US011596442B2

(12) United States Patent
Samchukov et al.

(10) Patent No.: US 11,596,442 B2
(45) Date of Patent: Mar. 7, 2023

(54) DYNAMIZATION TABS PROVIDING COMPONENT INTERCONNECTIVITY FOR EXTERNAL FIXATION DEVICES

(71) Applicants: Texas Scottish Rite Hospital for Children, Dallas, TX (US); Orthofix S.R.L., Verona (IT)

(72) Inventors: Mikhail L. Samchukov, Coppell, TX (US); Alexander M. Cherkashin, Flower Mound, TX (US); John D. Ross, Ovilla, TX (US); Karen D. Standefer, Flower Mound, TX (US); Daniele Venturini, Povegliano Veronese (IT); Andrea Ottoboni, Rovigo (IT)

(73) Assignees: Texas Scottish Right Hospital for Children, Dallas, TX (US); Orthofix S.R.L., Bussolengo Verona (IT)

( * ) Notice: Subject to any disclaimer, the term of this patent is extended or adjusted under 35 U.S.C. 154(b) by 758 days.

(21) Appl. No.: 16/448,794

(22) Filed: Jun. 21, 2019

(65) Prior Publication Data
US 2020/0397481 A1    Dec. 24, 2020

(51) Int. Cl.
*A61B 17/64* (2006.01)
*A61B 17/66* (2006.01)
*A61B 17/60* (2006.01)

(52) U.S. Cl.
CPC ............ *A61B 17/66* (2013.01); *A61B 17/645* (2013.01); *A61B 17/6416* (2013.01); *A61B 17/6475* (2013.01); *A61B 2017/606* (2013.01)

(58) Field of Classification Search
CPC ... A61B 17/62; A61B 17/6491; A61B 17/645; A61B 17/6441; A61B 2017/606; A61B 17/6466; A61B 17/6475; A61B 16/6483
See application file for complete search history.

(56) References Cited

U.S. PATENT DOCUMENTS

| 3,977,397 | A | * | 8/1976 | Kalnberz | ............... A61B 17/62 606/56 |
| 6,162,223 | A | * | 12/2000 | Orsak | ................ A61B 17/6425 606/59 |
| 8,439,914 | B2 | | 5/2013 | Ross et al. | |

(Continued)

OTHER PUBLICATIONS

Definition of "along", http://www.thefreedictionary.com/along, accessed Sep. 7, 2022.*

*Primary Examiner* — Jan Christopher L Merene
(74) *Attorney, Agent, or Firm* — Haynes and Boone, LLP

(57) ABSTRACT

Dynamization tabs and methods of use are provided. Dynamization tabs may be used with an external fixation ring or other fixator device as part of a therapeutic treatment of bone fractures or malformations. The device forms a connection between one or more fixation struts and an external fixation ring so as to introduce controllable amounts of movement or dynamization to the arrangement of the struts and the fixator. By introducing controlled amounts of dynamization, therapeutic benefits can be derived in the enhanced, accelerated bone formation, mineralization and remodeling of the underlying bone. Dynamization tabs may comprise a strut connector, a mechanical biasing or dynamizing device, and a ring connector. Many different forms for introducing controlled amounts of dynamization are disclosed.

17 Claims, 79 Drawing Sheets

(56) References Cited

U.S. PATENT DOCUMENTS

| | | |
|---|---|---|
| 8,444,644 B2 | 5/2013 | Ross et al. |
| 8,574,232 B1 | 11/2013 | Ross et al. |
| 8,864,750 B2 | 10/2014 | Ross et al. |
| 9,078,700 B2 | 7/2015 | Ross et al. |
| 9,155,559 B2 | 10/2015 | Ross et al. |
| 9,289,238 B2 | 3/2016 | Ross et al. |
| 9,295,493 B2 | 3/2016 | Ross et al. |
| 9,381,042 B2 | 7/2016 | Ross et al. |
| 9,456,849 B2 | 10/2016 | Ross et al. |
| 9,579,122 B2 | 2/2017 | Ross et al. |
| 9,681,892 B2 | 6/2017 | Ross et al. |
| 9,717,530 B1 | 8/2017 | Ross et al. |
| 9,808,289 B2 | 11/2017 | Ross et al. |
| 10,080,586 B2 | 9/2018 | Ross et al. |
| 10,130,391 B2 | 11/2018 | Ross et al. |
| 10,603,076 B2 | 3/2020 | Ross et al. |
| 10,743,918 B2 | 8/2020 | Samchukov et al. |
| 10,874,434 B2 | 12/2020 | Ross et al. |
| 2005/0203509 A1* | 9/2005 | Chinnaian .......... A61B 17/6491 606/54 |
| 2010/0305568 A1* | 12/2010 | Ross .................... A61B 17/62 606/56 |
| 2015/0305776 A1* | 10/2015 | Ross .................. A61B 17/6491 606/56 |
| 2018/0228515 A1* | 8/2018 | Ross .................. A61B 17/6491 |
| 2019/0365420 A1* | 12/2019 | Samchukov ....... A61B 17/6425 |
| 2020/0360057 A1 | 11/2020 | Samchukov et al. |
| 2020/0397481 A1 | 12/2020 | Samchukov et al. |
| 2021/0038263 A1 | 2/2021 | Ross et al. |
| 2021/0290270 A1 | 9/2021 | Venturini et al. |

\* cited by examiner

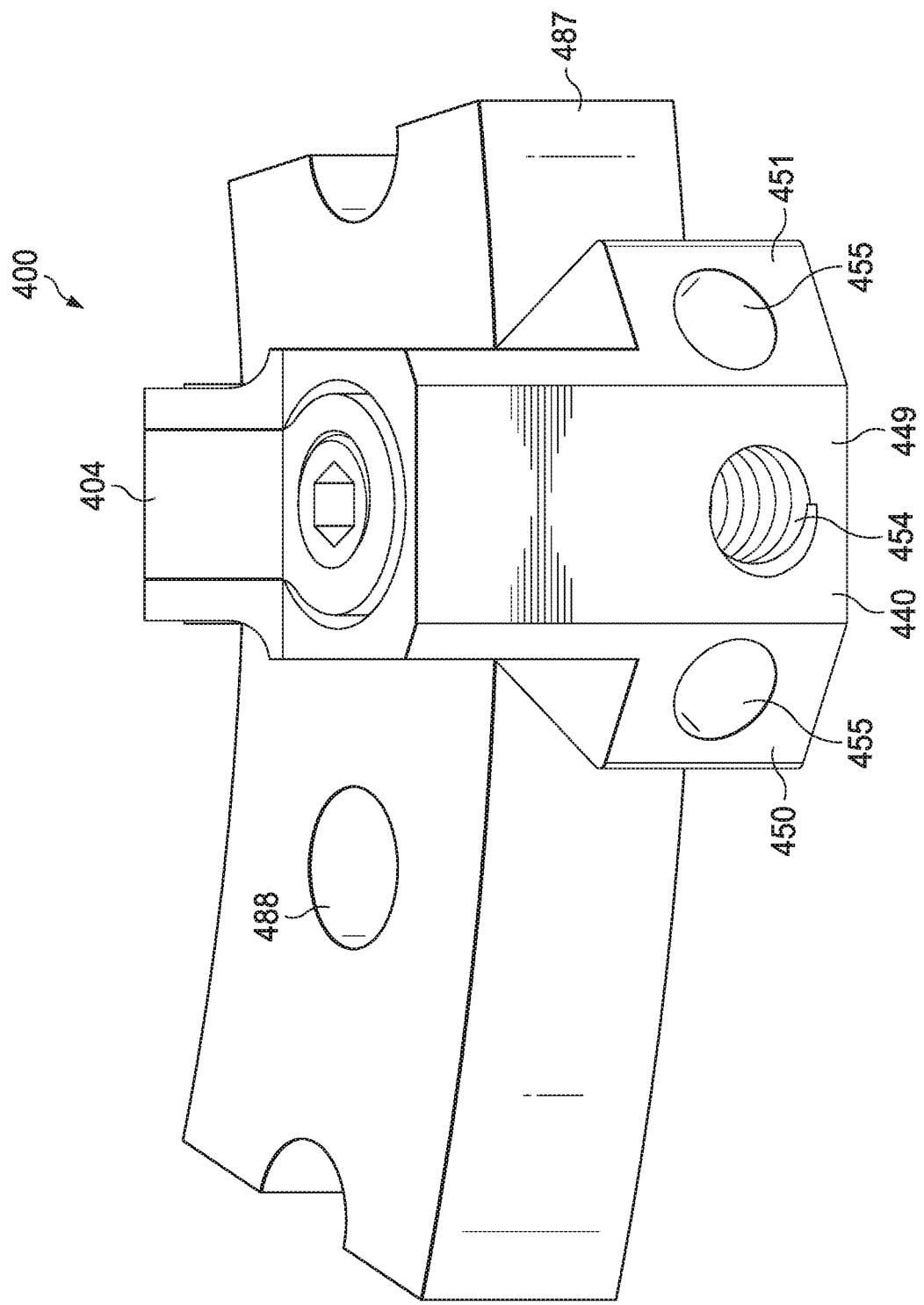

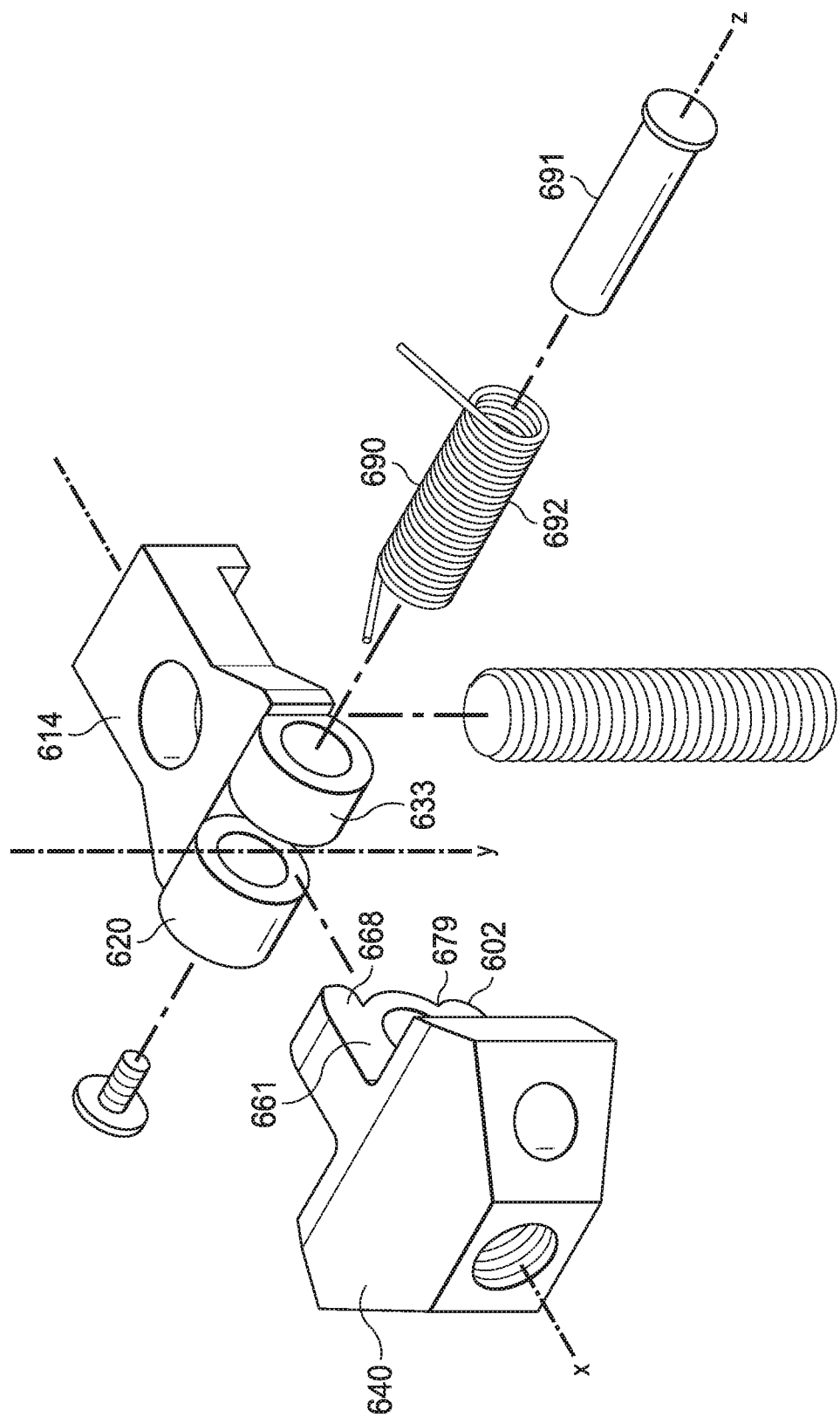

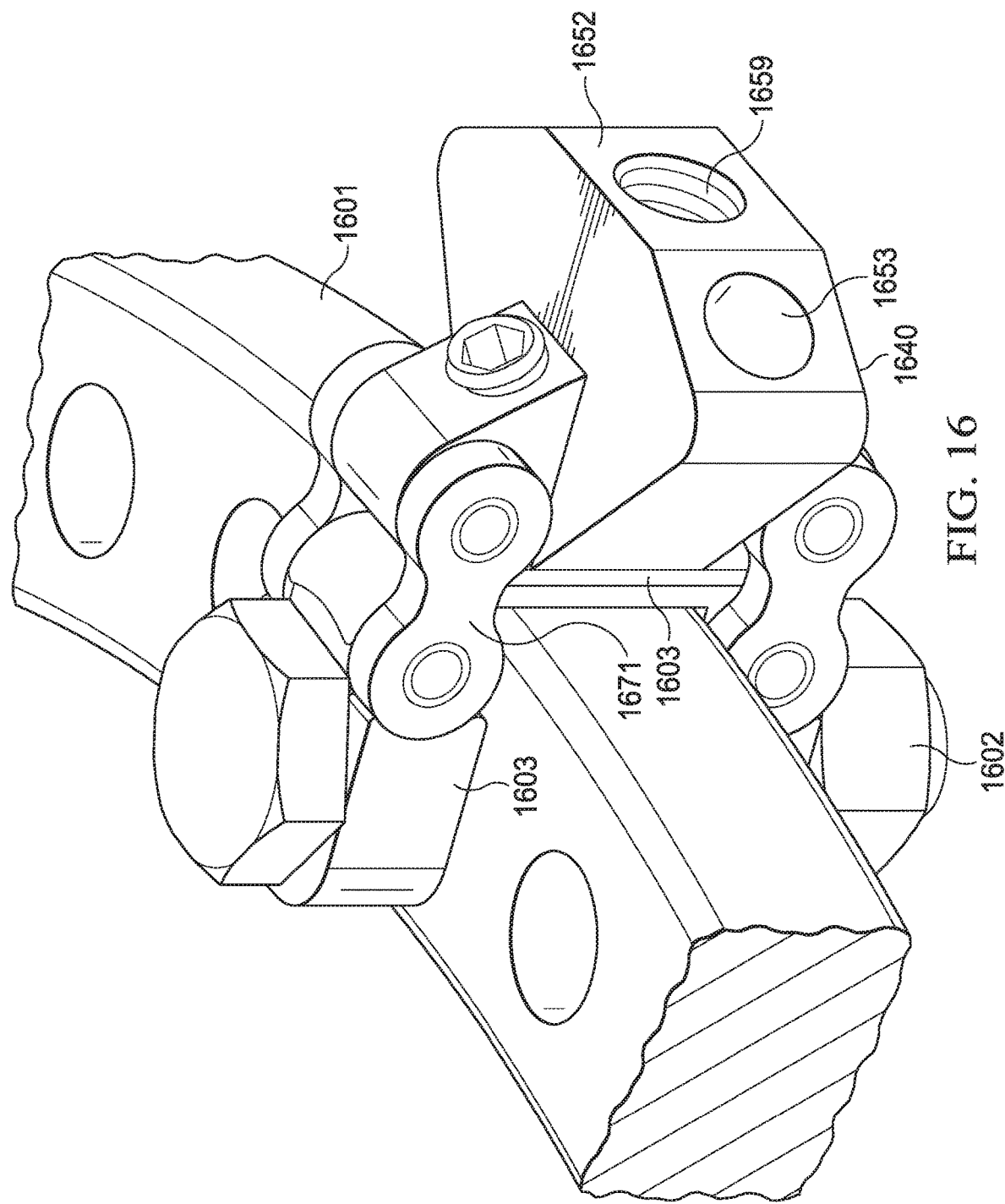

DYNAMIZATION TABS PROVIDING COMPONENT INTERCONNECTIVITY FOR EXTERNAL FIXATION DEVICES

TECHNICAL FIELD

The present disclosure relates in general to the field of external fixation, and more specifically, to dynamization tabs for joining external fixation struts to external fixation rings.

BACKGROUND OF THE DISCLOSURE

Without limiting the scope of the disclosure, this background is described in connection with external fixation devices and specifically in connection with dynamization tabs which are an advantageous means of connecting struts and/or rods to external fixation rings. Generally speaking, external fixation devices are commonly used devices in a variety of surgical procedures, e.g. limb lengthening, deformity correction, fracture reduction, etc., and in the treatment of non-unions, mal-unions, and bone defects. The process involves placing a rigid framework, made up of several rings, externally around a limb and attaching sections of the framework to relative bone segments using wires and half pins which are inserted into the bone. Opposite rings of the rigid framework are interconnected by either threaded or telescopic rods directly, or in conjunction with uniplanar or multi-planar hinges, allowing a surgeon to connect opposite rings that are not parallel to each other after manipulation with bone segments either rapidly or gradually over a period of time.

For example, in bone fracture reduction or non-union treatment, the wires and half pins are inserted into each bone segment and attached to the rings of the rigid framework. The rigid framework is used to acutely reduce a displacement and restore alignment between the bone segments. During this realignment, the orientations of opposite rings are often not parallel. The opposite rings of the rigid framework are connected together by threaded or telescopic rods with attached uniplanar or multi-planar hinges, allowing the opposite bone segment to be rigidly fixed until complete fracture healing or bone consolidation is complete.

For many bone treatments, the introduction of controlled destabilization can accelerate bone healing and significantly improve the strength of the fracture and distraction bone regenerate. The gradual increase of load is an important part of the healing process. In order to achieve this controlled destabilization, the external fixation devices may be dynamized. There are many ways of achieving dynamization. For a unilateral fixator, these include removing its bars, sliding the bars further away from the bone, removing some of its pins, and/or releasing tension or compression from the system. For a circular frame, these include removing some of its wires, releasing tension from the wires, partially removing its connection rods between rings, partially removing rings from a ring block, and/or releasing tension or compression from the system. These techniques may be problematic, however, because they often result in wide variations in the level of instability and may not effectively limit the dynamization to a desired direction or axis of movement.

One solution to this problem has been the introduction of dynamization modules into the threaded rods, i.e. struts, which connect the opposite rings of the rigid framework. This solution provides for a convenient method of introducing a desired amount of dynamization into the system in a manner which may be controlled in both intensity and direction. This solution, however, requires orientation of all dynamization modules parallel to each other and to the longitudinal axis of the bone or other desired direction of axial dynamization. This requirement can be achieved in traditional circular external fixation devices with external rings interconnected by 3-4 threaded or telescopic rods oriented parallel to each other. In hexapod-type external fixation devices, with 6 (six) telescopic struts oriented not parallel to each other and to the desired direction of dynamization, introduction of dynamization modules to the struts will result in reduction of overall stability of the system without possibility of controlled dynamization. This may result in undesirable translation of bone segments and problems with bone healing. In order to provide controlled dynamization in those cases, axial micromotion should be applied directly to the ring tabs.

SUMMARY

A dynamization device is described herein. According to one embodiment, the dynamization device includes a longitudinal axis, a vertical axis, and a transverse axis. The dynamization tab may further comprise a ring connector, a strut connector, and a biasing mechanism. The ring connector may have a proximal end, a distal end, and a first stabilizer, wherein the first stabilizer comprises a distal end and a proximal end and is positioned along the longitudinal axis of the dynamization tab. The first stabilizer may further comprise a top surface, a bottom surface, and a radial bore extending parallel to the vertical axis of the dynamization tab from the top surface to the bottom surface and configured to accept a connecting bolt. The ring connector may further comprise a second stabilizer having a distal end and a proximal end and is positioned inferior to and parallel with the first stabilizer. The second stabilizer may further comprise a top surface, a bottom surface, a radial bore extending parallel to the vertical axis of the dynamization tab from the top surface to the bottom surface and configured to accept the connecting bolt. The ring connector may further comprise a third stabilizer having a superior end and an inferior end and is positioned parallel to the vertical axis of the dynamization tab such that the superior end is in contact with the proximal end of the bottom surface of the first stabilizer and the inferior end is in contact with the proximal end of the top surface of the second stabilizer. The strut connector may comprise a proximal end, a distal end, and a head, wherein the head includes a proximal end and a distal end and is positioned along the longitudinal axis of the dynamization tab. The head of the strut connector may further comprise a top surface, a bottom surface, and a first distal-facing surface. The first distal-facing surface may comprise a locking-screw aperture having a partial bore extending from the distal end of the head toward the proximal end of the head. The head of the strut connector may also comprise second and third distal-facing surfaces, each of which may comprise a strut aperture having a partial bore extending from the distal end of the head toward the proximal end of the head. The head of the strut connector may also comprise a proximal-facing surface comprising a top edge and a bottom edge, the proximal-facing surface being positioned parallel to the transverse axis of the dynamization tab and in a manner such that the top edge is in contact with the top surface of the head and the bottom edge is in contact with the bottom surface of the head, and such that the proximal-facing surface comprises the proximal end of the head. The strut connector may also comprise a strut connector knuckle that can be positioned along the transverse axis of the dynamization tab in such a manner that it is in contact with the proximal-facing surface of the head of the strut connector. The strut connector knuckle may further comprise a superior member having a top surface and a bottom surface, and an inferior member having a top surface and a bottom surface. The dynamization tab may also comprise a biasing mechanism comprised of either an elastomeric material or flexible plastic, the biasing mechanism being positioned along the longitudinal axis of the dynamization tab. The biasing mechanism may be further comprised of a proximal end and a distal end, a biasing lip comprising a top surface and a bottom surface wherein the biasing lip may be positioned at the distal end of the biasing mechanism and along the longitudinal axis of the dynamization tab in such a manner that the top surface of the biasing lip is in contact with the bottom surface of the superior member of the strut connector knuckle and the bottom surface of the biasing lip is in contact with the top surface. The biasing mechanism may further comprise a biasing tab having a top surface that is positioned such that it is in contact with the bottom surface of the first stabilizer and can provide a mechanical bias when the strut connector is displaced from the longitudinal axis of the dynamization tab. The biasing mechanism may further comprise a bottom surface that is positioned such that it is in contact with the top surface of the second stabilizer and provides bias when the strut connector is displaced from the longitudinal axis of the dynamization tab. The biasing mechanism may further comprise a biasing tab elliptical bore extending parallel to the vertical axis of the dynamization tab in such a manner that the biasing mechanism may be displaced along the longitudinal axis of the dynamization tab. The biasing mechanism may be arranged such that proximal displacement decreases the strut connector's ability to rotate about the transverse axis of the dynamization tab and distal displacement increases the strut connector's ability to rotate about the transverse axis of the dynamization tab.

According to another embodiment, a dynamization tab may have a longitudinal axis, a vertical axis, and a transverse axis. The dynamization tab may be comprised of a ring connector, a strut connector, and a biasing mechanism. The ring connector may comprise a proximal end and a distal end and be positioned parallel to the longitudinal axis of the dynamization tab. The ring connector may comprise a stabilizer that is positioned parallel to the longitudinal axis of the dynamization tab, wherein the stabilizer comprises a top surface, a bottom surface, a proximal edge that is positioned parallel to the transverse axis of the dynamization tab and has a length equal to n, and a distal edge that is positioned parallel to the transverse axis of the dynamization tab, distal to the proximal edge, and has a length x, wherein x is greater than n. The ring connector may further comprise a ring connector elliptical bore extending parallel to the vertical axis of the dynamization tab from the top surface of the stabilizer to the bottom surface of the stabilizer and configured to accept a connector bolt. The ring connector elliptical bore may be further configured to allow the ring connector to be displaced along the longitudinal axis of the dynamization tab in a proximal manner and in a distal manner. The strut connector may have a proximal end and a distal end and further comprise a locking screw bushing, wherein the locking screw bushing comprises a threaded, cylindrical tube positioned along the longitudinal axis of the dynamization tab in such a manner that the longitudinal axis of the dynamization tab comprises the longitudinal axis of the threaded cylindrical tube. The locking screw bushing may be configured to accept a locking screw. The strut connector may further comprise first and second strut bushings that comprise threaded cylindrical tubes with first and second ends, positioned radially to the longitudinal axis of the dynamization tab in a manner such that the first ends are distal to the second ends, the first and second strut bushings being configured to accept strut-connecting screws. The biasing mechanism of the dynamization device may be comprised of either an elastomeric material or flexible plastic and be positioned along the longitudinal axis of the dynamization tab. The biasing mechanism may be further comprised of a first stabilizer, wherein the first stabilizer comprises a distal end and a proximal end and is positioned along the longitudinal axis of the dynamization tab. The first stabilizer may further comprise a top surface positioned such that it is in contact with the bottom surface of the ring connector stabilizer. The first stabilize may also comprise a bottom surface. The first stabilizer may further comprise a first biasing mechanism bore, extending parallel to the vertical axis of the dynamization tab from the top surface of the first stabilizer to the bottom surface of the first stabilizer and configured to accept the connecting bolt. The biasing mechanism may further comprise a second stabilizer that comprises a superior end and an inferior end and is positioned parallel to the vertical axis of the dynamization tab such that the superior end is in contact with the proximal end of the bottom surface of the first stabilizer. The biasing mechanism may further comprise a head with a proximal end and a distal end and which is positioned along the longitudinal axis of the dynamization tab. The head may further comprise a top surface positioned to be in contact with the bottom surface of the ring connector stabilizer in a manner such that the ring connector stabilizer applies bias when the head is displaced from the longitudinal axis of the dynamization tab. The head may also comprise a bottom surface and a first distal-facing surface having a locking-screw aperture. The locking screw aperture may comprise a partial bore extending from the distal end of the head toward the proximal end of the head and being configured to accept the locking screw bushing. The head may also comprise second and third distal-facing surfaces, each of which comprises a strut aperture having a partial bore that extends from the distal end of the head toward the proximal end of the head and being configured to accept the strut bushings.

According to another embodiment, a dynamization tab may have a longitudinal axis, a vertical axis, and a transverse axis and may comprise a ring connector, a strut connector, and a fastener. The ring connector may comprise a proximal end and a distal end and be positioned along the longitudinal axis of the dynamization tab. The ring connector may further comprise a top surface, a bottom surface, an anterior-facing surface, a posterior-facing surface, and a distal-facing surface. The ring connector may further comprise a first bore extending parallel and distal to the vertical axis of the dynamization tab, from the top surface of the ring connector to the bottom surface of the ring connector, and configured to accept a connecting bolt, the connecting bolt configured to secure the ring connector to a top surface of a ring. The ring connector may further comprise a second bore extending along the transverse axis of the dynamization tab and from the anterior-facing surface of the ring connector to the posterior-facing surface of the ring connector, the second bore being configured to accept a fastener. The strut connector of the dynamization tab may also have a proximal end and a distal end and may comprise a head. The head of the strut connector may be positioned along the longitudinal axis of the dynamization tab, the head further comprising a top surface, a bottom surface, a first distal-facing surface, and second and third distal facing surface. The first distal facing surface may comprise a top edge and a bottom edge wherein the proximal-facing surface being positioned parallel to the transverse axis of the dynamization tab in a manner such that the top edge is in contact with the top surface of the head and the bottom edge is in contact with the bottom surface of the head. The first distal facing surface may also comprise a locking-screw aperture comprising a partial bore extending from the distal end of the head toward the proximal end of the head. The head may further comprise second and third distal facing surfaces, each of which comprises a strut aperture having a partial bore extending from the distal end of the head toward the proximal end of the head. The strut connector may further comprise a strut connector knuckle having a proximal end and a distal end and being positioned along the longitudinal axis of the dynamization tab in a manner such that the distal end of the strut connector knuckle is in contact with the proximal end of the head. The strut connector knuckle may further comprise a first knob having a proximal end and a distal end and be positioned parallel to the longitudinal axis of the dynamization tab in a manner such that the distal end of the first knob is in contact with the proximal end of the head. The first knob may further comprise a top surface, a bottom surface, and an anterior-facing surface comprising a top edge and a bottom edge and being positioned such that the top edge of the anterior-facing surface is in contact with the top surface of the first knob and the bottom edge of the anterior-facing surface is in contact with the bottom surface of the first knob. The first knob may also comprise a posterior-facing surface having a top edge and a bottom edge and being positioned such that the top edge of the posterior-facing surface is in contact with the top surface of the first knob and wherein the bottom edge of the posterior-facing surface is in contact with the bottom surface of the first knob. In addition, the posterior-facing surface may be in contact with the anterior-facing surface of the ring connector. The first knob may also comprise a first knob bore extending along the transverse axis of the dynamization tab, from the anterior-facing surface of the first knob to the posterior-facing surface of the first knob, the first knob bore being configured to accept the fastener. The strut connector knuckle may further comprise a second knob comprising a proximal end and a distal end and be positioned parallel to the longitudinal axis of the dynamization tab in a manner such that the distal end of the second knob is in contact with the proximal end of the head. The second knob may further comprise a top surface, a bottom surface, an anterior-facing surface comprising a top edge and a bottom edge and being positioned such that the top edge of the anterior-facing surface is in contact with the top surface of the second knob, the bottom edge of the anterior-facing surface is in contact with the bottom surface of the second knob, and the anterior-facing surface is in contact with the posterior-facing surface of the ring connector. The second knob may also comprise a second knob bore extending along the transverse axis of the dynamization tab from the anterior-facing surface of the second knob to the posterior-facing surface of the second knob, the second knob bore being configured to accept the fastener. The dynamization device may also comprise a fastener that may be positioned along the transverse axis of the dynamization tab in a manner such that the fastener passes through the first knob bore, the second knob bore, and the second bore of the ring connector and allows for rotation of the strut connector about the transverse axis of the dynamization tab, the rotation being limited in degree by contact between the bottom surface of the first knob and the top surface of the ring and by contact between the bottom surface of the second knob and the top surface of the ring. The fastener may further comprise a pin and a torsion spring, wherein the torsion spring is positioned such that the torsion spring applies bias when the strut connector is displaced from the longitudinal axis of the dynamization tab.

According to another embodiment, the dynamization tab has a longitudinal axis, a vertical axis, and a transverse axis, the dynamization tab comprising a ring connector having a proximal end and a distal end and being positioned along the longitudinal axis of the dynamization tab. The ring connector may further comprise a ring connector body having a proximal end and a distal end and being positioned along the longitudinal axis of the dynamization tab. The ring connector body may further comprise a top surface, a bottom surface, a first upper lateral surface, a second upper lateral surface; and a distal knob that is positioned at the distal end of the ring connector body and comprises a top surface and a bottom surface. The ring connector body may also comprise a first bore that extends from the top surface of the ring connector knob to the bottom surface of the ring connector knob and is parallel to the vertical axis of the dynamization tab, the first bore being configured to accept an adjustment screw. The ring connector body may also comprise a second bore that extends from the first upper lateral surface of the ring connector body to the second upper lateral surface of the ring connector body and is positioned parallel to the transverse axis of the dynamization tab at the proximal end of the ring connector body, the second bore being configured to accept a pivot pin. The ring connector body may also include a connecting bolt that extends from the bottom surface of the ring connector body and is positioned parallel to the vertical axis of the dynamization tab and is configured to accept a connecting nut. The ring connector body may also comprise a first roughened surface having a plurality of ridges on the bottom surface of the ring connector body, the first roughened surface being positioned at the distal end of the ring connector body in a manner such that it may contact a surface of the external fixation ring and provide a frictional connection that limits rotation of the ring connector with respect to an external fixation ring. The ring connector body may further comprise a second roughened surface comprising a plurality of ridges on the bottom surface of the ring connector body, the second roughened surface being positioned at the proximal end of the ring connector body in a manner such that it may contact a surface of the external fixation ring and provide a frictional connection that limits rotation of the ring connector with respect to an external fixation ring. The ring connector body may also comprise a first motion limiting face positioned at the distal end of the ring connector body and parallel to the transverse axis of the dynamization tab in a manner such that the first notch is parallel and superior to the bottom surface of the ring connector body. The dynamization device may also comprise a strut connector having a proximal end and a distal end and being positioned along the longitudinal axis of the dynamization tab such that the strut connector is in contact with the ring connector. The strut connector may further comprise a head that comprises a proximal end and a distal end and is positioned along the longitudinal axis of the dynamization tab. The head may further comprise a top surface, a bottom surface, and a first distal-facing surface. The first distal-facing surface may comprise a top edge and a bottom edge, wherein the first distal-facing surface may be positioned parallel to the transverse axis of the dynamization tab and in a manner such that the top edge is in contact with the top surface of the head and the bottom edge is in contact with the bottom surface of the head. The strut connector may also comprise a locking screw aperture comprising a partial bore extending from the distal end of the head towards the proximal end of the head, the locking screw aperture being configured to accept a locking screw. The second and third distal-facing surfaces, each of the second and third distal-facing surfaces comprising a strut aperture comprising a partial bore, the partial bore extending from the distal end of the head towards the proximal end of the head, the strut aperture being configured to secure the strut connector to a strut. The strut connector may also comprise a second motion limiting face positioned at the proximal end of the head and in contact with the top surface of the head in a manner such that, the degree of rotational displacement of the strut connector about the transverse axis of the dynamization tab is limited by contact between the second motion limiting face of the strut connector and the first motion limiting face of the ring connector body. The strut connector may also comprise a first arm comprising a proximal end and a distal end, wherein the first arm is positioned along the longitudinal axis of the dynamization tab and further comprises a top surface, and a bottom surface positioned such that it is parallel to the longitudinal axis of the dynamization tab. The strut connector may also comprise a first inner wall surface, a first lateral wall surface, and a first lateral pin bore extending through the first lateral wall surface and the first inner wall surface so that the first lateral pin bore is parallel to the transverse axis of the dynamization tab, the first lateral pin bore being configured to accept the pivot pin. The strut connector may also comprise a second arm having a proximal end and a distal end, wherein the second arm is positioned along the longitudinal axis of the dynamization tab and further comprises a top surface, a bottom surface, the bottom surface being positioned such that it is parallel to the longitudinal axis of the dynamization tab, a second inner wall surface, a second lateral wall surface, and a second lateral pin bore extending through the second lateral wall surface and the second inner wall surface so that the second lateral pin bore is parallel to the transverse axis of the dynamization tab, the second lateral pin bore being configured to accept the pivot pin. The first and second arms may be connected by a lateral member at a proximal end of the arms. Generally speaking, the ring connector can be mated with the strut connector so that the first and second lateral pin bores of the first and second arms are aligned with the second bore of the ring connector so that a pivot pin pivotably secures to the ring connector and to the strut connector and allows the strut connector to pivot about the transvers axis with respect to the ring connector. The first and second upper lateral surfaces of the ring connector can slidably engage with the first and second inner wall surfaces of the strut connectors when the ring connector is pivotably secured to the strut connector. Also disclosed is a biasing element comprising a compression spring positioned between the bottom surface of the distal knob of the ring connector and the bottom of the ring connector aperture such that the biasing element provides a mechanical bias that opposes the pivotal movement of the strut connector with respect to the ring connector. The device may also include an adjustment screw disposed within the threaded bore of the ring connector that can be driven to traverse the threaded bore; wherein when a distal end of the adjustment screw is driven to impinge upon the bottom of the ring connector aperture, the pivotal movement of the strut connector with respect to the ring connector is limited; and wherein when a the distal end of the adjustment screw is driven away from the bottom of the ring connector aperture, pivotal movement of the strut connector with respect to the ring connector can be controllably engaged.

According to another embodiment, a dynamization tab may include a longitudinal axis, a vertical axis, and a transverse axis, and comprise a ring connector, a strut connector, and a biasing mechanism. The ring connector may comprise a proximal end, a distal end, a superior end, and an inferior end. The ring connector may further comprise a first stabilizer having a distal end and a proximal end and be positioned along the longitudinal axis of the dynamization tab. The first stabilizer may further comprise a top surface, a bottom surface, a first stabilizer bore extending along the vertical axis of the dynamization tab from the top surface of the first stabilizer to the bottom surface of the first stabilizer and being configured to accept a connecting bolt. The ring connector may further comprise a second stabilizer having a distal end and a proximal end and be positioned inferior to and parallel with the first stabilizer. The second stabilizer may further comprise a top surface, a bottom surface, a second stabilizer bore extending along the vertical axis of the dynamization tab from the top surface of the second stabilizer to the bottom surface of the second stabilizer, and be configured to accept the connecting bolt. The ring connector may further comprise a third stabilizer having a superior end and an inferior end and be positioned parallel to the vertical axis of the dynamization tab such that the superior end of the third stabilizer is in contact with the proximal end of the bottom surface of the first stabilizer and the inferior end of the third stabilizer is in contact with the top surface of the second stabilizer. The ring connector may further comprise a ring connector knuckle having a superior end and an inferior end and be positioned along the vertical axis of the dynamization tab in a manner such that the inferior end of the ring connector knuckle is in contact with the top surface of the first stabilizer. The ring connector knuckle may further comprise a top surface, a bottom surface, an anterior-facing surface, a posterior-facing surface, and a proximal-facing surface having a top edge and a bottom edge. The posterior-facing surface is positioned parallel to the vertical axis of the dynamization tab in such a manner that the top edge of the proximal-facing surface is in contact with the top surface of the ring connector knuckle and the bottom edge of the proximal-facing surface is in contact with the bottom face of the ring connector knuckle, the proximal-facing surface being convexly-shaped with respect to the vertical axis of the dynamization tab. The ring connector knuckle may also comprise a distal-facing surface having a top edge and a bottom edge and be positioned parallel to the vertical axis of the dynamization tab in such a manner that the top edge of the distal-facing surface is in contact with the top surface of the ring connector knuckle and the bottom edge of the distal-facing surface is in contact with the bottom surface of the ring connector knuckle, the distal-facing surface being convexly-shaped with respect to the vertical axis of the dynamization tab. The ring connector knuckle may further comprise a ring connector knuckle bore extending along the vertical axis of the dynamization tab from the top surface of the ring connector knuckle to the bottom surface of the ring connector knuckle and is configured to accept the connecting bolt. The dynamization device may further comprise a strut connector having a proximal end, a distal end, a superior end, and an inferior end. The strut connector may further comprise a head having a proximal end and a distal end and be positioned along the longitudinal axis of the dynamization tab. The head of the strut connector may further comprise a top surface, a bottom surface, a first distal-facing surface comprising a locking-screw aperture. The locking screw aperture may comprise a partial bore extending from the distal end of the head toward the proximal end of the head. The head of the strut connector may further comprise second and third distal-facing surfaces, each of which comprises a strut aperture having a partial bore extending from the distal end of the head toward the proximal end of the head. The strut connector may also comprise a strut connector knuckle having a proximal end and a distal end and be positioned along the longitudinal axis of the dynamization tab. The strut connector knuckle may further comprise a top surface, bottom surface, a strut connector knuckle bore extending along the vertical axis of the dynamization tab, from the top surface of the strut connector knuckle to the bottom surface of the strut connector knuckle. The strut connector knuckle may further comprise an anterior-facing surface, wherein the anterior-facing surface is configured to be in contact with the posterior-facing surface of the ring connector knuckle in such a manner that rotation of the strut connector about the vertical axis of the dynamization tab is prohibited. The strut connector knuckle may further comprise a posterior-facing surface that may be configured to be in contact with the anterior-facing surface of the ring connector knuckle in such a manner that rotation of the strut connector about the vertical axis of the dynamization tab is prohibited. The strut connector knuckle may further comprise a proximal-facing surface comprising a top edge and a bottom edge and be positioned parallel to the vertical axis of the dynamization tab in such a manner that the top edge of the proximal-facing surface is in contact with the top surface of the strut connector knuckle and the bottom edge of the proximal-facing surface is in contact with the bottom surface of the strut connector knuckle, the proximal-facing surface being concavely-shaped with respect to the vertical axis of the dynamization tab and positioned such that the proximal-facing surface of the strut connector knuckle bore is in contact with the distal-facing surface of the ring connector knuckle. The strut connector knuckle may further comprise a distal-facing surface, wherein the distal-facing surface comprises a top edge and a bottom edge and is positioned parallel to the vertical axis of the dynamization tab in such a manner that the top edge of the distal-facing surface is in contact with the top surface of the strut connector knuckle and the bottom edge of the distal-facing surface is in contact with the bottom surface of the strut connector knuckle, the distal-facing surface being concavely-shaped with respect to the vertical axis of the dynamization tab and positioned such that the distal-facing surface of the strut connector knuckle bore is in contact with the proximal-facing surface of the ring connector knuckle. The dynamization device may also comprise a biasing mechanism having a superior end and an inferior end, wherein the biasing mechanism may be positioned along the vertical axis of the dynamization tab. The biasing mechanism may further comprise a connector bolt comprising a superior end and an inferior end, wherein the connector bolt is a threaded bolt that may be configured to traverse along the vertical axis of the dynamization tab in such a manner that it passes through the ring connector knuckle bore, the first stabilizer bore, and the second stabilizer bore. The biasing mechanism may further comprise a fastener having a superior end and an inferior end, wherein the fastener is positioned such that its superior end comprises the superior end of the biasing mechanism, and the inferior end of the fastener is in contact with the connector bolt in a manner such that rotation of the fastener around the vertical axis of the dynamization tab translates to rotation of the connector bolt around the vertical axis of the dynamization tab. The biasing mechanism may further comprise an oscillating spring comprising a superior end and an inferior end, positioned along the vertical axis of the dynamization tab in a manner such that the superior end is in contact with the fastener, the inferior end is in contact with the top surface of the strut connector knuckle, and compression of the oscillating spring provides a biasing force when the strut connector is displaced from the longitudinal axis of the dynamization tab.

According to another embodiment, a dynamization tab may include a longitudinal axis, a vertical axis, and a transverse axis, and may comprise a ring connector, a strut connector, and a fastener. The ring connector may include a proximal end, a distal end, a superior end, and an inferior end. The ring connector may further comprise a first stabilizer having a distal end and a proximal end and be positioned along the longitudinal axis of the dynamization tab. The first stabilizer may further comprise a top surface, a bottom surface, and a radial bore extending parallel to the vertical axis of the dynamization tab from the top surface to the bottom surface and configured to accept a connecting bolt. The ring connector may further comprise a second stabilizer having a distal end and a proximal end and be positioned inferior to and parallel with the first stabilizer. The second stabilizer may further comprise a top surface, a bottom surface, and a radial bore extending parallel to the vertical axis of the dynamization tab from the top surface to the bottom surface and configured to accept the connecting bolt. The ring connector may further comprise a third stabilizer having a superior end and an inferior end and be positioned parallel to the vertical axis of the dynamization tab such that the superior end is in contact with the proximal end of the bottom surface of the first stabilizer and the inferior end is in contact with the proximal end of the top surface of the second stabilizer. The ring connector may further comprise a ring connector knuckle, wherein the ring connector knuckle comprises an anterior end, a posterior end, a proximal end, and a distal end and is positioned along the longitudinal axis of the dynamization tab in a manner such that the proximal end is in contact with the distal end of the first stabilizer. The ring connector knuckle may further comprise a first circular knob having an anterior face and a posterior face and be positioned along the transverse axis of the dynamization tab in a manner such that the anterior face and the posterior face are perpendicular to the top surface and the bottom surface of the first stabilizer. The first circular knob may further comprise a bore extending from the anterior face to the posterior face and a second circular knob having an anterior face and a posterior face and be positioned along the transverse axis of the dynamization tab in a manner such that the anterior face and the posterior face are perpendicular to the top surface and the bottom surface of the first stabilizer. The second circular knob may further comprise a bore extending from the anterior face to the posterior face. The dynamization device may further comprise a strut connector having a proximal end, a distal end, a superior end, an inferior end. The strut connector may further comprise a head having a proximal end and a distal end and be positioned along the longitudinal axis of the dynamization tab. The head of the strut connector may further comprise a top surface, a bottom surface, a first distal-facing surface comprising a locking-screw aperture having a partial bore extending from the distal end of the head toward the proximal end of the head, and second and third distal-facing surfaces, each of which comprises a strut aperture having a partial bore extending from the distal end of the head toward the proximal end of the head. The head of the strut connector may further comprise a proximal-facing surface having a top edge and a bottom edge, the proximal-facing surface being positioned parallel to the transverse axis of the dynamization tab and in a manner such that the top edge is in contact with the top surface of the head and the bottom edge is in contact with the bottom surface of the head, and such that the proximal-facing surface comprises the proximal end of the head. The strut connector may further comprise a strut connector knuckle having a proximal end and a distal end and be positioned along the longitudinal axis of the dynamization tab in a manner such that the distal end is in contact with the proximal end of the head. The strut connector knuckle may further comprise a first knob having a distal end and a proximal end and be positioned parallel to the longitudinal axis of the dynamization tab in a manner such that the distal end is in contact with the proximal end of the head. The first knob may further comprise a top surface having a proximal end and a distal end, the top surface being curved at the proximal end, a bottom surface having a proximal end and a distal end, the proximal and distal end connected by a curved face, and a motion-limiting face having a superior edge and an inferior edge and positioned such that the superior edge is in contact with the proximal end of the top surface and the inferior edge is in contact with the proximal end of the bottom surface. The strut connector knuckle may further comprise a second knob having a distal end and a proximal end and positioned inferior to the first knob and parallel to the longitudinal axis of the dynamization tab in a manner such that the distal end is in contact with the proximal end of the head. The second knob further comprising a top surface having a proximal end and a distal end, the proximal and distal end connected by a curved face. The second knob also comprising a bottom surface having a proximal end and a distal end, the bottom surface being curved at the proximal end. The second knob also comprising a motion-limiting face having a superior edge and an inferior edge and positioned such that the superior edge is in contact with the proximal end of the top surface and the inferior edge is in contact with the proximal end of the bottom surface. The dynamization device further comprising a fastener that may be positioned along the transverse axis of the dynamization tab in a manner such that the fastener passes through the bore of the first circular knob and the bore of the second circular knob, is in contact with the bottom surface of the first knob of the strut connector knuckle and the top surface of the second knob of the strut connector knuckle, and allows for rotation of the strut connector about the transverse axis of the dynamization tab, the rotation being limited in degree by contact between the motion-limiting face of the first knob of the strut connector knuckle and the top surface of the first stabilizer of the ring connector and by contact between the motion-limiting face of the second knob of the strut connector knuckle and the bottom surface of the first stabilizer of the ring connector. The fastener may further comprise a pin and a torsion spring configured to apply bias then the strut connector is displaced from the longitudinal axis of the dynamization tab.

According to another embodiment, the dynamization device may include a longitudinal axis, a vertical axis, and a transverse axis. The dynamization tab may further comprise a ring connector, a strut connector, and a biasing mechanism. According to one embodiment, a ring connector may include a proximal end and a distal end. The ring connector may further comprise a first stabilizer having a proximal and a distal end and be positioned along the longitudinal axis of the dynamization tab. The ring connector may further comprise a top surface, a bottom surface, a first stabilizer bore, wherein the first stabilizer bore extends parallel to the vertical axis of the dynamization tab from the top surface of the first stabilizer to the bottom surface of the first stabilizer. The first stabilizer bore may be positioned proximal to the vertical axis of the dynamization tab and configured to accept a connector bolt. The ring connector may further comprise a second stabilizer comprising a superior and an inferior end, the second stabilizer being positioned parallel to the vertical axis of the dynamization tab in such a manner that the superior end is in contact with the proximal end of the first stabilizer. The ring connector may further comprise a ring connector knuckle, comprising a superior end and an inferior end, the ring connector knuckle being positioned parallel to the vertical axis of the dynamization tab in such manner that the superior end is in contact with the distal end of the first stabilizer. The ring connector knuckle may further comprise a top edge, a bottom edge, a distal-facing surface, wherein the distal-facing surface is positioned along the vertical axis of the dynamization tab and convexly-shaped in relation to the vertical axis of the dynamization tab, the distal-facing surface further comprising a radial track donor, the radial track donor positioned such that it is perpendicular to the transverse axis of the dynamization tab. The dynamization device may further comprise a strut connector having a proximal end and a distal end, and be positioned along the longitudinal axis of the dynamization tab in such a manner that the proximal end is in contact with the distal end of the ring connector. The strut connector may further comprise a head having a proximal end and a distal end and positioned along the longitudinal axis of the dynamization tab. The head may further comprise a top surface, a bottom surface, a first distal-facing surface, the first distal-facing surface comprising a locking-screw aperture, the locking screw aperture comprising a partial bore, the partial bore extending from the distal end of the head toward the proximal end of the head. The head may further comprise second and third distal-facing surfaces, each of which comprises a strut aperture having a partial bore extending from the distal end of the head toward the proximal end of the head. The strut connector may further comprise a strut connector knuckle having a superior end and an inferior end and being positioned parallel to the vertical axis of the dynamization tab such that the superior end is in contact with the top surface of the head of the strut connector and the inferior end is in contact with the bottom surface of the head of the strut connector. The strut connector knuckle further comprising a top edge that in contact with the top surface of the head of the strut connector, a bottom edge that is in contact with the bottom surface of the head of the strut connector, and a proximal-facing surface that may be positioned along the vertical axis of the dynamization tab and be concavely-shaped with respect to the vertical axis of the dynamization tab. The proximal-facing surface may further comprise a radial track acceptor being positioned such that it is perpendicular to the transverse axis of the dynamization tab and configured to accept the radial track donor of the distal-facing surface of the ring connector knuckle. The dynamization device may further comprise a biasing mechanism having a superior member that is comprised of either an elastomeric material or flexible plastic and is positioned parallel to the transverse axis of the dynamization tab. The superior member may be further comprised of a top surface, a bottom surface being positioned such that it is in contact with the top surface of the head of the strut connector in such a manner that the superior member applies bias when the strut connector is displaced from the longitudinal axis of the dynamization tab, a proximal-facing surface having a top edge and a bottom edge and being positioned such that the top edge is in contact with the top surface of the superior member and the bottom edge is in contact with the bottom surface of the superior member and in a manner such that increased distance between the top edge and the bottom edge limits rotation of the strut connector about the transverse axis of the dynamization tab. The biasing member further comprising an inferior member comprised of either an elastomeric material or flexible plastic and positioned parallel to the transverse axis of the dynamization tab. Wherein the inferior member may be further comprised of a top surface being positioned such that it is in contact with the bottom surface of the head of the strut connector in such a manner that the inferior member applies bias when the strut connector is displaced from the longitudinal axis of the dynamization tab, a bottom surface, a proximal-facing surface comprising a top edge and a bottom edge, wherein the proximal-facing surface being positioned such that the top edge is in contact with the top surface of the inferior member and the bottom edge is in contact with the bottom surface of the inferior member and in a manner such that increased distance between the top edge and the bottom edge limits rotation of the strut connector about the transverse axis of the dynamization tab.

According to another embodiment, the dynamization device may include a longitudinal axis, a vertical axis, and a transverse axis. The dynamization tab may further comprise a ring connector, a strut connector, and a biasing mechanism. According to one embodiment, a ring connector may include a proximal and a distal end and further comprise a first stabilizer. The first stabilizer may comprise a proximal end and a distal end and be positioned parallel to the longitudinal axis of the dynamization tab. The first stabilizer may further comprise a top surface, a bottom surface, and a first stabilizer bore extending along the vertical axis of the dynamization tab from the top surface of the first stabilizer to the bottom surface of the stabilizer, the first stabilizer bore being configured to accept a connector bolt and the connector bolt being configured to secure the ring connector to a ring. The ring connector may further comprise a second stabilizer having a superior and an inferior end and be positioned parallel to the vertical axis of the dynamization tab in such a manner that the superior end is in contact with the proximal end of the first stabilizer. The ring connector may further comprise a track donor having a superior end and an inferior end and being positioned parallel to the vertical axis of the dynamization tab in such a manner that the superior end is in contact with the top surface of the first stabilizer and the inferior end is in contact with the bottom surface of the first stabilizer. The strut connector may comprise a proximal end and a distal end and be positioned along the longitudinal axis of the dynamization tab. The strut connector may further comprise a head that comprises a proximal end and a distal end and is positioned along the longitudinal axis of the dynamization tab. The head may further comprise a top surface, a bottom surface, a first distal-facing surface having a locking-screw aperture that comprises a partial bore extending from the distal end of the head toward the proximal end of the head. The head may further comprise second and third distal-facing surfaces, each of which comprises a strut aperture having a partial bore extending from the distal end of the head toward the proximal end of the head. The strut connector may further comprise a strut connector stabilizer having a proximal and a distal end and being positioned parallel to the longitudinal axis of the dynamization tab in such a manner that the distal end of the strut connector stabilizer is in contact with the proximal end of the head. The strut connector stabilizer further comprises a top surface, a bottom surface, a strut connector stabilizer bore extending along the vertical axis from the top surface of the strut connector stabilizer to the bottom surface of the strut connector stabilizer, the strut connector stabilizer bore being configured to accept a connecting bolt. The strut connector may further comprise a track acceptor having a superior and an inferior end, the track acceptor being positioned parallel to the vertical axis of the dynamization tab such that the superior end is in contact with the top surface of the head of the strut connector and the inferior end is in contact with the bottom surface of the head of the strut connector, the track acceptor being further configured to accept the track donor of the ring connector. The dynamization device further comprising a biasing mechanism having a superior end and an inferior end and positioned superior to the strut connector stabilizer in a manner such that the inferior end of the biasing mechanism is in contact with the top surface of the strut connector stabilizer and in a manner such that when the strut connector is displaced from the longitudinal axis of the dynamization tab, the biasing mechanism applies a biasing force which returns the strut connector to its original position. The biasing mechanism further comprises at least one of a compression spring, an elastomeric material, and flexible plastic.

According to another embodiment, the dynamization device may include a longitudinal axis, a vertical axis, and a transverse axis. The dynamization tab may further comprise a connector and a biasing mechanism. According to one embodiment, the connector may include a proximal end and a distal end, the connector being positioned along the longitudinal axis of the dynamization tab. The connector may further comprise a ring connector having a proximal end, a distal end, an anterior face, and a posterior face, and further comprising a first stabilizer having a proximal end and a distal end. The first stabilizer may be positioned parallel to the longitudinal axis of the dynamization tab and further comprise a top surface and a bottom surface. The ring connector may further comprise a second stabilizer having a superior end and an inferior end and be positioned parallel to the vertical axis of the dynamization tab in a manner such that the superior end of the second stabilizer is in contact with the proximal end of the first stabilizer. The ring connector may further comprise a biasing groove having an anterior end and a posterior end, the biasing groove being concavely shaped with respect to the transverse axis and being positioned along the transverse axis. The biasing groove may be positioned such that the anterior end of the biasing groove is in contact with the anterior face of the ring connector, the posterior end of the biasing groove is in contact with the posterior face of the ring connector, and the biasing groove bisects the ring connector between the proximal end and the distal end. The connector may further comprise a head having a proximal end and a distal end and positioned along the longitudinal axis of the dynamization tab, the head further comprising a top surface, a bottom surface, a first distal-facing surface having a locking-screw aperture including a partial bore extending from the distal end of the head toward the proximal end of the head. The head of the connector may further comprise second and third distal-facing surfaces, each of which comprises a strut aperture having a partial bore extending from the distal end of the head toward the proximal end of the head. The connector may further comprise a connector bore extending along the vertical axis from the top surface of the first stabilizer to the bottom surface of the first stabilizer, the connector bore being an elliptical bore with a flat anterior face and a flat posterior face and being positioned between the anterior end of the biasing groove and the posterior end of the biasing groove. The dynamization tab may further comprise a biasing mechanism including a biasing nut having a superior end and an inferior end and being positioned along the vertical axis in a manner such that the inferior end of the biasing nut is in contact with the biasing groove of the ring connector, the inferior end of the biasing nut being convexly shaped with respect to the transverse axis of the dynamization tab in a manner such that it allows for displacement of the connector about the transverse axis of the dynamization tab. The biasing mechanism may further comprise a connector bolt having a superior end and an inferior end and being positioned along the transverse axis of the dynamization tab in a manner such that the superior end is in contact with the biasing nut, the connector bolt being configured to be accepted by the connector bore. The connect bolt further comprises an anterior face with a flat surface and a posterior face with a flat surface, the anterior and posterior faces being in contact with the flat anterior face of the connector bore of the connector and the posterior face of the connector bolt being in contact with the flat posterior face of the connector bore of the connector in a manner which allows for the rotation of the connector about the transverse axis of the dynamization tab. The biasing mechanism may further comprise a biasing spring, the biasing spring having a superior end and an inferior end and being positioned along the vertical axis of the dynamization tab in a manner such that the superior end is in contact with the bottom surface of the first stabilizer of the ring connector, the biasing spring being configured to apply a biasing force when the connector is displaced from the longitudinal axis of the dynamization tab.

According to another embodiment, the dynamization device may include a longitudinal axis, a vertical axis, and a transverse axis. The dynamization tab may further comprise a connector and a biasing mechanism. According to this embodiment, a connector may include a proximal end and a distal end, and be positioned along the longitudinal axis of the dynamization tab. The connector may further comprise a ring connector having a proximal end, a distal end, and a first stabilizer having a proximal end and a distal end and being positioned parallel to the longitudinal axis of the dynamization tab. The first stabilizer may further comprise a top surface and a bottom surface. The ring connector may further comprise a second stabilizer having a superior end and an inferior end and being positioned parallel to the vertical axis of the dynamization tab in a manner such that the superior end of the second stabilizer is in contact with the proximal end of the first stabilizer. The ring connector may further comprise a connector bore extending along the vertical axis from the top surface of the first stabilizer to the bottom surface of the first stabilizer, the connector bore being configured to accept a connecting bolt. The connector may further comprise a head having a proximal end and a distal end and is positioned along the longitudinal axis of the dynamization tab. The head may further comprise a top surface, a bottom surface, a first distal-facing surface having a locking-screw aperture comprising a partial bore extending from the distal end of the head toward the proximal end of the head. The head may further comprise second and third distal-facing surfaces, each of which comprises a strut aperture having a partial bore extending from the distal end of the head toward the proximal end of the head. The dynamization tab may further comprise a biasing mechanism having a proximal end and a distal end and is comprised of a flexible plastic or elastomeric material. The biasing mechanism may further comprise a bottom surface and a top surface that is configured to be in contact with the ring connector in a manner such that the biasing mechanism applies a biasing force when the head of the connector is displaced from the longitudinal axis of the dynamization tab. The biasing mechanism may further comprise a proximal edge that may be positioned parallel to the transverse axis of the dynamization tab and have a length equal to n. The biasing mechanism may further comprise a distal edge, wherein the distal edge is positioned parallel to the transverse axis of the dynamization tab, distal to the proximal edge, and has a length x, wherein x is greater than n. The biasing mechanism may further comprise a biasing mechanism bore, extending parallel to the vertical axis of the dynamization tab from the top surface of the biasing mechanism to the bottom surface of the biasing mechanism and configured to accept a connector bolt, the biasing mechanism bore being further configured to allow the biasing mechanism to be displaced along the longitudinal axis of the dynamization tab in a proximal manner and in a distal manner such that proximal displacement restricts the ability of the connector to rotate about the transverse axis of the dynamization tab.

According to another embodiment, the dynamization device may include a longitudinal axis, a vertical axis, and a transverse axis and may comprise a strut connector, a ring connector, and a biasing mechanism. According to this embodiment, a strut connector may include a proximal end, a distal end, and be positioned along the longitudinal axis of the dynamization tab. The strut connector may further comprise a top surface, a bottom surface, and a first distal-facing surface having a top edge and a bottom edge, the proximal-facing surface being positioned parallel to the transverse axis of the dynamization tab and in a manner such that the top edge is in contact with the top surface of the head and the bottom edge is in contact with the bottom surface of the head. The first distal-facing surface may further comprise a locking-screw aperture, the locking screw aperture comprising a partial bore extending from the distal end of the head toward the proximal end of the head. The strut connector may further comprise second and third distal facing surfaces, each of which comprises a strut aperture with a partial bore extending from the distal end of the head toward the proximal end of the head. The dynamization device may further comprise a ring connector having a proximal end, a distal end, and a first stabilizer having a proximal end and a distal end and being positioned parallel and superior to the longitudinal axis of the dynamization tab. The first stabilizer may further comprise a top surface, a bottom surface, a first connector bore extending from the top surface of the first stabilizer to the bottom surface of the first stabilizer and being configured to accept a connecting bolt. The first stabilizer may further comprise a second connector bore extending from the top surface of the first stabilizer to the bottom surface of the first stabilizer and being configured to accept a connecting bolt. The ring connector may further comprise a second stabilizer having a proximal end and a distal end and being positioned parallel and inferior to the longitudinal axis of the dynamization tab, the second stabilizer further comprising a top surface, a bottom surface, a first connector bore extending from the top surface of the second stabilizer to the bottom surface of the second stabilizer and being configured to accept a connecting bolt, and a second connector bore extending from the top surface of the second stabilizer to the bottom surface of the second stabilizer and being configured to accept a connecting bolt. The dynamization tab may further comprise a biasing mechanism having a proximal end and a distal and being positioned along the longitudinal axis in a manner such that the proximal end of the biasing mechanism is in contact with the distal end of the ring connector and the distal end of the biasing mechanism is in contact with the proximal end of the strut connector. The biasing mechanism may further comprise a first biasing region having a proximal end and a distal end and being positioned such that the proximal end of the first biasing region is in contact with the ring connector and the distal end of the first biasing region is in contact with the strut connector. The first biasing region may further comprise one or more biasing plates, the biasing plates being placed parallel to one another and to the longitudinal axis of the dynamization tab in a manner such that there is space between each of the plates, the plates being comprised of a flexible plastic or other elastomeric material and configured such that the first biasing region applies a biasing force when the strut connector is displaced from the longitudinal axis of the dynamization tab. The biasing mechanism may further comprise a second biasing region having a proximal end and a distal end and being positioned such that the proximal end of the second biasing region is in contact with the ring connector and the distal end of the second biasing region is in contact with the strut connector, the second biasing region further comprising one or more biasing plates being placed parallel to one another and to the longitudinal axis of the dynamization tab in a manner such that there is space between each of the plates, the plates being comprised of a flexible plastic or other elastomeric material and configured such that the second biasing region applies a biasing force when the strut connector is displaced from the longitudinal axis of the dynamization tab.

According to another embodiment, the dynamization device may include a longitudinal axis, a vertical axis, and a transverse axis and may comprise a strut connector, a ring connector, and a biasing mechanism. According to this embodiment, a ring connector may comprise a first ring connecting apparatus having a superior end and an inferior end and being positioned parallel to the vertical axis of the dynamization tab in a manner such that the superior end is in contact with a ring. The first connecting apparatus may further comprise a first connecting bore extending from the superior end to the inferior end and being configured to accept a first connecting bolt. The ring connector may further comprise a second ring connecting apparatus having a superior end and an inferior end and being positioned parallel to the vertical axis of the dynamization tab in a manner such that the superior end is in contact with a ring, the second connecting apparatus further comprising a second ring connecting bore extending from the superior end to the inferior end and being configured to accept a second ring connecting bolt. The dynamization device may further comprise a strut connector having a top surface and a bottom surface and being positioned along the longitudinal axis of the dynamization tab. The strut connector may further comprise a first distal-facing surface having a locking-screw aperture, a second and third distal-facing surfaces, each of which further comprising a strut aperture, and an adjustment bore being a partial bore extending from the top surface of the strut connector towards the bottom surface of the strut connector. The adjustment bore may be configured to accept an adjustment bolt. The dynamization device may further comprise a biasing mechanism being positioned along the transverse axis of the dynamization tab in a manner such that it is parallel and inferior to the ring. The biasing mechanism may further comprise a first biasing region having an anterior end and a posterior end and being positioned such that the posterior end is in contact with the strut connector. The first biasing region further comprising a top surface, a bottom surface, and one or more biasing plates positioned between the top surface and the bottom surface of the first biasing region, parallel to one another and to the transverse axis of the dynamization tab in a manner such that there is space between each of the plates. Each of the biasing plates may comprise a flexible plastic or other elastomeric material and configured such that the second biasing region applies a biasing force when the strut connector is displaced from the longitudinal axis of the dynamization tab. The biasing mechanism may further comprise a second biasing region having an anterior end and a posterior end and being positioned such that the anterior end is in contact with the strut connector. The second biasing region may further comprise a top surface, a bottom surface, and one or more biasing plates, wherein the biasing plates are positioned between the top surface and the bottom surface of the second biasing region, parallel to one another and to the transverse axis of the dynamization tab in a manner such that there is space between each of the plates. The biasing plates may be comprised of a flexible plastic or other elastomeric material and configured such that the second biasing region applies a biasing force when the strut connector is displaced from the longitudinal axis x of the dynamization tab. The biasing mechanism may further comprise an adjustment mechanism positioned along the vertical axis and further comprising an adjustment bolt having a superior end and an inferior end, positioned such that the superior end is in contact with a ring and the inferior end is in contact with the adjustment bore of the strut connector. The biasing mechanism may further comprise a first adjustment nut being positioned such that it is in contact with the ring. The biasing mechanism may further comprise a second adjustment nut being positioned inferior to the first adjustment nut and configured such that increased distance between the first adjustment nut and the second adjustment nut translates to a decreased ability for the strut aperture to be displaced from the longitudinal axis of the dynamization tab.

According to another embodiment, the dynamization device may include a longitudinal axis, a vertical axis, and a transverse axis and may comprise a strut connector, a ring connector, and a biasing mechanism. According to this embodiment, the ring connector may comprise a superior member having a distal end and a proximal end and being positioned parallel and superior to the longitudinal axis. The superior member may further comprise a top surface, a bottom surface, a first drive pin bore, a second drive pin bore, and a third drive pin bore, each of the first, second, and third drive pin bores being positioned such that it extends parallel to the vertical axis of the dynamization tab from the top surface of the superior member to the bottom surface of the superior member, and wherein each of the first, second, and third drive pin bores being configured to accept a first drive pin, a second drive pin, and a third drive pin, respectively. The superior member may further comprise a set screw bore being positioned proximal to the first, second, and third drive pin bores such that it extends parallel to the vertical axis of the dynamization tab from the top surface of the superior member to the bottom surface of the superior member, the set screw bore being configured to accept a first set screw. The superior member may further comprise a ring connector bore being positioned proximal to the first, second, and third drive pin bores and proximal to the set screw bore and in a manner such that it is parallel to the vertical axis of the dynamization tab and extends from the top surface of the superior member to the bottom surface of the superior member, the ring connector bore being configured to accept a connecting bolt. The superior member may further comprise a first and a second stabilizing feature, each of the first and second stabilizing features extending from the bottom surface of the superior member and parallel to the vertical axis. The ring connector may further comprise an inferior member having a distal end and a proximal end and being positioned parallel and inferior to the longitudinal axis, the inferior member further comprising a top surface, a bottom surface, and a first drive pin bore, a second drive pin bore, and a third drive pin bore, each of the first, second, and third drive pin bores being positioned such that it extends parallel to the vertical axis of the dynamization tab from the top surface of the inferior member to the bottom surface of the inferior member, each of the first, second, and third drive pin bores being configured to accept the first drive pin, the second drive pin, and the third drive pin, respectively. The ring connector may further comprise a set screw bore being positioned proximal to the first, second, and third drive pin bores and such that it extends parallel to the vertical axis of the dynamization tab from the top surface of the inferior member to the bottom surface of the inferior member, the set screw bore being configured to accept a second set screw. The ring connector may further comprise a ring connector bore being positioned proximal to the first, second, and third drive pin bores and proximal to the set screw bore and in a manner such that it is parallel to the vertical axis of the dynamization tab and extends from the top surface of the superior member to the bottom surface of the superior member, the ring connector bore being configured to accept the connecting bolt. The ring connector may further comprise a first and a second stabilizing feature, each of which extends from the top surface of the inferior member and parallel to the vertical axis. The dynamization tab may further comprise a strut connector having a distal end and a proximal end and being positioned along the longitudinal axis of the dynamization tab. The strut connector may further comprise a top surface being positioned such that it is in contact with the bottom surface of the superior member of the ring connector, a bottom surface, a first drive pin bore, a second drive pin bore, and a third drive pin bore, each of the first, second, and third drive pin bores being positioned such that it extends parallel to the vertical axis of the dynamization tab from the top surface of the strut connector to the bottom surface of the strut connector, each of the first, second, and third drive pin bores being configured to accept the first drive pin, the second drive pin, and the third drive pin, respectively. The strut connector may further comprise a first stabilizing feature cavity being configured to house the first stabilizing feature of the superior member and the first stabilizing feature of the inferior member in a manner such that rotation of the strut connector about the vertical axis of the dynamization tab is limited by contact between the first stabilizing feature cavity and the first stabilizing features of the superior member and the inferior member, respectively. The strut connector may further comprise a second stabilizing feature cavity being configured to house the second stabilizing feature of the superior member and the second stabilizing feature of the inferior member in a manner such that rotation of the strut connector about the vertical axis of the dynamization tab is limited by contact between the second stabilizing feature cavity and the second stabilizing features of the superior member and the inferior member, respectively. The strut connector may further comprise first, second, and third distal-facing surfaces, each of the first, second, and third distal-facing surfaces comprising a strut aperture having a partial bore extending from the distal end of the strut connector towards the proximal end of the strut connector and being configured to secure a strut to the strut connector. The dynamization device may further comprise a biasing mechanism having a first linear bearing comprising a low friction material and being positioned parallel to the vertical axis of the dynamization tab in a manner such that it is in contact with the bottom surface of the superior member and the top surface of the strut connector, the first linear bearing being further configured to traverse at least a part of the first drive pin bore of the strut connector and to accept the first drive pin. The biasing mechanism may further comprise a second linear bearing comprising a low friction material and being positioned parallel to the vertical axis of the dynamization tab in a manner such that it is in contact with the bottom surface of the strut connector, the second linear bearing being configured to traverse at least a part of the second drive pin bore of the strut connector and to accept the second drive pin. The biasing mechanism may further comprise a third linear bearing comprising a low friction material and being positioned parallel to the vertical axis of the dynamization tab in a manner such that it is in contact with the bottom surface of the strut connector. The third linear bearing being configured to traverse at least part of the drive pin bore of the strut connector and to accept the third driving pin. The biasing mechanism may further comprise a first drive pin being configured to traverse the first drive pin bore of the superior member, the first drive pin bore of the inferior member, the first drive pin bore of the strut connector, and the first linear bearing in a manner such that when the strut connector is displaced from the longitudinal axis of the dynamization tab, the displacement is limited to axial displacement parallel to the vertical axis of the dynamization tab. The biasing mechanism may further comprise a second drive pin being configured to traverse the second drive pin bore of the superior member, the second drive pin bore of the inferior member, the second drive pin bore of the strut connector, the second linear bearing, and a first spring in a manner such that when the strut connector is displaced from the longitudinal axis of the dynamization tab, the displacement is limited to axial displacement parallel to the vertical axis of the dynamization tab. The biasing mechanism may further comprise a third drive pin, the third drive pin being configured to traverse the third drive pin bore of the superior member, the third drive pin bore of the inferior member, the third drive pin bore of the strut connector, the third linear bearing, and a second spring in a manner such that when the strut connector is displaced from the longitudinal axis of the dynamization tab, the displacement is limited to axial displacement parallel to the vertical axis of the dynamization tab. The biasing mechanism may further comprise a first set screw being positioned such that it is parallel to the vertical axis of the dynamization tab and in contact with the top surface of the strut connector, the first set screw being configured to traverse the set screw bore of the superior member of the ring connector in a manner such that as the first set screw is tightened, movement of the strut connector along the vertical axis of the dynamization tab is limited. The biasing mechanism may further comprise a second set screw being positioned such that it is parallel to the vertical axis of the dynamization tab and in contact with the bottom surface of the strut connector, the second set screw being configured to traverse the set screw bore of the inferior member of the ring connector in a manner such that as the second screw is tightened, movement of the strut connector along the vertical axis of the dynamization tab is limited. The biasing mechanism may further comprise a first spring being positioned such that it is parallel to the vertical axis of the dynamization tab in a manner such that it is in contact with the bottom surface of the strut connector and the top surface of the inferior member of the ring connector, the first spring configured such that when the strut connector is displaced from the longitudinal axis of the dynamization tab, the first spring provides a sufficient biasing force to return the strut connector to its original position. The biasing mechanism may further comprise a second spring, the second spring being positioned such that it is parallel to the vertical axis of the dynamization tab in a manner such that it is in contact with the bottom surface of the strut connector and the top surface of the inferior member of the ring connector, the second spring being configured such that when the strut connector is displaced from the longitudinal axis of the dynamization tab, the second spring provides a sufficient biasing force to return the strut connector to its original position.

According to another embodiment, the dynamization device may include a longitudinal axis, a vertical axis, and a transverse axis and may comprise a strut connector, a ring connector, and a biasing mechanism. According to this embodiment, a ring connector may comprise a first stabilizer having a distal end and being positioned superior and parallel to the longitudinal axis of the dynamization tab, the first stabilizer further comprising a ring connector bore. The ring connector may further comprise a second stabilizer having a distal end and being positioned inferior and parallel to the longitudinal axis of the dynamization tab, the second stabilizer further comprising a ring connector bore. The ring connector may further comprise a third stabilizer having a superior end, an inferior end, an anterior-facing surface, and a posterior-facing surface, and being positioned parallel to the vertical axis of the dynamization tab in a manner such that the superior end of the third stabilizer is in contact with the distal end of the first stabilizer and the inferior end of the third stabilizer is in contact with the distal end of the second stabilizer. The third stabilizer may further comprise a first pin bore positioned parallel to the longitudinal axis of the dynamization tab in a manner such that the first pin bore extends from the anterior-facing surface of the ring connector to the posterior-facing surface of the ring connector, the first pin bore being configured to accept a first pin. The ring connector may further comprise a second pin bore positioned parallel to the longitudinal axis of the dynamization tab in a manner such that the second pin bore extends from the anterior-facing surface of the ring connector to the posterior-facing surface of the ring connector, the second pin bore being configured to accept a second pin. The dynamization device may further comprise a strut connector having a distal end and a proximal end and being positioned along the longitudinal axis of the dynamization tab. The strut connector may further comprise a head having a top surface and a bottom surface, the head further comprising first, second, and third distal-facing surfaces. Each of the first, second, and third distal-facing surfaces may comprise a strut aperture having a partial bore extending from the distal end of the strut connector towards the proximal end of the strut connector and being configured to secure a strut to the strut connector. The strut connector may further comprise a first knob being positioned parallel to the vertical axis of the dynamization tab in a manner such that the first knob is in contact with the top surface of the head. The first knob may further comprise an anterior-facing surface, a posterior-facing surface, and a third pin bore being positioned parallel to the longitudinal axis of the dynamization tab in a manner such that the third pin bore extends from the anterior-facing surface of the first knob to the posterior-facing surface of the first knob, the third pin bore being configured to accept a third pin. The strut connector may further comprise a second knob being positioned parallel to the vertical axis of the dynamization tab in a manner such that the second knob is in contact with the bottom surface of the head. The second knob may further comprise an anterior-facing surface, a posterior-facing surface, and a fourth pin bore, the fourth pin bore being positioned parallel to the longitudinal axis of the dynamization tab in a manner such that the fourth pin bore extends from the anterior-facing surface of the second knob to the posterior-facing surface of the second knob, the fourth pin bore being configured to accept a fourth pin. The strut connector may further comprise a first set screw bore extending in an angular fashion from the proximal end of the strut connector towards the distal end of the strut connector, the first set screw bore being configured to accept a first set screw. The strut connector may further comprise a second set screw bore extending in an angular fashion from the proximal end of the strut connector towards the distal end of the strut connector, the second set screw bore being configured to accept a second set screw. The dynamization device may further comprise a biasing mechanism having a hinging mechanism positioned such that the hinging mechanism allows for the strut connector to be rotationally displaced from the longitudinal axis of the dynamization tab. The hinging mechanism may further comprise a first pin having an anterior end and a posterior end and being positioned superior and parallel to the longitudinal axis of the dynamization tab in a manner such that the first pin traverses the first pin bore of the third stabilizer of the ring connector. The hinging mechanism may further comprise a second pin having an anterior end and a posterior end and being positioned inferior and parallel to the longitudinal axis of the dynamization tab in a manner such that the second pin traverses the second pin bore of the third stabilizer of the ring connector. The hinging mechanism may further comprise a third pin having an anterior end and a posterior end and being positioned superior and parallel to the longitudinal axis of the dynamization tab in a manner such that the third pin traverses the third pin bore of the first knob of the strut connector. The hinging mechanism may further comprise a fourth pin having an anterior end and a posterior end and being positioned inferior and parallel to the longitudinal axis of the dynamization tab in a manner such that the fourth pin traverses the fourth pin bore of the second knob of the strut connector. The hinging mechanism may further comprise a first link comprising a first eye and a second eye and being positioned such that the first eye accepts and secures the posterior end of the first pin and the second eye accepts and secures the posterior end of the third pin. The hinging mechanism may further comprise a second link comprising a first eye and a second eye and being positioned such that the first eye accepts and secures the anterior end of the first pin and the second eye accepts and secures the anterior end of the third pin. The hinging mechanism may further comprise a third link comprising a first eye and a second eye and being positioned such that the first eye accepts and secures the posterior end of the second pin and the second eye accepts and secures the posterior end of the fourth pin. The hinging mechanism may further comprise a fourth link comprising a first eye and a second eye and being positioned such that the first eye accepts and secures the anterior end of the second pin and the second eye accepts and secures the anterior end of the fourth pin. The biasing mechanism may further comprise an elastic element comprised of an elastomeric material or a spring and being positioned in a manner such that the elastic element is in contact with the third stabilizer of the ring connector, applies a biasing force, when the strut connector is displaced from the longitudinal axis of the dynamization tab, sufficient to return to the strut connector to its original position. The biasing mechanism may further comprise a first set screw being configured to traverse the first set screw bore and be in contact with the elastic element in a manner such that as the first set screw is tightened, rotational movement of the strut connector about the transverse axis is limited. The biasing mechanism may further comprise the second set screw, the second set screw being configured to traverse the second set screw bore and be in contact with the elastic element in a manner such that as the second set screw is tightened, rotational movement of the strut connector about the transverse axis is limited.

According to another embodiment, the dynamization device may include a longitudinal axis, a vertical axis, and a transverse axis and may comprise a strut connector, a ring connector, and a biasing mechanism. According to this embodiment, a ring connector may comprise a first stabilizer being positioned parallel to the longitudinal axis of the dynamization tab, the first stabilizer comprising a top surface, a bottom surface, and a ring connector bore extending from the top surface of the first stabilizer to the bottom surface of the first stabilizer, the ring connector bore being configured to accept a connecting bolt. The ring connector may further comprise a second stabilizer having a superior end and an inferior end and being positioned parallel to the vertical axis of the dynamization tab, the second stabilizer further comprising a distal-facing surface, a proximal-facing surface, a spring recess, the spring recess comprising a partial bore extending from the distal-facing surface of the second stabilizer towards the proximal-facing surface of the second stabilizer, the spring recess being configured to accept a biasing spring. The second stabilizer may further comprise a ring connector knob having an anterior-facing surface and a posterior-facing surface and further comprising a hinge pin bore, the pin bore extending from the anterior-facing surface of the ring connector knob to the posterior-facing surface of the ring connector knob and being configured to accept a hinge pin. The dynamization device may further comprise a strut connector having a distal end, a proximal end, an anterior-facing surface, and a posterior-facing surface, and being positioned along the longitudinal axis of the dynamization tab. The strut connector may further comprise a head having a top surface and a bottom surface and further comprising first, second, and third distal-facing surfaces, each of the first, second, and third distal-facing surfaces comprising a strut aperture having a partial bore extending from the distal end of the strut connector towards the proximal end of the strut connector and being configured to secure a strut to the strut connector. The strut connector may further comprise a strut connector knob, the strut connector knob being positioned parallel to the vertical axis of the dynamization tab in a manner such that the strut connector knob is in contact with the top surface of the head of the strut connector. The strut connector knob may further comprise a spring recess comprising a partial bore extending from the proximal end of the strut connector towards the distal end of the strut connector and being configured to accept a biasing spring, and a set screw bore, extending in an angular fashion from the proximal end of the strut connector towards the distal end of the strut connector, the set screw bore being configured to accept a set screw. The strut connector may further comprise a strut connector recess being positioned at the proximal end of the strut connector and being configured to accept at least a portion of the ring connector knob. The strut connector may further comprise a hinge pin bore extending from the anterior-facing surface of the strut connector to the posterior-facing surface of the strut connector, the hinge pin bore being configured to accept the hinge pin. The dynamization device may further comprise a biasing mechanism comprising a hinge pin positioned along the transverse axis of the dynamization tab in a manner such that it traverses the hinge pin bore of the strut connector and the hinge pin bore of the ring connector and allows for the rotational displacement of the strut connector about the transverse axis of the dynamization tab. The biasing mechanism may further comprise a biasing spring positioned superior and parallel to the longitudinal axis in a manner such that it is in contact with the spring recess of the ring connector and the spring recess of the strut connector, and applies a biasing force, as the strut connector is displaced from the longitudinal axis of the dynamization tab, sufficient to return the strut connector to its original position. The biasing mechanism may further comprise a set screw being configured to traverse the set screw bore of the strut connector and be in contact with the ring connector knob in a manner such that as the set screw is tightened, rotational movement of the strut connector about the transverse axis of the dynamization tab is limited.

According to another embodiment, the dynamization device may include a longitudinal axis, a vertical axis, and a transverse axis and may comprise a strut connector, a ring connector, and a biasing mechanism. According to this embodiment, a ring connector may comprise a first stabilizer having a distal end and being positioned superior and parallel to the longitudinal axis of the dynamization tab, the first stabilizer further comprising a ring connector bore. The ring connector may further comprise a second stabilizer having a distal end and being positioned inferior and parallel to the longitudinal axis of the dynamization tab, the second stabilizer further comprising a ring connector bore. The ring connector may further comprise a third stabilizer having a first wall, comprising a first pin bore, the first pin bore being positioned parallel to the transverse axis of the dynamization tab and configured to accept a first pin. The third stabilizer of the ring connector may further comprise a second wall comprising a first pin bore, the first pin bore being positioned parallel to the transverse axis of the dynamization tab and configured to accept the first pin. The third stabilizer of the ring connector may further comprise a third wall comprising a second pin bore, the second pin bore being positioned parallel to the transverse axis of the dynamization tab and configured to accept a second pin. The third stabilizer of the ring connector may further comprise a fourth wall comprising a second pin bore, the second pin bore being positioned parallel to the transverse axis of the dynamization tab and configured to accept the second pin. In addition, the third stabilizer of the ring connector may further comprise a distal-facing surface, positioned parallel to the vertical axis of the dynamization tab. The dynamization device may further comprise a strut connector positioned along the longitudinal axis and comprising a head having a top surface and a bottom surface, the head further comprising first, second, and third distal-facing surfaces. Each of the first, second, and third distal-facing surfaces comprising a strut aperture, the strut aperture comprising a partial bore extending from the distal end of the strut connector towards the proximal end of the strut connector and being configured to secure a strut to the strut connector. The strut connector may further comprise a first knob being positioned in a manner such that it is in contact with the top surface of the head of the strut connector, the first knob comprising a top surface, an anterior-facing surface, a posterior-facing surface, and a stadium bore extending from the anterior-facing surface of the first knob to the posterior-facing surface of the first knob and being configured to accept the first pin. The strut connector may further comprise a second knob being positioned in a manner such that it is in contact with the bottom surface of the head of the strut connector, the second knob comprising a bottom surface, an anterior-facing surface, a posterior-facing surface, and a stadium bore extending from the anterior-facing surface of the second knob to the posterior-facing surface of the second knob and being configured to accept the second pin. The strut connector may further comprise a set screw bore, the set screw bore extending inferior and parallel to the longitudinal axis of the dynamization tab, the set screw bore being configured to accept a set screw. The strut connector may further comprise an elastic element housing, the elastic element housing comprising a partial bore extending from the top surface of the first knob of the strut connector towards the bottom surface of the second knob of the strut connector, the elastic element housing being positioned along the vertical axis and configured to accept an elastic element. The strut connector may further comprise a proximal-facing surface, the proximal-facing surface being positioned proximal and parallel to the vertical axis of the dynamization tab and in contact with the distal-facing surface of the ring connector in a manner such that rotational displacement of the strut connector about the transverse axis is limited. The dynamization device may further comprise a biasing mechanism comprising a first pin being positioned superior and parallel to the transverse axis of the dynamization tab in a manner such that it traverses the first pin bore of the first wall of the third stabilizer, the stadium bore of the first knob of the strut connector, and the first pin bore of the second wall of the third stabilizer in a manner such that the strut connector may be displaced along the vertical axis of the dynamization tab. The biasing mechanism further comprising a second pin, the second pin being positioned inferior and parallel to the transverse axis of the dynamization tab in a manner such that it traverses the second pin bore of the third wall, the stadium bore of the second knob of the strut connector, and the second pin bore of the fourth wall of the third stabilizer in a manner such that the strut connector may be displaced along the vertical axis of the dynamization tab. The biasing mechanism further comprising an elastic element comprising a spring or an elastomeric material and being positioned along the vertical axis in a manner such that it traverses the elastic element housing of the strut connector and applies a biasing force, when the strut connector is displaced from the longitudinal axis of the dynamization tab, sufficient to return the strut connector to its original position. Lastly, the biasing mechanism may further comprise a set screw being configured to traverse the set screw bore of the strut connector and be in contact with the elastic element in a manner such that as the set screw is tightened, axial movement of the strut connector along the vertical axis of the dynamization tab is limited.

According to another embodiment, the dynamization device may include a longitudinal axis, a vertical axis, and a transverse axis and may comprise a strut connector, a ring connector, and a biasing mechanism. According to this embodiment, the ring connector may comprise a first stabilizer being positioned superior and parallel to the longitudinal axis of the dynamization tab and comprising a ring connector bore. The ring connector may further comprise The ring connector may further comprise a second stabilizer, the second stabilizer being positioned inferior and parallel to the longitudinal axis of the dynamization tab and comprising a ring connector bore. The strut connector may comprise a strut connector, positioned along the longitudinal axis and comprising a head having a top surface and a bottom surface, the head further comprising first, second, and third distal-facing surfaces, each of the first, second, and third distal-facing surfaces comprising a strut aperture, the strut aperture comprising a partial bore extending from the distal end of the strut connector towards the proximal end of the strut connector and being configured to secure a strut to the strut connector. The strut connector may further comprise a set screw and a first dynamization stop bore extending from the top surface of the head of the strut connector to the bottom surface of the head of the strut connector and being positioned parallel to the vertical axis of the dynamization tab, the first dynamization stop bore being configured to accept a first dynamization stop. The strut connector may further comprise a second dynamization stop bore, the second dynamization stop bore extending from the top surface of the head of the strut connector to the bottom surface of the head of the strut connector and being positioned parallel to the vertical axis of the dynamization tab, the second dynamization stop bore being configured to accept a second dynamization stop. The biasing mechanism may comprise a first biasing region being positioned superior and parallel to the longitudinal axis of the dynamization tab and comprising one or more biasing plates, the biasing plates being placed parallel to one another and to the longitudinal axis of the dynamization tab in a manner such that there is space between each of the plates, the plates being comprised of a flexible plastic or other elastomeric material and configured such that the first biasing region applies a biasing force when the strut connector is displaced from the longitudinal axis of the dynamization tab. The biasing mechanism may comprise a second biasing region being positioned inferior and parallel to the longitudinal axis of the dynamization tab and comprising one or more biasing plates, the biasing plates being placed parallel to one another and to the longitudinal axis of the dynamization tab in a manner such that there is space between each of the plates, the plates being comprised of a flexible plastic or other elastomeric material and configured such that the second biasing region applies a biasing force when the strut connector is displaced from the longitudinal axis of the dynamization tab. The biasing mechanism may further comprise a first dynamization stop, the first dynamization stop comprising a post comprising a superior end, an inferior end, and a central axis, the post being configured to traverse the first dynamization stop bore of the strut connector in a manner such that the post is allowed to rotate about its central axis. The first dynamization stop may further comprise an elastic ring, the elastic ring being configured to be in contact with the inferior end of the post in a manner such that it secures the post within the first dynamization stop bore of the strut connector. The first dynamization stop may further comprise a first dynamization stop tab, positioned parallel to the longitudinal axis of the dynamization tab and at the superior end of the post, the dynamization stop tab being configured to limit the ability of the strut connector to be displaced from the longitudinal axis of the dynamization tab when placed between any two plates of the first biasing region. The biasing mechanism may further comprise a second dynamization stop comprising a post comprising a superior end, an inferior end, and a central axis, the post being configured to traverse the second dynamization stop bore of the strut connector in a manner such that the post is allowed to rotate about its central axis. The second dynamization stop may further comprise an elastic ring, the elastic ring being configured to be in contact with the superior end of the post in a manner such that it secures the post within the second dynamization stop bore of the strut connector. The first dynamization stop may further comprise a second dynamization stop tab, positioned parallel to the longitudinal axis of the dynamization tab and at the inferior end of the post, the dynamization stop tab being configured to limit the ability of the strut connector to be displaced from the longitudinal axis of the dynamization tab when placed between any two plates of the second biasing region.

According to another embodiment, the dynamization device may include a longitudinal axis, a vertical axis, and a transverse axis and may comprise a strut connector, a ring connector, and a biasing mechanism. According to this embodiment, a ring connector body may a proximal end and a distal end and being positioned along the longitudinal axis of the dynamization tab, the ring connector body further comprising a top surface, a bottom surface, a first lateral surface, a second lateral surface, a proximal surface, and a distal surface having a curved profile with respect to the vertical axis of the dynamization tab. The ring connector body further comprising a first bore that extends from the top surface to the bottom surface and is parallel to the vertical axis of the dynamization tab, the first bore being threaded to accept a connecting bolt. The ring connector body further comprising a second bore that extends from the first lateral surface to the second lateral surface and is positioned parallel to the transverse axis of the dynamization tab at the proximal end of the ring connector body, wherein the second bore comprises a plurality of flat surfaces that are parallel to the transverse axis. The ring connector body may comprise a lateral width measured between the first lateral surface and a second lateral surface. The ring connector body further comprising a connecting bolt comprising a threaded portion and smooth portion and is positioned parallel to the vertical axis of the dynamization tab and is configured to accept a connecting nut, wherein the threaded portion securely engages with the first bore of the ring connector body. The ring connector body further comprising a connecting nut having a flanged surface with a diameter that is greater than the lateral width of the ring connector body, wherein the connecting nut is threadably engaged with the threaded portion of the connecting bolt such that its flanged surface faces the top surface of the ring connector. The device may also comprise a strut connector comprising a proximal end and a distal end and being positioned along the longitudinal axis of the dynamization tab such that the strut connector is in contact with the ring connector body. The strut connector may further comprise a head comprising a proximal end and a distal end, the head further comprising a top surface, a bottom surface, and a first distal-facing surface. The first distal-facing surface may comprise a top edge and a bottom edge, the first distal-facing surface being positioned parallel to the transverse axis of the dynamization tab and in a manner such that the top edge is in contact with the top surface of the head and the bottom edge is in contact with the bottom surface of the head. The head of the strut connector may further compromise a locking screw aperture comprising a partial bore extending from the distal end of the head towards the proximal end of the head, the locking screw aperture being configured to accept a locking screw and second and third distal-facing surfaces, each of the second and third distal-facing surfaces comprising a strut aperture comprising a partial bore, the partial bore extending from the distal end of the head towards the proximal end of the head, each strut aperture being configured to secure the strut connector to a strut. The strut connector body may further comprise a first arm comprising a proximal end and a distal end, wherein the first arm is positioned along the longitudinal axis of the dynamization tab and further comprise a top surface, a bottom surface, a first inner wall surface, a first lateral wall surface, and a first lateral pin bore comprising circular aperture extending through the first lateral wall surface to the first inner wall surface so that the first lateral pin bore is parallel to the transverse axis of the dynamization tab. The strut connector body may further comprise a first longitudinal cantilever bore extending from a proximal end of the first arm into the first arm and is parallel to the longitudinal axis of the device, wherein the first longitudinal cantilever bore further comprises a smaller circumference at a distal end of the bore, and a larger circumference at a proximal end of the bore. The strut connector body may further comprise a second arm comprising a proximal end and a distal end, wherein the second arm is positioned along the longitudinal axis of the dynamization tab and further comprises a top surface, a bottom surface, a second inner wall surface, a second lateral wall surface, and a second lateral pin bore extending through the second lateral wall surface and the second inner wall surface so that the second lateral pin bore is parallel to the transverse axis of the dynamization tab, the second lateral pin bore being configured to accept the pivot pin. The strut connector body may further comprise a second longitudinal cantilever bore extending from a proximal end of the second arm into the second arm and is parallel to the longitudinal axis of the device and is sized to receive a second cantilever element, wherein the second longitudinal cantilever bore further comprises a smaller circumference at a distal end of the bore, and a larger circumference at a proximal end of the bore. The first and second arms may comprise a lateral width measured between the first inner wall surface and the second inner wall surface, wherein the lateral width of the first and second arms is less than the diameter of the flanged surface of the connecting nut. The device may further comprise a pivot pin having a longitudinal axis that is aligned with the transverse axis of the device, the pivot pin comprising a first lateral end having a cylindrical shape that pivotally mates with the first lateral pin bore of the first arm of the strut connector, the first lateral end further comprising a cantilever bore that is substantially orthogonal to the longitudinal axis of the pivot pin, a second lateral end having a cylindrical shape that pivotally mates with the second lateral pin bore of the second arm of the strut connector the first second lateral end further comprising, and a medial section comprising a plurality of flat surfaces that are parallel to the transverse axis of the device and securely mate with the plurality of flat surfaces of the second bore of the ring connector body, wherein the pivot pin pivotally connects the strut connector with the ring connector body so that the strut connector may pivot about the transverse axis of the device so that the first and second lateral surfaces of the ring connector body slidably engage with the first and second inner wall surfaces of the first and second arms of the strut connector, a first elastic element having a proximal end and a distal end, wherein the first elastic element is positioned within the first longitudinal cantilever bore and within the cantilever bore at the first lateral end of the pivot pin, wherein the distal end of the first elastic element is mated with the smaller circumference at the distal end of the first longitudinal cantilever bore, and wherein the proximal end of the first elastic element has an outer circumference that is smaller than the circumference of the first longitudinal cantilever bore at its proximal end. The device may further comprise a second elastic element having a proximal end and a distal end, wherein the second elastic element is positioned within the second longitudinal cantilever bore and within the cantilever bore at the second lateral end of the pivot pin, wherein the distal end of the second elastic element is mated with the smaller circumference at the distal end of the second longitudinal cantilever bore, and wherein the proximal end of the second elastic element has an outer circumference that is smaller than the circumference of the second longitudinal cantilever bore at its proximal end. Wherein, the first and second elastic elements provide a mechanical bias that resist the pivotal movement of the strut connector with respect to the ring connector body, and wherein the connecting nut can be adjustably positioned along the threaded portion of the connecting bolt so that when the flanged surface of the connecting nut impinges upon the top surface of the ring connector body, the flanged surface of the connecting nut prevents pivotal movement of the strut connector with respect to the ring connector body, and when the flanged surface of the connecting nut is displaced away from the top surface of the ring connector body, pivotal movement of the strut connector with respect to the ring connector body can be controllably engaged.

BRIEF DESCRIPTION OF THE DRAWINGS

Some embodiments of this disclosure may be understood by referring, in part, to the present disclosure and the accompanying drawings, wherein:

FIG. 4M illustrates another perspective side view of an alternative embodiment of a hinged dynamization tab;

FIG. 6E illustrates another exploded perspective view of an embodiment of a hinge with torsion spring in a dynamization tab;

FIG. 16 illustrates a perspective view of an embodiment of an alternative dynamization device mounted to a ring fixator;

DETAILED DESCRIPTION

Figure 1A:
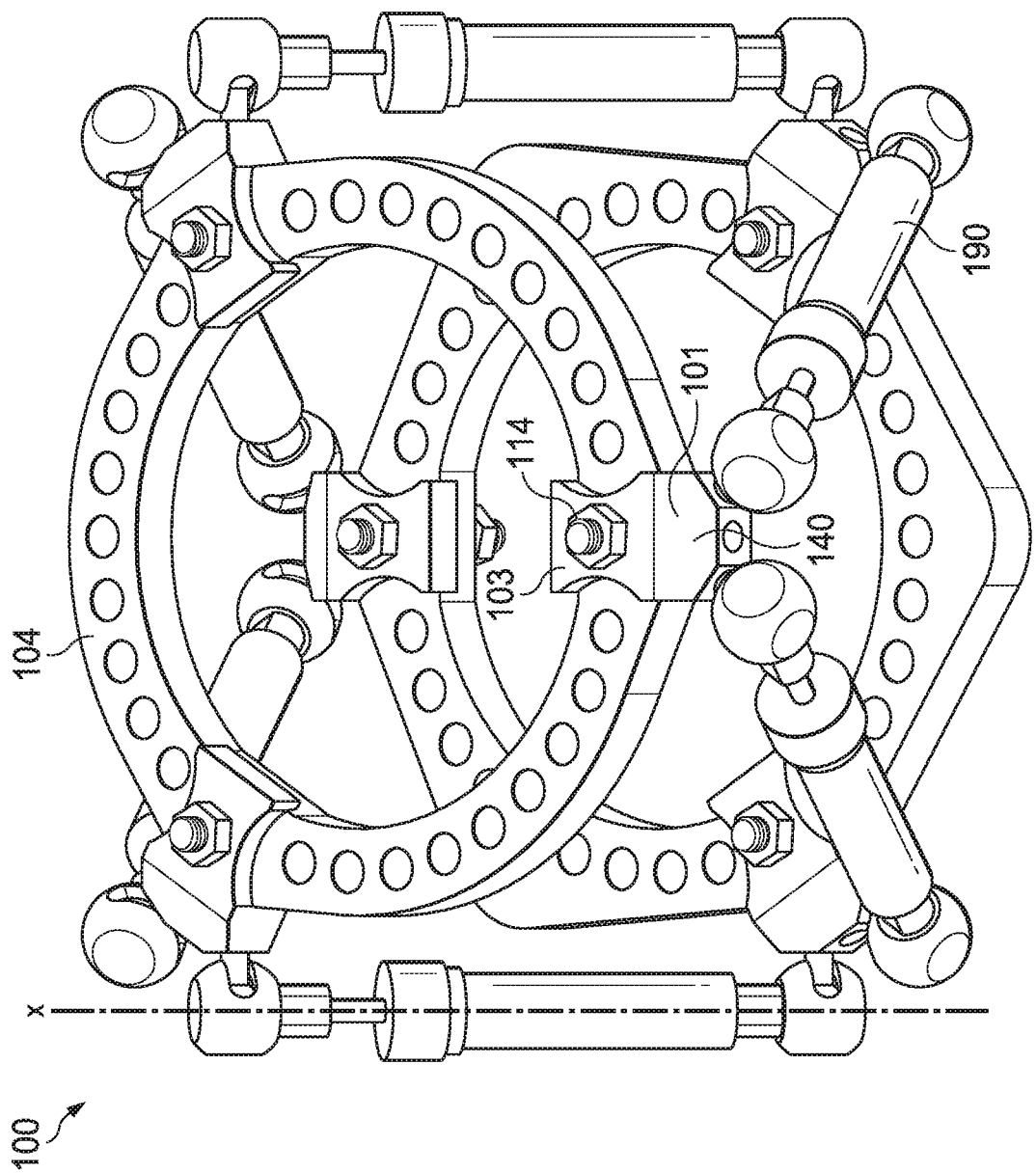
FIG. 1A illustrates a perspective view of one embodiment of a dynamization device connected to a hexapod arrangement.

While making and using various embodiments of the present disclosure discussed below, it should be appreciated that the present disclosure provides many applicable inventive concepts which can be embodied in a wide variety of specific contexts. The specific embodiments discussed in this disclosure are merely illustrative of specific ways to make and use the disclosed material and do not limit the scope of the disclosure.

To facilitate the understanding of this disclosure, a number of terms are defined below. Terms defined herein have meanings as commonly understood by a person of ordinary skill in the areas relevant to the present disclosure. Terms such as "a," "an," and "the," are not meant to refer only to a single entity, but to include the general class of which a specific example may be used for illustration. The terminology herein is used to describe specific embodiments of the disclosure, but their usage does not limit the disclosure, except as outlined in the claims.

The present disclosure relates generally to a dynamization tab which allows for an either traditional or hexapod external fixation device to introduce dynamization in a controlled manner and in such a way that the dynamization module is external to a strut and/or threaded rod. The arrangement of the different elements of the dynamization tab allows for highly controlled bone dynamization, which in turn provides improvement in the final strength of the bone. Further, the dynamization tab may be produced using relatively simple and cost-effective means. Biasing in the system can be varied in both length and flexibility, depending on the arrangement and/or composition of the elements, maximizing the bone dynamization based on factors such as the type bone break or separation, the bone being remodeled or grown, the position of the bone break or separation, the gender, age, weight, metabolism of the patient, and if the patient is taking drugs or receiving therapies that could accelerate or reduce bone reformation, growth, or mineralization and remodeling. The controllable flexibility introduced by biasing allows an external fixation device to provide a proper amount of stabilization at different stages of a patient's healing process. For example, when using an external fixation device on fractured bones, the external fixation device needs to be stable to prevent movement of the fractured bones that may cause deformity. However, if the external fixation device is too stable, at times, that may have its own disadvantages. There are several advantages to controlled destabilization of the external fixation device when a callous begins to form on the fractured bones. One such advantage is exerting sufficient loading force and pressure to the patient's body part to accelerate the healing process, which is optimal if the exertion is controlled. The loading process may proceed gradually during the mineralization phase of the fracture healing process (direct dynamization) or before the mineralization phase during the soft callus formation (reversed dynamization), which in both cases results in accelerated bone healing and a stronger union of the fractured tissues.

FIG. 1A illustrates a dynamization tab 101 as it may be arranged with respect to an external fixation device 100. A dynamization tab 101 may generally comprise a ring connector 103, a strut connector 140, and a biasing mechanism (not shown). In some embodiments, a ring connector 103 may reversibly couple a dynamization tab 101 to a ring 104 of an external fixation device 100 through a connecting bolt 114 or other means. A dynamization tab 101 may further comprise a strut connector 140, which may be used to reversibly couple the dynamization tab 101 to one or more struts 190 (the term "strut" as used in this disclosure, may refer to one or a plurality of struts, threaded rods, non-threaded rods, other means of connecting two opposite rings of an external fixation device 100, or any combination thereof).

Figure 1B:
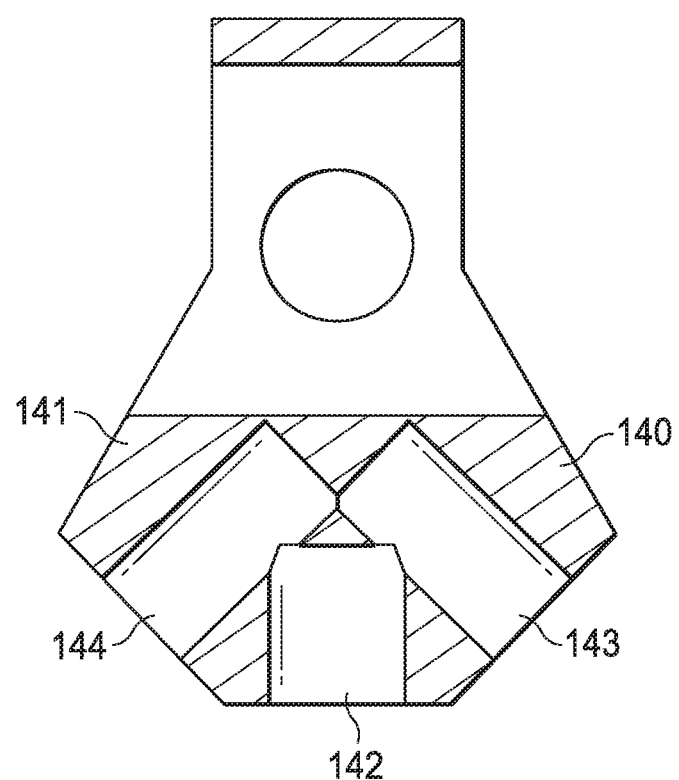
FIG. 1B illustrates a cross-sectional view of an embodiment of a dynamization tab.

FIG. 1B includes a cross-sectional illustration of an embodiment of a dynamization tab 101 taken through plane A with a strut connector 140 comprising a head 141 with a locking screw aperture 142. Further, the head 141 comprises a first strut aperture 143 and a second strut aperture 144, each of which may be configured to secure the dynamization tab 101 to one or more struts by accepting a strut fastener. A strut fastener may be a screw, bolt, or other type of fastener. The locking screw aperture 142 may be configured to accept a locking screw, which may be configured to secure the strut fasteners when they are placed inside of the strut apertures 143, 144. The locking screw may secure the strut fasteners through contact with the strut fasteners in a manner which prevents the movement of the strut fasteners with respect to the strut apertures 143, 144 when the locking screw is in place. Several examples of such a locking arrangement are found in U.S. Pat. No. 9,295,493, which is hereby incorporated by reference into this patent.

Referring now back to FIG. 1A, the dynamization tab 101 may further comprise a biasing mechanism (not shown) which provides a degree of flexibility in the dynamization tab 101 which translates to axial flexibility along the length of the strut 190. The freedom of the strut to extend along its axis X may be limited by the biasing mechanism of the dynamization tab 101, as the biasing mechanism, according to some embodiments, may apply a biasing force when the strut connector 140 is displaced. The biasing force may be sufficient to return the strut connector to its resting position. The biasing mechanism of the dynamization tab 101 may be a spring, coiled spring, tension/extension spring, compression spring, torsion spring, constant spring, variable spring, flat spring, machined spring, cantilever spring, helical spring, volute spring, tension or extension spring, hairspring or balance spring, leaf spring, V-spring, Belleville spring, a constant-force spring, gas spring, mainspring, progressive rate coil spring, spring washer, torsion spring, wave spring, or lengths of resilient material such as rubber or other elastic or elastomeric material.

Generally speaking, the flex-hinge dynamization tab (flex hinge) provides two rigid components; the first being a ring connector used to secure the flex hinge to an external fixation ring and the second being a strut connector to secure one or more struts to the flex hinge. Further, the flex hinge provides a flexible member, arranged between the ring connector and the external fixation ring, which is connected to the strut connector in a manner that allows the strut connector to oscillate under loading. The range of motion of the strut connector is easily adjustable due to a slot in the flexible member, allowing the flexible member and the strut connector to be adjusted with respect to the external fixation ring.

Figure 2A:
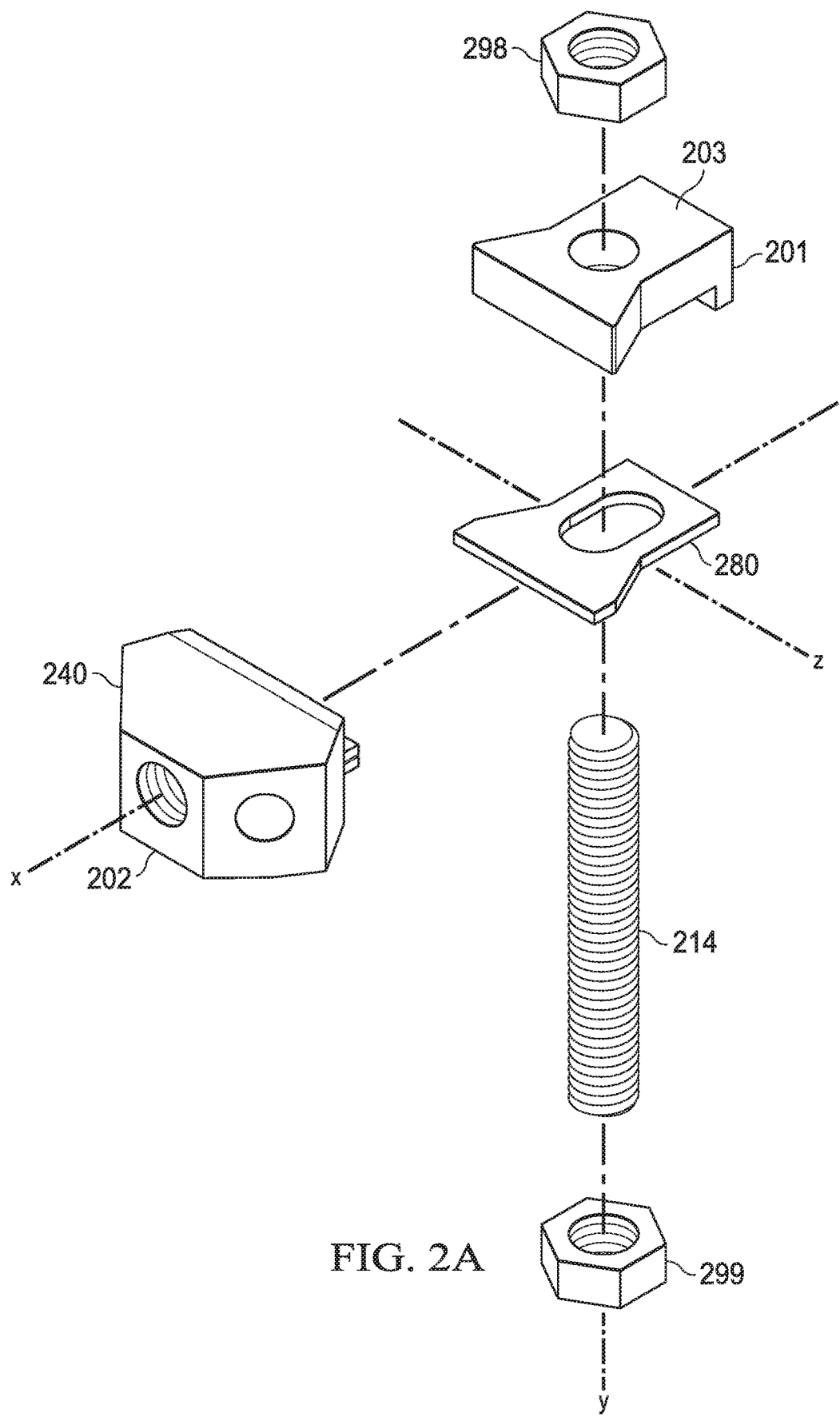
FIG. 2A illustrates an exploded view of an embodiment of a flex-hinge dynamization tab.

FIG. 2A illustrates an exploded view of an embodiment of a flex-hinge dynamization tab (flex hinge) 200. Generally speaking, the flex-hinge dynamization tab 200 provides two rigid components; the first being a ring connector 203 used to secure the flex hinge 200 to an external fixation ring and the second being a strut connector 240 to secure one or more struts to the flex hinge 200. Further, the flex hinge 200 provides a flexible member 280, arranged between the ring connector 203 and the external fixation ring, which is connected to the strut connector 240 in a manner that allows the strut connector 240 to translate under loading. The range of motion of the strut connector 240 is easily adjustable due to a slot in the flexible member 280, allowing the flexible member and the strut connector to be adjusted with respect to the external fixation ring. In FIG. 2A, the flex-hinge 200 has a longitudinal axis X, a vertical axis Y, and a transverse axis Z defined therein and comprises a proximal end 201, a distal end 202, a ring connector 203, a strut connector 240, and a biasing mechanism 280. Further, the flex-hinge 200 may comprise a connecting bolt 214, a first connecting nut 298 and a second connecting nut 299. In these embodiments, the connecting bolt 214, the first connecting nut 298, and the second connecting nut 299 are configured to secure the flex-hinge 200 to an external fixation ring, discussed above.

Figure 2B:
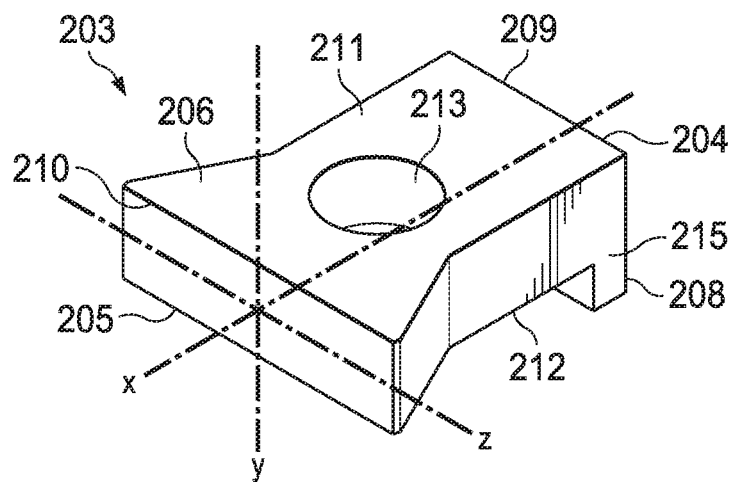
FIG. 2B illustrates a ring connector used in one embodiment of the flex-hinge dynamization tab.

Illustrated in FIG. 2B, the ring connector 206 of the flex-hinge, according to an embodiment, may have a proximal end 204 and a distal end 205 and may further comprise a first stabilizer 206 and a second stabilizer 208. The first stabilizer 206 of the ring connector 203 has a proximal end 209 and a distal end 210 and is positioned along the longitudinal axis X of the flex-hinge. The first stabilizer 206 may further comprise a top surface 211, a bottom surface 212, and a circular bore 213. The circular bore 213 of the first stabilizer, according to an embodiment, extends parallel to the vertical axis Y of the flex-hinge from the top surface of the first stabilizer 211 to the bottom surface of the first stabilizer 212. Further, the circular bore 213 of the first stabilizer 206 may be configured to accept the connecting bolt 214 of FIG. 2A. The second stabilizer 208 of the ring connector 203 comprises a superior end 215 and is positioned parallel to the vertical axis Y of the flex-hinge in such a manner that the superior end 215 is in contact with the proximal end of the bottom surface 212 of the first stabilizer 206.

Figure 2C:
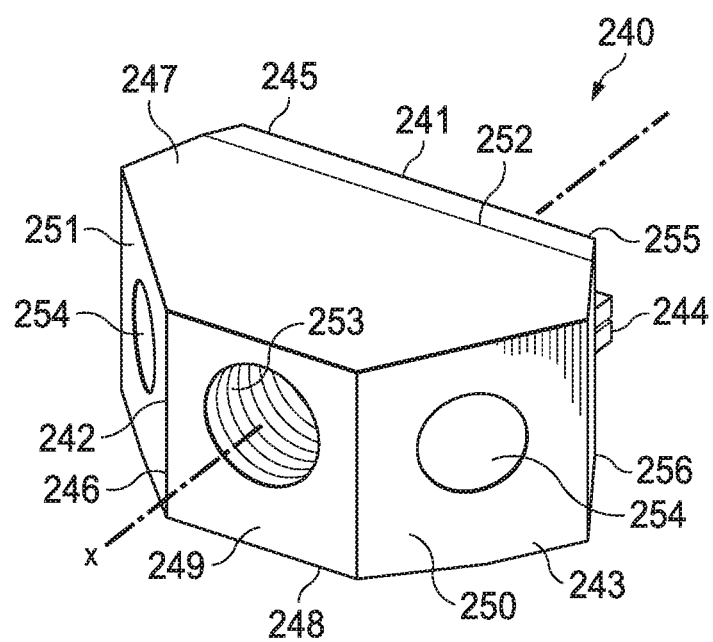
FIG. 2C illustrates a strut connector used in one embodiment of the flex-hinge dynamization tab.
Figure 2D:
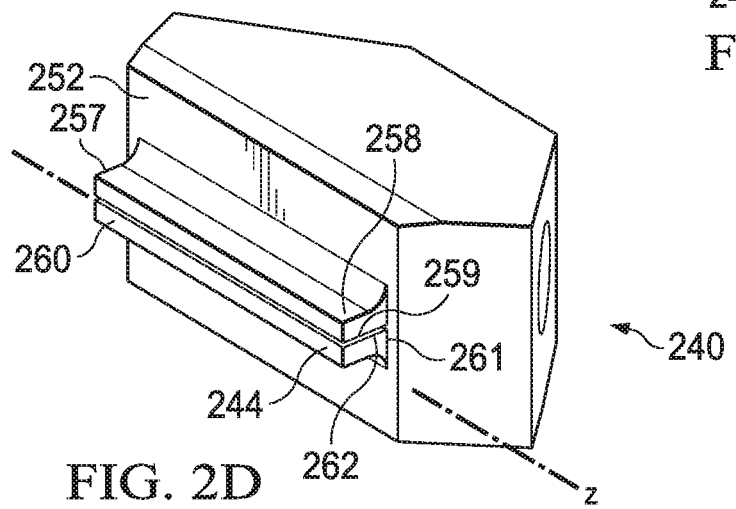
FIG. 2D illustrates another view of a strut connector used in one embodiment of the flex-hinge dynamization tab.

In the embodiment of FIG. 2C, the strut connector 240 has a proximal end 241 and a distal end 242 and further comprises a head 243 and a strut connector knuckle 244. The head 243 of the strut connector also has a proximal end 245 and a distal end 246 and is positioned along the longitudinal axis X of the flex-hinge. In some embodiments, the head of the strut connector 243 may further comprise a top surface 247, a bottom surface 248, a first distal-facing surface 249, a second distal-facing surface 250, a third distal-facing surface 251, and a proximal-facing surface 252. The first distal-facing surface 249 of the head may further comprise a locking-screw aperture 253, the locking-screw aperture 253 being a partial bore that extends from the distal end of the head 246 toward the proximal end of the head 245. The locking-screw aperture 253 may be configured to accept a locking screw, configured in such a manner that the locking screw restricts the movement of strut connector screws discussed below. The second distal-facing surface 250 and the third distal-facing surface 251 may each include a strut aperture 254. According to some embodiments, each strut aperture 254 may comprise a partial bore, extending from the distal end of the head 246 toward the proximal end of the head 245. Each of the strut apertures 254 may be configured to accept a strut connector screw, which may attach the flex-hinge to a strut. The proximal-facing surface 252 of the head may comprise a top edge 255 and a bottom edge 256 and may be positioned parallel to the vertical axis Y of the hinged tab in such a manner that the top edge of the proximal-facing surface 252 is in contact with the top surface of the head 247 and the bottom edge of the proximal-facing surface 256 is in contact with the bottom surface of the head 248. In some embodiments, the proximal-facing surface 252 may comprise the proximal end of the head 245. The strut connector knuckle 244 of FIG. 2D is positioned along the transverse axis Z of the flex-hinge in such a manner that it is in contact with the proximal-facing surface of the head 252. The strut connector knuckle 244 may further comprise a superior member 257 and an inferior member 260, each of which may further comprise a top surface 258, 261 and a bottom surface 259, 262, respectively.

Figure 2E:
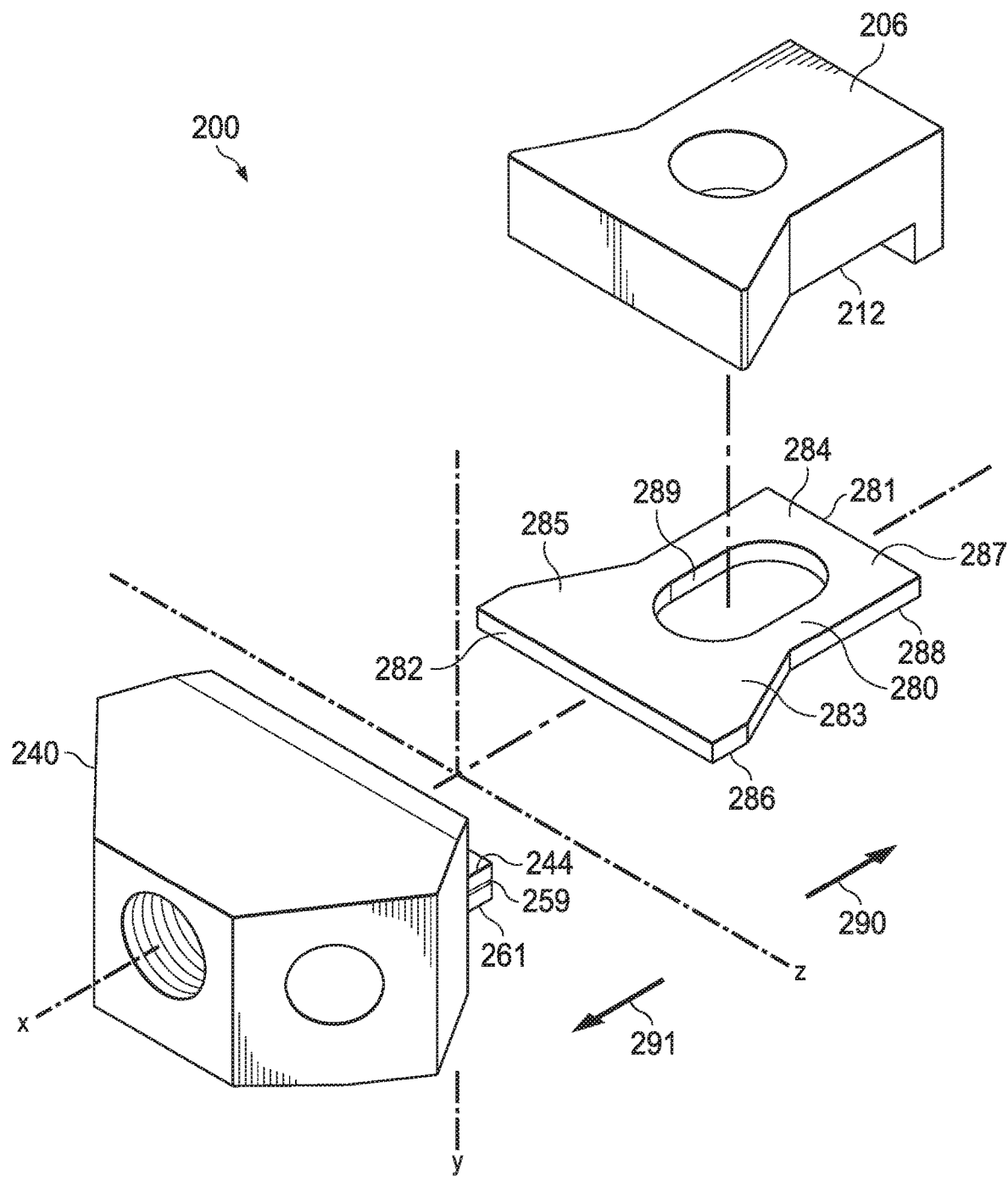
FIG. 2E illustrates another exploded view of an embodiment of a flex-hinge dynamization tab.

Referring now to FIG. 2E, the biasing mechanism 280 of the flex-hinge 200 may, according to some embodiments, be comprised of an elastomeric material or a flexible plastic. The elastomeric or flexible nature of the material comprising the biasing mechanism 280 may allow for pivoting of the strut connector 240 about the transverse axis Z of the flex-hinge 200 and, further, provide bias which returns the strut connector 240 to its original position when displaced. In an embodiment, the biasing mechanism 280 is positioned along the longitudinal axis X of the flex-hinge 200 and further comprises a proximal end 281, a distal end 282, a biasing lip 283, and a biasing tab 284. The biasing lip 283 includes a top surface 285 and a bottom surface 286 and is positioned at the distal end of the biasing mechanism 282, along the longitudinal axis X of the flex-hinge 200 in such a manner that the top surface of the biasing lip 285 is in contact with the bottom surface of the superior member 259 of the strut connector knuckle 244 and the bottom surface of the biasing lip 286 is in contact with the top surface of the inferior member 261 of the strut connector knuckle 244. The biasing lip 285 may be secured to the superior member 259 and inferior member 261 with a variety of means, including, for example, a clamp, an adhesive or glue, or a fastener, such as a screw. The biasing tab 284, according to some embodiments, may comprise a top surface 287, a bottom surface 288, and a biasing tab stadium bore 289. The top surface of the biasing tab 287 may be positioned such that it is in contact with the bottom surface of the first stabilizer 212 and the bottom surface of the biasing tab 288 may be positioned such that it is in contact with the external fixation ring, each providing bias when the strut connector 240 is pivotally displaced along the transverse axis Z of the flex-hinge 200. The biasing tab stadium bore 289, according to some embodiments, extends parallel to the vertical axis Y of the flex-hinge 200 and from the top surface of the biasing tab 287 to the bottom surface of the biasing tab 288 in such a manner that allows the biasing mechanism 280 to be displaced along the longitudinal axis X of the flex-hinge 200 with respect to the ring connector 206. Proximal displacement 290 of the biasing mechanism 280 may decrease the ability of the strut connector 240 to rotate about the transverse axis Z of the flex-hinge 200, while distal displacement 291 of the biasing mechanism 280 may increase the ability of the strut connector 240 to rotate about the transverse axis Z of the flex-hinge 200.

Figures 3A, 3B:
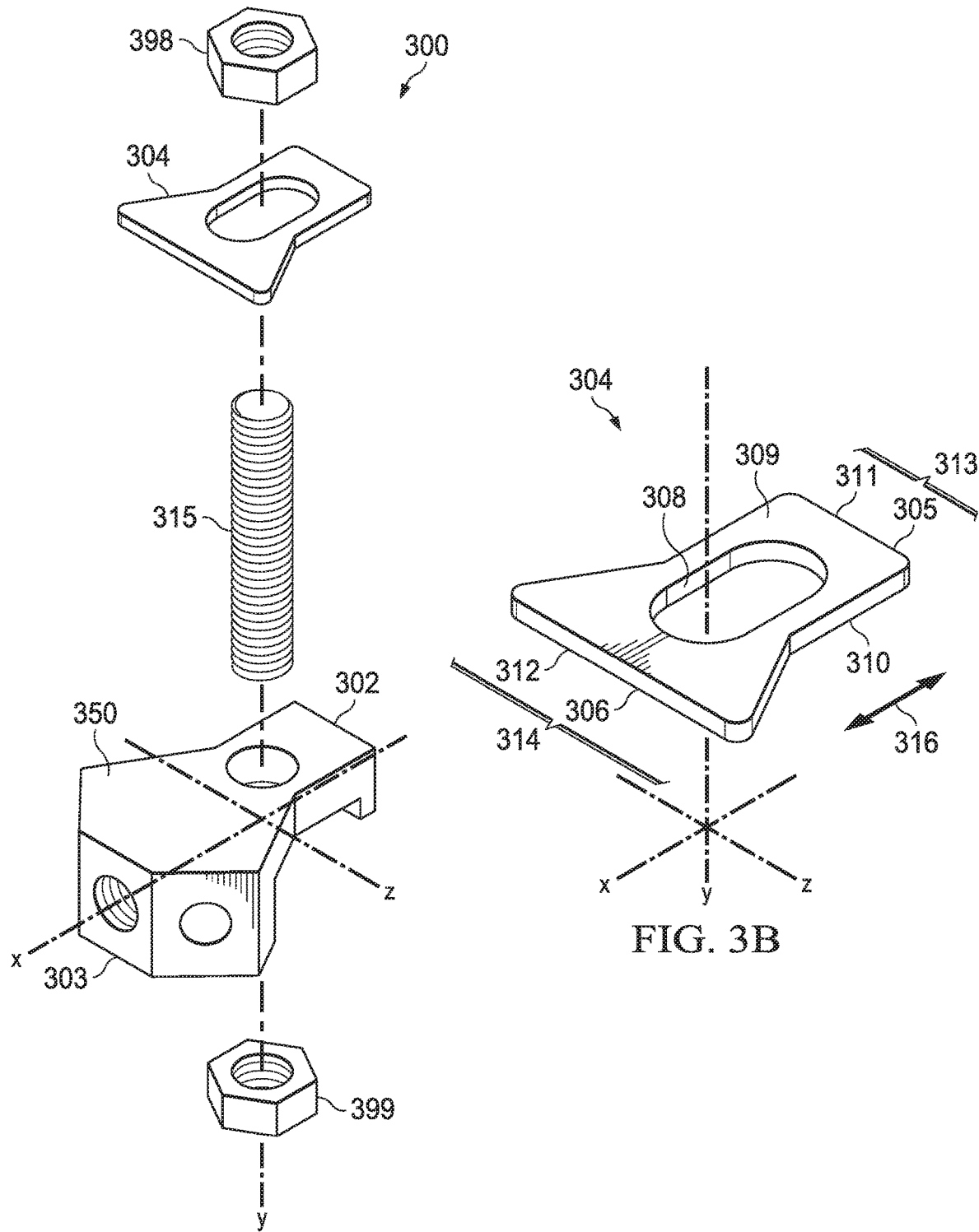
FIG. 3A illustrates an alternative embodiment for an elastic dynamization tab.
FIG. 3B illustrates the slotted member used with an alternative embodiment for an elastic dynamization tab.

An alternative embodiment for dynamization tab 300 (i.e., an elastic tab) is depicted in FIG. 3A. The elastic tab 300 provides for dynamization through a strut connector and ring connector made from an elastic material with properties for permitting dynamization of the attached struts. Further, the elastic tab provides for a slotted washer or rigid material component 304 which may be secured to the external fixation ring with the strut and ring connector. Adjustment of the slotted washer or rigid material component 304 either towards the limb or away from the limb allows the for the translation of the strut along the vertical axis to be adjusted appropriately. The elastic tab 300 has a longitudinal axis X, a vertical axis Y, and a transverse axis Z defined therein and comprises a proximal end 302, a distal end 303, a slotted member 304, and a biasing mechanism 350. Further, according to some embodiments, the elastic tab 300 may comprise a connecting bolt 315, a first connecting nut 398, and a second connecting nut 399. In these embodiments, the connecting bolt 315, the first connecting nut 398, and the second connecting nut 399 are configured to secure the elastic tab 300 to an external fixation ring, discussed above.

Illustrated in FIG. 3B, the slotted member 304 may comprise a proximal end 305 and a distal end 306 and be positioned parallel to the longitudinal axis X of the elastic tab. The slotted member 304 may further comprise a stabilizer 307 and a slotted member stadium bore 308. According to some embodiments, the stabilizer 307 of the slotted member 304 is positioned parallel to the longitudinal axis X of the elastic tab and has a top surface 309, a bottom surface 310, a proximal edge 311, and a distal edge 312. In the embodiment of FIG. 3B, the proximal edge of the stabilizer 311 has a length 313 equal to n and the distal edge of the stabilizer 312 has a length 314 equal to d and the length of the distal edge 314, d, is greater than the length of the proximal edge 313, n. Both the proximal edge 311 and the distal edge 312 may be positioned parallel to the transverse axis Z of the elastic tab. In some embodiments, the slotted member stadium bore 308 may extend parallel to the vertical axis Y of the elastic tab, from the top surface of the stabilizer 309 to the bottom surface of the stabilizer 310 and may be configured to accept the connecting bolt 315 of FIG. 3A. The slotted member stadium bore 308 may be further configured to allow displacement 316 of the slotted member 304 in both a proximal and distal manner along the longitudinal axis X of the elastic tab.

Figure 3C:
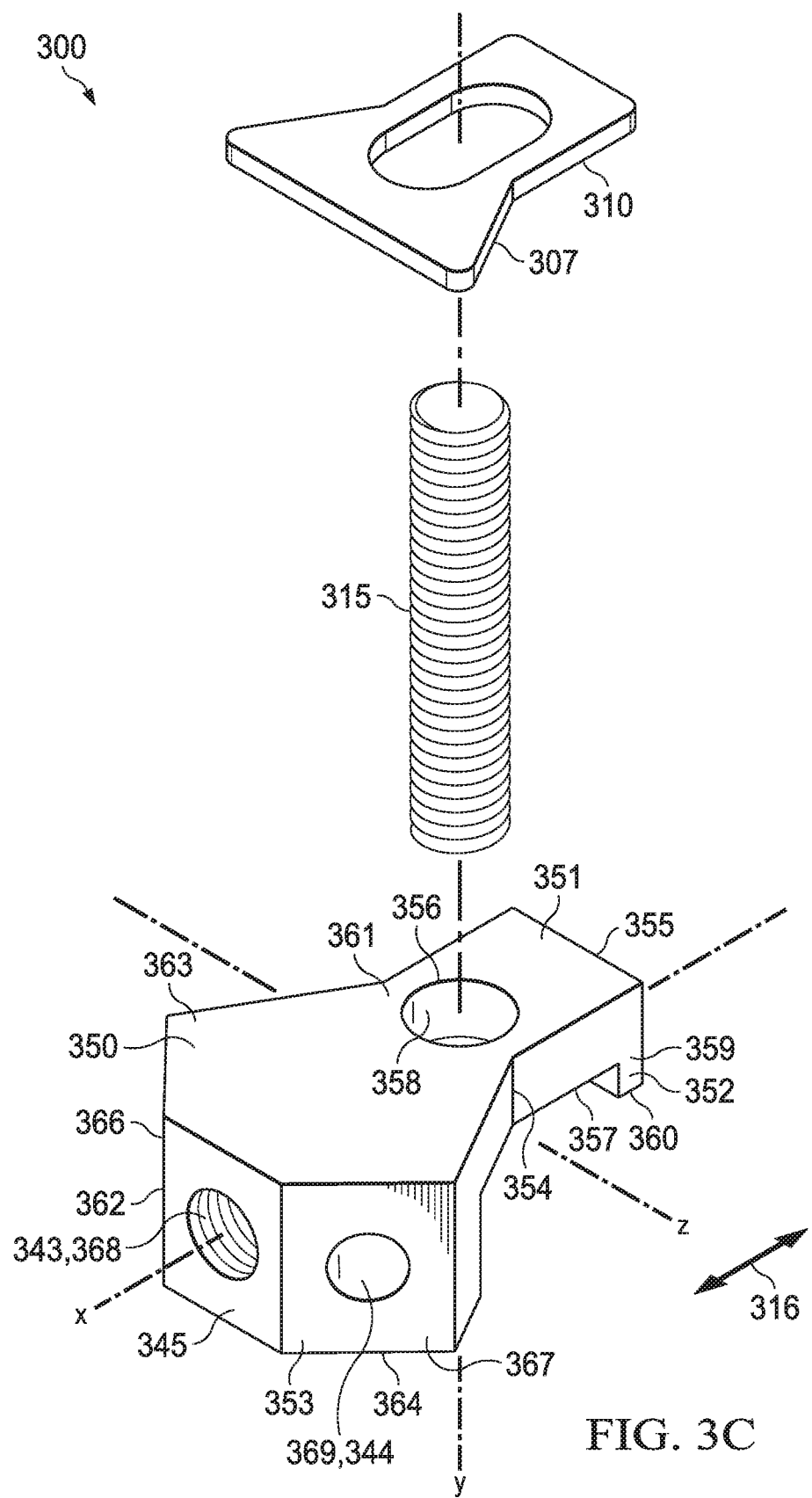
FIG. 3C illustrates a closer exploded view of an alternative embodiment for an elastic dynamization tab.

FIG. 3C illustrates an embodiment of the biasing mechanism 350 of the elastic tab 300. The biasing mechanism 350 may be comprised of an elastomeric material or a flexible plastic and be positioned along the longitudinal axis X of the elastic tab 300. Further, the biasing mechanism may have a first stabilizer 351, a second stabilizer 352, and a head 353. In some embodiments, the first stabilizer of the biasing mechanism 351 may comprise a distal end 354 and a proximal end 355 and be positioned along the longitudinal axis X of the elastic tab 300. The first stabilizer 351 may further comprise a top surface 356, positioned such that it is in contact with bottom surface of the slotted member stabilizer 307, a bottom surface 357, and a first biasing mechanism bore 358. The first biasing mechanism bore 358 may extend parallel to the vertical axis Y of the elastic tab 300 from the top surface of first stabilizer 356 to the bottom surface of the first stabilizer 357. In some embodiments, the first biasing mechanism bore 358 may be configured to accept the connecting bolt 315. The biasing mechanism 350 may further comprise a second stabilizer 352, which may have a superior end 359 and an inferior end 360. In the embodiment of FIG. 3C, the second stabilizer 352 is positioned parallel to the vertical axis Y of the elastic tab 300 in a manner such that the superior end 359 is in contact with the proximal end of the bottom surface of the first stabilizer 310. The head of the biasing mechanism 353 may comprise a proximal end 361, a distal end 362, a top surface 363, a bottom surface 364, a first distal-facing surface 365, a second distal-facing surface 366, and a third distal-facing surface 367. In some embodiments, the head may be positioned along the longitudinal axis X of the elastic tab 300. The top surface of the head 363 may be positioned to be in contact with the bottom surface of the slotted member stabilizer 310. In this arrangement, the slotted member stabilizer 307 applies bias when the head 353 is displaced along the longitudinal axis Y of the elastic tab 300. The first distal-facing surface 365 may comprise a locking screw aperture 363, which may be a partial bore extending from the distal end of the head 362 to the proximal end of the head 361. The locking screw aperture may be configured to accept a locking-screw bushing 343, which may comprise a threaded, cylindrical tube positioned along the longitudinal axis of X of the elastic tab 300 and which may be configured to accept a locking screw. The second distal-facing surface 366 and the third distal-facing surface 367 of the biasing mechanism head 353 may each comprise a strut aperture 369. Each of the strut apertures 369 may comprise a partial bore which extends from the distal end of the head 362 to the proximal end of the head 361. Each may be configured to accept a strut bushing 344 which, in some embodiments, are threaded, cylindrical tubes which may be configured to accept strut-connecting screws.

Figure 4A:
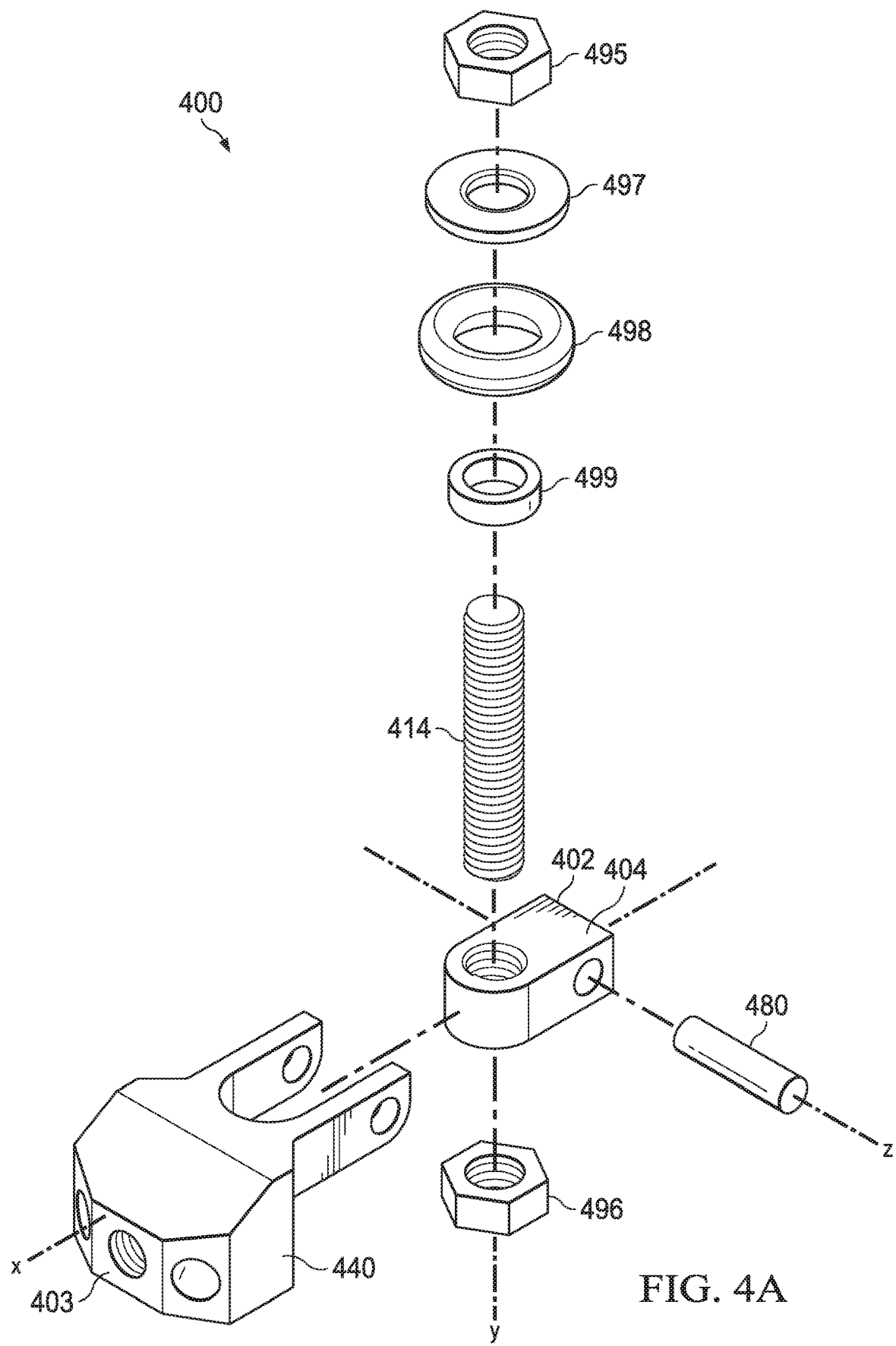
FIG. 4A illustrates an exploded perspective view of an embodiment of a hinged dynamization tab.

FIG. 4A is an exploded perspective view of an embodiment of a hinged tab dynamization tab (hinged tab 400) of the present disclosure. The hinged tab 400 has a longitudinal axis X, a vertical axis Y, and a transverse axis Z defined therein and comprises a proximal end 402, a distal end 403, a ring connector 404, a strut connector 440, and a pivot pin 480, which may comprise a pivot pin that provides an axis of rotation that is aligned with the transverse axis Z. Further, according to some embodiments, the hinged tab 400 may comprise a connecting bolt 414, a first connecting nut 495, a second connecting nut 496, a first connecting washer 497, a biasing element 498, and a third sleeve 499. The biasing element 498 may comprise a compressible silicone O-Ring, a coiled compressing ring, or a compressible wave spring. The outer circumference of the biasing element 498 may align with the space between the two arms of the hinged tab 403 so that the upper surface of the hinged tab 403 contacts the lower surface of the biasing element 498. The third sleeve 499 may act as a spacer that is slightly lower in height than the biasing element 498. This allows the first connecting nut 495 to be tightened down securely on the connecting bolt 414 with respect to the ring connector 404. Being slightly lower in height creates a mechanical pre-load (bias) on the arms of the hinged tab 403 when the first connecting nut 495 is torqued down onto the connecting bolt 414. If the nut 495 is not securely locked down, it can become loosened over time during mechanical operation. When a load is applied to the distal end 403 of the strut connector 440, it pivots about axis pin 480 and further compresses the biasing element 498. Also, the fixed preload and uniform spring constant of the biasing element 498 can provide substantially equal dynamization from multiple dynamization tabs on a frame. When dynamization is not desired, the biasing element 498 and the third sleeve 499 are removed and a rigid construct is created when the first connecting nut 495 and the first connecting washer 497 are torqued down against the hinged tab 400. The first connecting washer 497 distributes evenly the force applied by the first connecting nut 495 onto the biasing element 498 as the first connecting nut 495 is driven downwards. The third sleeve fits inside the biasing element 498 to hold it in place around the connecting bolt and protect the bolt threads from damaging the biasing element 498. In these embodiments, the connecting bolt 414, first connecting nut 495, second connecting nut 496, first connecting washer 497, biasing element 498, and third sleeve 499 are configured to secure the hinged tab 400 to an external fixation ring, discussed above.

Figure 4B:
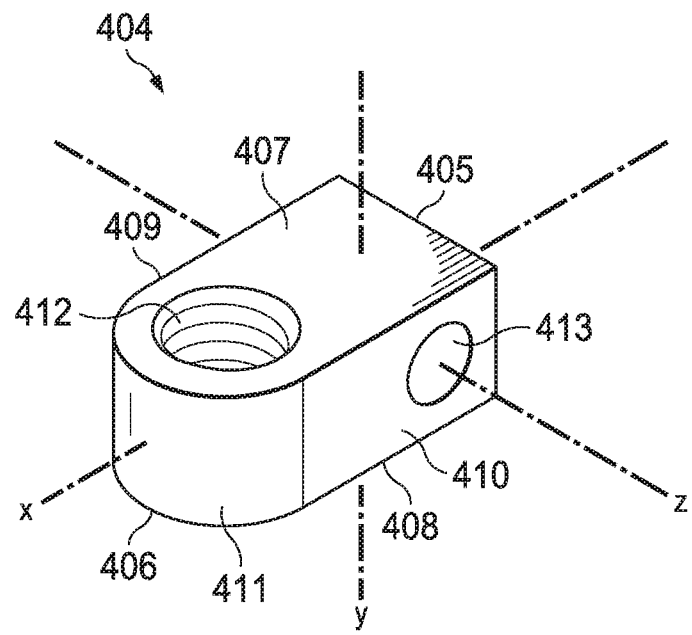
FIG. 4B illustrates a perspective view of a ring connector used with an embodiment of a hinged dynamization tab.

In the embodiment illustrated in FIG. 4B, the ring connector 404 has a proximal end 405 and a distal end 406 and is positioned along the longitudinal axis X of the hinged tab 400. The ring connector 404 may further comprise a top surface 407, a bottom surface 408, a first surface 409, a second surface 410, a distal-facing surface 411, a first bore 412, and a second bore 413. In some embodiments, the first bore 412 extends parallel and distal to the vertical axis Y of the hinged tab from the top surface of the ring connector 407 to the bottom surface of the ring connector 408. The first bore 412 may be threaded to threadably engage the connecting bolt 414. The second bore 413 may extend along the transverse axis Z of the hinged tab from the first surface 409 of the ring connector to the second surface 410 of the ring connector and may be configured to accept the biasing mechanism of FIG. 4A. The pivot pin 480 may be suitable for a press fit in bore 413 (See FIG. 4B), but a loose or rotational fit through the bores in the arms in the strut connector 440.

Figure 4C:
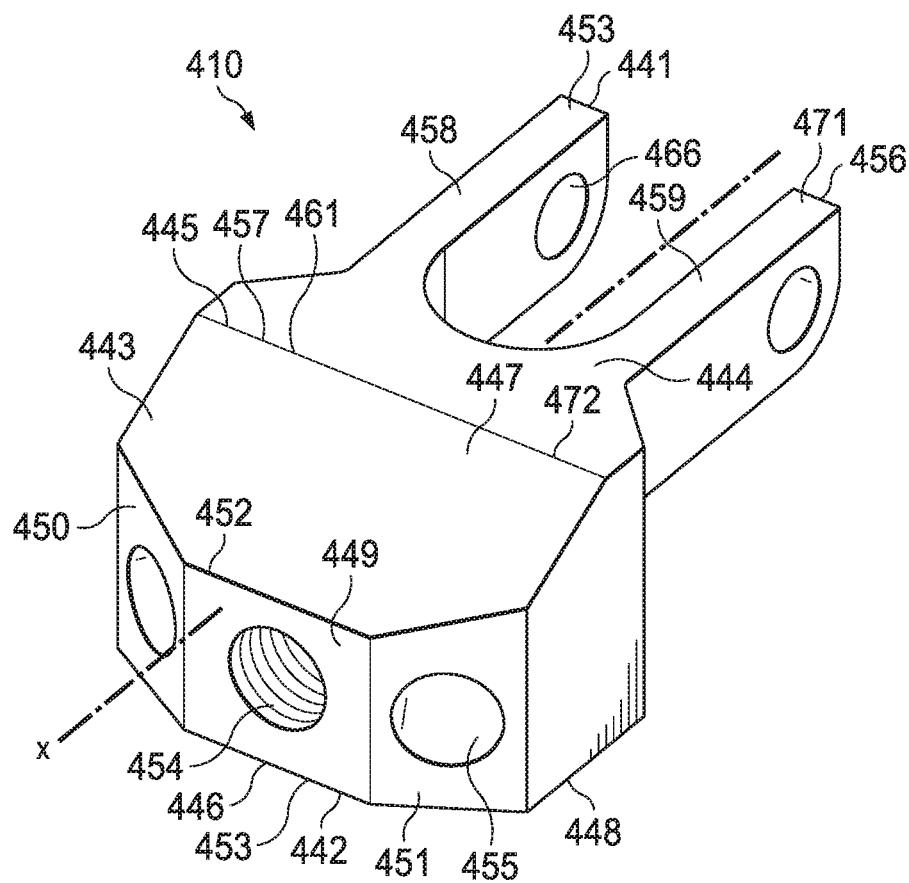
FIG. 4C illustrates a perspective view of a strut connector used with an embodiment of a hinged dynamization tab.

The hinged tab may further comprise a strut connector 440, illustrated in FIG. 4C. In some embodiments, the strut connector 440 may have a proximal end 441 and a distal end 446 and may further comprise a head 443 and strut connector knuckle 444. The head 443 may have a proximal end 445 and a distal end 446 and be positioned along the longitudinal axis X of the hinged tab. The head 443 may further comprise a top surface 447, a bottom surface 448, a first distal-facing surface 449, a second distal-facing surface 450, and a third distal-facing surface 451. The first distal-facing surface of the head 449, according to some embodiments, comprises a top edge 452 and a bottom edge 453 and is positioned parallel to the transverse axis Z of the hinged tab in a manner such that the top edge 452 is in contact with the top surface of the head 447 and the bottom edge 453 is in contact with the bottom surface of the head 448. The first distal-facing surface of the head 449 may further comprise a locking-screw aperture 454, which may be a partial bore that extends from the distal end of the head 446 towards the proximal end of the head 445 and may be configured to accept a locking screw. The second distal-facing surface 450 and the third distal-facing surface 451 may each comprise a strut aperture 455, which may be a partial bore that extends from the distal end of the head 446 to the proximal end of the head 445 and may be each be configured to secure a strut to the strut connector 440.

In some embodiments, the strut connector 440 may further comprise a strut connector knuckle 444. The strut connector knuckle 444 may have a proximal end 456 and a distal end 457 and be positioned along the longitudinal axis X of the hinged tab in a manner such that the distal end of the strut connector knuckle 457 is in contact with the proximal end of the head 445. The strut connector knuckle 444 may further comprise a first arm 458 and a second arm 459, shown in FIG. 4C. The first arm 458 comprises a proximal end 460 and a distal end 461 and is positioned parallel to the longitudinal axis X of the hinged tab in a manner such that the distal end 461 is in contact with the proximal end of the head 445. The second arm 459 comprises a proximal end 471 and a distal end 472 and is positioned parallel to the longitudinal axis X of the hinged tab in a manner such that the distal end 472 is in contact with the proximal end of the head 445.

Figure 4D:
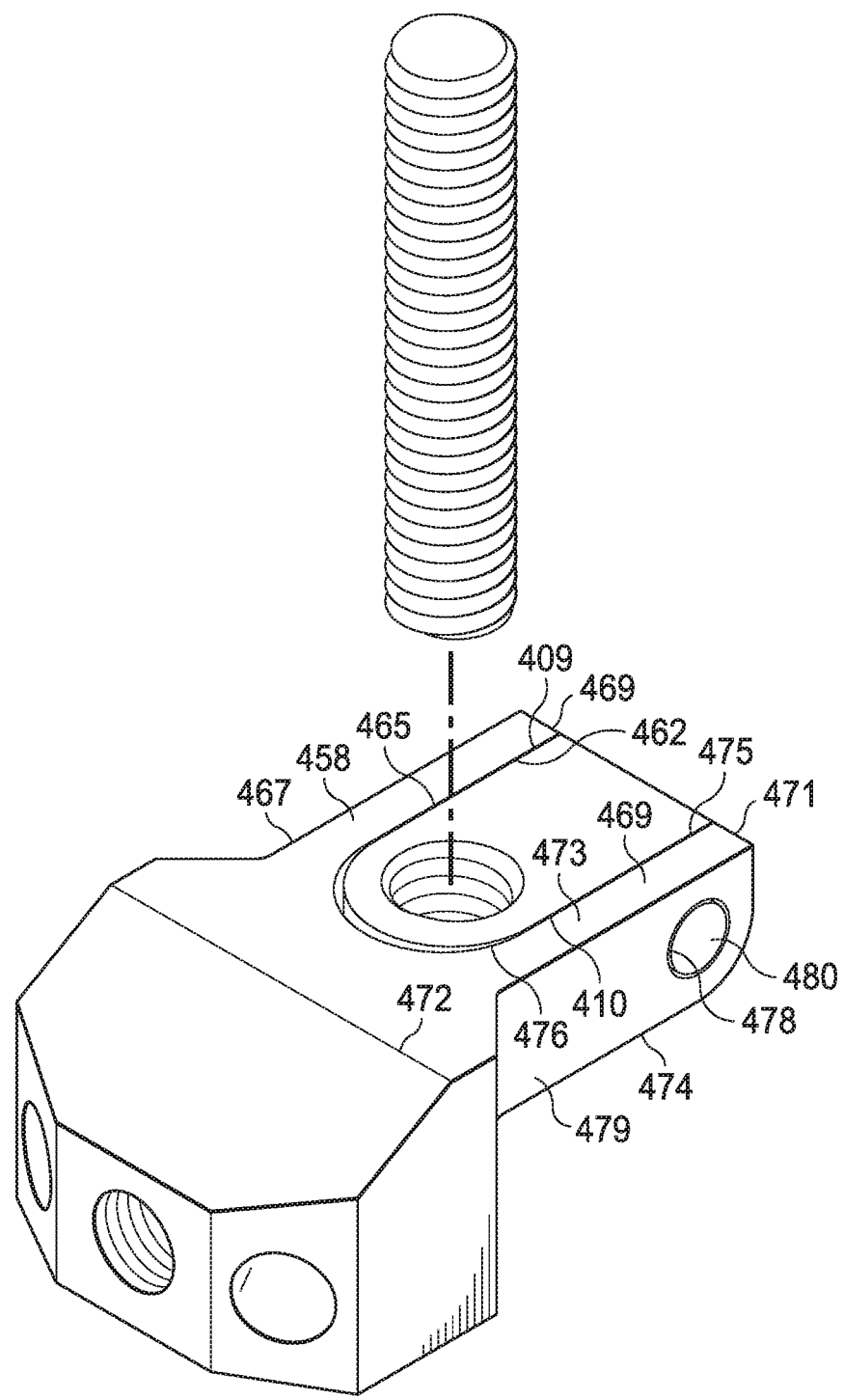
FIG. 4D illustrates another perspective view of an embodiment of a hinged dynamization tab.

Referring now to FIG. 4D, the first arm of the strut connector knuckle 458 may further comprise a top surface 462, a bottom surface (not shown), a first surface (464, not shown), a second surface 465, and a first arm bore (element 466 of FIG. 4C). The first surface 464 of the first arm comprises a top edge 467 and a bottom edge (not shown) and is positioned such that the top edge 467 is in contact with the top surface of the first arm 462 and the bottom edge 468 is in contact with the bottom surface of the first arm (not shown). The second surface 465 of the first arm comprises a top edge 469 and a bottom edge (not shown) and is positioned such that the top edge 469 is in contact with the top surface of the first arm 462, the bottom edge (not shown) is in contact with the bottom surface of the first arm (not shown), and the second facing surface 465 is in contact with the first surface of the ring connector 409. The first arm bore (not shown) extends along the transverse axis Z of the hinged tab from the first surface of the first arm (not shown) to the second surface of the first arm 465 and is configured to accept the pivot pin 480.

According to some embodiments, the second arm of the strut connector 469 comprises a proximal end 471 and a distal end 472 and is positioned parallel to the longitudinal axis X of the hinged tab such that the distal end of the second arm 472 is in contact with the proximal end of the head 445. The second arm 459 may further comprise a top surface 473, a bottom surface 474, a first surface 475, a second surface 479, and a second arm bore 478. According to the embodiment of FIG. 4D, the first surface 475 comprises a top edge 476 and a bottom edge (not shown) and is positioned such that the top edge 476 is in contact with the top surface of the second arm 473, the bottom edge (not shown) is in contact with the bottom surface of the second arm 474, and the first surface 475 is in contact with the second surface of the ring connector 410. The transverse axis Z of the hinged tab from the second surface of the second arm 475 to the first surface of the second arm 479 and is, according to some embodiments, configured to accept the pivot pin 480.

The pivot pin 480 of FIG. 4D may comprise a cylindrical pin. The pivot pin 480 is positioned along the transverse axis Z of the hinged tab such that the pivot pin 480 passes through the first arm bore 466, the second arm bore 478, and the second bore of the ring connector 412. In this manner, the pivot pin 480 allows for pivoting of the strut connector 440 about the transverse axis Z of the hinged tab. This pivoting is limited, according to some embodiments, by contact between the bottom surface of the first arm 463 and the external fixation ring and between the bottom surface of the second arm 474 and the external fixation ring. As the strut connector 440 is displaced along the longitudinal axis Y of the hinged tab, the pivot pin 480 applies a biasing force, returning the strut connector 440 to its original position.

In another alternative embodiment, the circular pivot dynamization tab (circular pivot tab), the rotation of the strut connector may be limited to a single plane due to modifications to the ring connector. In this embodiment, the strut connector is in contact with a cylindrical member of the ring connector that has flat sides which restrict the side-to-side movement of the strut connector. Further, the embodiment provides that a threaded cap be placed in contact with the oscillating biasing mechanism which allows for easy adjustment of dynamization. One advantage of this configuration is the relatively long lever arm between the axis of the pivot pin 480 and the distal end 446 of the strut connector 440 where the struts are connected. The arms of the strut connector knuckle 444 also limit the movement of the strut connector to rotational movement of the strut connector 440 about the axis of the pivot pin 480, thus providing greater control over the amount of dynamization to be applied to the patient. Furthermore, the hinged tab dynamization tab (hinged tab) generally helps protect the bolt 414 from fatigue stress, which may occur in other designs when biasing mechanisms oscillate. The tab 440 can angulate without directly contacting the bolt 414.

Figure 4E:
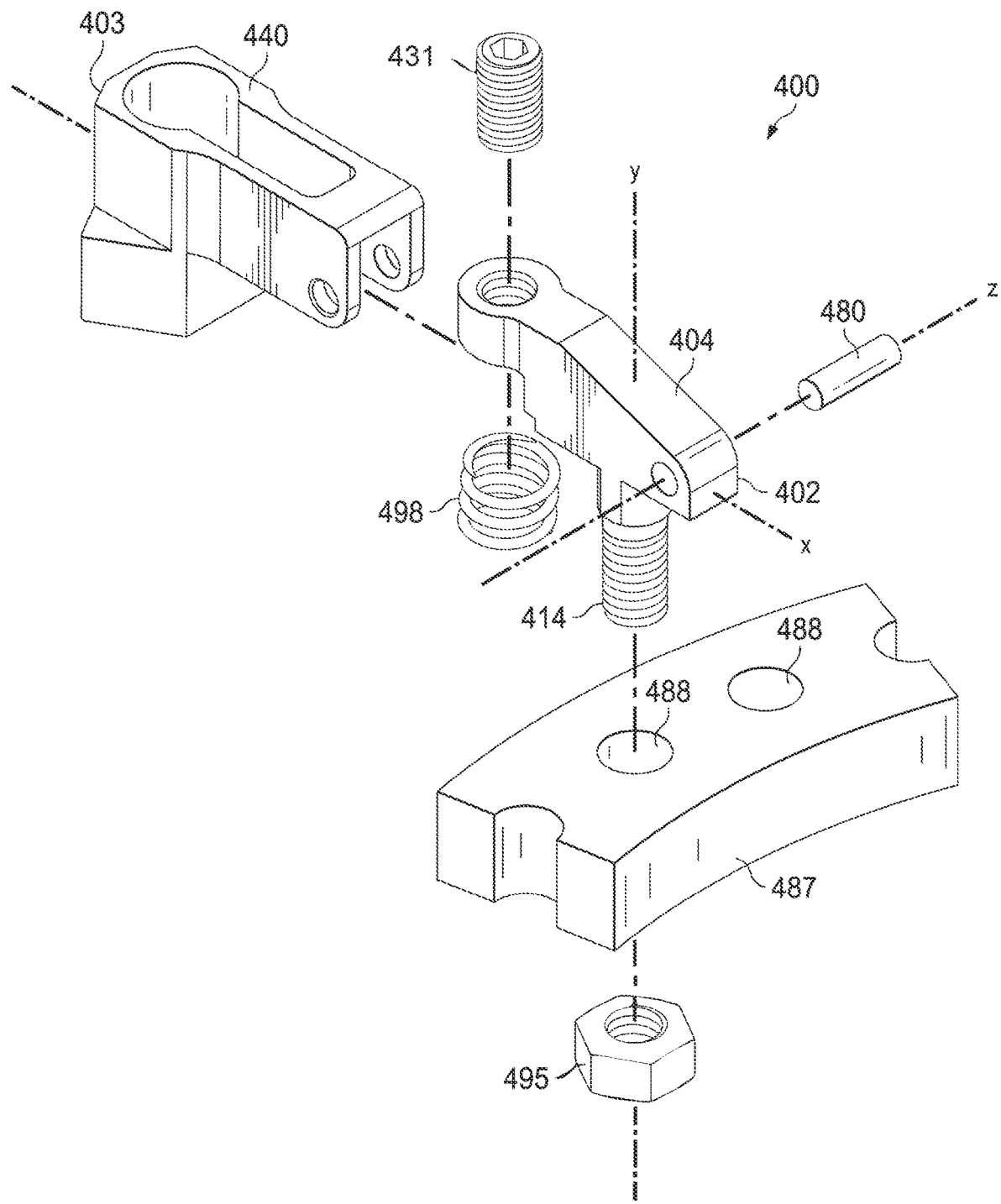
FIG. 4E illustrates an exploded perspective view of an alternative embodiment of a hinged dynamization tab.

FIG. 4E is an exploded perspective view of an embodiment of a hinged tab dynamization tab (hinged tab 400) of the present disclosure. The hinged tab 400 has a longitudinal axis X, a vertical axis Y, and a transverse axis Z defined therein and comprises a proximal end 402, a distal end 403, a ring connector 404, a strut connector 440, and a pivot pin 480 that provides an axis of rotation that is aligned with the transverse axis Z. Further, according to some embodiments, the hinged tab 400 may comprise a connecting bolt 414, a first connecting nut 495, a biasing element 498, and an adjustment screw 431. The biasing element 498 may comprise a coiled compressing ring or a compressible wave spring. Also shown in FIG. 4E is a ring 487 with a plurality of apertures 488 passing from the top surface of the ring to the bottom surface. The apertures 488 have a sufficient size to allow the connecting bolt 414 to pass entirely through the ring 487 so that the first connecting nut 495 may secure the hinged tab 400 to the ring 487.

Figure 4F:
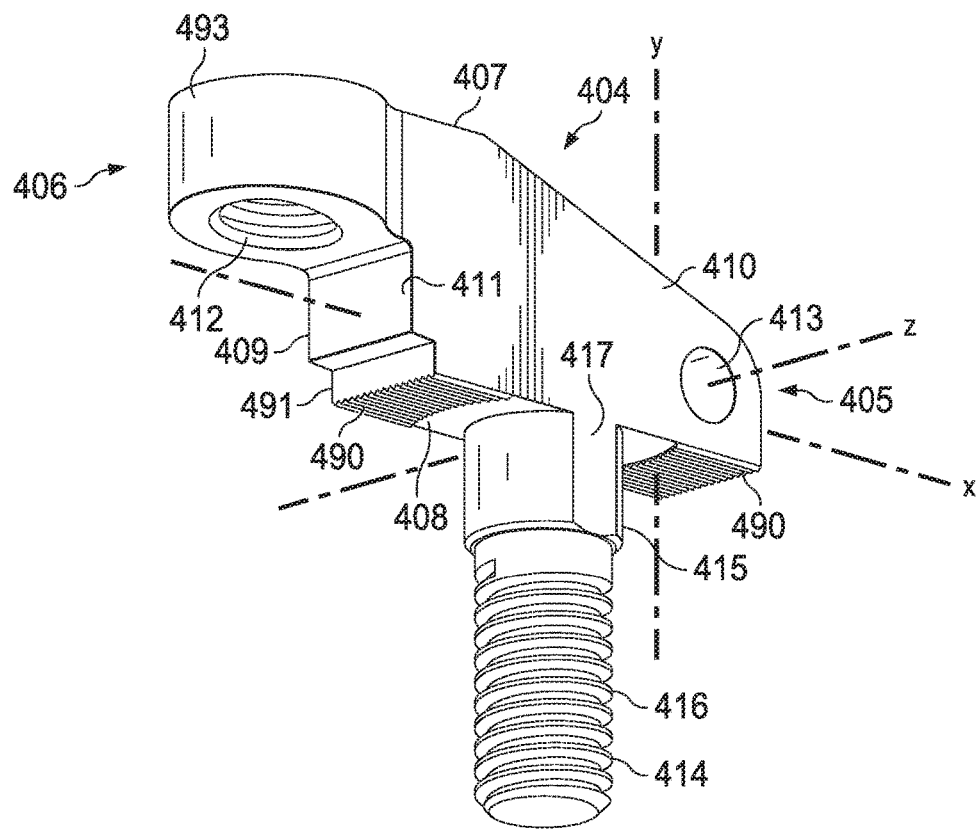
FIG. 4F illustrates a perspective view of a ring connector used with an alternative embodiment of a hinged dynamization tab.

Another perspective view of the ring connector 404 is depicted in FIG. 4F. In FIG. 4F, the connecting bolt 414 is parallel to or aligned with the vertical axis Y. The connecting bolt 414 includes a smooth portion 415 and a threaded portion 416. The outer diameter of the smooth portion 415 of the connecting bolt 414 is approximately the same as the inner diameter of ring apertures 488 so that the ring connector 404 may be fitted securely to the ring 487. The lateral sides of the smooth portion 415 of the connecting bolt 414 may also include at least one flat 417 comprising a planar surface that is aligned with an upper lateral surface 410 of the ring connector 404. The ring connector 404 has a proximal end 405 and a distal end 406 and is positioned along the longitudinal axis X of the hinged tab 400. The ring connector 404 may further comprise a top surface 407, a bottom surface 408, a first upper lateral surface 409, a second upper lateral surface 410, a distal-facing surface 411, a threaded bore 412, and a second bore 413. In some embodiments, the threaded bore 412 extends parallel and distal to the vertical axis Y from the top surface of the ring connector 407 to a bottom surface of the ring connector 408. The threaded bore 412 may be placed within a distal knob 493 that is placed at a distal end of the ring connector 404. The distal knob 493 have a generally cylindrical shape between the top surface 408 and the bottom surface 409.

Figure 4G:
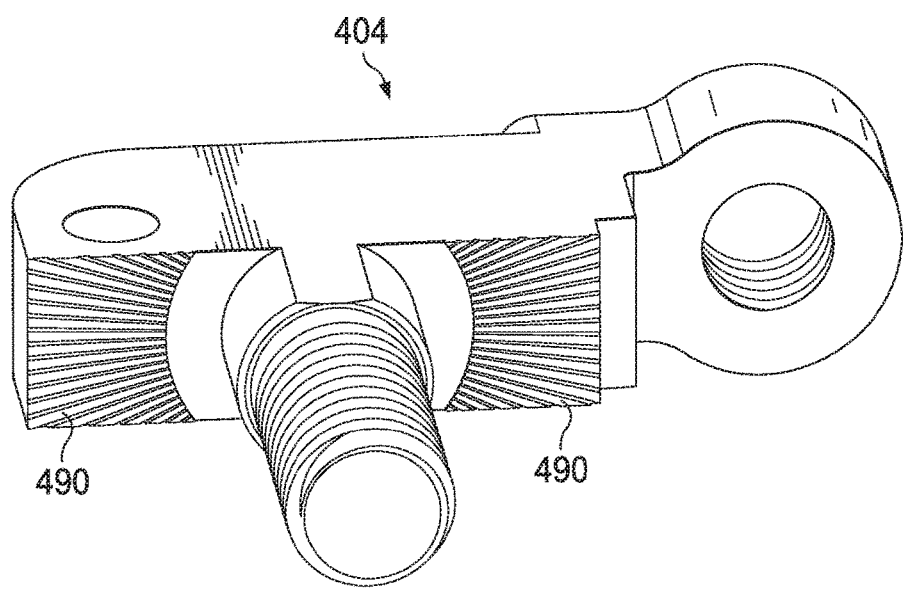
FIG. 4G illustrates another perspective view of a ring connector used with an alternative embodiment of a hinged dynamization tab.

The threaded bore 412 may threadably engage with the adjustment screw 431, as depicted in FIG. 4E. The second bore 413 may extend along the transverse axis Z of the hinged tab 400 from the first upper lateral surface 409 of the ring connector to the second upper lateral surface 410 of the ring connector and may be configured to accept the pivot pin 480 of FIG. 4E. The pivot pin 480 may be suitable for a press fit in bore 413 (See FIG. 4B), but a loose or rotational fit through the bores in the arms in the strut connector 440, as will be explained below. The bottom surface 408 of the ring connector 404 may also include one or more roughened surfaces 490, which create friction with the upper surface of the ring 487 and therefore inhibit rotation of the ring connector 404 with respect to the ring 487. According to one embodiment, the roughened surfaces may comprise a series of ridges or teeth that are approximately 0.25 mm in height and have a cross-sectional "V" profile with sides that have angles at approximately 90 degrees with respect to each other. The bottom surface 408 may also include a motion limiting face 491 that can mate with a corresponding lip or edge portion in the strut connector 440. An alternative embodiment of the roughened surfaces 490 is depicted in FIG. 4G. As shown in this figure, the roughened surfaces may comprise a radial pattern of ridges or teeth that have a height of approximately 0.25 mm and have a cross-sectional "V" profile with sides that have angles at approximately 90 degrees with respect to each other.

Figure 4H:
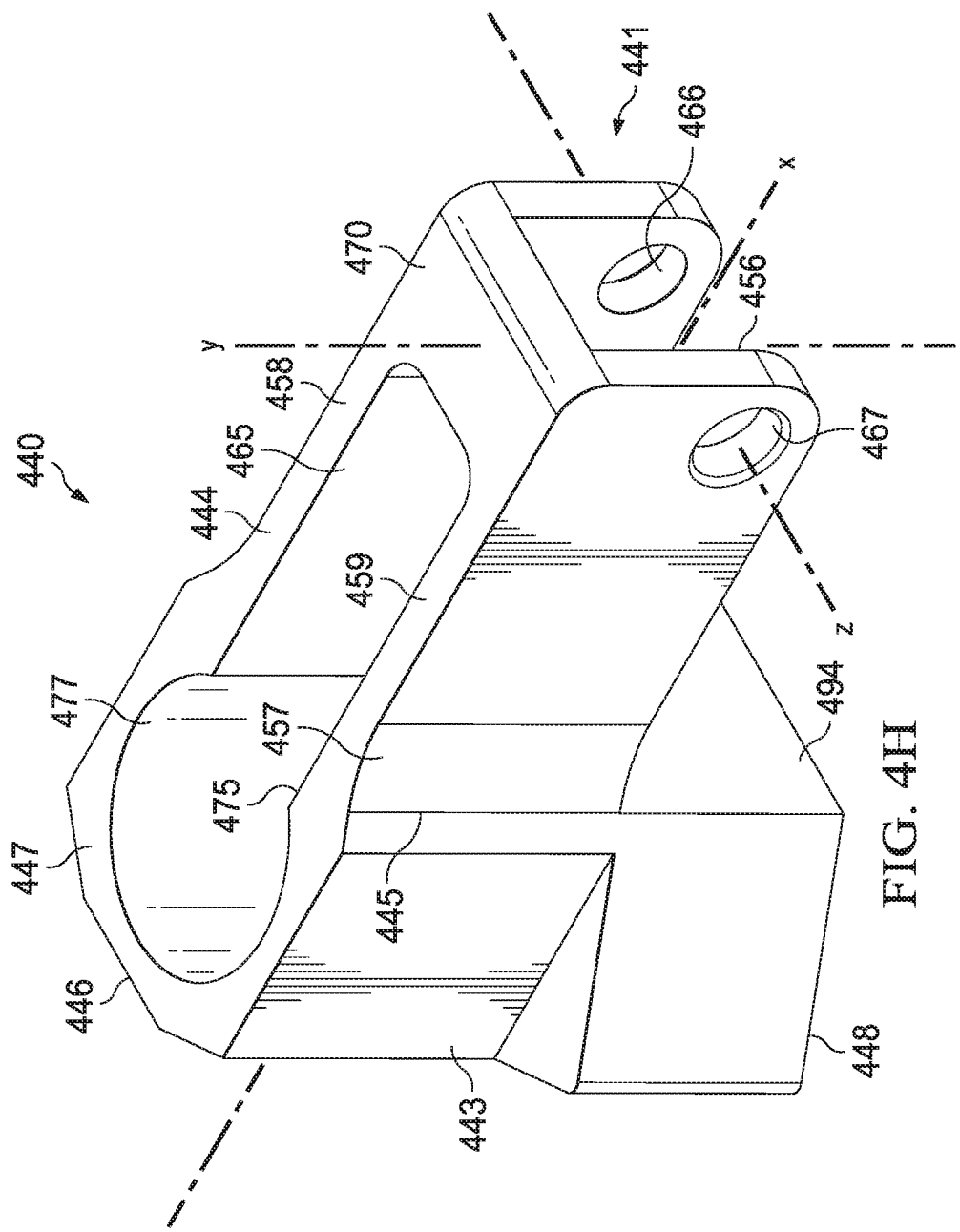
FIG. 4H illustrates a perspective view of a strut connector used with an alternative embodiment of a hinged dynamization tab.

The hinged tab 400 may further comprise a strut connector 440, as illustrated in FIG. 4H. In some embodiments, the strut connector 440 may have a proximal end 441 and a distal end 446 and may further comprise a head 443 and strut connector knuckle 444. The head 443 may have a proximal end 445 and a distal end 446 and be positioned along the longitudinal axis X of the hinged tab 440. The proximal end 445 of the strut connector 440 may also include a flat or curved surface 494 that can impinge upon the outer surface of the ring 487. The head 443 may further comprise a top surface 447, a bottom surface 448, a first distal-facing surface 449, a second distal-facing surface 450, and a third distal-facing surface 451 (See FIG. 4I). In some embodiments, the strut connector knuckle 444 may comprise a proximal end 456 and a distal end 457 and be positioned along the longitudinal axis X of the hinged tab 440 so that the distal end 457 of the strut connector knuckle is in contact with the proximal end 445 of the head. The strut connector knuckle 444 may further comprise a first arm 458 and a second arm 459. The first arm 458 may be positioned parallel to the longitudinal axis X of the hinged tab so that the distal end 457 is in contact with the proximal end 445 of the head. The second arm 459 may also be positioned parallel to the longitudinal axis X of the hinged tab so that the distal end 457 is in contact with the proximal end 445 of the head. The proximal ends of the first and second arms (458, 459) may be connected by a lateral member 470, which forms a rigid connection between the first and second arms (458, 459) and further strengthens the proximal end 441 of the strut connector 440.

The first arm 458 of the strut connector knuckle may further comprise a first arm bore 466 that is sized to receive the pivot pin 480. Similarly, the second arm 459 may further comprise a second arm bore 467 that extends along the transverse axis Z of the hinged tab 400 and is sized to receive the pivot pin 480. The first arm 458 also comprises a first inner wall 465 that may be placed in contact with the first upper lateral surface 409 of the ring connector 404 when those components are mated together. The second arm 459 of the strut connector knuckle 440 may also comprise a second arm bore 467 that extends along the transverse axis Z of the hinged tab 400 and is sized to receive the pivot pin 480. The second arm 459 also comprises a second inner wall 475 that may be placed in contact with the second upper lateral surface 410 of the ring connector 404 when those components are mated together. The relatively large surface areas of the first and second inner walls (465, 475) that are in contact with the first and second upper lateral surfaces (409, 410) allow the strut connector 440 to pivot about the transverse axis Z with respect to the ring connector 404 while minimizing any lateral displacement that may occur along the transverse axis Z.

The head 443 of the strut connector 440 may also comprise a ring connector aperture 477 that is formed in the top surface of the head and extends down into the head. According to one embodiment, the ring connector aperture 477 has a generally cylindrical shape with an inner circumference that is large enough to accommodate the distal knob 493 of the ring connector 404 (depicted in FIG. 4F). Further, the inner circumference of the ring connector aperture 477 is large enough to allow the strut connector 440 to pivot about the transverse axis Z of the hinged tab 400 without the outer walls of the distal knob 493 impinging upon the inner walls of the ring connector aperture 477. The ring connector aperture 477 is also large enough to allow the biasing element 498 to fit within the aperture and form a biasing mechanism between the bottom surface of the ring connector aperture 477 and the lower surface of the distal knob 493 of the ring connector 404.

Figure 4I:
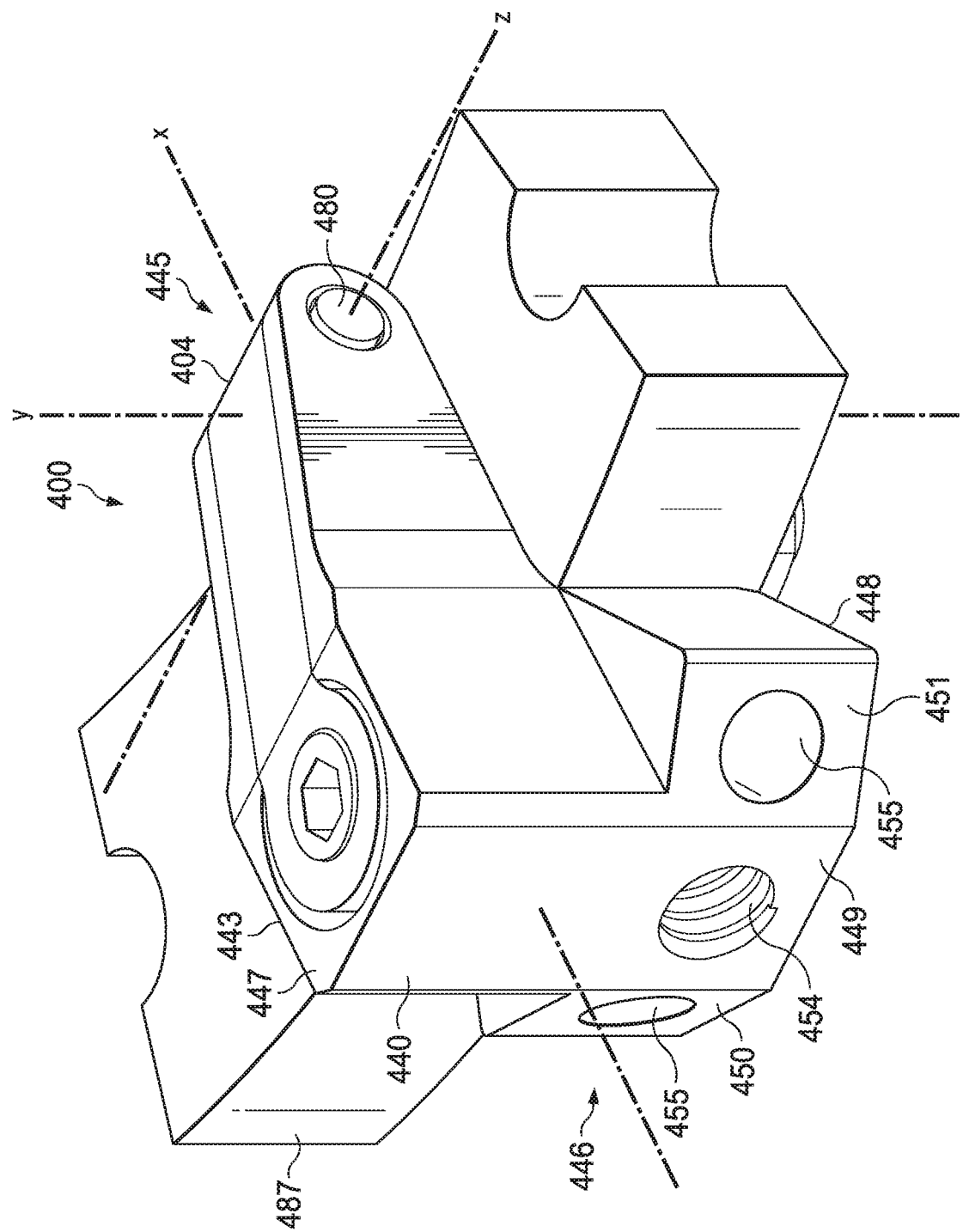
FIG. 4I illustrates another perspective view of an alternative embodiment of a hinged dynamization tab.

An alternative perspective view of the hinged tab 400 that is connected to the ring 487 is depicted in FIG. 4I. In FIG. 4I, the strut connector 440 is mated to the ring connector 404 so that the pieces are pivotally connected by the pivot pin 480. In this arrangement, the strut connector is allowed to pivot about the transverse axis Z of the hinged tab 400, while the ring connector 404 remains fixed to the ring 487. The head 443 of the strut connector 440 may further comprise a top surface 447, a bottom surface 448, a first distal-facing surface 449, a second distal-facing surface 450, and a third distal-facing surface 451. The first distal-facing surface 449 may further comprise a locking-screw aperture 454, which may be a partial bore that extends from the distal end of the head 446 towards the proximal end of the head 445 and may be threaded to accept a locking screw. The second distal-facing surface 450 and the third distal-facing surface 451 may further comprise a strut aperture 455, which may be a partial bore that extends from the distal end of the head 446 to the proximal end of the head 445 and may be each be configured to secure a strut to the strut connector 440.

Figure 4J:
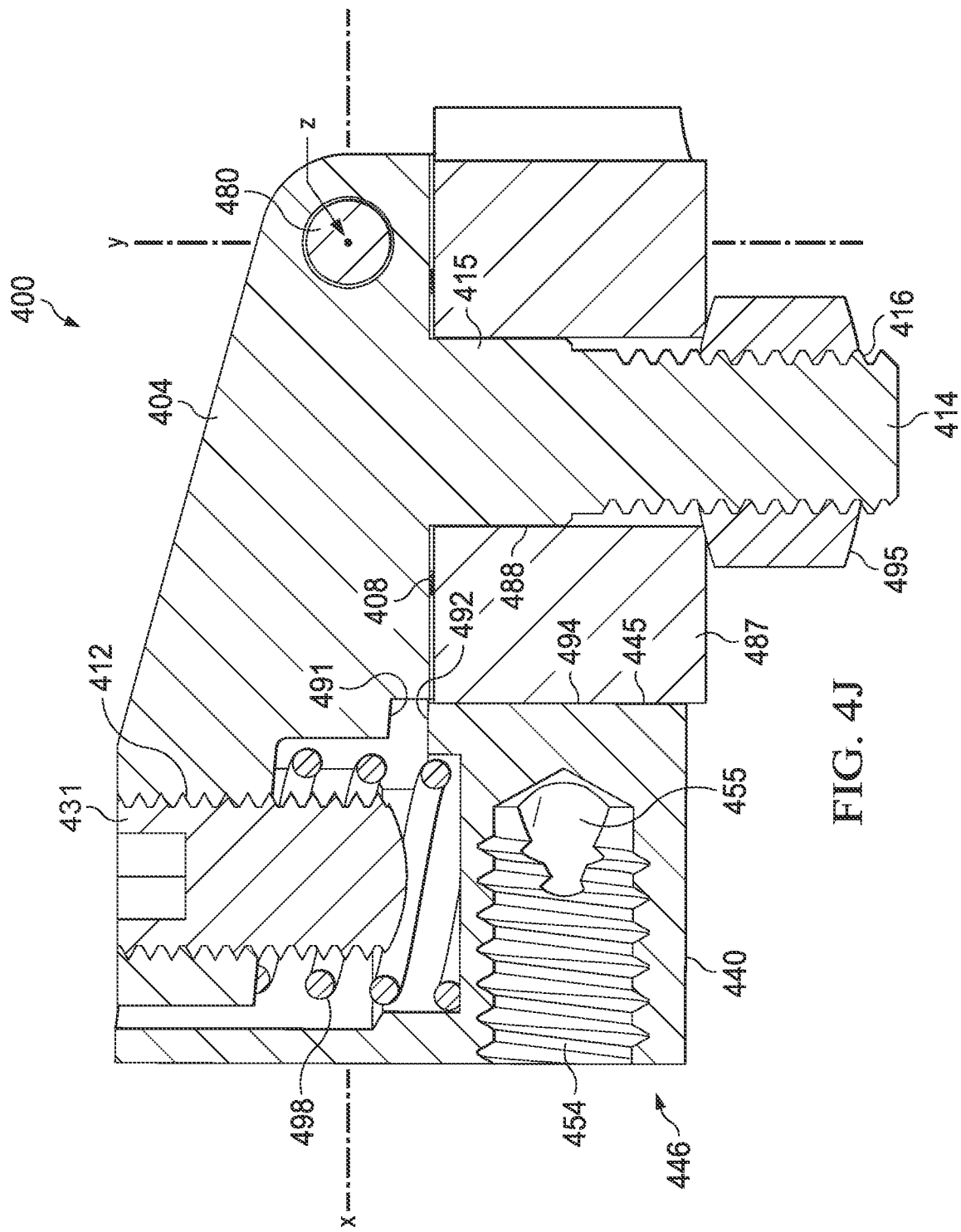
FIG. 4J illustrates a cross-sectional view of an alternative embodiment of a hinged dynamization tab.

A cross-sectional view of the hinged tab 400 taken along the longitudinal axis X is depicted in FIG. 4J. In FIG. 4J, the pivotal connection of the ring connector 404 to the strut connector 440 through the pivot pin 480 is illustrated. The connection of the ring connector 404 to the ring 487 by virtue of the connecting nut 495 on the threaded portion 416 of the connecting bolt 414 is also depicted in FIG. 4J. As described above, the outer diameter of the smooth portion 415 of the connecting bolt is substantially similar to the inner diameter of the ring aperture 488. As such, by tightening the connecting nut 495 onto the connecting bolt 414, the ring connector 404 can be secured onto the ring 487. Also depicted in FIG. 4J is a cross-sectional view of the locking-screw aperture 454, which may be a partial bore that extends from the distal end of the head 446 towards the proximal end of the head 445 and may be threaded to accept a locking screw. The proximal end of the locking-screw aperture 454 intersects with the proximal end of strut aperture 455 so that the proximal end of the locking screw can impinge upon proximal end of a strut connector. Accordingly, the locking screw may secure the strut fasteners through contact with the strut fasteners in a manner that prevents the movement of the strut fasteners with respect to the strut apertures 455 when the locking screw is in place. Several examples of such a locking arrangement are found in U.S. Pat. No. 9,295,493, hereby incorporated by reference into this patent.

The bottom surface 408 of the ring connector 404 may also include a first motion limiting face 491 that can mate with a corresponding second motion limiting face 492 of the strut connector 440. When the strut connector 440 is pivoted in a clockwise direction with respect to the transverse axis Z, the second motion limiting face 492 will pivot until it comes in contact with the first motion limiting face 491. At this point, no further rotation of the strut connector 440 with respect to the ring connector 404 will be permitted. In addition, the biasing element 498 will be compressed as the strut connector 440 is pivoted in a clockwise direction with respect to the transverse axis Z. The compression applies a force against the bottom surface of the distal knob 493 of the ring connector 404 and against the bottom of the ring connector aperture 477. This biasing force also presses the flat or curved surface 494 against the outer surface of the ring 487 when the hinged tab 400 is mounted to the ring 487. This provides an advantage in which the biasing force of the flat or curved surface 494 of the strut connector against the outer surface of the ring 487 will hold the hinged tab in place on the ring 487 until the connecting nut 495 can be tightened onto the connecting bolt 414.

Also shown in FIG. 4J is the adjustment screw 431 that is placed in the threaded bore 412 of the ring connector 404. As the adjustment screw 431 is driven down into threaded bore 412, the distal end of the adjustment screw will impinge upon the bottom of the ring connector aperture 477 in the strut connector 440. This prevents any relative pivotal movement of the strut connector 440 with respect to the ring connector 404, and thus any dynamization of the fixation struts with respect to the fixation rings 487. As the adjustment screw 431 is backed out in threaded bore 412, the distal end of the adjustment screw moves away from the bottom of the ring connector aperture 477 in the strut connector 440. This introduces a controllable amount of "play" or pivotal movement of the strut connector 440 with respect to the ring connector 404, thus permitting a controlled amount of dynamization of the fixation struts with respect to the fixation rings 487. By controlling the relative position of the adjustment screw 431 within the threaded bore 412 of the ring connector 404, the amount of dynamization of the fixation struts with respect to the fixation rings 487 can be controlled.

Figure 4K:
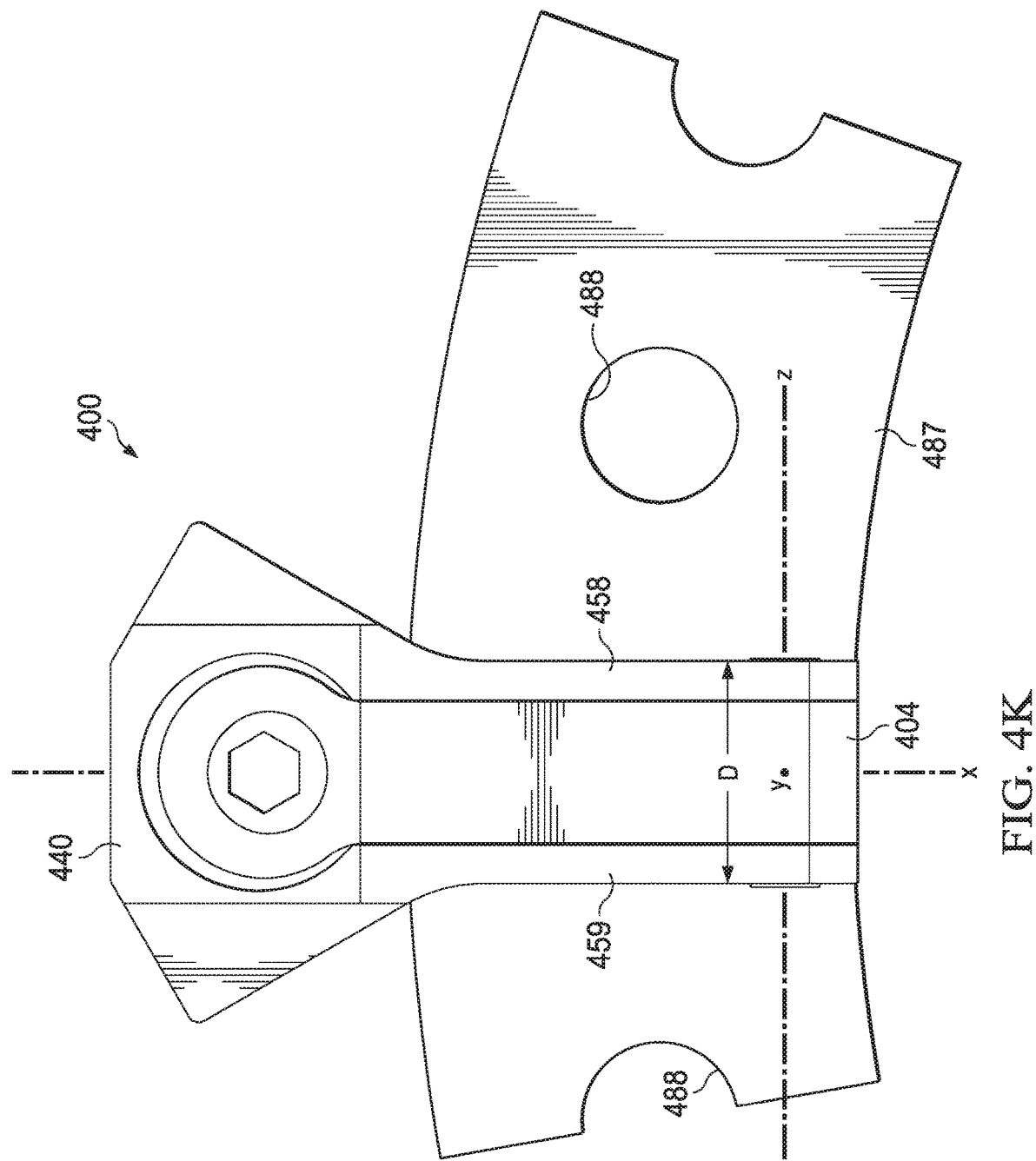
FIG. 4K illustrates a top view of an alternative embodiment of a hinged dynamization tab.

A top view of one embodiment of the hinged tab 400 is depicted in FIG. 4K. In FIG. 4K, the arms 458 and 459 of the strut connector 440 are depicted as mated to the first and second upper lateral surfaces of the ring connector to allow the strut connector 440 to pivot about the transverse axis Z with respect to the ring connector 404 while minimizing any lateral displacement that may occur along the transverse axis Z. One advantage of this embodiment of the hinged tab 400 is that it has a relatively narrow width D along the transverse axis Z. As a result of this, access to the adjacent apertures 488 in the ring 487 is maintained. This allows other devices, fixation equipment, mounting wires, or other accessories to be attached at more locations around the circumference of the ring 487 than on other embodiments.

Figure 4L:
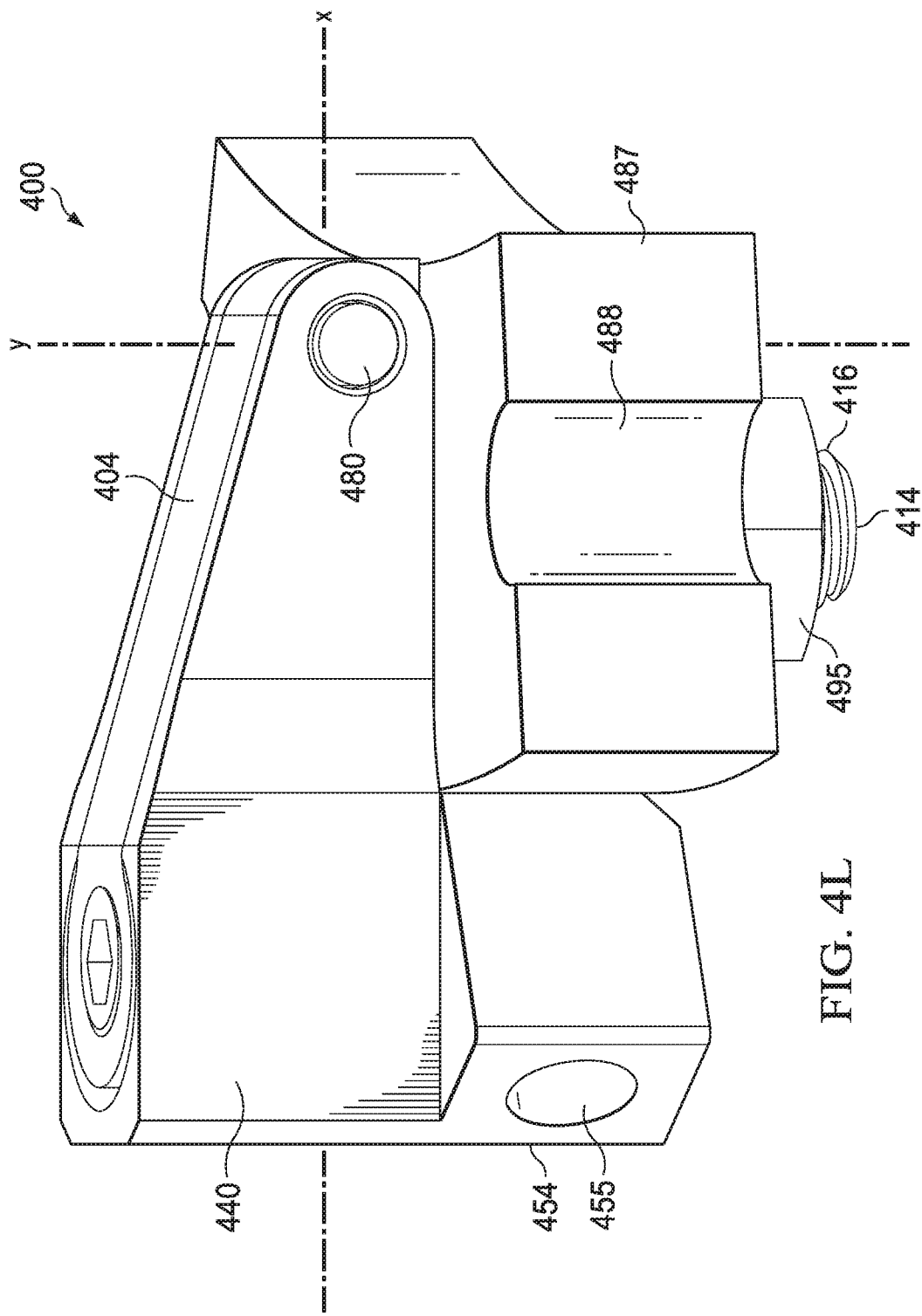
FIG. 4L illustrates a perspective side view of an alternative embodiment of a hinged dynamization tab.

A side view of one embodiment of the hinged tab 400 is depicted in FIG. 4L. In FIG. 4L, the pivotable attachment of the strut connector 440 with respect to the ring connector 404 is depicted. The pivotable attachment of these components is provided by the pivot pin 480 that is mounted along the transverse axis Z of the hinged tab 400. The connecting nut 495 that is mounted on the threaded portion 416 of the connecting bolt 414 is also depicted. In addition, the placement of the locking-screw aperture 454 and the strut apertures 455 along the vertical axis Y to align with the midpoint of the ring 487 is depicted. By aligning the end of the fixation struts with the midpoint of the ring 487, the mathematical modeling of the placement of the struts and the amount of displacement of the lengths of the struts can be simplified. This presents another advantage of this embodiment with respect to other embodiments of this invention. Yet another side view of the hinged tab 400 is depicted in FIG. 4M.

Figure 5A:
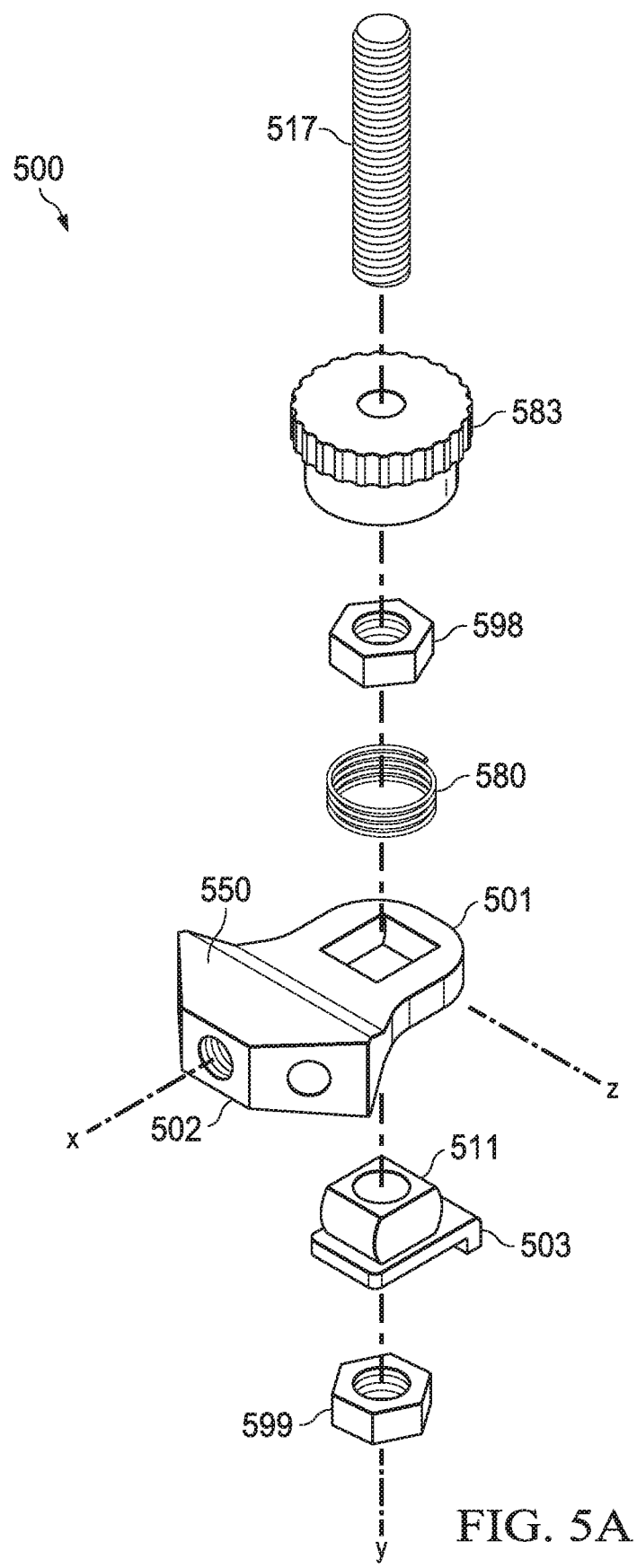
FIG. 5A illustrates an exploded perspective view of an embodiment of a circular pivot dynamization tab.

FIG. 5A is an exploded perspective view of an embodiment of a circular pivot tab 500 of the present disclosure. The circular pivot tab 500 has a longitudinal axis X, a vertical axis Y, and a transverse axis Z defined therein and comprises a proximal end 501, a distal end 502, a ring connector 503, a strut connector 550, a biasing mechanism 580, and a fastener 583. Further, according to some embodiments, the circular pivot tab 500 may comprise a connecting bolt 517, a first connecting nut 598, and a second connecting nut 599. In these embodiments, the connecting bolt 517, first connecting nut 598, and second connecting nut 599, are configured to secure the circular pivot tab 500 to an external fixation ring, discussed above.

Figure 5B:
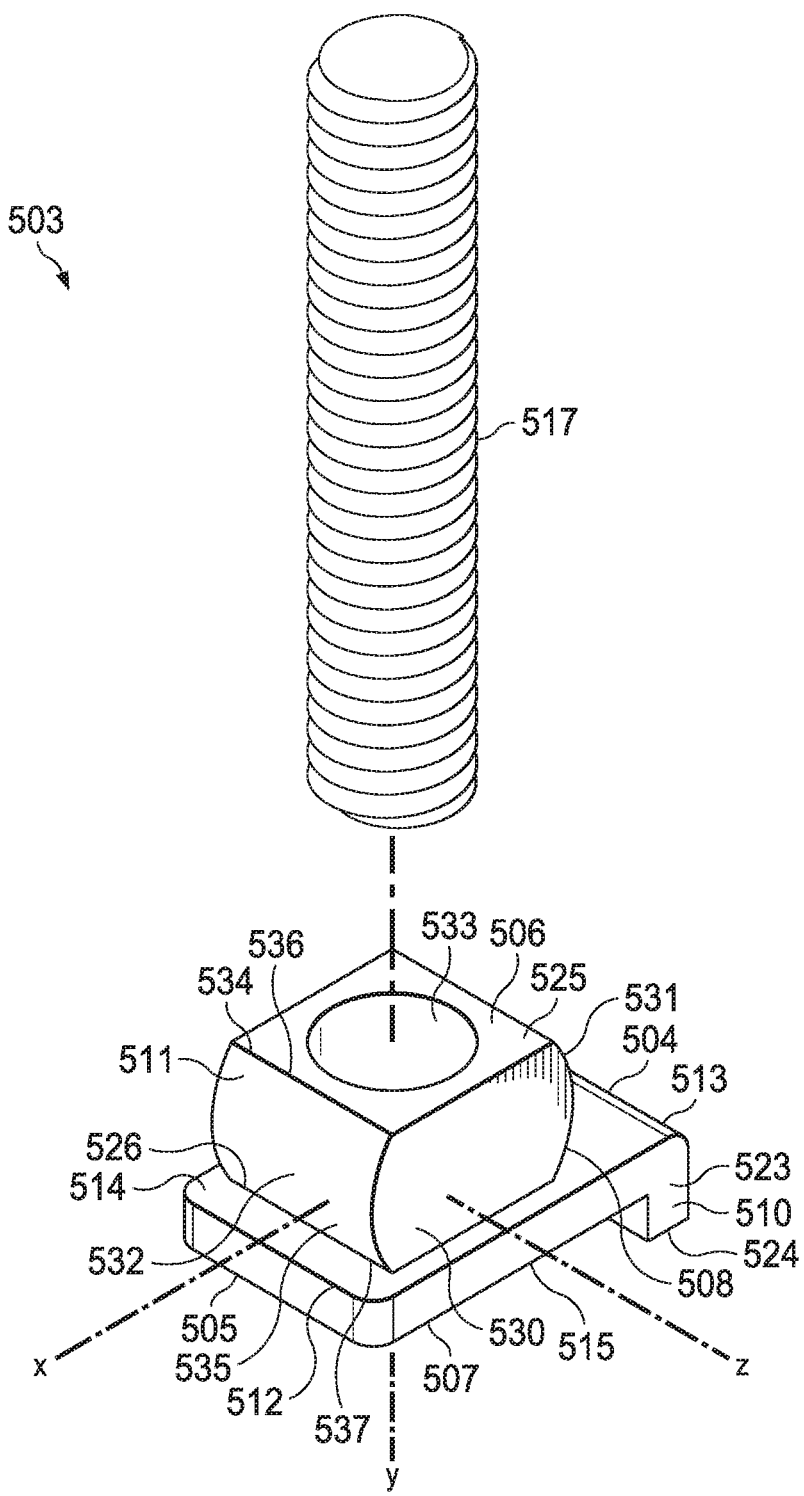
FIG. 5B illustrates an exploded perspective view of a ring connector of a circular pivot dynamization tab.

Illustrated in FIG. 5B, the ring connector 503 has a proximal end 504, a distal end 505, a superior end 506, and an inferior end 507. The ring connector 503 further comprises a first stabilizer 508, a second stabilizer 510, and ring connector knuckle 511. The first stabilizer of the ring connector 508 has a distal end 512 and a proximal end 513 and is positioned along the longitudinal axis X of the circular pivot tab. According to some embodiments, the first stabilizer 508 may further comprise a top surface 514, a bottom surface 515, and a first stabilizer bore (not shown). The first stabilizer bore (not shown) may extend along the vertical axis Y of the circular pivot tab from the top surface of the first stabilizer 514 to the bottom surface of the first stabilizer 515 and may be configured to accept a connecting bolt 517. The second stabilizer of the ring connector 510 may comprise a superior end 523 and an inferior end 524. In some embodiments, the second stabilizer 510 may be positioned parallel to the vertical axis Y of the circular pivot tab in a manner such that the superior end 523 is in contact with the bottom surface of the first stabilizer 515.

The ring connector 503 may further comprise a ring connector knuckle 511, as illustrated in FIG. 5B. The ring connector knuckle 511 may have a superior end 525, an inferior end 526, and be positioned along the vertical axis Y of the dynamization tab in a manner such that the inferior end 526 is in contact with the top surface of the first stabilizer 514. According to some embodiments, the ring connector knuckle 511 may further comprise a top surface 527, a bottom surface 528, a first surface (not shown), a second surface 530, a proximal-facing surface 531, a distal-facing surface 532, and a ring connector knuckle bore 533. In these embodiments, the proximal-facing surface 531 may comprise a top edge 534 and a bottom edge 535 and be positioned parallel to the vertical axis Y of the dynamization tab in such a manner that the top edge 534 is in contact with the top surface of the ring connector knuckle 527 and the bottom edge 535 is in contact with the bottom surface of the ring connector knuckle 528. As shown in FIG. 5B, the proximal-facing surface of the ring connector knuckle 531 may be convexly shaped with respect to the vertical axis Y of the circular pivot tab. The distal-facing surface of the ring connector knuckle 532 may comprise a top edge 536 and a bottom edge 537 and be positioned parallel to the vertical axis Y of the circular pivot tab in a manner such that the top edge 536 is in contact with the top surface of the ring connector knuckle 527 and the bottom edge 537 is in contact with the bottom surface of the ring connector knuckle 528. The distal-facing surface of the ring connector knuckle 532 may be convexly shaped with respect to the vertical axis Y of the circular pivot tab. The ring connector knuckle bore 533, according to some embodiments, extends along the vertical axis Y of the circular pivot tab from the top surface of the ring connector knuckle 527 to the bottom surface of the ring connector knuckle 528. The ring connector knuckle bore 533 may be configured to accept a connecting bolt 517.

Figure 5C:
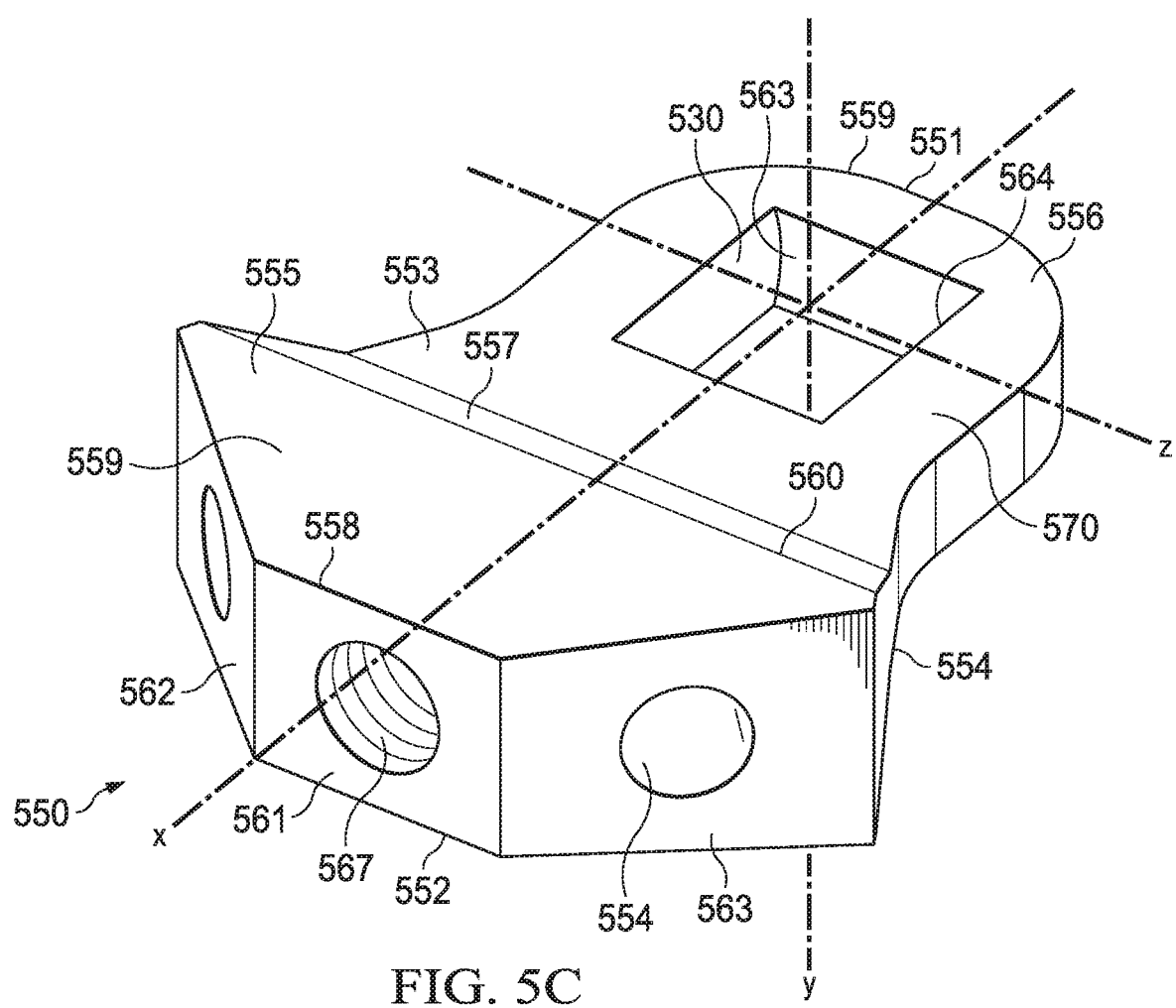
FIG. 5C illustrates an exploded perspective view of a strut connector of a circular pivot dynamization tab.

FIG. 5C illustrates an embodiment of a strut connector of a circular pivot tab 550. The strut connector 550 may comprise a proximal end 551, a distal end 552, a superior end 553, and an inferior end 554, and be positioned along the longitudinal axis X of the circular pivot tab. The strut connector 550 may further comprise a head 555 and a strut connector knuckle 556. The head of the strut connector 555, according to some embodiments, may comprise a proximal end 557, a distal end 558, a top surface 559, a bottom surface 560, a first distal-facing surface 561, a second distal-facing surface 562, and a third distal-facing surface 563. The first distal-facing surface 561 may comprise a locking-screw aperture 567 which may be a partial bore extending from the distal end of the head 558 towards the proximal end of the head 557. The second distal-facing surface 562 and the third distal-facing surface 563 may each comprise a strut aperture 558 that, according to some embodiments, may each be a partial bore extending from the distal end of the head 558 towards the proximal end of the head 557 and may be configured to secure struts to the circular pivot tab. The strut connector knuckle 556 of FIG. 5C may comprise a proximal end 559, a distal end 560, a top surface 570, a bottom surface (not shown), and a strut connector knuckle bore 563. The strut connector knuckle bore 563 may extend from the top surface 570 of the strut connector knuckle 556 to the bottom surface of the strut connector knuckle.

Figure 5D:
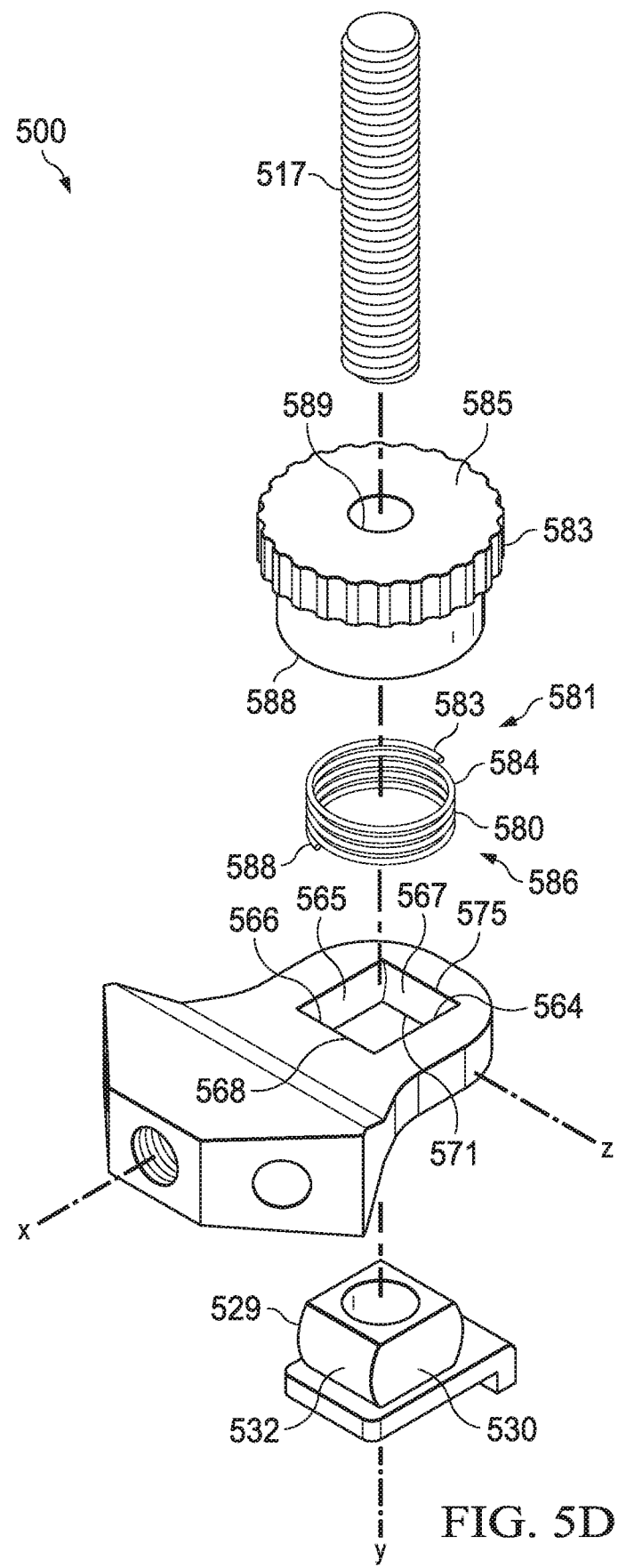
FIG. 5D illustrates another exploded perspective view of an embodiment of a circular pivot dynamization tab.

Referring now to FIG. 5D, the strut connector knuckle bore 563 may further comprise an first side surface 564, a second side surface 565, a proximal-facing surface 566 and a distal-facing surface 567. The first side surface of the strut connector knuckle bore 564 may be configured to be in contact with the second side surface of the ring connector knuckle 530 in such a manner that pivoting of the strut connector 550 about the vertical axis Y of the circular pivot tab is diminished. Similarly, the second side surface 565 of the strut connector knuckle bore may be configured to be in contact with the first surface 529 of the ring connector knuckle in such a manner that pivoting of the strut connector 550 about the vertical axis Y of the circular pivot tab is diminished. The proximal-facing surface of the strut connector knuckle bore 566 comprises a top edge 568 and a bottom edge (not shown). The proximal-facing surface 566, according to some embodiments, is positioned parallel to the vertical axis Y of the circular pivot tab in such a manner that the top edge of the proximal-facing surface 568 is in contact with the top surface of the strut connector knuckle 561 and the bottom edge 569 is in contact with the bottom surface of the strut connector knuckle 562. In the embodiment of FIG. 5D, the proximal-facing surface 566 of the strut connector knuckle bore is concavely shaped with respect to the vertical axis Y of the circular pivot tab. The proximal-facing 566 surface of the strut connector knuckle bore may be configured to be in contact with the convexly shaped, distal-facing surface of the ring connector knuckle 532, in a manner such that the two surfaces allow for pivoting of the strut connector 550 about the transverse axis Z of the circular pivot tab. The distal-facing surface of the strut connector knuckle bore 567 comprises a top edge 575 and a bottom edge 571 and is positioned parallel to the vertical axis Y of the circular pivot tab in a manner such that the top edge 575 is in contact with the top surface of the strut connector knuckle 561 and the bottom edge 571 is in contact with the bottom surface of the strut connector knuckle 562. In some embodiments, the distal-facing surface of the ring connector knuckle 567 may be concavely shaped with respect to the vertical axis Y of the circular pivot tab and be configured to be in contact with the convexly shaped, proximal-facing surface of the ring connector knuckle 531 in such a manner that the two surfaces allow for pivoting of the strut connector 550 about the transverse axis Z of the circular pivot tab.

The circular pivot tab 500 may further comprise a biasing mechanism 580. As illustrated in FIG. 5D, the biasing mechanism 580 may comprise a superior end 581 and an inferior end 586 and be positioned along the vertical axis Y of the circular pivot tab 500. The biasing mechanism 580 may further comprise a connecting bolt 517, a fastener 583, and a coil spring 584. The connecting bolt 517 may be a threaded bolt that is configured to traverse along the vertical axis Y of the circular pivot tab in a manner such that it passes through the ring connector knuckle bore 533, the first stabilizer bore (not shown), and a fastener bore 589. The fastener 583 may comprise a superior end 585, an inferior end 586, and the fastener bore 589 and be positioned such that the superior end of the fastener 585 comprises the superior end of the biasing mechanism 581 and the inferior end of the fastener 586 is in contact with the coil spring 584. The fastener bore 589 may be a threaded bore that extends from the superior end of the fastener 585 to the inferior end of the fastener 588 and may be configured to accept the connecting bolt 517. The coil spring 584 may comprise a superior end 587 and an inferior end 588 and be positioned along the vertical axis Y of the circular pivot tab 500 in a manner such that the superior end of the coil spring 584 is in contact with the fastener 583 and the inferior end of the coil spring 588 may be in contact with the top surface of the strut connector knuckle 556. The coil spring 584 may be positioned such that translation of the fastener 583 along the vertical axis Y of the circular pivot tab 500 translates to the compression or decompression of the coil spring 584. In some embodiments, compression of the coil spring 584 may translate to restricted pivoting of the strut connector 550 about the transverse axis Z of the circular pivot tab 500 and decompression of the coil spring 584 may translate to a greater freedom of pivoting of the strut connector 550 about the transverse axis Z of the circular pivot tab 500. Further, the coil spring 584 may be configured to provide a biasing force when the strut connector 550 is pivoted about the transverse axis Z of the circular pivot tab 500, returning the strut connector 550 to its original position.

In another embodiment, the hinge with torsion spring (hinge with torsion spring), the tab itself behaves as a hinge. In this embodiment, the strut connector and ring connector junction is loaded with a horizontal torsion spring, allowing the strut connector to oscillate under loading, as well as providing the biasing force needed to return the strut connector to a resting position. Further, the degree of oscillation is limited by two motion-limiting faces present on the strut connector, which limit the degree by contact with the ring connector. Adjustments to the degree of dynamization may be made through the use of different torsion springs, as appropriate.

Figure 6A:
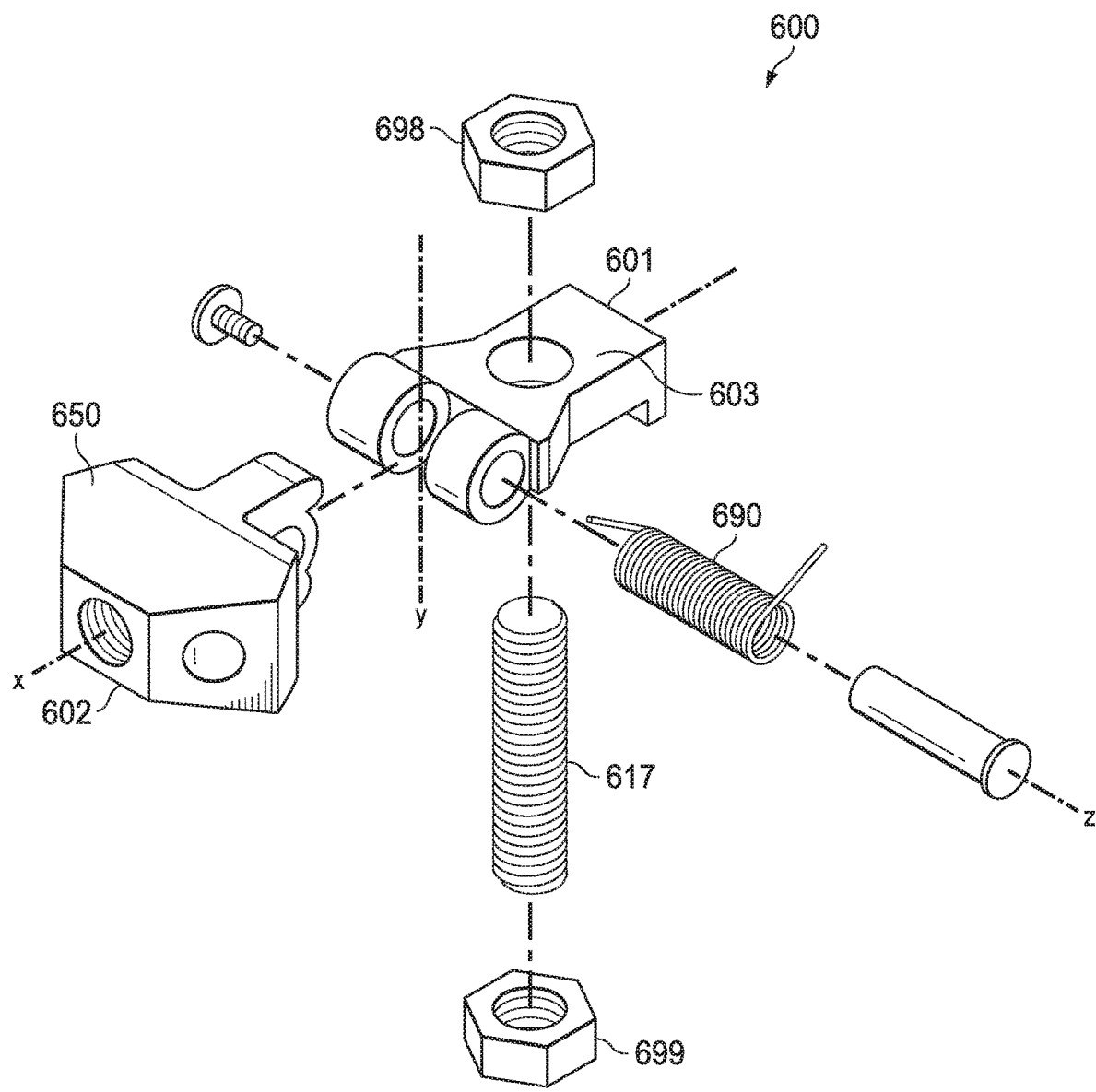
FIG. 6A illustrates an exploded perspective view of an embodiment of a hinge with torsion spring in a dynamization tab.

FIG. 6A is an exploded perspective view of an embodiment of a hinge with torsion spring 600 of the present disclosure. The hinge with torsion spring 600 has a longitudinal axis X, a vertical axis Y, and a transverse axis Z defined therein and comprises a proximal end 601, a distal end 602, a ring connector 603, a strut connector 650, and a biasing mechanism 690. Further, according to some embodiments, the hinge with torsion spring 600 may comprise a connecting bolt 617, a first connecting nut 698, and a second connecting nut 699. In these embodiments, the connecting bolt 617, first connecting nut 698, and second connecting nut 699, are configured to secure the hinge with torsion spring 600 to an external fixation ring, discussed above.

Figure 6B:
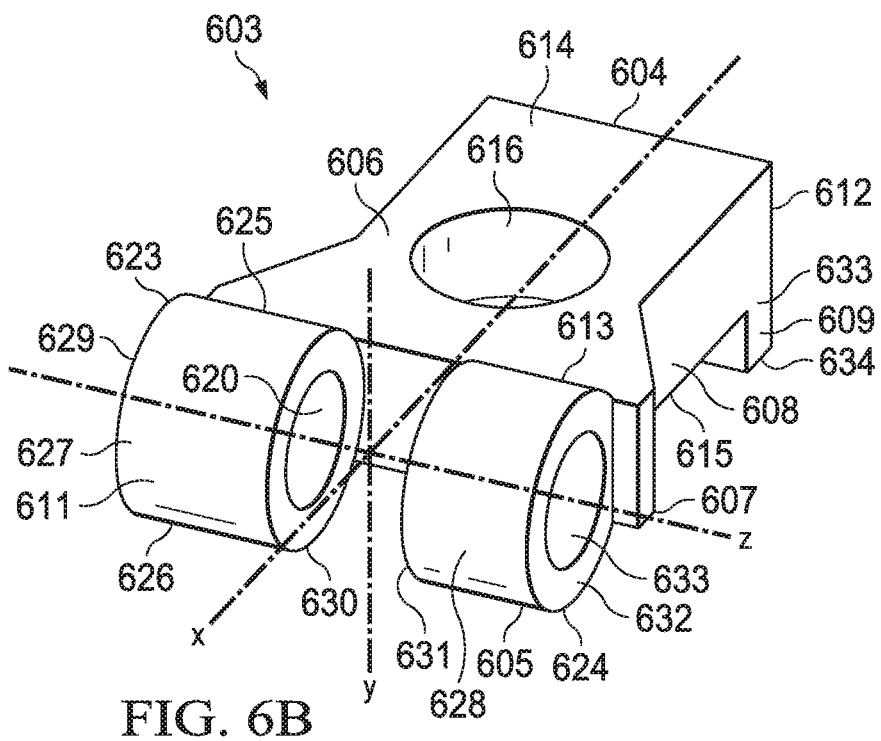
FIG. 6B illustrates a perspective view of an embodiment of a ring connector with a hinge and torsion spring in a dynamization tab.

In the embodiment of FIG. 6B, the ring connector 603 of the hinge with torsion spring has a proximal end 604, a distal end 605, a superior end 606, and an inferior end 607. The ring connector 603 may further comprise a first stabilizer 608, a second stabilizer 609, and a ring connector knuckle 611. The first stabilizer 608 of the ring connector 603 has a distal end 613 and a proximal end 612 and may be positioned along the longitudinal axis X of the hinge with torsion spring 600. It may further comprise a top surface 614, a bottom surface 615, and a circular bore 616 which extends parallel to the vertical axis Y of the hinge with torsion spring from the top surface of the first stabilizer 614 to the bottom surface of the first stabilizer 615 and may be configured to accept the connecting bolt 617. The second stabilizer of the ring connector 609 may comprise a superior end 623 and an inferior end 624 and be positioned parallel to the vertical axis Y of the hinge with torsion spring in a manner such that the superior end 623 is in contact with the bottom surface of the first stabilizer 615. The ring connector 603 may further comprise a ring connector knuckle 611, which may comprise a first end 623, a second end 624, a proximal end 625, and a distal end 626. The ring connector knuckle 611, according to some embodiments, may be positioned along the longitudinal axis X of the hinge with torsion spring in a manner such that the proximal end 625 is in contact with the distal end of the first stabilizer 613. The ring connector knuckle 611 may comprise a first circular arm 627 and a second circular arm 628. The first circular arm 627 may have an first face 629 and a second face 630 and be positioned along the transverse axis of the hinge with torsion spring in such a manner that the first face 629 and the second face 630 are perpendicular to the top surface of the first stabilizer 614 and the bottom surface of the first stabilizer 615. Further, the first circular arm may comprise a first arm bore 620, which may extend from the first face of the first circular arm 629 to the second face of the first circular arm 630 and be configured to accept the biasing mechanism 690. The second circular arm 628 may have a first face 631 and a second face 632 and be positioned along the transverse axis of the hinge with torsion spring in such a manner that the first face 631 and the second face 632 are perpendicular to the top surface of the first stabilizer 614 and the bottom surface of the first stabilizer 615. Further, the second circular arm may comprise a second arm bore 633, which may extend from the first face of the second circular arm 631 to the second face of the first circular arm 632 and be configured to accept the biasing mechanism 690.

Figure 6C:
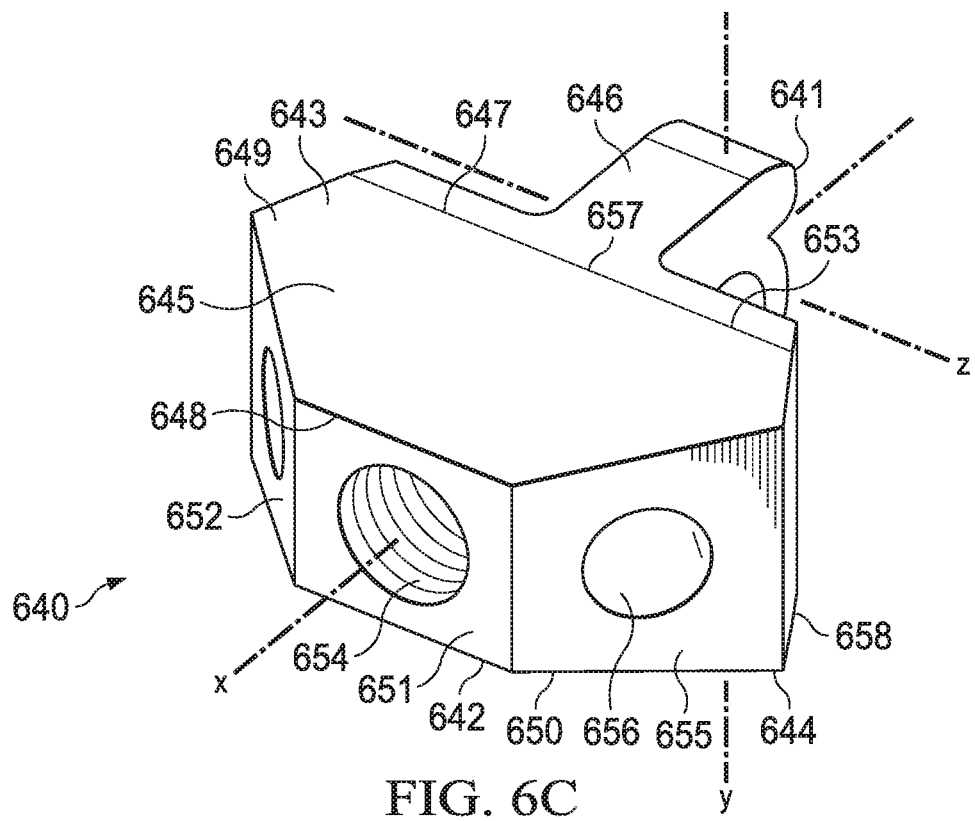
FIG. 6C illustrates a perspective view of an embodiment of a strut connector with a hinge and torsion spring in a dynamization tab.

The strut connector of the hinge with torsion spring 640, illustrated in FIG. 6C, has a proximal end 641, a distal end 642, a superior end 643, an inferior end 644, and further comprises a head 645 and a strut connector knuckle 646. The head of the strut connector 645, according to some embodiments, comprises a proximal end 647, a distal end 648, a top surface 649, a bottom surface 650, a first distal-facing surface 651, a second distal-facing surface 652, a third distal-facing surface 655, and a proximal-facing surface 653 and is positioned along the longitudinal axis X of the hinge with torsion spring. The first distal-facing surface 651 may comprise a locking-screw mechanism 654, which may be a partial bore extending from the distal end of the head 648 towards the proximal end of the head 647. The second distal-facing surface 652 and the third distal-facing surface 655 may each comprise a respective strut aperture 656, which may be a partial bore extending from the distal end of the distal end of the head 648 towards the proximal end of the head 647. The proximal-facing surface of the head 653 of FIG. 6C comprises a top edge 657 and a bottom edge 658 and is positioned parallel to the transverse axis Z of the hinge with torsion spring in a manner such that the top edge 657 is in contact with the top surface of the head 649 and the bottom edge 658 is in contact with the bottom surface of the head 650. In some embodiments, the proximal-facing surface of the head 653 may comprise the proximal end of the head 647.

Figure 6D:
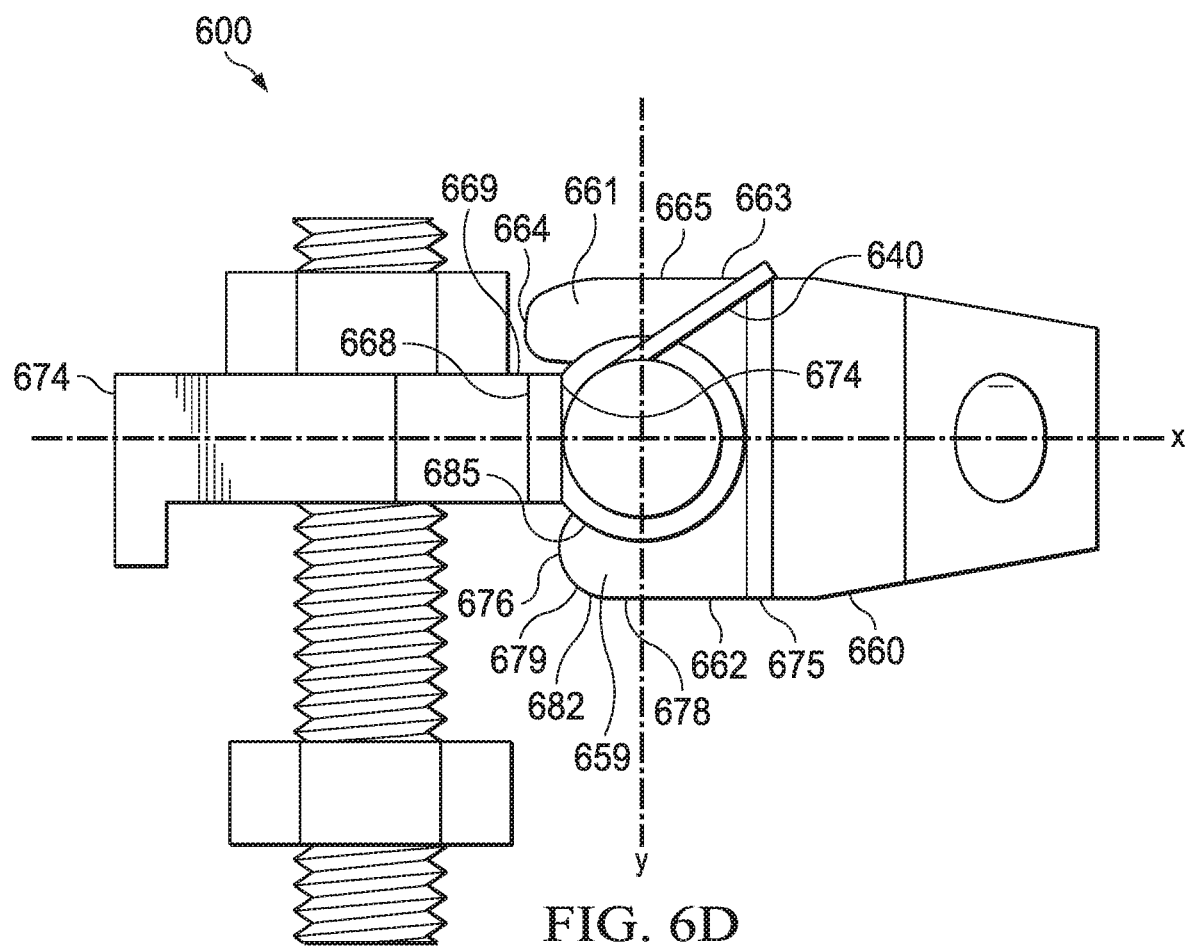
FIG. 6D illustrates an side view of an embodiment of a hinge with torsion spring in a dynamization tab.

Referring now to FIG. 6D, the strut connector knuckle 646 has a proximal end 659, a distal end 660 and is positioned along the longitudinal axis of the hinge with torsion spring 600 in a manner such that the distal end 660 is in contact with the proximal end of the head 647. In some embodiments, the strut connector knuckle 646 may further comprise a first arm 661 and a second arm 662. The first arm 661 has a distal end 663 and a proximal end 664 and is positioned parallel to the longitudinal axis X of the hinge with torsion spring in a manner such that the distal end 663 is in contact with the proximal end of the head 647. The first arm 661 may further comprise a top surface 665 with a curved proximal end 669 and a motion-limiting face 668. The motion-limiting face of the first arm 668 may have a superior edge 673 and an inferior edge 674 and may be positioned such that the superior edge 673 is in contact with the curved proximal end of the first arm 669. The second arm of the strut connector knuckle 662 may have a distal end 675 and a proximal end 676 and be positioned inferior to the first arm 661 and parallel to the longitudinal axis X of the hinge with torsion spring 600 in a manner such that the distal end 675 is in contact with the proximal end of the head 647. In the embodiment of FIG. 6D, the second arm 662 further comprises a bottom surface 678 with a curved proximal end 682 and a motion limiting face 679. The motion-limiting face 679 has a an inferior edge 685 and is positioned such that the inferior edge 685 is in contact with the curved proximal end of the bottom surface 682.

In the embodiment of FIG. 6E, the biasing mechanism of the hinge with torsion spring 690 is positioned along the transverse axis Z of the hinge with torsion spring and comprises a pin 691 and a torsion spring 692. Further, the biasing mechanism 690 is positioned such that it passes through the first arm bore of the ring connector knuckle 620 and the second arm bore of the ring connector knuckle 633; and between the first arm of the strut connector knuckle 661 and the second arm of the strut connector knuckle 662, in a manner such that it allows for the pivoting of the strut connector 640 about the transverse axis Z of the hinge with torsion spring 600. In some embodiments, the pivoting of the strut connector 640 may be limited in degree by contact between (a) the motion-limiting face of the strut connector knuckle first arm 668 and the top surface of the ring connector first stabilizer 614, and (b) the motion-limiting face of the strut connector knuckle second arm 679 and the top surface of the ring connector first stabilizer 614. Further, the torsion spring of the biasing mechanism 692 may be configured to apply a biasing force when the strut connector 640 is displaced along the longitudinal axis Y of the hinge with torsion spring 600, returning the strut connector 640 to its original position.

Another embodiment, the large radius hinge dynamization tab (large radius hinge), provides that dynamization occurs as the strut connector moves along a radial track between the strut connector and the ring connector. In this embodiment, the range of motion, i.e. degree of oscillation under loading, is limited by two elastic members or "stops," placed at the opposing ends of the radial track. The stops allow for dynamization by being flexible enough to allow the strut connector to move along the track, but also provide the biasing force necessary to return the strut connector to its resting position. The degree of oscillation, and therefore dynamization, may be adjusted by placing the stops either (1) further apart, or (2) closer together, as appropriate.

Figure 7A:
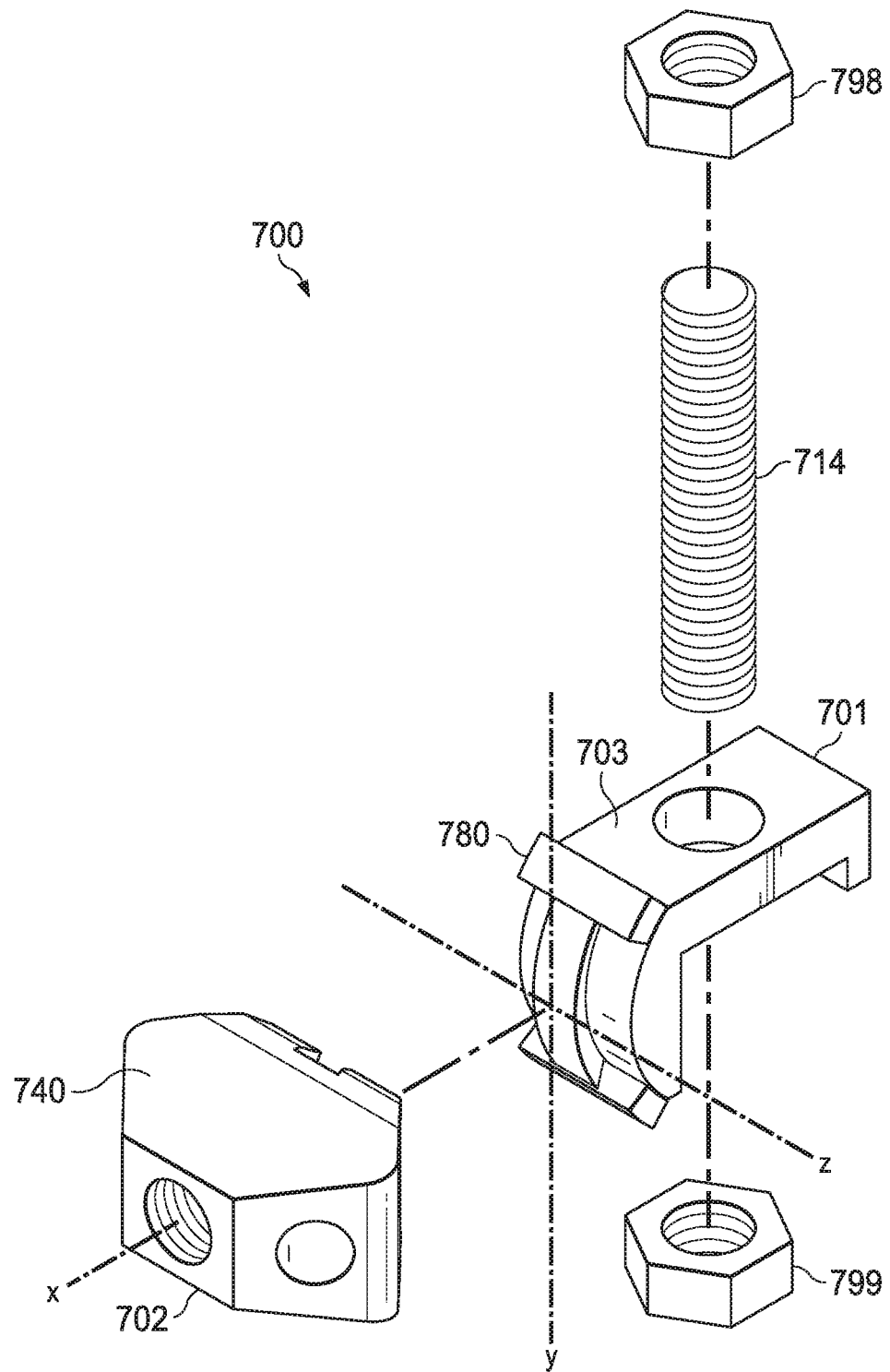
FIG. 7A illustrates an exploded perspective view of an embodiment of a large radius hinge in a dynamization tab.

FIG. 7A is an exploded perspective view of an embodiment of a large radius hinge 700 of the present disclosure. The large radius hinge 700 has a longitudinal axis X, a vertical axis Y, and a transverse axis Z defined therein and comprises a proximal end 701, a distal end 702, a ring connector 703, a strut connector 740, and a biasing mechanism 780. Further, according to some embodiments, the large radius hinge 700 may comprise a connecting bolt 714, a first connecting nut 798, and a second connecting nut 799. In these embodiments, the connecting bolt 714, first connecting nut 798, and second connecting nut 799, are configured to secure the large radius hinge 700 to an external fixation ring, discussed above.

Figure 7B:
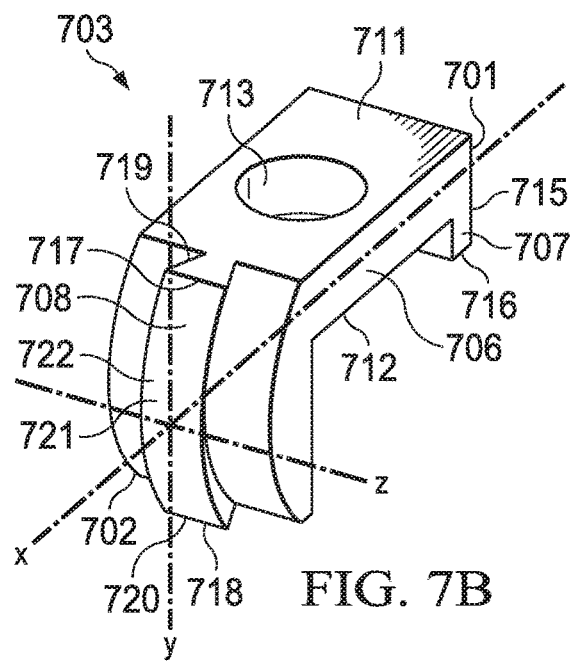
FIG. 7B illustrates a perspective view of a ring connector of a large radius hinge in a dynamization tab.

Illustrated in FIG. 7B, the ring connector 703 of the large radius hinge 700 may have a proximal end 701 and a distal end 702 and be further comprised of a first stabilizer 706, a second stabilizer 707, and a ring connector knuckle 708. The first stabilizer 706 is positioned parallel to the longitudinal axis X of the large radius hinge 700 and comprises a top surface 711, a bottom surface 712, and a first stabilizer bore 713. The first stabilizer bore 713, according to some embodiments, may extend parallel to the vertical axis Y of the large radius hinge 700 from the top surface of the first stabilizer 711 to the bottom surface of the first stabilizer 712. Further, the first stabilizer bore 713 may be configured to accept the connecting bolt 714. The second stabilizer 707 of FIG. 7B comprises a superior end 715 and an inferior end 716 and is positioned parallel to the vertical axis Y of the large radius hinge 700 in a manner such that the superior end 715 is in contact with the proximal end of the first stabilizer 709. The ring connector knuckle 708, according to some embodiments, may have a superior end 717 and an inferior end 718 and be positioned parallel to the vertical axis Y of the large radius hinge 700 in such a manner that the superior end 717 is in contact with the distal end of the first stabilizer 710. The ring connector knuckle 708 may further comprise a top edge 719, a bottom edge 720, and a distal-facing surface 721. In some embodiments, the distal-facing surface of the ring connector knuckle 721 may be convexly shaped with respect to the vertical axis Y of the large radius hinge 700 and may further comprise a radial track donor 722. The radial track donor 722, as illustrated in FIG. 7B, may be positioned such that it is perpendicular to the transverse axis Z of the large radius hinge 700.

Figure 7C:
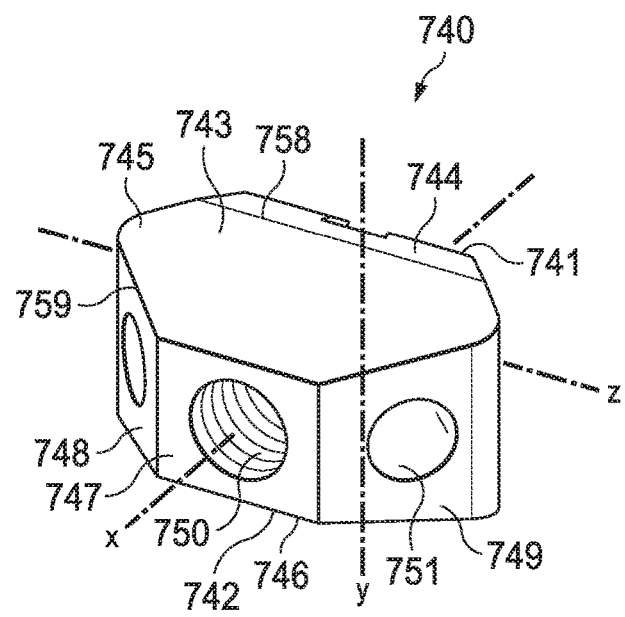
FIG. 7C illustrates a perspective view of a strut connector of a large radius hinge in a dynamization tab.

Referring now to FIG. 7C, the strut connector 740 may have a proximal end 741 and a distal end 742 and be positioned along the longitudinal axis X of the large radius hinge 700 in such a manner that the proximal end of the strut connector 741 is in contact with the distal end of the ring connector 705 of FIG. 7B. The strut connector 740 may further comprise a head 743 and a strut connector knuckle 744. The head 743 may have a proximal end 758 and a distal end 759, be positioned along the longitudinal axis X of the large radius hinge 700, and further comprise a top surface 745, a bottom surface 746, a first distal-facing surface 747, a second distal-facing surface 748, and a third distal-facing surface 749. The first distal-facing surface 747 may include a locking screw aperture 750, the locking-screw aperture 750 being a partial bore that extends from the distal end of the head 759 toward the proximal end of the head 758 and being configured to accept a locking screw. Each of the second distal-facing surface 748 and the third distal-facing surface 749 may include a respective strut aperture 751, the strut aperture 751 being a partial bore that extends from the distal end of the head 759 toward the proximal end of the head 758 and each being configured to connect the strut connector 740 to a strut.

Figure 7D:
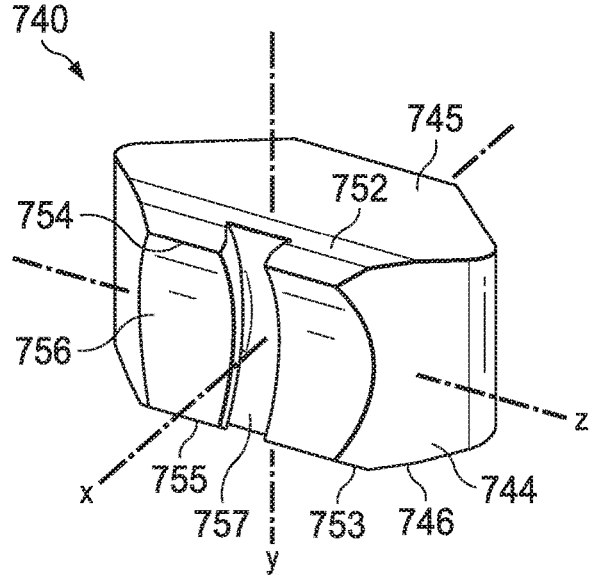
FIG. 7D illustrates another perspective view of a strut connector of a large radius hinge in a dynamization tab.

Illustrated in FIG. 7D, the strut connector knuckle 744, according to some embodiments, may include a superior end 752 and an inferior end 753 and be positioned parallel to the vertical axis Y of the large radius hinge 700 in a manner such that the superior end of the strut connector knuckle 752 is in contact with the top surface of the head 745 and the inferior end of the strut connector knuckle 753 is in contact with the bottom surface of the head 746. The strut connector knuckle 744 may further comprise a top edge 754, a bottom edge 755, and a proximal-facing surface 756. In some embodiments, the top edge of the strut connector knuckle 754 is in contact with the top surface of the head 745 and the bottom edge 755 is in contact with the bottom surface of the head 746. The proximal-facing surface 756 is positioned along the vertical axis Y of the large radius hinge 700 and may be concavely shaped with respect to the vertical axis Y. The proximal-facing surface 756 may further comprise a radial track acceptor 757, which may be positioned such that it is perpendicular to the transverse axis Z of the large radius hinge 700 and configured to accept the radial track donor 722 of FIG. 7B and to allow for the pivoting of the strut connector 740 about the transverse axis Z of the large radius hinge 700.

Figure 7E:
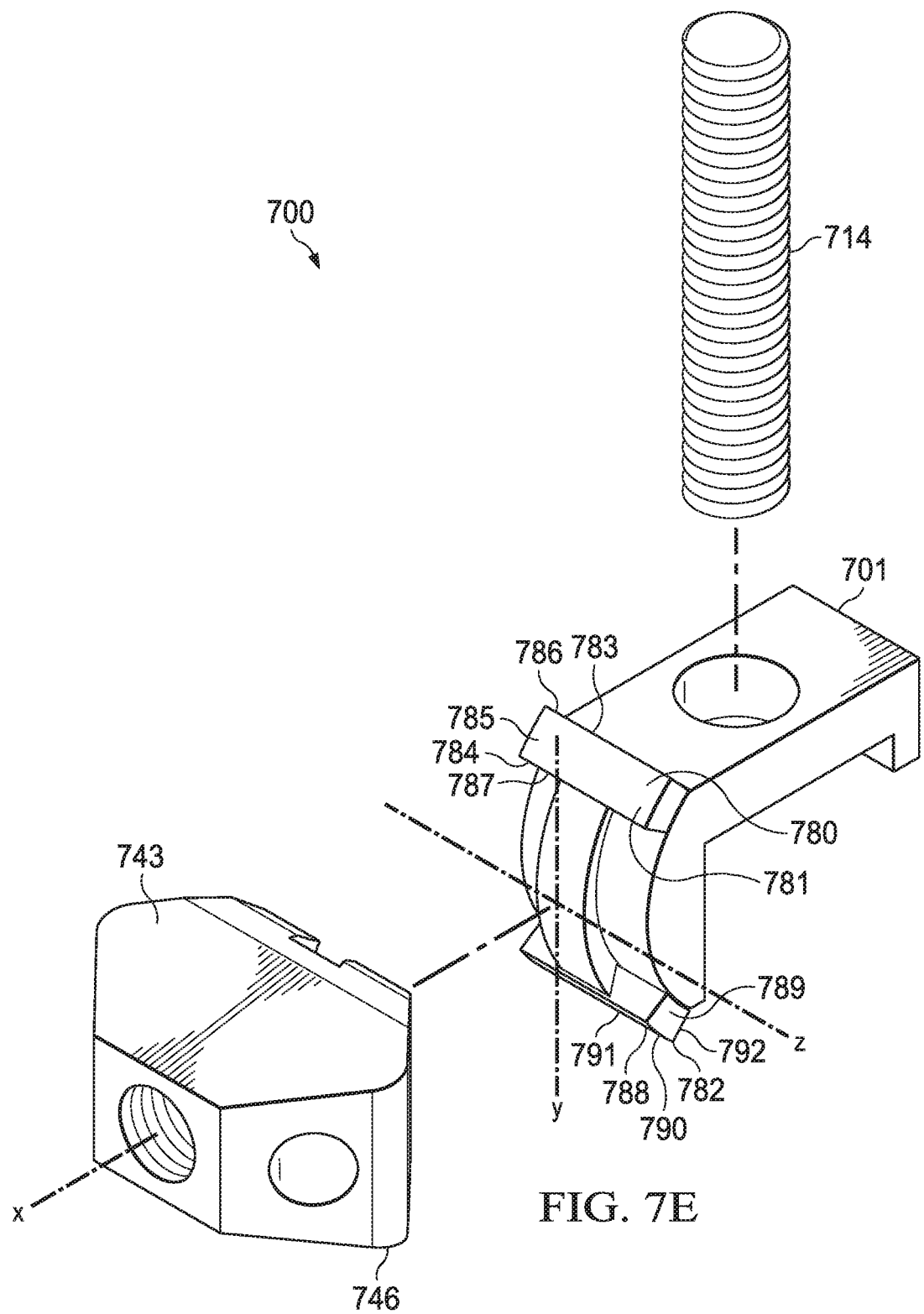
FIG. 7E illustrates another exploded perspective view of an embodiment of a large radius hinge in a dynamization tab.

In the embodiment of FIG. 7E, the biasing mechanism 780 of the large radius hinge 700 comprises a superior member 781 and an inferior member 782. Each of the superior member 781 and the inferior member 782 may be comprised of either an elastomeric material or a flexible plastic. The superior member 781 is positioned parallel to the transverse axis Z of the large radius hinge 700 and is further comprised of a top surface 783, a bottom surface 784, and a proximal-facing surface 785. The bottom surface of the superior member 784 may be positioned such that it is in contact with the top surface of the strut connector head 743 and in a manner such that it applies a biasing force when the strut connector 740 is displaced along the longitudinal axis Y of the large radius hinge 700. The proximal-facing surface of the superior member 785 comprises a top edge 786 and a bottom edge 787 and is positioned such that the top edge of the proximal-facing surface 786 is in contact with the top surface of the superior member 783 and the bottom edge of the proximal-facing surface 787 is in contact with the bottom surface of the superior member 784. In some embodiments, as the distance between the top edge of the proximal-facing surface 786 and the bottom edge of the proximal-facing surface 787 increases, the freedom of the strut connector 740 to pivot will be increasingly limited about the transverse axis Z of the large radius hinge 700. In the embodiment of FIG. 7E, the inferior member of the biasing mechanism 782 is positioned parallel to the transverse axis Z of the large radius hinge 700 and comprises a top surface 788, a bottom surface 789, and a proximal-facing surface 790. The top surface of the inferior member 788 is positioned such that it is in contact with the bottom surface of the strut connector head 746 and such that the inferior member 782 applies a biasing force when the strut connector 740 is displaced along the longitudinal axis Y of the large radius hinge 700. The proximal-facing surface of the inferior member 790 comprises a top edge 791 and a bottom edge 792 and is positioned such that the top edge of the proximal-facing surface 791 is in contact with the top surface of the inferior member 788 and the bottom edge of the proximal-facing surface 792 is in contact with the bottom surface of the inferior member 789. According to some embodiments, as the distance between the top edge of the proximal-facing surface 791 and the bottom edge of the proximal-facing surface 792 increases, the freedom of the strut connector 740 to pivot about the transverse axis Z of the large radius hinge 700 will be increasingly limited.

An alternative embodiment, the axial translation dynamization tab (axial translator), provides for dynamization in a single plane, i.e. up and down. The strut connector is allowed to move along a track between the strut connector and ring connector, providing oscillation under loading. Generally speaking, a biasing mechanism such as a spring or other elastic member is placed between the underside of the external fixation ring and a tab on the lower side of the strut connector which provides the biasing force necessary to return the strut connector to its resting position.

Figure 8A:
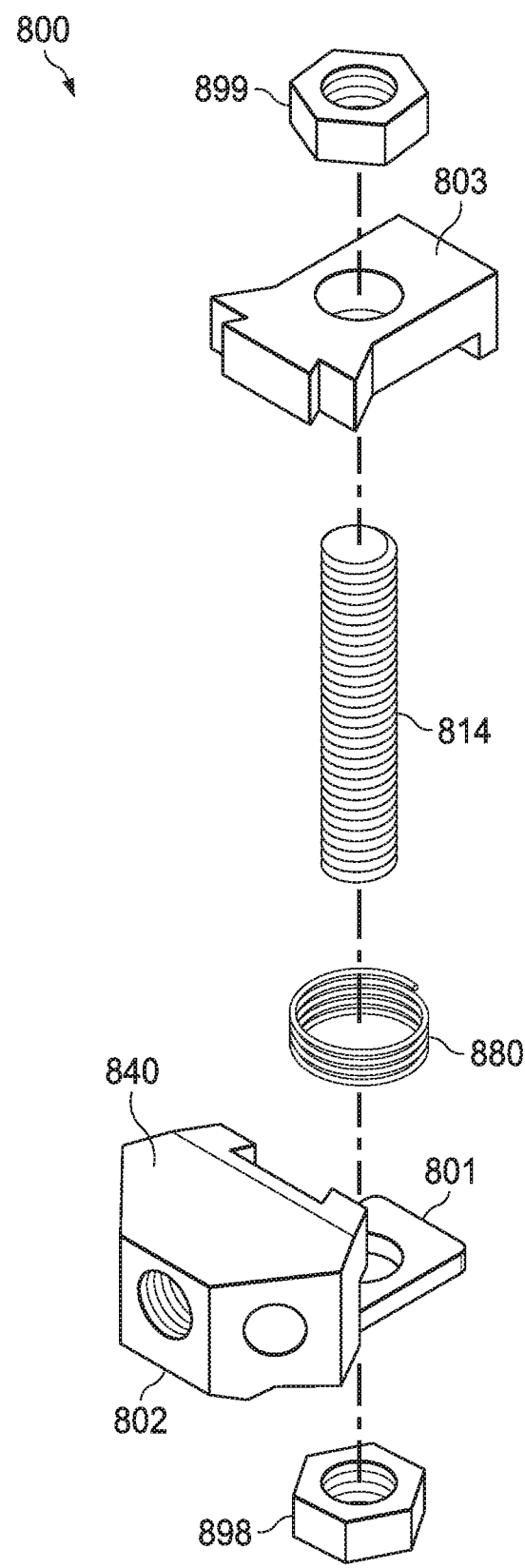
FIG. 8A illustrates an exploded perspective view of an embodiment of an axial translator in a dynamization tab.

FIG. 8A is an exploded perspective view of an embodiment of an axial translator 800 of the present disclosure. The axial translator 800 has a longitudinal axis X, a vertical axis Y, and a transverse axis Z defined therein and comprises a proximal end 801, a distal end 802, a ring connector 803, a strut connector 840, and a biasing mechanism 880. Further, according to some embodiments, the axial translator 800 may comprise a connecting bolt 814, a lower connecting nut 898, and an upper connecting nut 899. In these embodiments, the connecting bolt 814, lower connecting nut 898, and upper connecting nut 899 are configured to secure the axial translator 800 to an external fixation ring, as discussed above.

Figure 8B:
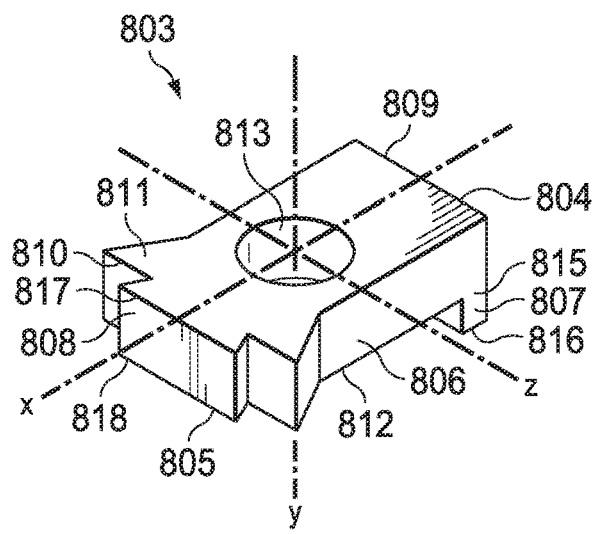
FIG. 8B illustrates a perspective view of a ring connector of an axial translator in a dynamization tab.

In the embodiment of FIG. 8B, the ring connector 803 comprises a proximal end 804, a distal end 805, a first stabilizer 806, a second stabilizer 807, and a dovetail notch 808. The first stabilizer 806 may have a proximal end 809 and a distal end 810 and be positioned parallel to the longitudinal axis X of the axial translator. Further, it may comprise a top surface 811, a bottom surface 812, and a first stabilizer bore 813 which extends along the vertical axis Y of the axial translator from the top surface of the first stabilizer 811 to the bottom surface of the first stabilizer 812. The first threaded bore 813 may be configured to accept the connecting bolt 814. The second stabilizer 807 may comprise a superior end 815 and an inferior end 816 and may be positioned parallel to the vertical axis Y of the axial translator in such a manner that the superior end 815 is in contact with the bottom surface of the first stabilizer 812. In some embodiments, the dovetail notch 808 comprises a superior end 817 and an inferior end 818 and is positioned parallel to the vertical axis Y of the axial translator in such a manner that the superior end 817 is in contact with the top surface of the first stabilizer 811 and the inferior end 818 is in contact with the bottom surface of the first stabilizer 812.

Figure 8C:
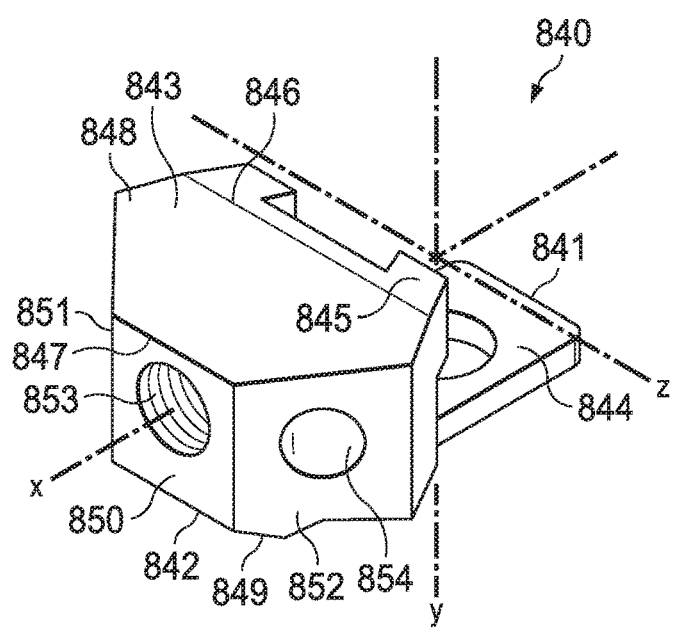
FIG. 8C illustrates a perspective view of a strut connector of an axial translator in a dynamization tab.

Referring now to FIG. 8C, the strut connector of the axial translator 840 may have a proximal end 841 and a distal end 842 and be positioned along the longitudinal axis X of the axial translator. In some embodiments, the strut connector 840 further comprises a head 843, a strut connector stabilizer 844, and a dovetail groove 845. The head of the strut connector 843 may comprise a proximal end 846, a distal end 847, a top surface 848, a bottom surface 849, a first distal-facing surface 850, a second distal-facing surface 851, and a third distal-facing surface 852. The first distal-facing surface of the head 850 may comprise a locking-screw aperture 853, which may be a partial bore that extends from the distal end of the head 847 towards the proximal end of the head 846 and be configured to accept a locking screw. Each of the second distal-facing surface 851 and the third distal-facing surface 852 may comprise a strut aperture 854, which may be a partial bore that extends from the distal end of the head 847 to the proximal end of the head 846 and be configured to secure the strut connector 840 to a strut.

Figure 8D:
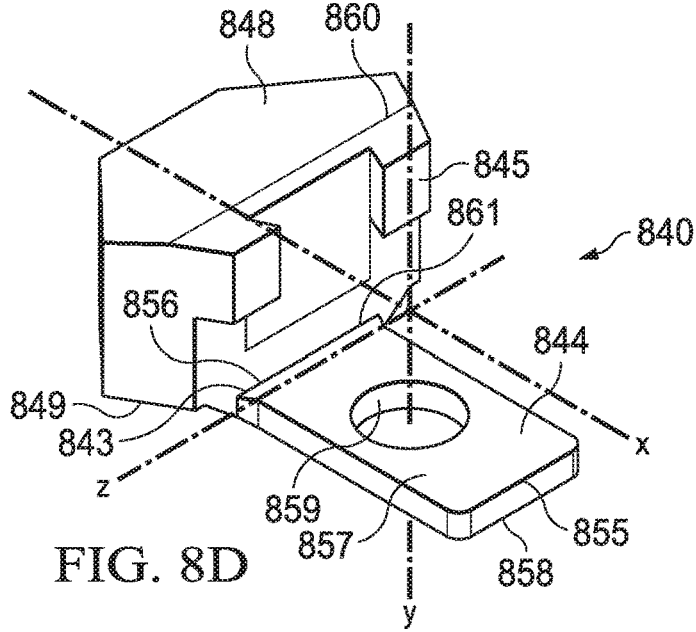
FIG. 8D illustrates another perspective view of a strut connector of an axial translator in a dynamization tab.

In the embodiment of FIG. 8D, the strut connector stabilizer 844 comprises a proximal end 855 and a distal end 856 and is positioned parallel to the longitudinal axis X of the axial translator in a manner such that the distal end 856 is in contact with the proximal end of the head 843. The strut connector stabilizer may further comprise a top surface 857, a bottom surface 858, and a strut connector stabilizer bore 859 which may extend along the vertical axis Y of the axial translator from the top surface of the strut connector stabilizer 857 to the bottom surface of the strut connector stabilizer 858 and be configured to accept the connecting bolt 814 of FIG. 8A. The dovetail groove 845 may comprise a superior end 860 and an inferior end 861 and be positioned parallel to the vertical axis Y of the axial translator in a manner such that the superior end 860 is in contact with the top surface of the head 848 and the inferior end 861 is in contact with the bottom surface of the head 849. The dovetail groove 845 may be configured to accept the dovetail notch 808 of FIG. 8B. The movement of the dovetail notch 808 of FIG. 8B within the dovetail groove 845 of FIG. 8D may allow for the strut connector 840 to be displaced parallel to the vertical axis Y of the axial translator.

Figure 8E:
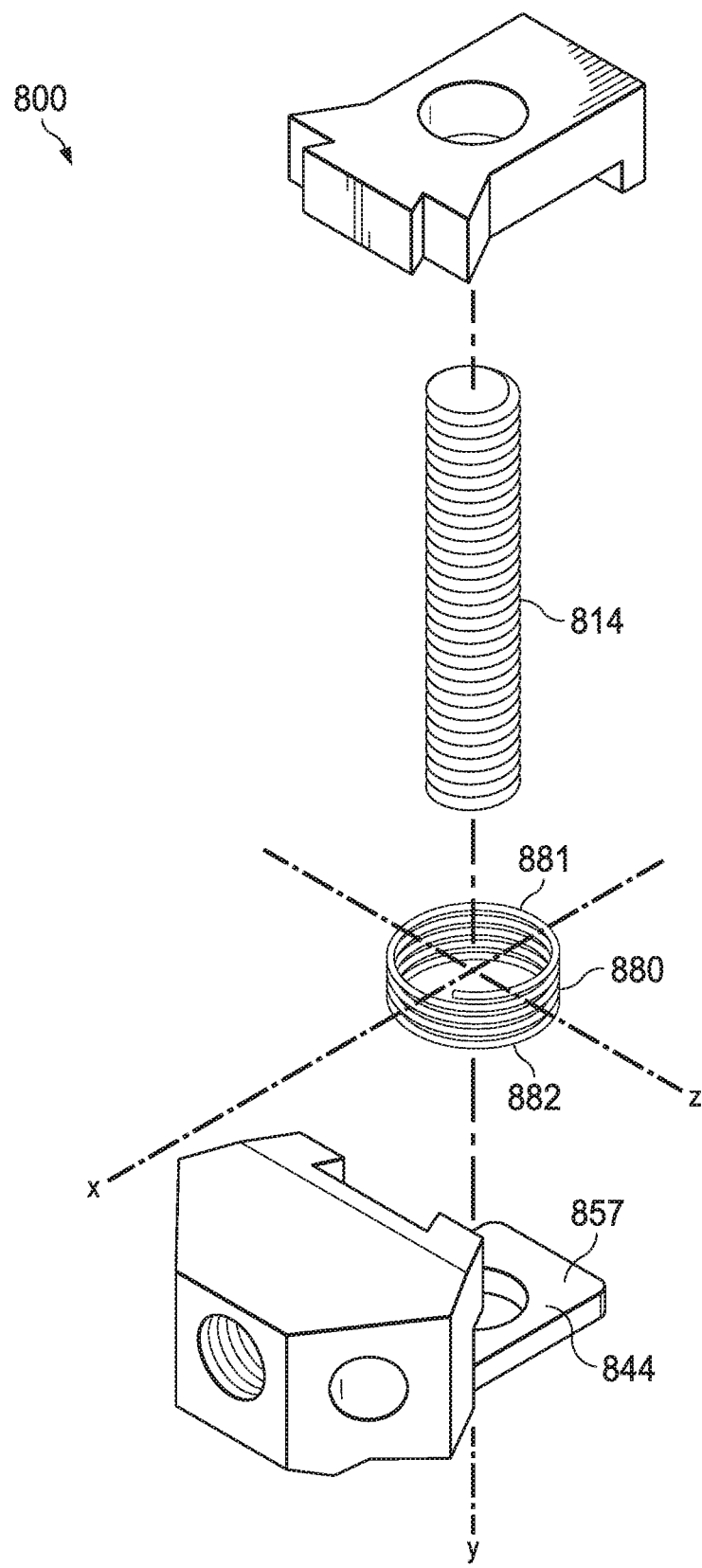
FIG. 8E illustrates another exploded perspective view of an embodiment of an axial translator in a dynamization tab.

Illustrated in FIG. 8E, the biasing mechanism 880 may comprise a superior end 881 and an inferior end 882 and be positioned superior to the strut connector stabilizer 844 in a manner such that the inferior end of the biasing mechanism 882 is in contact with the top surface of the strut connector stabilizer 857. Further, the superior end 881, according to some embodiments, may be in contact with a lower surface of the ring connector. The biasing mechanism may comprise a compression spring, a flexible plastic, an elastomeric material, or any other material which may apply a biasing force when the strut connector 840 is displaced along the longitudinal axis Y of the axial translator 800.

Figure 9A:
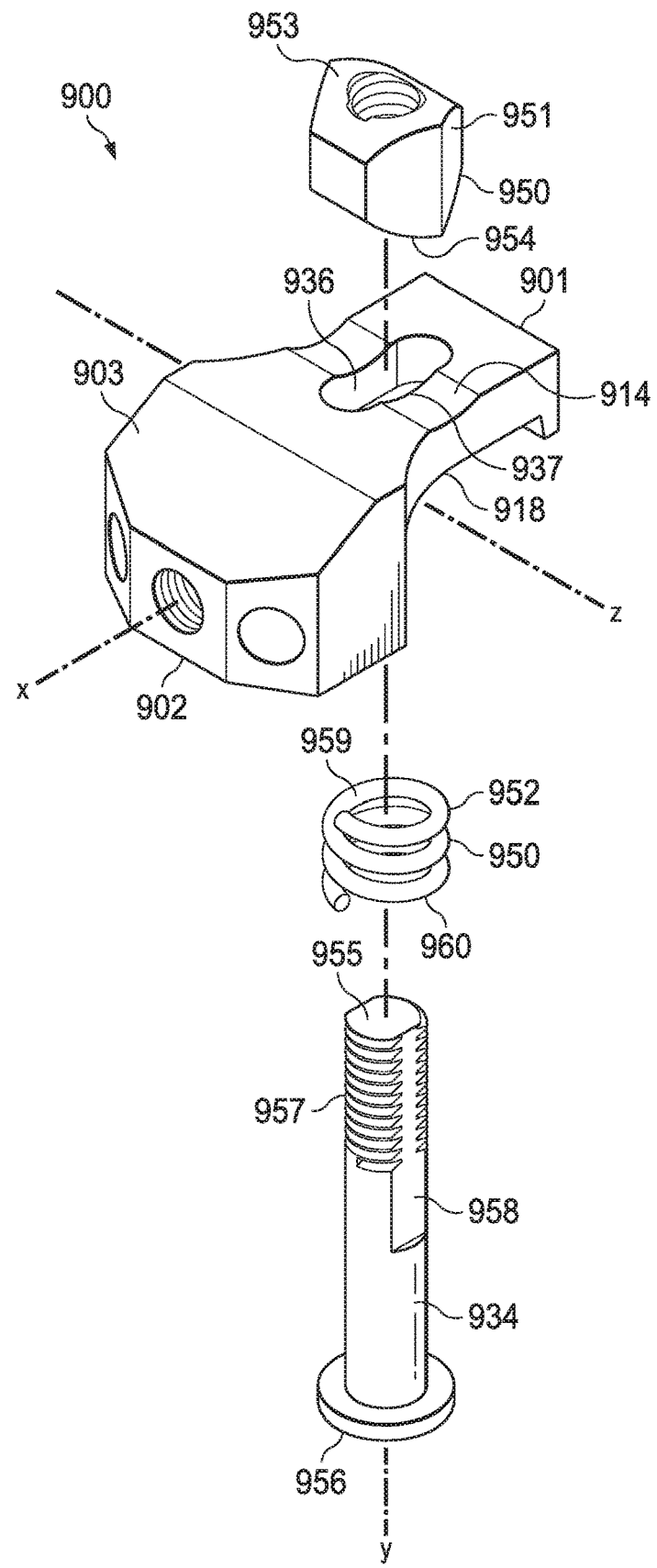
FIG. 9A illustrates an exploded perspective view of an alternative embodiment of a dynamization tab.

FIG. 9A is an exploded perspective view of an embodiment of an alternative dynamization tab 900 of the present disclosure. The embodiment depicted in FIG. 9A has a longitudinal axis X, a vertical axis Y, and a transverse axis Z defined therein and comprises a proximal end 901, a distal end 902, a connector 903, and a biasing mechanism 950. This embodiment allows for highly adjustable dynamization through the use of a rounded nut 951, screwed onto a connecting bolt 934 on the top of the tab 900, and sitting in a groove 914 for pivoting. In this embodiment, the back of the tab 900 may extend into the inner diameter of the external fixation ring to prevent tab rotation. Further, the nut 951 is adjustable to allow an increase or decrease in the range of motion (i.e., dynamization) allowed in the tab 900 during treatment.

Figure 9B:
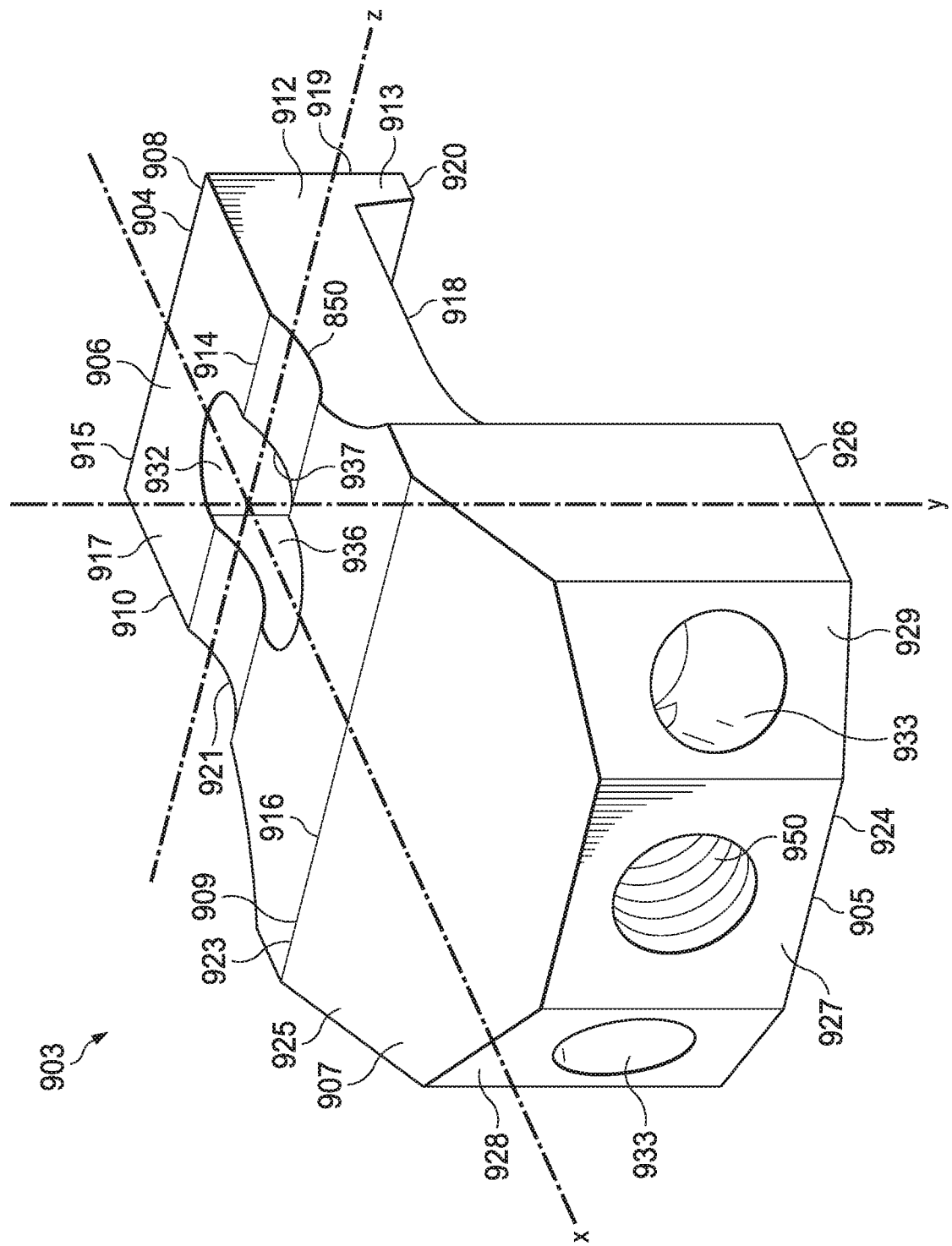
FIG. 9B illustrates a perspective view of a strut connector in an alternative embodiment of a dynamization tab.

A closer view of the connector component 903 of this embodiment is depicted in FIG. 9B. In FIG. 9B, the connector 903 has a proximal end 904 and a distal end 905 and comprises a ring connector 906, a head 907, and a connector bore 932. The ring connector 906 comprises a proximal end 904, a distal end 905, a first face 910, and a second face 911. The ring connector 906 may further comprise a first stabilizer 912, a second stabilizer 913, and a biasing groove 914. The first stabilizer 912 has a proximal end 915, a distal end 916, a top surface 917, and a bottom surface 918, and may be positioned parallel to the longitudinal axis X of the tab 900. The second stabilizer 913, according to some embodiments, has a superior end 919 and an inferior end 920 and is positioned parallel to the vertical axis Y of the tab 900 in a manner such that the superior end 919 is in contact with the proximal end of the first stabilizer 915. The biasing groove 914 of FIG. 9B comprises a first end 921 and a second end 922 and is concavely shaped with respect to the transverse axis Z of the bolt with spring. The biasing groove 914 may be positioned along the transverse axis Z of the tab 900 in such a manner that the first end 921 is in contact with the first face of the ring connector 910 and the second end 922 is in contact with the second face of the ring connector 911. In some embodiments, the biasing groove 914 bisects the ring connector 906 between the proximal end 908 and the distal end 909.

The head of the connector 907, as illustrated in FIG. 9B, comprises a proximal end 923, a distal end 924, a top surface 925, a bottom surface 926, a first distal-facing surface 927, a second distal-facing surface 928, and a third distal-facing surface 929. The first distal-facing surface may comprise a locking-screw mechanism 930, which may comprise a partial bore extending from the distal end of the head 924 towards the proximal end of the head 923 and be threaded to receive a locking screw. The second distal-facing surface 928 and the third distal-facing surface 929 may respectively comprise one or more strut apertures 933, which may each be a partial bore that extends from the distal end of the head 924 towards the proximal end of the head 923 and may be configured to secure the connector 903 to a strut. The connector bore 932, according to some embodiments, may extend along the vertical axis Y of the tab 900 from the top surface of the first stabilizer 917 to the bottom surface of the first stabilizer 918. The connector bore 932 of FIG. 9B may comprise a stadium shape, with a flat first face 936 and a flat second face 937 positioned between the first end of the biasing groove 921 and the second end of the biasing groove 922.

Referring now back to FIG. 9A, the biasing mechanism 950 further comprises a biasing nut 951, a connecting bolt 934, and a biasing spring 952. The biasing nut 951 comprises a superior end 953 and an inferior end 954 and is positioned along the vertical axis Y of the bolt with spring in a manner such that the inferior end 954 is in contact with the biasing groove 914. The inferior end of the biasing nut 954 may, in some embodiments, be convexly shaped with respect to the transverse axis of the bolt with spring 952 in a manner such that it allows for the pivoting of the connector 903 about the transverse axis Z of the bolt with spring 952. The convex face of the biasing nut 951 and the matching concave shape of the biasing groove 914 of the connector 903 also serve as a détente to prevent accidental rotation of the biasing nut during use of the dynamization tab 900. The connecting bolt 934 may have a superior end 955 and an inferior end 956 and be positioned along the vertical axis Y of the tab 900 in a manner such that the superior end 955 is in contact with the biasing nut 951. Further, the connecting bolt 934 may comprise an first planar face 957 and a second planar face 958, where each of the faces (957, 958) comprises a flat surface. The first face 957 of the connecting bolt 934 may be configured to be in contact with the first face 936 of the connector bore and the second face 958 of the connecting bolt 934 may be configured to be in contact with the second face 937 of the connector bore in a manner which allows for pivoting of the connector 903 about the transverse axis Z of the tab 900 while diminishing pivoting of the connector 903 about the vertical axis Y of the tab 900. The first and second faces (957, 958) on the connecting bolt 934 also serve to prevent the connecting bolt 934 from rotating within the connector 903 once the desired level of dynamization has been set. Undesirable rotation of the connecting bolt 934 could loosen connector 903 with respect to the fixation ring, thereby allowing increasing amounts of dynamization in the tab 900, which could be undesirable. The biasing spring 952, according to some embodiments, may comprise a superior end 959 and an inferior end 960 and be positioned along the vertical axis Y of the of the bolt with spring 900 in a manner such that the superior end 959 is in contact with the bottom surface of the ring connector first stabilizer 918. The biasing spring 952 may be configured to apply a biasing force when the connector 903 is displaced along the vertical axis Y of the tab 900.

Figure 9C:
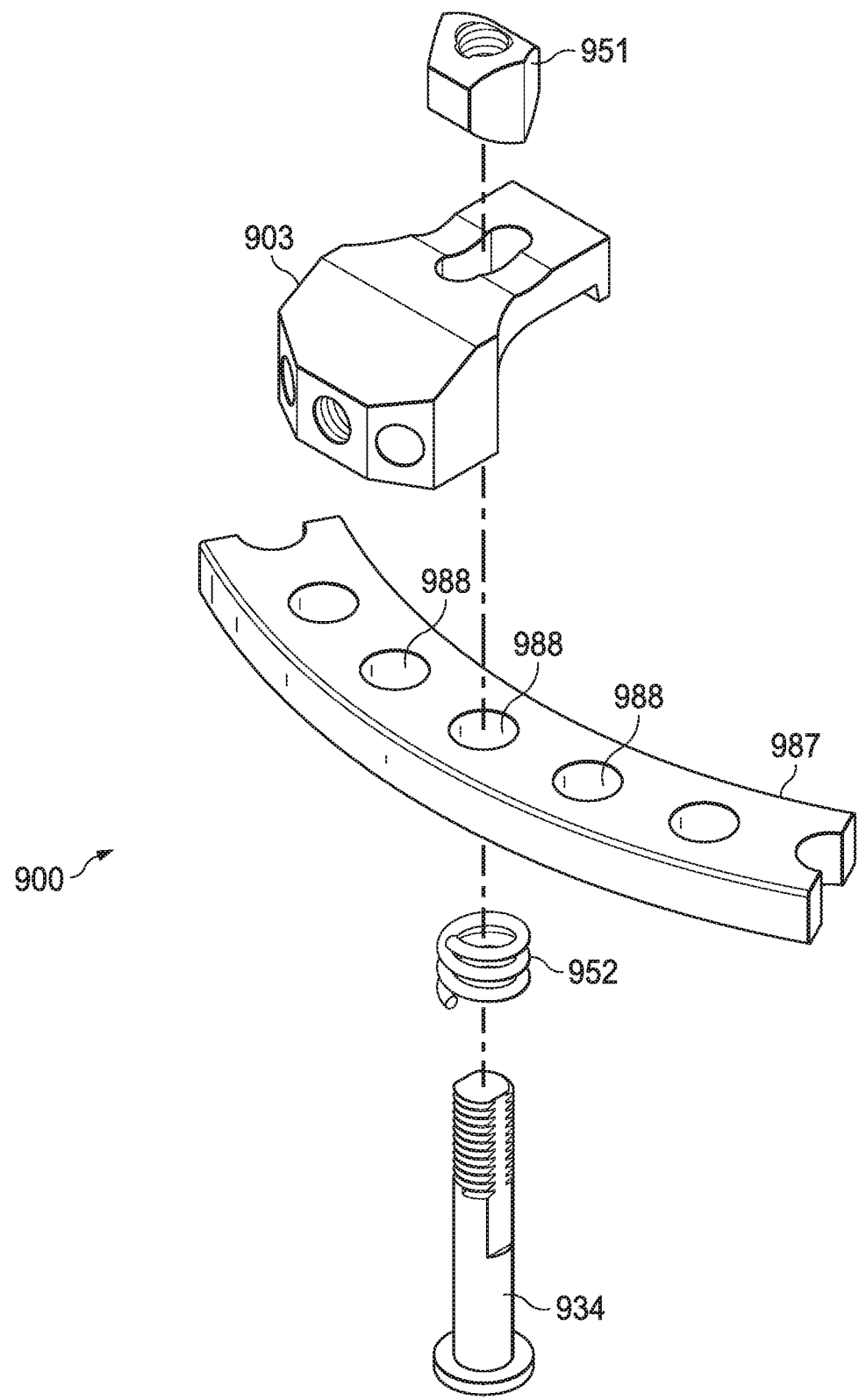
FIG. 9C illustrates another exploded perspective view of an alternative embodiment of a dynamization tab.

FIG. 9C is an exploded perspective view of an embodiment of an alternative dynamization tab 900 and how it can be connected to an external fixation ring 987. In FIG. 9C, the biasing spring 952 is placed underneath the external fixation ring 987 but aligned with the vertical axis Y of the device 900. As such, the connecting bolt 934 will pass through the biasing spring 952 before entering one of the holes (988) in the external fixation ring 987. According to one embodiment, the diameter of the holes 988 in the fixation ring 987 are larger than the diameter of the connecting bolt 934. This allows a small amount of play between connecting bolt 934 and the holes 988 in the external fixation ring 987, thus allowing the connecting bolt 934 to angulate slightly during the dynamization process. This reduces the mechanical stress and fatigue on the connecting bolt 934 during the dynamization process. The placement of the biasing spring 952 underneath the external fixation ring 987 provides an axial force along the axis of the connecting bolt 934, but still allows the connecting bolt 934 to angulate during dynamization. When the biasing nut 951 has been fully driven down against the connector component 903, the biasing spring 952 is fully compressed and yields zero dynamization. This embodiment allows for highly adjustable dynamization through the use of a rounded nut 951, screwed onto a connecting bolt 934 on the top of the tab 900, and sitting in a groove 914 for pivoting. In this embodiment, the back of the tab 900 may extend into the inner diameter of the external fixation ring 987 to prevent tab rotation. Further, the nut 951 is adjustable to allow an increase or decrease in the range of motion (i.e., dynamization) allowed in the tab 900 during treatment.

Figure 10A:
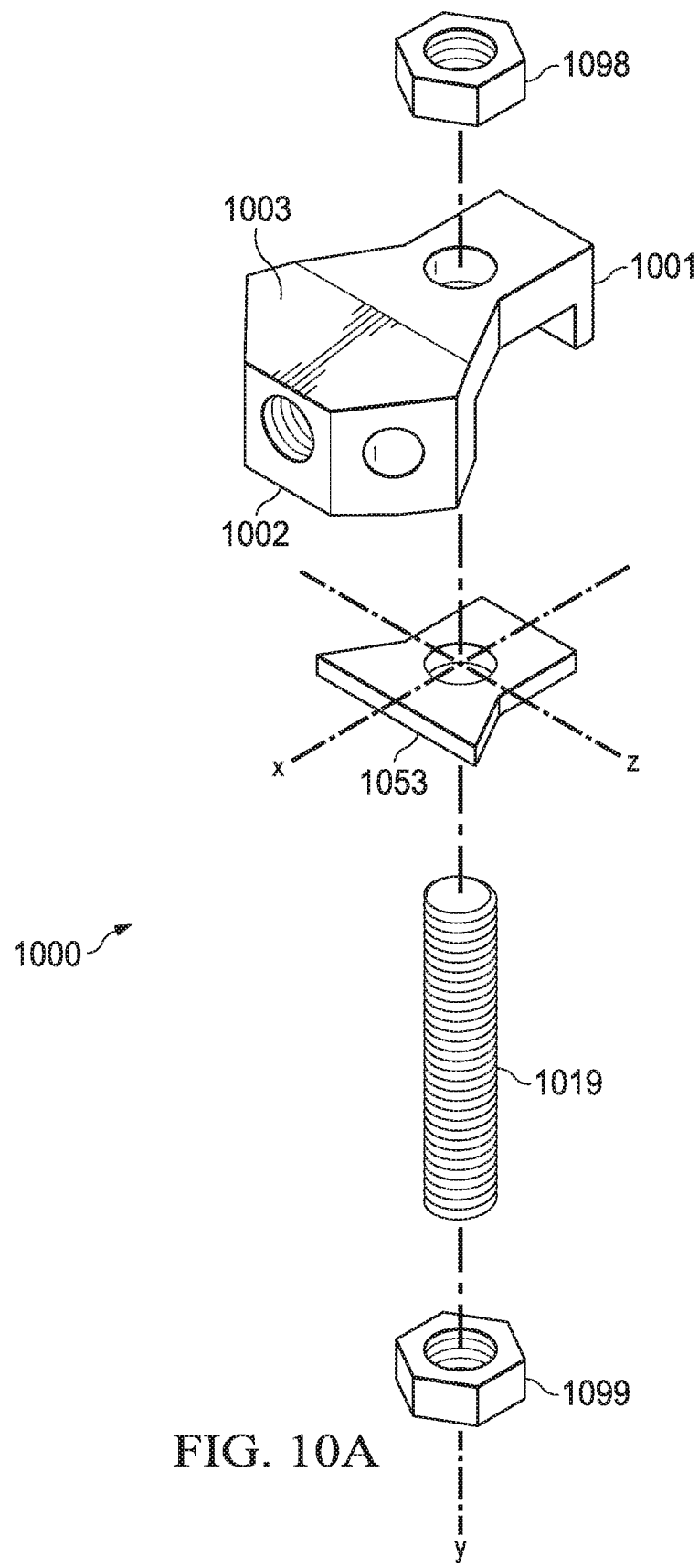
FIG. 10A illustrates an exploded perspective view of an embodiment of an alternative dynamization device.

FIG. 10A is an exploded perspective view of an embodiment of an alternative dynamization device 1000 of the present disclosure. In FIG. 10A, an elastic washer device provides for dynamization by placing an elastic washer or biasing mechanism 1050 between a dynamization tab 1003 and an external fixation ring to allow movement under loading. Further, the biasing mechanism 1050 may provide the necessary biasing force to return the tab 1003 to its resting position when displaced. In this embodiment, rotation of the tab 1003 may be prevented by moving the tab into the inner diameter of the ring. The biasing mechanism 1050 may be easily removed from the tab 1003 to eliminate dynamization from the device 1000. In FIG. 10A, the device 1000 has a longitudinal axis X, a vertical axis Y, and a transverse axis Z defined therein and comprises a proximal end 1001, a distal end 1002, a connector 1003 and a biasing mechanism 1053. Further, according to some embodiments, the device 1000 may comprise a connecting bolt 1019, a first connecting nut 1098, and a second connecting nut 1099. In these embodiments, the connecting bolt 1019, first connecting nut 1098, and second connecting nut 1099 are configured to secure the device 1000 to an external fixation ring, as discussed above.

Figure 10B:
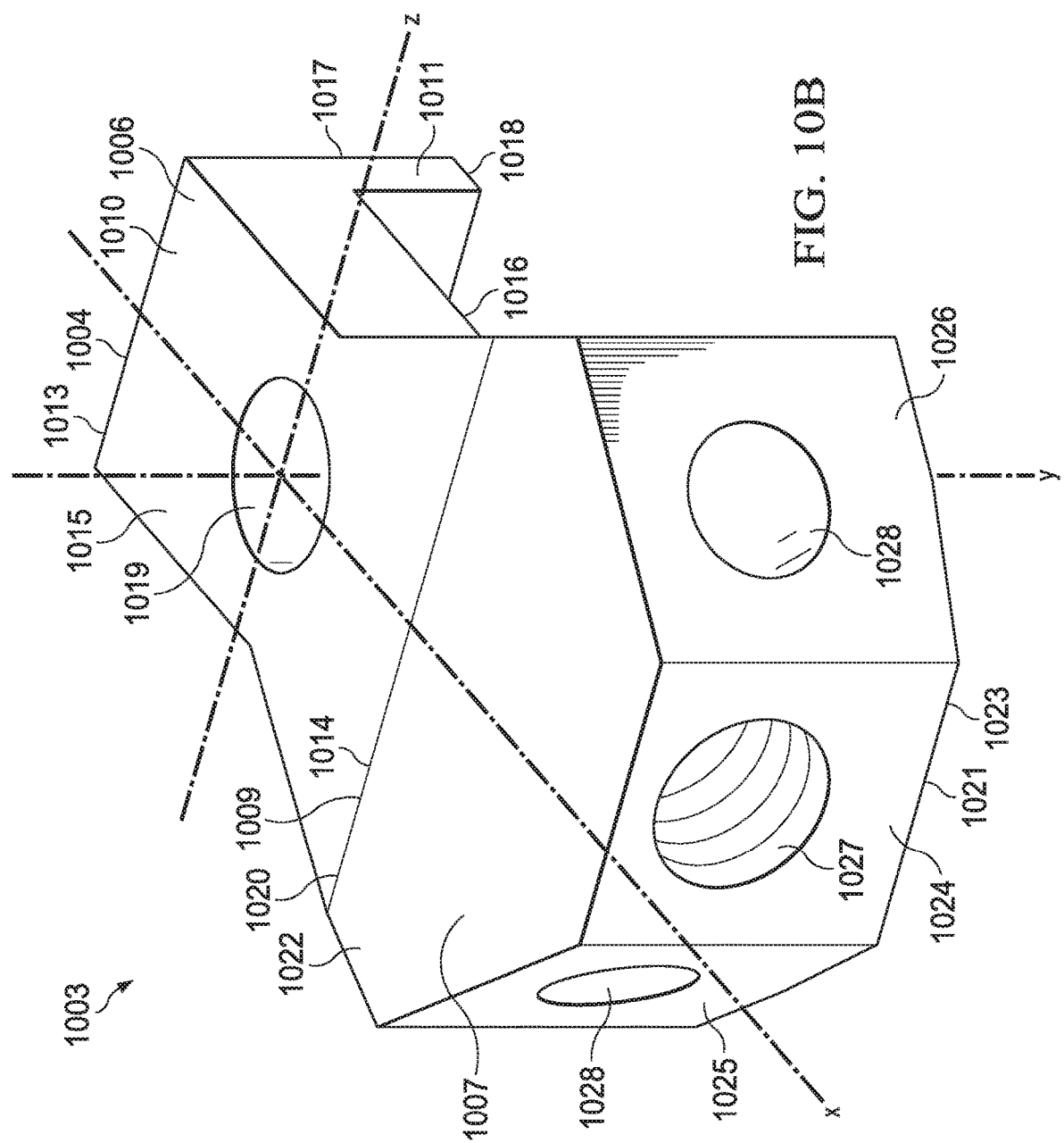
FIG. 10B illustrates a perspective view of a strut connector in an alternative dynamization device.

FIG. 10B illustrates an embodiment of a connector 1003. The connector may comprise a ring connector 1006 and a head 1007. The ring connector 1006 may have a proximal end 1004 and a distal end 1009 and may further comprise a first stabilizer 1010 having a proximal end 1013 and a distal end 1014, a second stabilizer 1011, and a connector bore 1019. The first stabilizer 1010 may further comprise a top surface 1015 and a bottom surface 1016. Further, the second stabilizer 1011, having a superior end 1017 and in inferior end 1018, may be positioned parallel to the vertical axis Y of the elastic washer 1000 in a manner such that the superior end 1017 is in contact with the proximal end of the first stabilizer 1013. The connector bore 1012, according to some embodiments, extends along the vertical axis Y of the elastic washer from the top surface of the first stabilizer 1015 to the bottom surface of the first stabilizer 1016 and may be configured to accept the connecting bolt, as shown in FIG. 10A. The connector 1003 may further comprise a head 1007 having a proximal end 1020 and a distal end 1021 and further comprising a top surface 1022, a bottom surface 1023, a first distal-facing surface 1024, a second distal-facing surface 1025, and a third distal facing surface 1026. The first distal-facing surface of the head 1024 may further comprise a locking screw aperture 1027 which may be a partial bore extending from the distal end of the head 1021 towards the proximal end of the head 1020. Each of the second distal-facing surface 1025 and the third distal-facing surface 1026 may additionally comprise a strut aperture 1028, each of which may be a partial bore extending from the distal end of the head 1021 towards the proximal end of the head 1020 and may be configured to secure the connector 1003 to a strut.

Figure 10C:
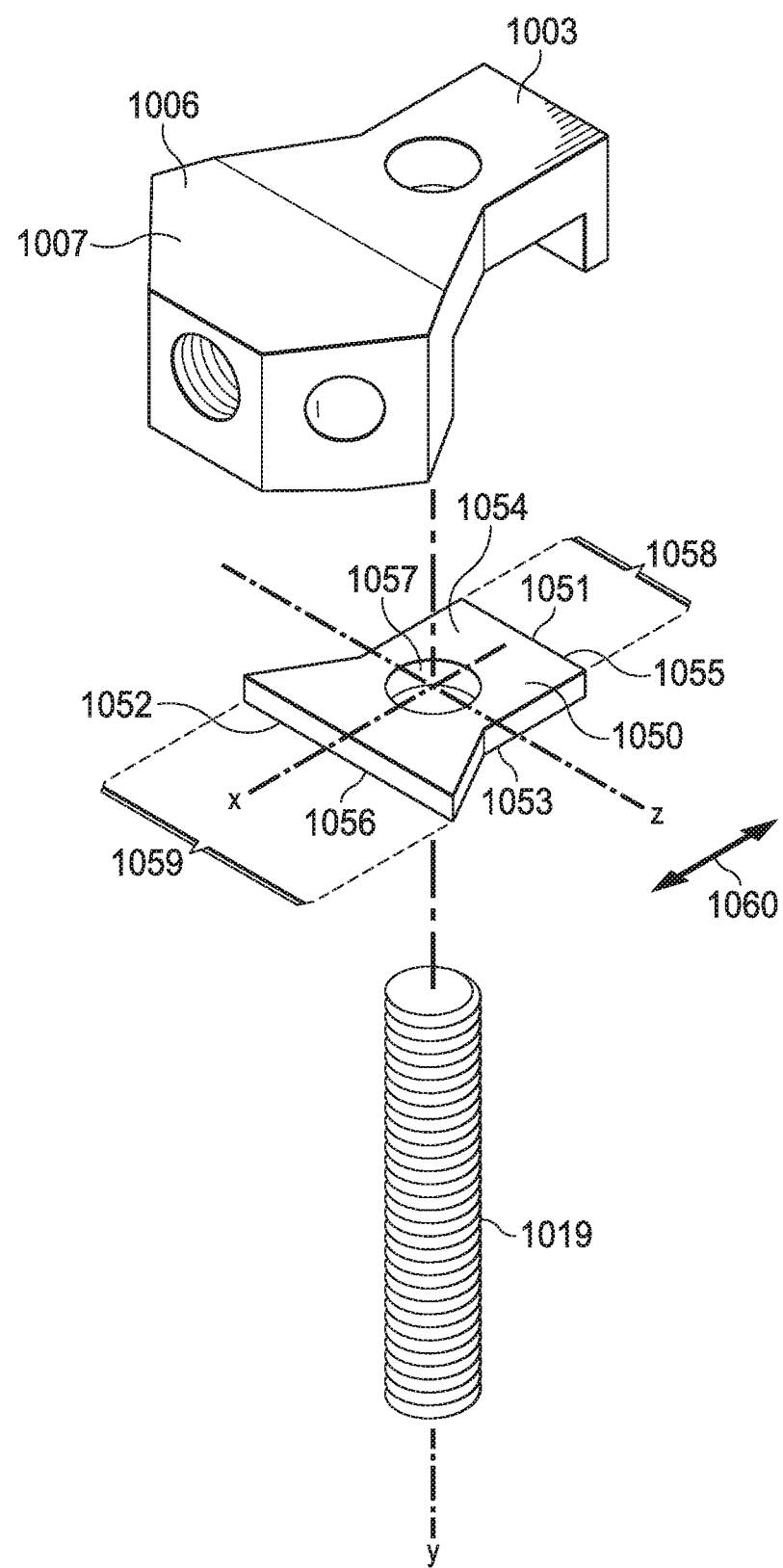
FIG. 10C illustrates another exploded perspective view of an alternative embodiment of a dynamization tab.

Illustrated in FIG. 10C, the biasing mechanism 1050 of the device 1000 has a proximal end 1051 and a distal end 1052 and may be comprised of a flexible plastic or other elastomeric material. The biasing mechanism 1050 may further comprise a bottom surface 1053, a top surface 1054, a proximal edge 1055, a distal edge 1056, and a biasing mechanism bore 1057. According to some embodiments, the top surface of the biasing mechanism 1054 may be configured to be in contact with the ring connector 1006 in a manner such that the biasing mechanism 1050 applies a biasing force when the head of the connector 1007 is displaced along the vertical axis Y of the device 1000. Further, each of the proximal edge 1055 and the distal edge 1056 of the biasing mechanism may be positioned parallel to the transverse axis Z of the elastic washer and may each comprise a length, where the length of the distal edge 1059 is greater than the length of the proximal edge 1058. In the embodiment of FIG. 10C, the biasing mechanism bore extends parallel to the vertical axis Y of the device 1000 from the top surface of the biasing mechanism 1054 to the bottom surface of the biasing mechanism 1053 and may be configured to accept the connecting bolt 1019. Further, according to some embodiments, the biasing mechanism bore 1057 may be further configured to allow the biasing mechanism 1050 to be longitudinally displaced (at displacement action 1060) along the longitudinal axis X of the device 1000 in a proximal and/or distal manner. When displacement 1060 is in the proximal direction, the displacement 1060 may restrict the ability of the connector 1008 to rotate about the transverse axis Z of the dynamization tab 1000.

As an alternative, a spring can be used (rather than the elastic washer 1053 as shown in FIG. 10A). This allows the biasing force and deflection distance (deflection angle) to be regulated by the nut 1098 placed on the superior side of the device 1000. Dynamization of the device 1000 can be eliminated by pre-compressing the spring by driving the nut 1098 against the superior side of the device 1000. The spring embodiment of the device 1000 provides more versatility in that it can be easily regulated or locked without having to disassemble and remove components.

Figure 11A:
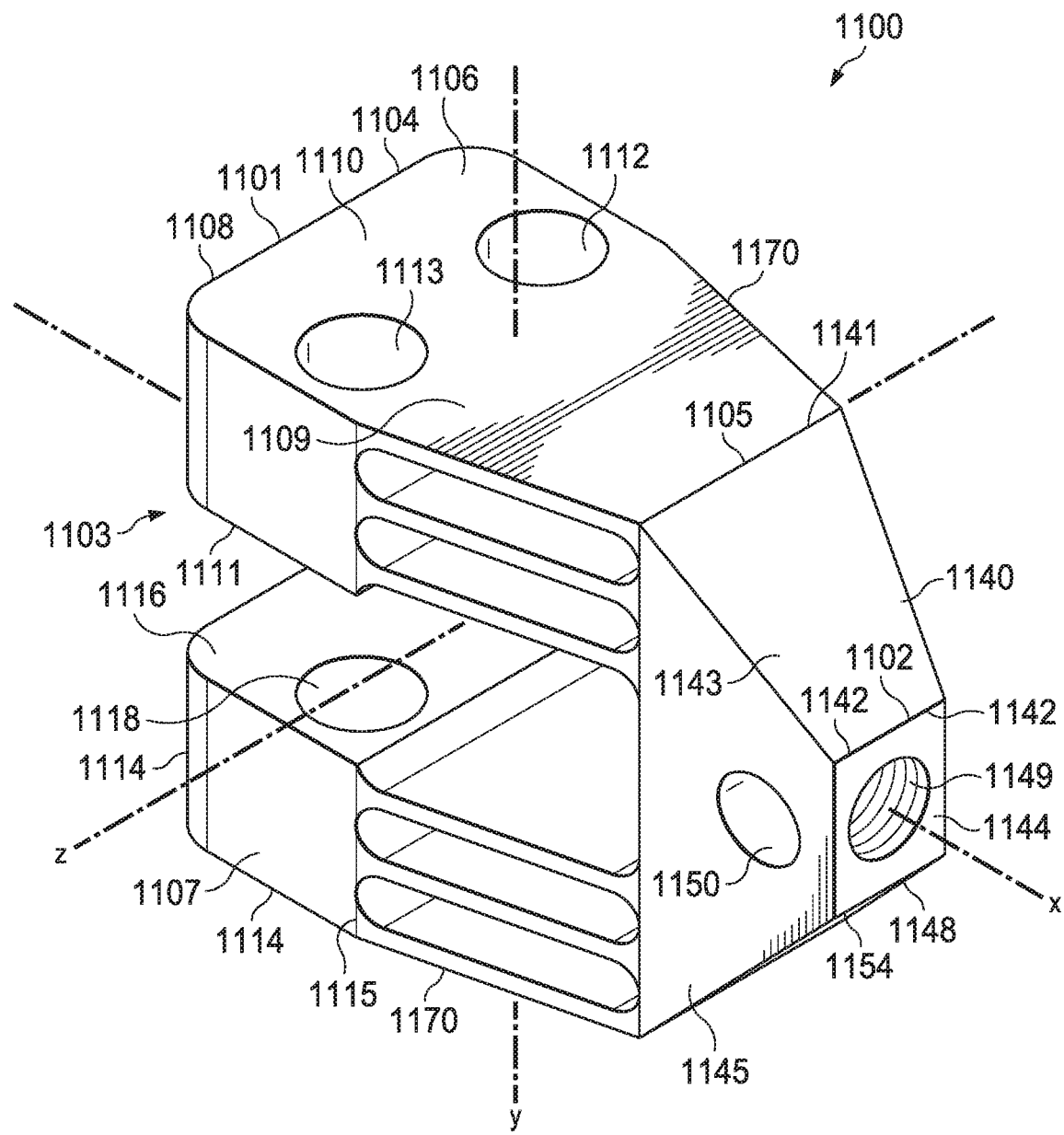
FIG. 11A illustrates a perspective view of an alternative embodiment of a dynamization tab.

An alternative embodiment of a dynamization tab 1100 is depicted in FIG. 11A. In FIG. 11A, the spring dynamization tab (spring tab), provides dynamization through a plate-shaped geometry which allows for dynamization under loading. In this embodiment, the tab itself is spring-shaped, allowing for the tab 1100 to deform under loading, while still providing the necessary biasing force to return the tab to its original shape. Further, the tab is secured to an external fixation ring with two connecting bolts to prevent unwanted rotation. In FIG. 11A, the spring tab 1100 has a longitudinal axis X, a vertical axis Y, and a transverse axis Z defined therein and comprises a proximal end 1101, a distal end 1102, a ring connector 1103, a strut connector 1140, and a biasing mechanism 1170. Further, according to some embodiments, the spring tab 1100 may comprise one or more connecting bolts (not shown), as well as first and second connecting nuts (not shown) to secure the spring tab 1100 to an external fixation ring, as discussed above.

According to some embodiments, the ring connector 1103 of the spring tab 1100 has a proximal end 1108 and a distal end 1109 and is positioned parallel to the longitudinal axis X of the spring tab 1100. The ring connector 1103 may further comprise a first stabilizer 1106 and a second stabilizer 1107. The first stabilizer of the ring connector 1106 has a proximal end 1108 and a distal end 1109 and is positioned superior to the longitudinal axis X of the spring tab 1100. It may further comprise a top surface 1110, a bottom surface 1111, a first connector bore 1112, and a second connector bore 1113. Each of the first and second connector bores (1112,1113) may extend from the top surface of the first stabilizer 1110 to the bottom surface of the first stabilizer 1111 and may be configured to accept a connecting bolt (not shown). The second stabilizer of the ring connector 1107, according to some embodiments, has a proximal end 1114 and a distal end 1109 and is positioned parallel and inferior to the longitudinal axis X of the spring tab 1100. The second stabilizer 1107 may further comprise a top surface 1116, a bottom surface 1117, a first connector bore 1118, and a second connector bore (not shown). Each of the first connector bore 1118 and the second connector bore (not shown) may extend from the top surface of the second stabilizer 1116 to the bottom surface of the second stabilizer 1117 and be configured to accept a connecting bolt (not shown).

Figure 11B:
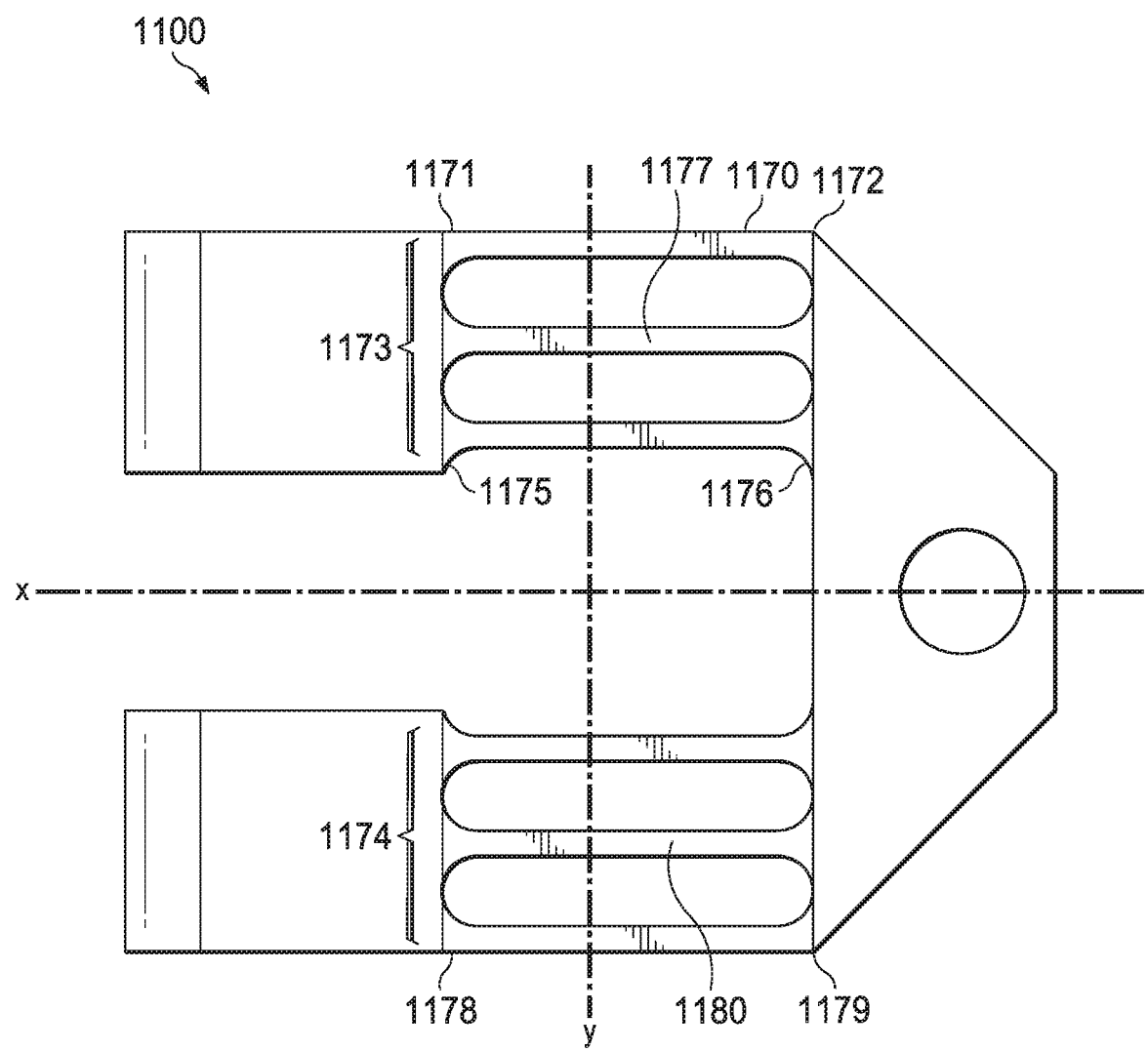
FIG. 11B illustrates a side view of alternative embodiment of a dynamization tab.

A side view of the spring tab 1100 is depicted in FIG. 11B. In FIG. 11B, the biasing mechanism 1170 of the spring tab 1100 has a proximal end 1171 and a distal end 1172 and is positioned along the longitudinal axis X of the spring tab 1100 in a manner such that the proximal end 1171 is in contact with the distal end of the ring connector 1105 and the distal end 1172 is in contact with the proximal end of the strut connector 1141. The biasing mechanism 1170 may further comprise a first biasing region 1173 and a second biasing region 1174. According to some embodiments, the first biasing region 1173 has a proximal end 1171 and a distal end 1172 and is positioned parallel and superior to the longitudinal axis X of the spring tab 1100 such that the proximal end 1171 is in contact with the ring connector 1103 and the distal end 1176 is in contact with the strut connector 1140. The first biasing region 1173 may comprise one or more biasing plates 1177, which may be comprised of a flexible plastic or other elastomeric material and, where there are more than one biasing plates 1177, may be positioned parallel to one another in a manner which is parallel to the longitudinal axis of the spring tab 1100 and provides space between each of the biasing plates 1177. The first biasing region 1173 may be configured such that it applies a biasing force when the strut connector 1140 is displaced along the vertical axis Y of the spring tab 1100. The second biasing region 1174 may have a proximal end 1178 and a distal end 1179 and be positioned parallel and inferior to the longitudinal axis X of the spring tab 1100 such that the proximal end 1178 is in contact with the ring connector 1103 and the distal end 1179 is in contact with the strut connector 1140. The second biasing region 1174 may comprise one or more biasing plates 1180, which may be comprised of a flexible plastic or other elastomeric material and, where there are more than one biasing plates 1180, may be positioned parallel to one another in a manner which is parallel to the longitudinal axis of the spring tab 1100 and provides space between each of the biasing plates 1180. The second biasing region 1174 may be configured such that it applies a biasing force when the strut connector 1140 is displaced along the vertical axis Y of the spring tab 1100.

The biasing regions, or even the entire tab, may be comprised of a material having appropriate elasticity and shape memory, such material can be selected from plastic, polymer, thermoplastic, metal, metal alloy, composite, resin, ultra-high-molecular-weight polyethylene (UHMW), a polytetrafluroethylene (PTFE), ABS plastic, PLA, polyamide, glass filled polyamide, epoxy, nylon, rayon, polyester, polyacrylate, wood, bamboo, bronze, titanium, steel, stainless steel, a cobalt chromium alloy, ceramic, wax, photopolymer, and polycarbonate. In certain non-limiting examples the polymer can be a thermoplastic polymer, a polyolefin, a polyester, a polysilicone, a polyacrylonitrile resin, a polystyrene, polyvinyl chloride, polyvinylidene chloride, polyvinyl acetate, a fluoroplastic, a phenolic resin, a urea resin, a melamine, an epoxy, a polyurethane, a polyamide, a polyacrylate resin, a polyketone, a polyimide, a polysulfone, a polycarbonate, a polyacetal, poly(hydroxynapthoic acid), a conductive polymer, a poly(3-hexylthiophene), a polyphenylene-vinylene, a poly(phenylene vinylene), a polyaniline, or combinations thereof. Other appropriate and biocompatible materials can be utilized. According to another embodiment, the biasing region or dynamization device can be fabricated by an additive printing process (e.g., a 3D printing process). The biasing region or dynamization device can also be fabricated by machining, forging or casting, based on the specific design and intended use of the device and the material comprising the device. Suitable materials include the medical grade and biocompatible plastics described above, or biocompatible metals, such as titanium, stainless steel, 316L stainless steel, cobalt-chromium, and alloys thereof. According to some embodiments, the devices can be made as a composite or hybrid device with a combination of plastic and metallic components. The selected material must have sufficient plasticity and shape memory to return to its original configuration after having been deformed many times.

Figure 12A:
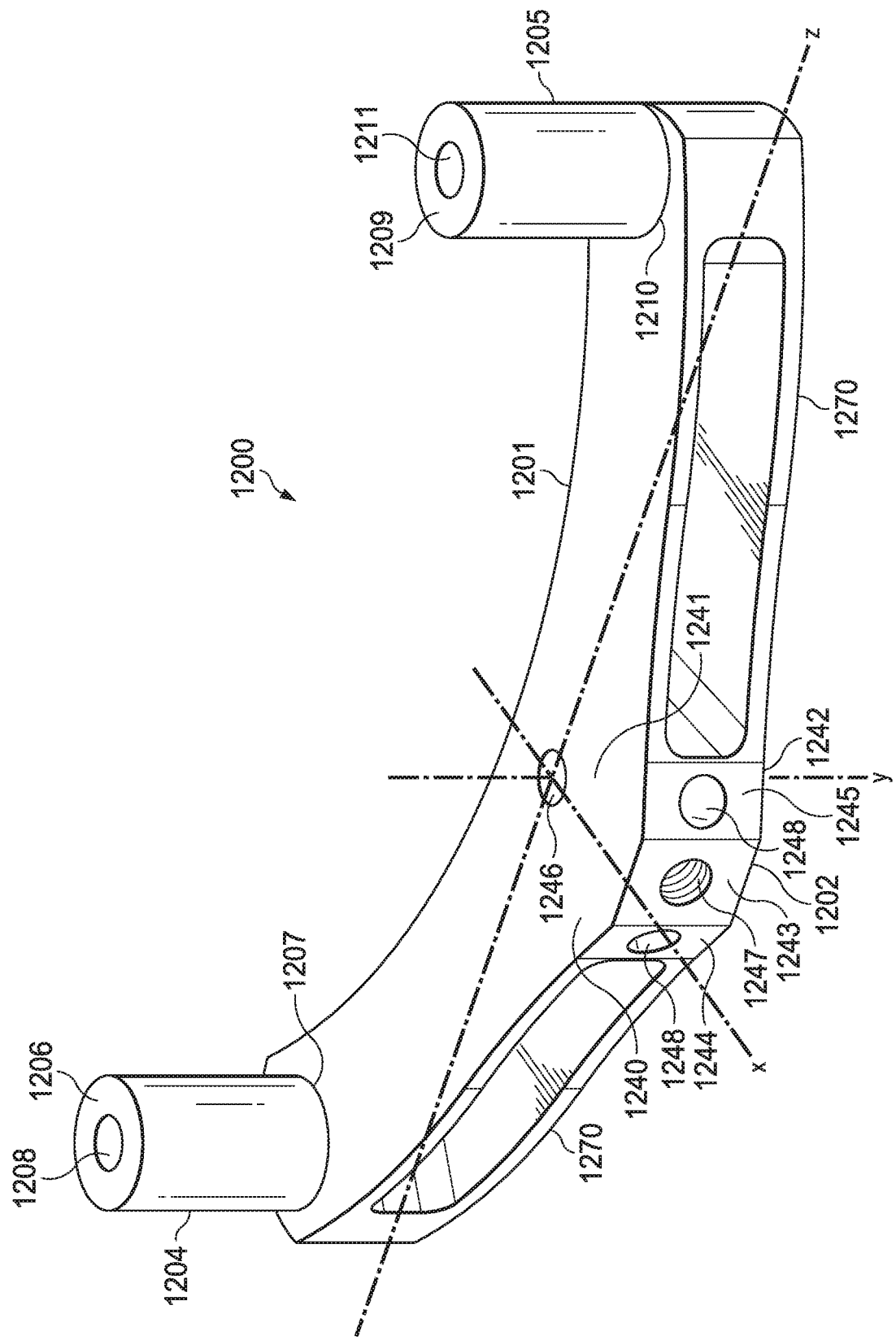
FIG. 12A illustrates a perspective view of an embodiment of a parallel tab dynamization device.

An alternative embodiment of the dynamization tab is depicted in FIG. 12A. In FIG. 12A, a parallel tab dynamization device 1200 provides a tab that is parallel to the external fixation ring and is fixed to the ring with an adjustable center bolt (not shown). In this embodiment, the tab deforms on either side of the bolt during loading, allowing for dynamization as well as the necessary biasing force to return the tab to its original shape. Generally speaking, the center bolt remains stationary while the ring moves up and down, along the vertical axis Y. In FIG. 12A, parallel tab 1200 has a longitudinal axis X, a vertical axis Y, and a transverse axis Z defined therein and comprises a proximal end 1201, a distal end 1202, first and second ring connectors (1204 and 1205), a strut connector 1240, and a biasing mechanism 1270.

According to some embodiments, the first ring connecting apparatus 1204 may have a superior end 1206 and an inferior end 1207 and be positioned parallel to the vertical axis Y of the parallel tab 1200 in such a manner that the superior end 1206 is in contact with a ring. The first ring connecting apparatus 1204 may further comprise a first ring connecting bore 1208, extending from the superior end of the first ring connecting apparatus 1206 to the inferior end of the first ring connecting apparatus 1207 and may be configured to accept a connecting bolt (not shown). The second ring connecting apparatus 1205, according to some embodiments, may have a superior end 1209 and an inferior end 1210 and be positioned parallel to the vertical axis Y of the parallel tab 1200 in such a manner that the superior end 1209 is in contact with a ring. The second ring connecting apparatus 1205 may additionally comprise a second ring connecting bore 1211 extending from the superior end of the second ring connecting apparatus 1209 to the inferior end of the second ring connecting apparatus 1210 and may be configured to accept a second ring connecting bolt (not shown). According to some embodiments, the first and/or second ring connecting apparatus may be comprised of a flexible plastic or other elastomeric material. A resilient, non-elastic material may also be used.

The strut connector 1240 of the parallel tab 1200, as illustrated in FIG. 12A, has a top surface 1241, a bottom surface 1242 and is positioned along the longitudinal axis X of the parallel tab 1200. The strut connector 1240 may further comprise a first distal-facing surface 1243, a second distal-facing surface 1244, a third distal-facing surface 1245, and an adjustment bore 1246. The first distal-facing surface 1243 may further comprise a locking-screw aperture 1247 which may be a partial bore extending from the distal end of the parallel tab 1202 towards the proximal end of the parallel tab 1201 and may be configured to accept a locking screw. The second distal-facing surface 1244 and the third distal-facing surface 1245 may each further comprise a respective strut aperture 1248 which may be a partial bore extending from the distal end of the parallel tab 1202 towards the proximal end of the parallel tab 1201 and may be configured to secure the parallel tab 1200 to a strut. The adjustment bore 1246 of the strut connector may extend along the vertical axis Y of the parallel tab 1200 from the top surface of the strut connector 1241 towards the bottom surface of the strut connector 1242 and be configured to accept an adjustment bolt (not shown). The adjustment bore 1246 may be a partial bore, extending only partially into the strut connector 1240, or may be a bore that extends completely from the top surface 1241 to the bottom surface 1242. In those embodiments where the adjustment bore 1246 extends fully from surface to surface, the parallel tab 1200 may comprise an additional nut to secure an adjustment bolt (not shown) in place.

Figure 12B:
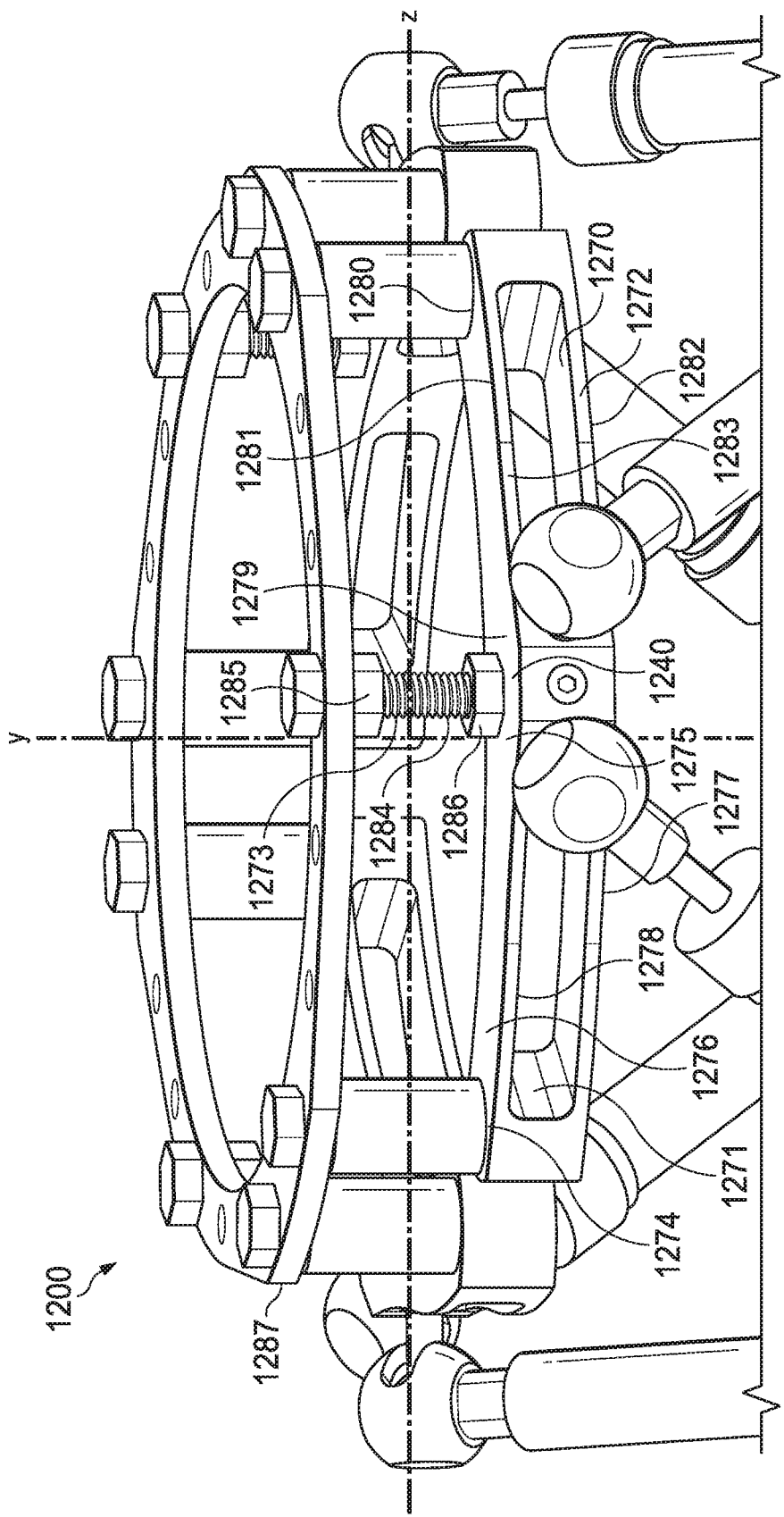
FIG. 12B illustrates another perspective view of an embodiment of a parallel tab dynamization device.

An embodiment with the connection of the parallel tab device 1200 to an external fixation ring 1287 and to the struts is depicted in FIG. 12B. In FIG. 12B, the biasing mechanism 1270 of the parallel tab 1200 is positioned along the transverse axis Z of the parallel tab 1200 in a manner such that it is parallel and inferior to the external fixation ring 1287. The biasing mechanism 1270 may comprise a first biasing region 1271, a second biasing region 1272, and an adjustment mechanism 1273. The first biasing region 1271, according to some embodiments, may have a first end 1274 and a second end 1275 and be positioned such that the second end 1275 is in contact with the strut connector 1240. The first biasing region 1271 may further comprise a top surface 1276, a bottom surface 1722, and one or more biasing plates 1278. The one or more biasing plates 1278 may be positioned between the top surface of the first biasing region 1276 and the bottom surface of the first biasing region 1277. Further, they may be positioned parallel to each other and to the transverse axis Z of the parallel tab 1200 in a manner such that, where there are two or more biasing plates 1278, there is space between each of the biasing plates 1278. Biasing plates 1278 of the first biasing region may be comprised of a flexible plastic or other elastomeric material and be configured such that the first biasing region 1271 provides a biasing force when the strut connector 1240 is displaced along the vertical axis Y of the parallel tab 1200. The second biasing region 1272, according to some embodiments, may have an first end 1279 and a second end 1280 and be positioned such that the first end 1279 is in contact with the strut connector 1240. The second biasing region 1272 may further comprise a top surface 1276, a bottom surface 1722, and one or more biasing plates 1278. The one or more biasing plates 1278 may be positioned between the top surface of the first biasing region 1276 and the bottom surface of the first biasing region 1277. Further, they may be positioned parallel to each other and to the transverse axis Z of the parallel tab 1200 in a manner such that, where there are two or more biasing plates 1278, there is space between each of the biasing plates 1278. Biasing plates of the first biasing region 1278 may be comprised of a flexible plastic or other elastomeric material and be configured such that the first biasing region 1271 provides a biasing force when the strut connector 1240 is displaced along the vertical axis Y of the parallel tab 1200.

The adjustment mechanism of FIG. 12B is positioned along the vertical axis Y of the parallel tab 1200 and comprises an adjustment bolt 1284, a first adjustment nut 1285, and a second adjustment nut 1286. The adjustment bolt 1284 may have a superior end 1288 and an inferior end 1289 and be positioned such that the superior end 1288 is in contact with the external fixation ring 1287 and the inferior end 1289 is in contact with the strut connector adjustment bore 1246 of FIG. 12A. Referring now back to FIG. 12B, the first adjustment nut 1285 may be configured such that it is secured to the adjustment bolt 1284 and in contact with the ring 1287. The second adjustment nut 1286 may be positioned inferior to the first adjustment nut 1285 and configured to be secured to the adjustment bolt 1284 in a manner such that increased distance (along the vertical axis Y of the parallel tab 1200) between the first adjustment nut 1285 and the second adjustment nut 1286 translates to diminished ability for the strut aperture 1240 to be displaced along the vertical axis Y of the parallel tab 1200.

The biasing regions, or even the entire tab, may be comprised of a material having appropriate elasticity and shape memory, such material can be selected from plastic, polymer, thermoplastic, metal, metal alloy, composite, resin, ultra-high-molecular-weight polyethylene (UHMW), a polytetrafluroethylene (PTFE), ABS plastic, PLA, polyamide, glass filled polyamide, epoxy, nylon, rayon, polyester, polyacrylate, wood, bamboo, bronze, titanium, steel, stainless steel, a cobalt chromium alloy, ceramic, wax, photopolymer, and polycarbonate. In certain non-limiting examples the polymer can be a thermoplastic polymer, a polyolefin, a polyester, a polysilicone, a polyacrylonitrile resin, a polystyrene, polyvinyl chloride, polyvinylidene chloride, polyvinyl acetate, a fluoroplastic, a phenolic resin, a urea resin, a melamine, an epoxy, a polyurethane, a polyamide, a polyacrylate resin, a polyketone, a polyimide, a polysulfone, a polycarbonate, a polyacetal, poly(hydroxynapthoic acid), a conductive polymer, a poly(3-hexylthiophene), a polyphenylene-vinylene, a poly(phenylene vinylene), a polyaniline, or combinations thereof. Other appropriate and biocompatible materials can be utilized. According to another embodiment, the biasing region or dynamization device can be fabricated by an additive printing process (e.g., a 3D printing process). The biasing region or dynamization device can also be fabricated by machining, forging or casting, based on the specific design and intended use of the device and the material comprising the device. Suitable materials include the medical grade and biocompatible plastics described above, or biocompatible metals, such as titanium, stainless steel, 316L stainless steel, cobalt-chromium, and alloys thereof. According to some embodiments, the devices can be made as a composite or hybrid device with a combination of plastic and metallic components. The selected material must have sufficient plasticity and shape memory to return to its original configuration after having been deformed many times.

Figure 13:
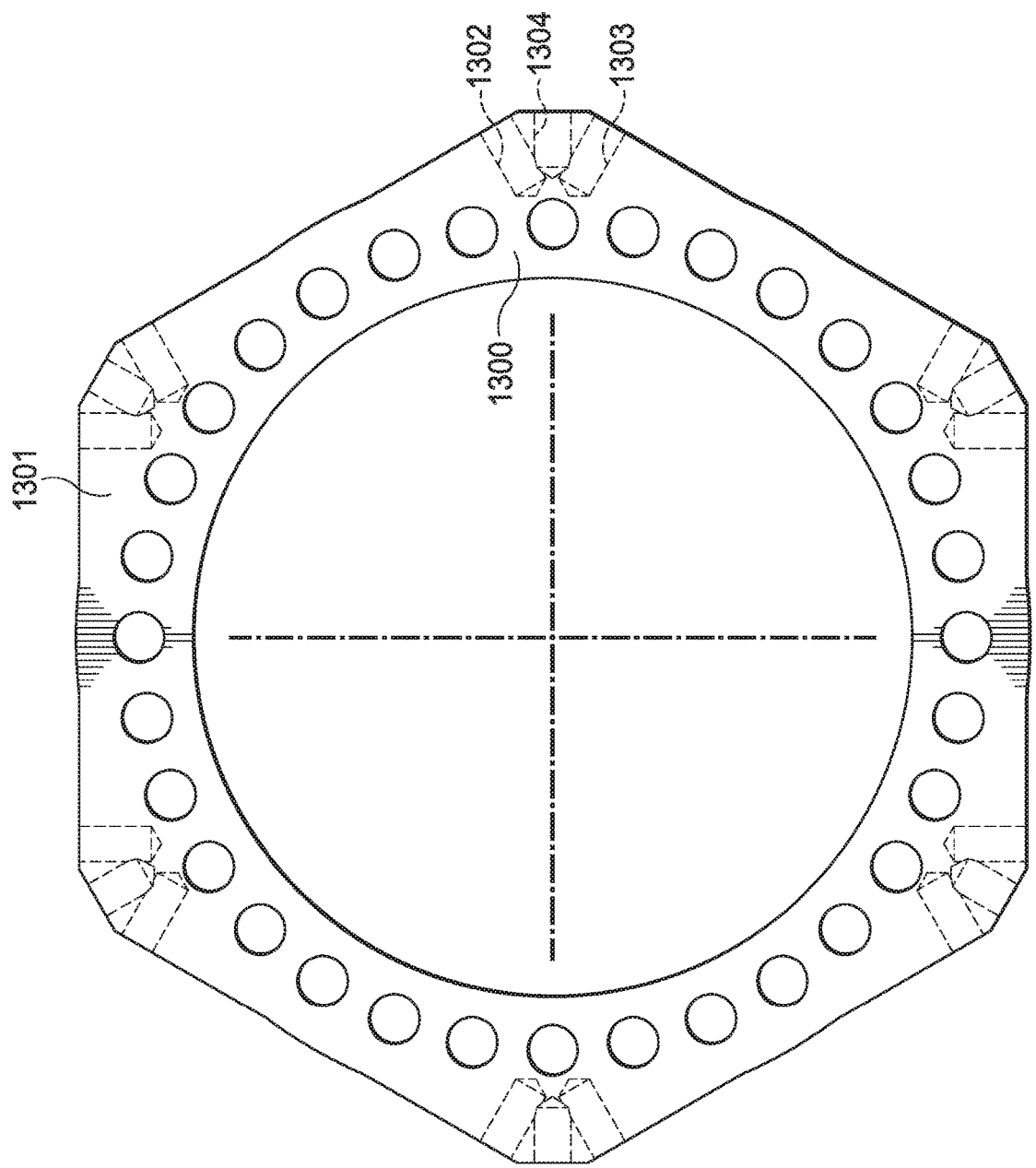
FIG. 13 illustrates a top view of another embodiment of a dynamization device that is integrated into an external fixation ring.

An alternative embodiment of the dynamization device 1300 is depicted in FIG. 13. In this alternative device 1300, a dynamization tab may be integrated (e.g., embedded) into an external fixation ring. In an example embodiment, a carbon fiber or similarly radiolucent material ring has a metal, e.g. aluminum or similar metal, tab imbedded in the ring. In some embodiments, the ring may have threaded metal tubes replacing the tab. While there are several ways that dynamization may be achieved in this arrangement, an example embodiment provides that the tab area of the ring itself has elastic properties which allow for dynamization under loading, as well as providing the necessary biasing force to return the ring to its resting conformation. In FIG. 13, an external fixation ring 1300 may be comprised of carbon fiber or similar radiolucent material with a tab (e.g. aluminum or similar metal) embedded in the external fixation ring 101 at the strut attachment point. The embedded tab 1301 may comprise a first strut bushing 1302 and a second strut bushing 1303, each configured to secure the ring 1300 to a strut (not shown). A bushing may be comprised of a tube comprising metal or other sufficiently rigid material to retain and hold a strut connector. In some embodiments, the bushing may be threaded. Further, the embedded tab 1301 may comprise a locking-screw bushing 1304, configured to accept a locking screw. In these embodiments, the locking-screw bushing 1304 and the first and second strut bushings 1302, 1303 may be imbedded in a rigid housing which may restrict the bushings 1302, 1303, 1304 from moving independently of one another. The rigid housing may be surrounded, in whole or in part, by a biasing zone, which may be a region within the external fixation ring 1300 comprised of flexible plastic or other elastomeric material. The biasing zone may be configured to be flexible enough to allow for the movement of the rigid housing, and subsequently the bushings 1302, 1303, 1304, within the external fixation ring 1301 during loading. Further, the biasing zone may be configured to provide a biasing force as the rigid housing and/or bushings 1302, 1303, 1304 are displaced along the longitudinal axis Y of the imbedded tab 1300.

The biasing regions, or even the entire tab, may be comprised of a material having appropriate elasticity and shape memory, such material can be selected from plastic, polymer, thermoplastic, metal, metal alloy, composite, resin, ultra-high-molecular-weight polyethylene (UHMW), a polytetrafluroethylene (PTFE), ABS plastic, PLA, polyamide, glass filled polyamide, epoxy, nylon, rayon, polyester, polyacrylate, wood, bamboo, bronze, titanium, steel, stainless steel, a cobalt chromium alloy, ceramic, wax, photopolymer, and polycarbonate. In certain non-limiting examples the polymer can be a thermoplastic polymer, a polyolefin, a polyester, a polysilicone, a polyacrylonitrile resin, a polystyrene, polyvinyl chloride, polyvinylidene chloride, polyvinyl acetate, a fluoroplastic, a phenolic resin, a urea resin, a melamine, an epoxy, a polyurethane, a polyamide, a polyacrylate resin, a polyketone, a polyimide, a polysulfone, a polycarbonate, a polyacetal, poly(hydroxynapthoic acid), a conductive polymer, a poly(3-hexyl-thiophene), a polyphenylene-vinylene, a poly(phenylene vinylene), a polyaniline, or combinations thereof. Other appropriate and biocompatible materials can be utilized. According to another embodiment, the biasing region or dynamization device can be fabricated by an additive printing process (e.g., a 3D printing process). The biasing region or dynamization device can also be fabricated by machining, forging or casting, based on the specific design and intended use of the device and the material comprising the device. Suitable materials include the medical grade and biocompatible plastics described above, or biocompatible metals, such as titanium, stainless steel, 316L stainless steel, cobalt-chromium, and alloys thereof. According to some embodiments, the devices can be made as a composite or hybrid device with a combination of plastic and metallic components. The selected material must have sufficient plasticity and shape memory to return to its original configuration after having been deformed many times.

Figure 14A:
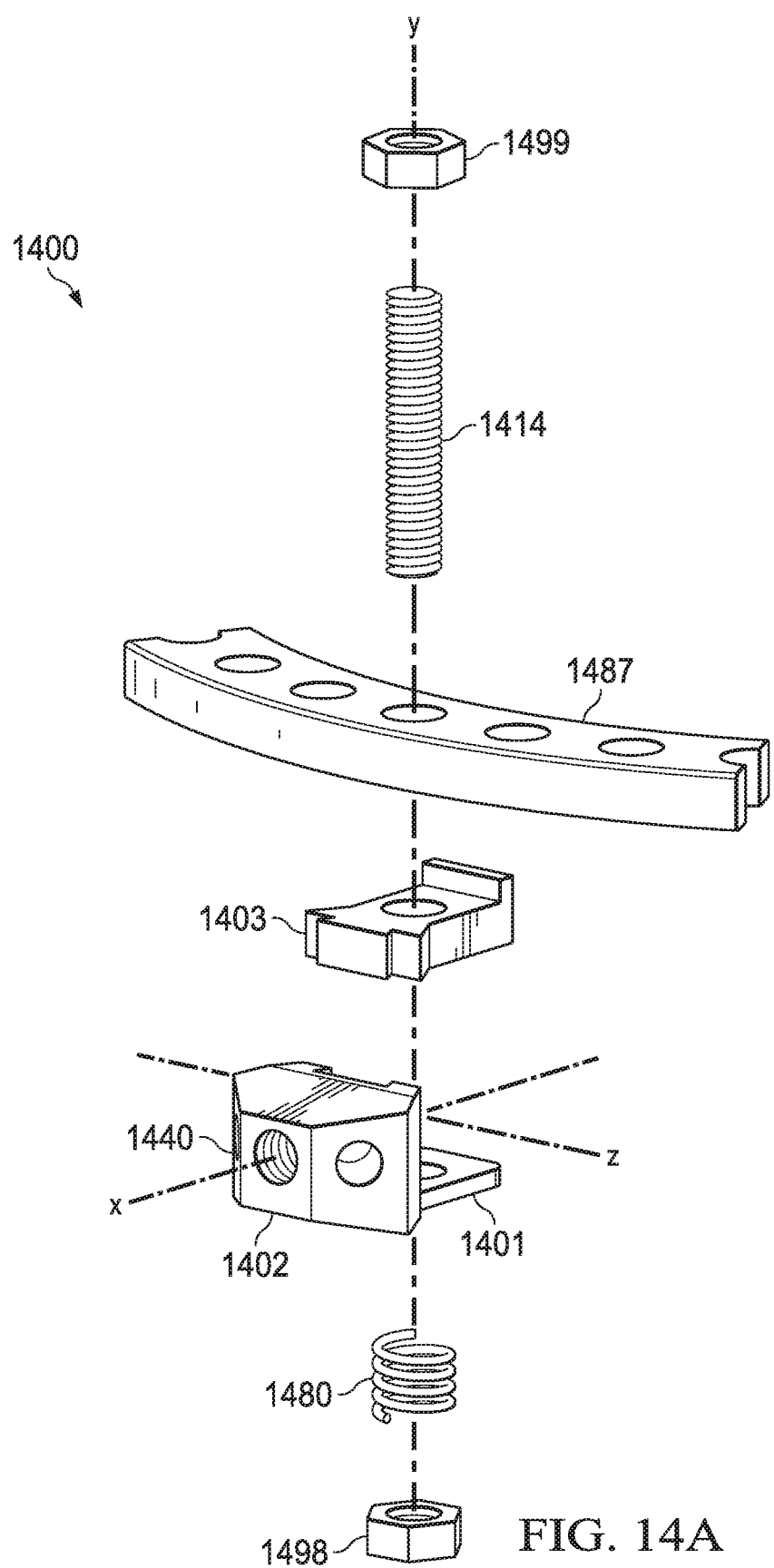
FIG. 14A illustrates an exploded perspective view of an embodiment of an axial translator dynamization device.

FIG. 14A is an exploded perspective view of an embodiment of an axial translator 1400 of the present disclosure. The axial translator 1400 has a longitudinal axis X, a vertical axis Y, and a transverse axis Z defined therein and comprises a proximal end 1401, a distal end 1402, a ring connector 1403, a strut connector 1440, and a biasing mechanism 1480. Further, according to some embodiments, the axial translator 1400 may comprise a connecting bolt 1414, a lower connecting nut 1498, and an upper connecting nut 1499. In these embodiments, the connecting bolt 1414, lower connecting nut 1498, and upper connecting nut 1499 are configured to secure the axial translator 1400 to an external fixation ring 1487, as discussed above. The structure of the strut connector 1440 of this embodiment may be substantially similar to the strut connector 840 depicted in FIG. 8C and described herein. Similarly, the structure of the ring connector 1403 of this embodiment may be substantially similar to the ring connector 803 depicted in FIG. 8C and described herein.

In the embodiment of FIG. 14A, the axial translation dynamization tab 1400, provides for dynamization in a single plane, i.e. up and down along the vertical axis Y of the device. The strut connector 1440 is allowed to move along a track between the strut connector 1440 and the ring connector 1403, providing oscillation or movement under loading. The dovetail locking arrangement between the strut connector 1440 and the ring connector 1403 provides a smooth and controlled axial movement of the strut connector 1440 along the vertical axis Y of the device. The degree of movement, or dynamization, can be controlled by loosening or tightening the lower connecting nut 1498.

Figure 14B:
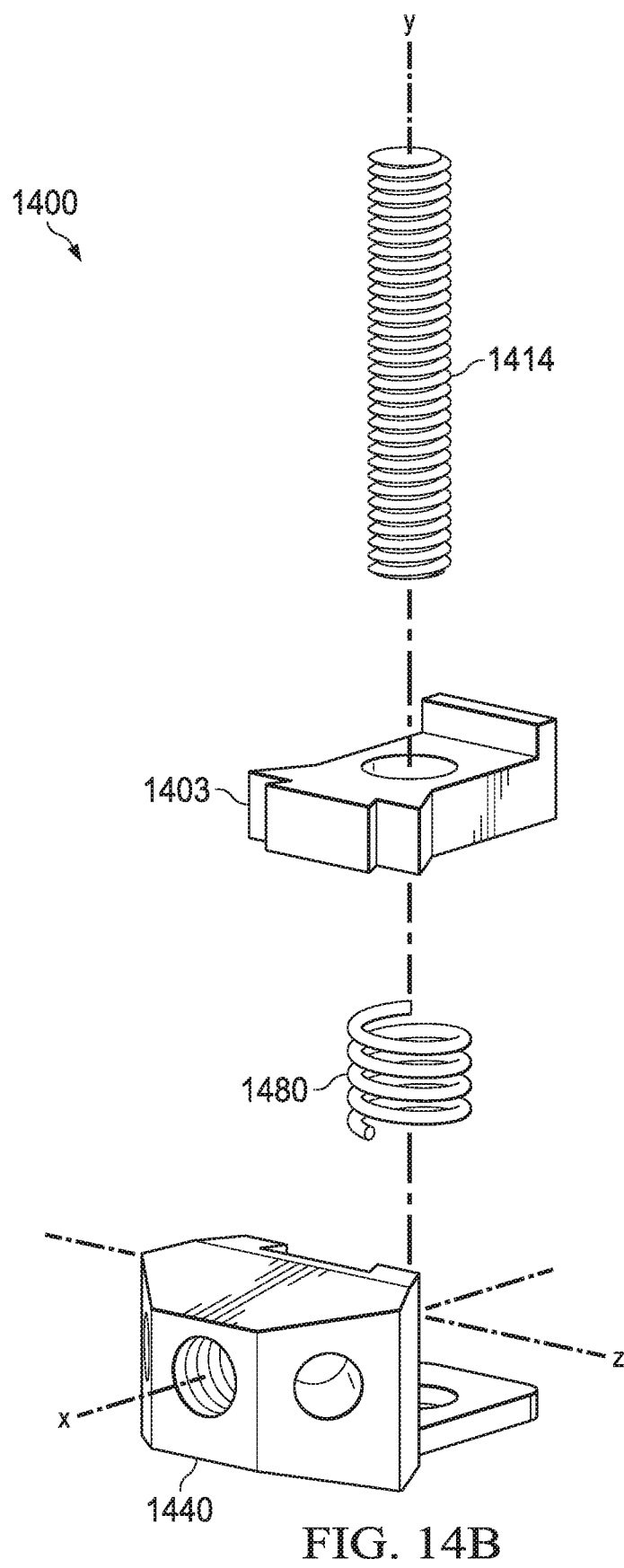
FIG. 14B illustrates another exploded perspective view of an embodiment of an axial translator dynamization device.

An alternative arrangement for the axial dynamization tab 1400 is depicted in FIG. 14B. In FIG. 14B, The axial translator 1400 has a longitudinal axis X, a vertical axis Y, and a transverse axis Z defined therein and comprises a ring connector 1403, a strut connector 1440, and a biasing mechanism 1480. Further, according to some embodiments, the axial translator 1400 may comprise a connecting bolt 1414, a lower connecting nut (not shown), and an upper connecting nut (not shown). In this embodiment, the connecting bolt 1414, lower connecting nut 1498, and upper connecting nut 1499 are configured to secure the axial translator 1400 to an external fixation ring (not shown). The structure of the strut connector 1440 of this embodiment may be substantially similar to the strut connector 840 depicted in FIG. 8C and described herein. Similarly, the structure of the ring connector 1403 of this embodiment may be substantially similar to the ring connector 803 depicted in FIG. 8C and described herein. In contrast to the embodiment in FIG. 14A, the biasing mechanism 1480 is positioned between the strut connector 1440 and the ring connector 1403. As such, the external fixation ring would be placed on the upper surface of the ring connector 1403 and an upper connecting nut would be secured to the connecting bolt 1414 on the upper surface of the external fixation ring. Similarly, the lower connecting nut would be secured to the connecting bolt 1414 on the bottom surface of the strut connector 1440.

Figure 14C:
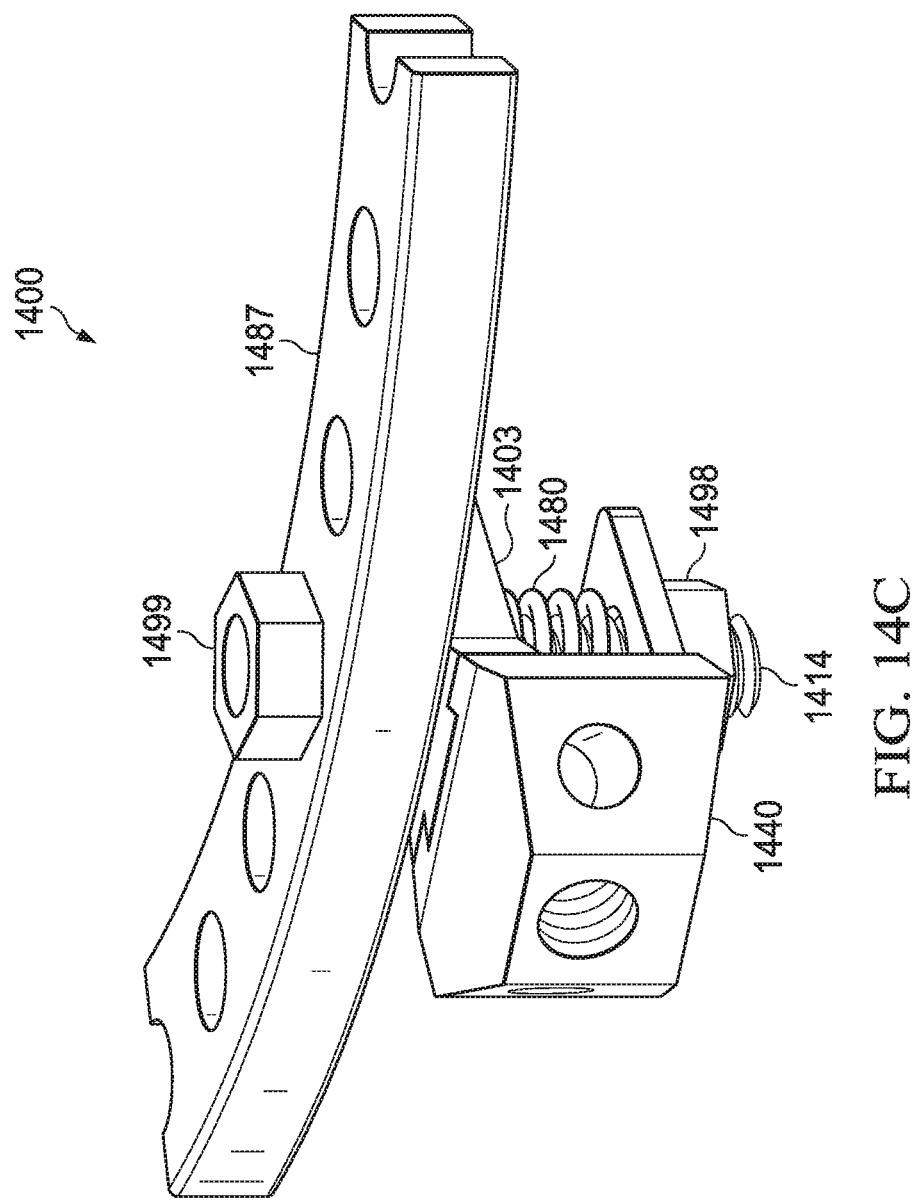
FIG. 14C illustrates a perspective view of an embodiment of an axial translator dynamization device.

In the embodiment of FIG. 14B, the axial translation dynamization tab 1400, provides for dynamization in a single plane, i.e. up and down along the vertical axis Y of the device. The strut connector 1440 is allowed to move along a track between the strut connector 1440 and the ring connector 1403, providing oscillation or movement under loading. The dovetail locking arrangement between the strut connector 1440 and the ring connector 1403 provides a smooth and controlled axial movement of the strut connector 1440 along the vertical axis Y of the device. The degree of movement, or dynamization, can be controlled by loosening or tightening the lower connecting nut 1498. The connection of the components of the axial translation dynamization tab of FIG. 14B to an external fixation ring 1487 is depicted in FIG. 14C.

Figure 15:
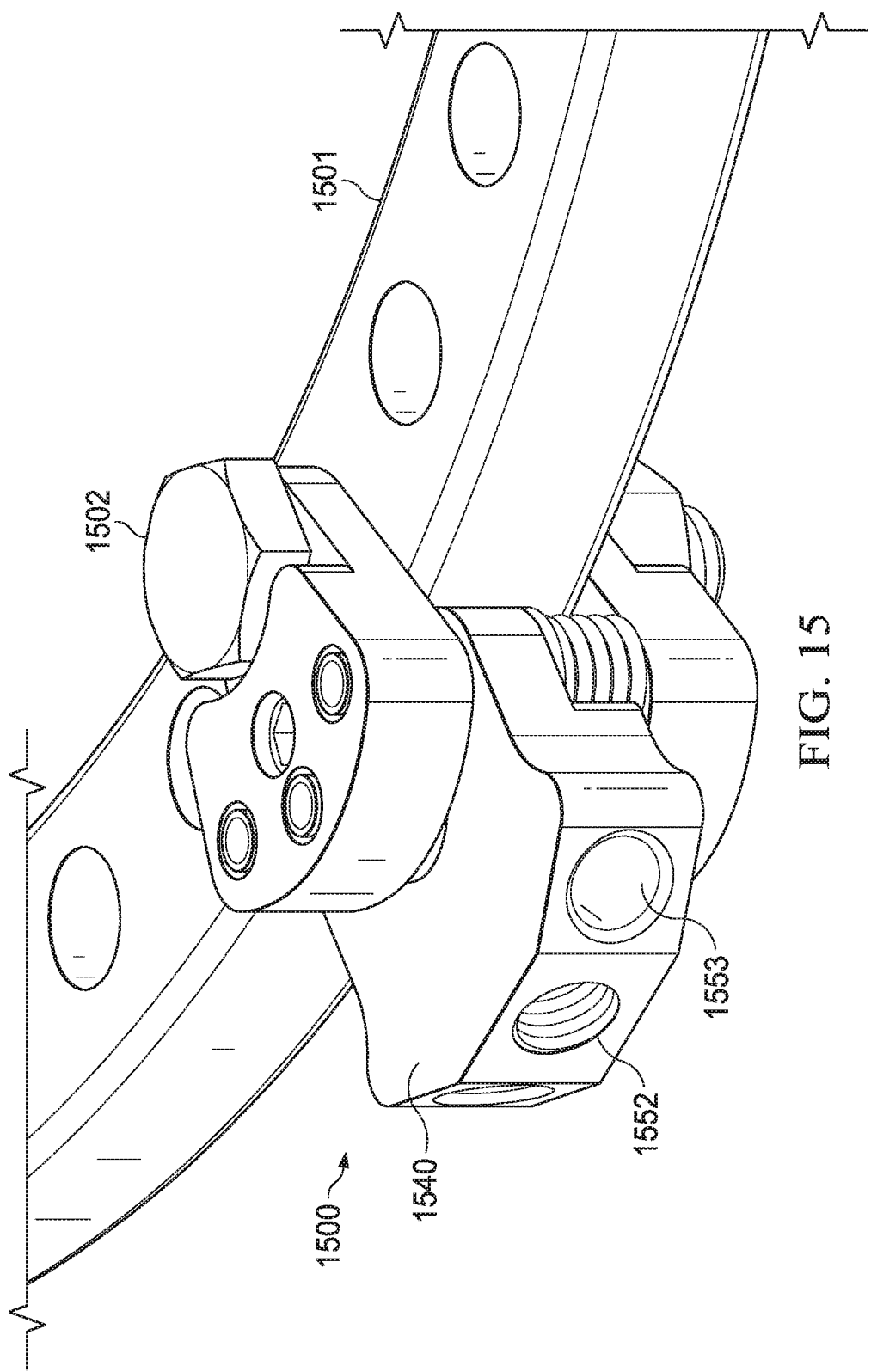
FIG. 15 illustrates a perspective view of an embodiment of an alternative dynamization device mounted to a ring fixator.

An alternate embodiment of a dynamization device is depicted in FIG. 15. In FIG. 15, a dynamization tab 1500 is connected to an external fixation ring 1501 by a connecting bolt 1502. The dynamization tab includes a ring connector 1503 and a strut connector 1540. Like the previous embodiments, the dynamization tab 1500 may also include one or more strut apertures 1553 to receive a strut fastener of an external fixation strut (not shown). Also shown in FIG. 15 is a locking screw aperture 1552, which can be used to secure the one or more of the external fixation struts to the dynamization tab 1500. The locking screw aperture 1552 may be configured to accept a locking screw, which may be configured to secure the strut fasteners when they are placed inside of the strut apertures 1553. As shown in FIG. 15, the locking screw aperture 1552 may be threaded to accept a correspondingly threaded locking screw. The locking screw may secure the strut fasteners through contact with the strut fasteners in a manner which prevents the movement of the strut fasteners with respect to the strut apertures 1553 when the locking screw is in place. Several examples of such a locking arrangement are found in U.S. Pat. No. 9,295,493, hereby incorporated by reference into this patent.

Figure 15A:
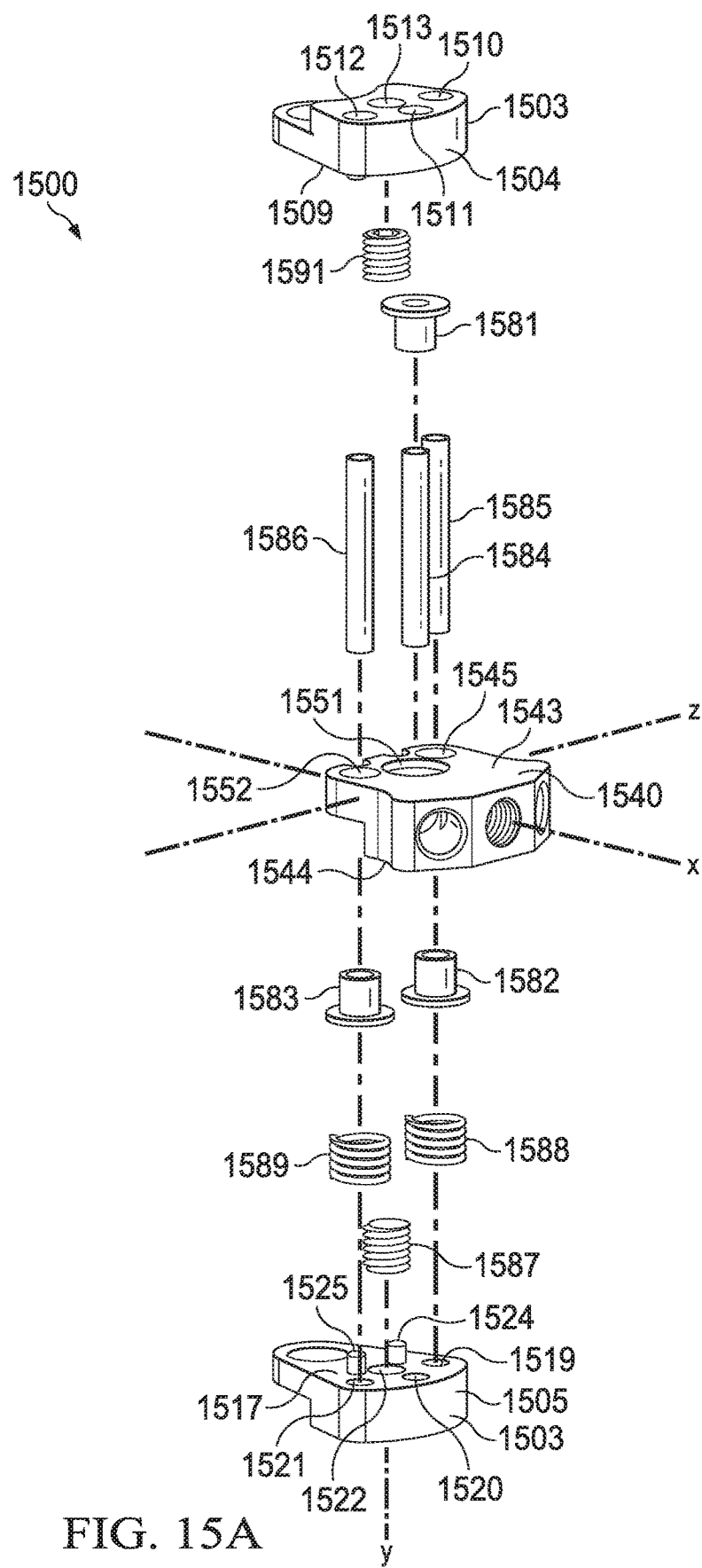
FIG. 15A illustrates an exploded perspective view of an embodiment of an alternative dynamization device.

Detailed illustrations of the dynamization device 1500 are found in FIGS. 15A-D. FIG. 15A is an exploded perspective view of an embodiment of a dynamization tab 1500, which may allow for limited axial translation along the axis Y, while minimizing the ability of the dynamization tab 1500 elements to rotate about the transverse axis Z. As shown, the dynamization tab 1500 may have a longitudinal axis X, a vertical axis Y, and a transverse axis Z, and may further comprise a ring connector 1503, a strut connector 1540, and a biasing mechanism. A ring connector 1503 may comprise a superior member 1504 and an inferior member 1505.

Figure 15B:
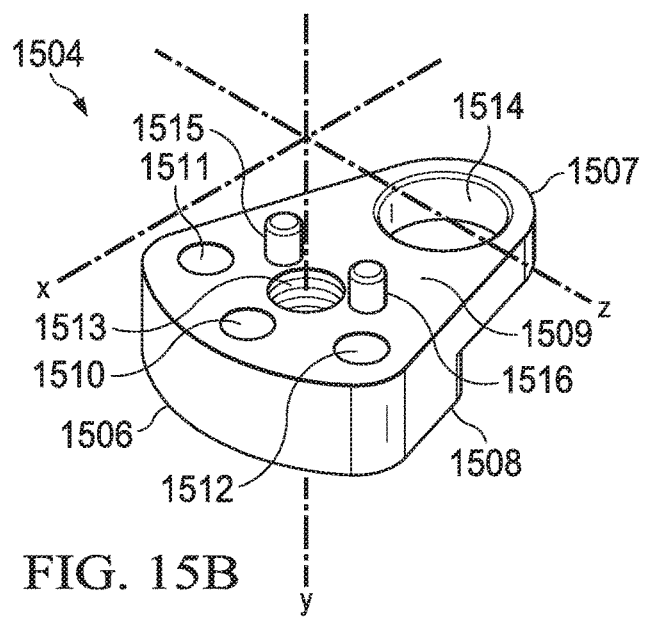
FIG. 15B illustrates a perspective view of the bottom surface of a superior member of an alternative dynamization device.

A perspective view of the bottom surface 1509 of the superior member 1504 is depicted in FIG. 15B. In FIG. 15B, the superior member 1504 may comprise a distal end 1506, a proximal end 1507 and be positioned parallel and superior to the longitudinal axis X of the dynamization tab 1500. The superior member 1504 may further comprise a top surface 1508, a bottom surface 1509, a first drive pin bore 1511, a second drive pin bore 1512, a third drive pin bore 1510, a set screw bore 1513, a ring connector bore 1514, a first stabilizing feature 1515, and a second stabilizing feature 1516. According to some embodiments, each of the first drive pin bore 1511, the second drive pin bore 1512, and the third drive pin bore 1510 may be positioned such that it extends from the top surface of the superior member 1508 to the bottom surface of the superior member 1509. Further, the first drive pin bore 1511, the second drive pin bore 1512, and the third drive pin bore 1510 may be configured to accept a first drive pin, a second drive pin, and a third drive pin (elements 1584, 1585, and 1586 of FIG. 15A), respectively.

The set screw bore 1513 may be positioned proximal to the drive pin bores 1510, 1511, 1512, and extend parallel to the vertical axis Y of the dynamization tab 1500 from the top surface of the superior member 1508 to the bottom surface of the superior member 1509. The set screw bore 1513 may be configured to accept a first set screw (element 1587 of FIG. 15A). The ring connector bore 1514 may be positioned proximal to the drive pin bores 1510, 1511, 1512, and extend parallel to the vertical axis Y of the dynamization tab 1500 from the top surface of the superior member 1508 to the bottom surface of the superior member 1509. The ring connector bore 1514 may be configured to accept a connecting bolt (not shown) and be used to reversibly couple the dynamization tab 1500 to an external fixation ring, as shown in FIG. 15. The superior member 1504 may further comprise a first stabilizing feature 1515 and a second stabilizing feature 1516, each extending from the bottom surface of the superior member 1509 and parallel to the vertical axis Y of the dynamization tab 1500. As shown in FIG. 15B, the first and second stabilizing features (1515, 1516) may comprise a cylindrical shape that protrudes from the bottom surface of the superior member 1509.

Figure 15C:
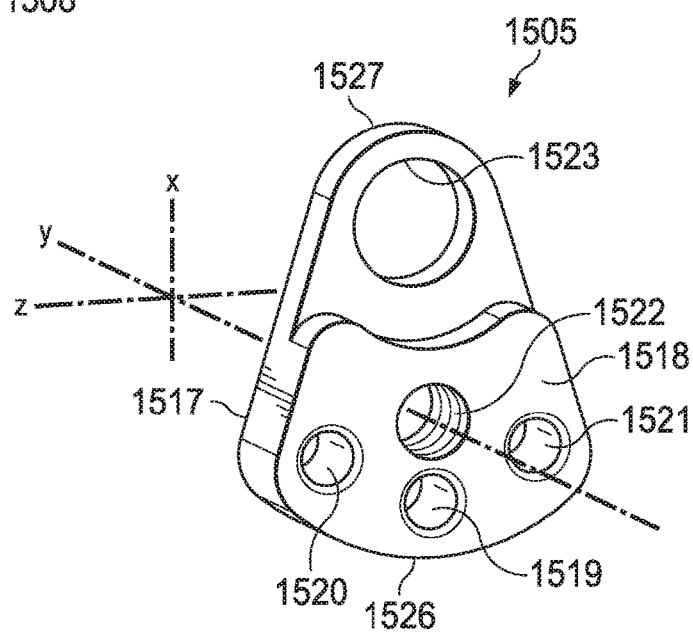
FIG. 15C illustrates a perspective view of the bottom surface of an inferior member of an alternative dynamization device.

A perspective view of the bottom surface 1518 of the inferior member 1505 is depicted in FIG. 15C. In FIG. 15C, the inferior member 1505 may comprise a distal end 1526, a proximal end 1527 and be positioned parallel and inferior to the longitudinal axis X of the dynamization tab 1500. The inferior member 1505 may further comprise a top surface 1517 (not shown), a bottom surface 1518, a first drive pin bore 1520, a second drive pin bore 1519, a third drive pin bore 1521, a set screw bore 1522, a ring connector bore 1523, a first stabilizing feature, and a second stabilizing feature that protrude from the top surface 1517 (similar to elements 1524 and 1525 of FIG. 15A). According to some embodiments, each of the first drive pin bore 1520, the second drive pin bore 1519, and the third drive pin bore 1521 may be positioned such that it extends from the top surface of the inferior member 1517 to the bottom surface of the inferior member 1518. Further, the first drive pin bore 1520, the second drive pin bore 1519, and the third drive pin bore 1521 may be aligned with the first, second, and third drive pin bores of the superior member 1504, respectively, to accept the first drive pin, the second drive pin, and the third drive pin (elements 1584, 1585, and 1586 of FIG. 15A).

The set screw bore of the inferior member 1522 may be positioned proximal to the drive pin bores of the inferior member 1519, 1520, 1521 and extend parallel to the vertical axis Y of the dynamization tab 1500 from the top surface of the inferior member 1517 to the bottom surface of the inferior member 1518. The set screw bore 1522 may be configured to accept a second set screw (element 1591 of FIG. 15A). The ring connector bore 1523 may be positioned proximal to the drive pin bores 1519, 1520, 1521, and extend parallel to the vertical axis Y of the dynamization tab 1500 from the top surface of the inferior member 1517 to the bottom surface of the inferior member 1518. The ring connector bore 1523 may be configured to accept a connecting bolt (not shown) and be used to reversibly couple the dynamization tab 1500 to an external fixation ring, as shown in FIG. 15. The inferior member 1505 may further comprise a first stabilizing feature and a second stabilizing feature (not shown, but similar to elements 1524 and 1525 of FIG. 15A), each extending from the top surface of the inferior member 1517 and parallel to the vertical axis Y of the dynamization tab 1500.

Preferably, the superior member 1504 and the inferior member 1505 may have an identical shape and configuration with identical first, second, and third drive pin bores, set screw bore, ring connector bore, and first and second stabilizing features. As such, the difference between the superior member 1504 and the inferior member 1505 would be that opposite sides of the members would be arranged as top and bottom surfaces. By utilizing identical shapes and configurations for the superior and inferior members, the fabrication can be simplified, and its cost reduced.

Figure 15D:
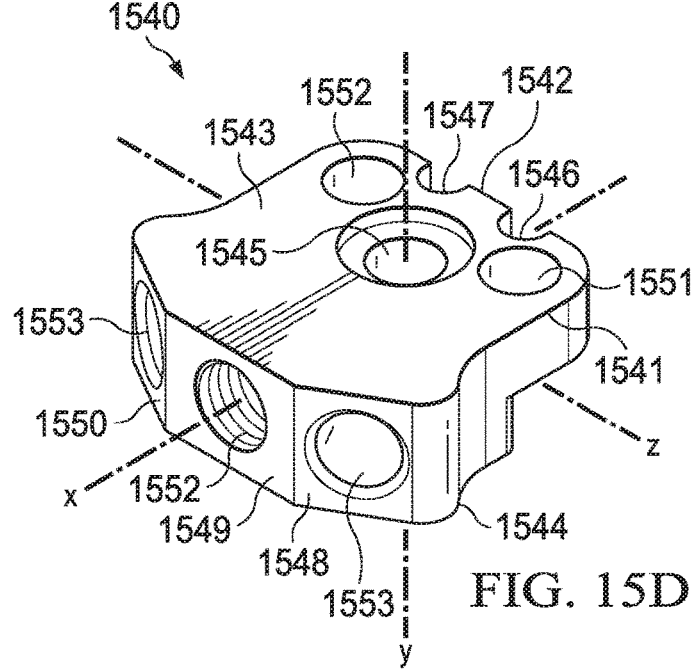
FIG. 15D illustrates a perspective view of a strut connector of an alternative dynamization device.

A dynamization tab 1500 may further comprise a strut connector 1540, illustrated in FIG. 15D. According to some embodiments, the strut connector 1540 may have a distal end 1541 and a proximal end 1542 and be positioned along the longitudinal axis X of the dynamization tab 1500. The strut connector 1540 may further comprise a top surface 1543, a bottom surface 1544, a first drive pin bore 1551, a second drive pin bore 1545, a third drive pin bore 1552, a first stabilizing feature cavity 1546, a second stabilizing feature cavity 1547, a first distal-facing surface 1548, a second distal facing surface 1549, and a third distal-facing surface 1550. The strut connector 1540 may be positioned such that the top surface of the strut connector 1543 is in contact with the bottom surface of the superior member of the ring connector 1509.

Each of the first drive pin bore 1551, the second drive pin bore 1545, and the third drive pin bore 1552, may extend parallel to the vertical axis Y of the dynamization tab 1500 from the top surface of the strut connector 1543 to the bottom surface of the strut connector 1544. The first drive pin bore 1545, the second drive pin bore 1551, and the third drive pin bore 1552 may be aligned with the first, second, and third drive pin bores of the superior member 1504 and the inferior member 1505, respectively, to accept the first drive pin, the second drive pin, and the third drive pin (elements 1584, 1585, and 1586 of FIG. 15A), respectively.

The first stabilizing feature cavity of the strut connector 1546 may be configured to mate with the first stabilizing feature 1515 of the superior member 1504 of the ring connector (see FIG. 15B) and the first stabilizing feature 1524 of the inferior member 1505 (see FIG. 15A) in a manner such that rotation of the strut connector 1540 about the vertical axis Y of the dynamization tab 1500 is limited by contact between the first stabilizing feature cavity 1546 and the corresponding stabilizing features. The second stabilizing feature cavity of the strut connector 1547 may be configured to mate with the second stabilizing feature 1516 of the superior member 1504 of the ring connector (see FIG. 15B) and the second stabilizing feature 1525 of the inferior member 1505 (see FIG. 15A) in a manner such that rotation of the strut connector 1540 about the vertical axis Y of the dynamization tab 1500 is limited by contact between the second stabilizing feature cavity 1547 and the corresponding stabilizing features. Preferably the shape of the first and second stabilizing feature cavities (1546 and 1547) should directly correspond to the shape of the first and second stabilizing features, respectively, so that the inferior and superior members (1504, 1505) will securely mate with the strut connector 1540.

Each of the first distal-facing surface 1548 and the third distal-facing surface 1550 may comprise a strut aperture 1553. The strut aperture 1553, according to some embodiments, may be a partial bore extending from the distal end of the strut connector 1541 towards the proximal end of the strut connector 1542 and may be configured to reversibly couple the strut connector 1540 to a strut. Also shown in FIG. 15D is a locking screw aperture 1552, which can be used to secure the one or more of the external fixation struts to the strut connector 1540. The locking screw aperture 1552 may be configured to accept a locking screw, which may be configured to secure the strut fasteners when they are placed inside of the strut apertures 1553. As shown in FIG. 15D, the locking screw aperture 1552 may be threaded to accept a correspondingly threaded locking screw. The locking screw may secure the strut fasteners through contact with the strut fasteners in a manner which prevents the movement of the strut fasteners with respect to the strut apertures 1553 when the locking screw is in place. Several examples of such a locking arrangement are found in U.S. Pat. No. 9,295,493, hereby incorporated by reference into this patent. While the embodiments of FIGS. 15A-D illustrate each of the first distal-facing surface 1548 and the third distal-facing surface 1550 comprising a respective strut aperture 1553, it should be appreciated that a strut aperture 1553 may be an element of any one or more of the distal-facing surfaces 1548, 1549, 1550, and is not necessarily an element of all three. For example, a first distal-facing surface 1548 may comprise a strut aperture 1553 and the second and third distal-facing surfaces 1549, 1550 may lack this element altogether.

Referring now back to FIG. 15A, a dynamization tab 1500 may further comprise a biasing mechanism. The biasing mechanism, according to some embodiments, may comprise a first linear bearing 1581, a second linear bearing 1582, a third linear bearing 1583, a first drive pin 1584, a second drive pin 1585, a third drive pin 1586, a first set screw 1587, a second set screw 1591, a first elastic member 1588, and a second elastic member 1589. The first, second, and third linear bearings (1581, 1582, 1583) may comprise a cylindrical sleeve with an annular collar positioned at one end and may be comprised of a low friction material. As shown in FIG. 15A, the first, second, and third linear bearings (1581, 1582, 1583) may be positioned parallel to the vertical axis Y of the dynamization tab 1500.

The first linear bearing 1581 may be positioned so that its annular collar is positioned in contact with the bottom surface 1509 of the of the superior member 1504 of the ring connector and be configured such that its cylindrical sleeve traverses at least part of the first drive pin bore 1551 of the strut connector 1540. As such, the outer diameter of the cylindrical sleeve of the first linear bearing 1581 should be similar to the inner diameter of the first drive pin bore 1551 of the strut connector 1540 to provide a smooth mating of these components. The first drive pin 1584 may be configured to traverse the first drive pin bore 1511 of the superior member 1504 of the ring connector, the first drive pin bore of the strut connector 1551, the first drive pin bore of the inferior member 1520, and the first linear bearing 1581.

The inner diameter of the first linear bearing 1581 should be similar to the outer diameter of the first drive pin 1584 to provide a smooth mating of these components. As mentioned previously, the low friction aspect of the first linear bearing 1581 facilitates the relative movement of the superior member 1504 with respect to the strut connector 1540 along the Y-Axis of the device in a smooth manner with minimal friction between the components.

The second linear bearing 1582 may be positioned such that annular collar is in contact with the upper surface 1517 of the inferior member 1505 and be configured such that its cylindrical sleeve traverses at least part of the second drive pin bore 1545 of the strut connector 1540. As such, the outer diameter of the cylindrical sleeve of the second linear bearing 1582 should be similar to the inner diameter of the second drive pin bore 1545 of the strut connector 1540 to provide a smooth mating of these components. The second drive pin 1585 may be configured to traverse the second drive pin bore 1512 of the superior member 1504, the second drive pin bore 1545 of the strut connector 1540, the second drive pin bore 1519 of the inferior member 1505, and the second linear bearing 1585.

The inner diameter of the second linear bearing 1582 should be similar to the outer diameter of the second drive pin 1585 to provide a smooth mating of these components. As mentioned previously, the low friction aspect of the second linear bearing 1582 facilitates the relative movement of the inferior member 1504 with respect to the strut connector 1540 along the Y-Axis of the device in a smooth manner with minimal friction between the components.

The third linear bearing 1583 may be positioned such that its annular collar is in contact with the upper surface 1517 of the inferior member 1505 and be configured such that its cylindrical sleeve traverses at least part of the third drive pin bore 1552 of the strut connector 1540. As such, the outer diameter of the cylindrical sleeve of the third linear bearing 1583 should be similar to the inner diameter of the third drive pin bore 1552 of the strut connector 1540 to provide a smooth mating of these components. The third drive pin 1586 may be configured to traverse the third drive pin bore 1510 of the superior member 1504, the third drive pin bore 1552 of the strut connector 1540, the third drive pin bore 1521 of the inferior member 1505, and the third linear bearing 1583.

The inner diameter of the third linear bearing 1583 should be similar to the outer diameter of the third drive pin 1586 to provide a smooth mating of these components. As mentioned previously, the low friction aspect of the third linear bearing 1583 facilitates the relative movement of the inferior member 1504 with respect to the strut connector 1540 along the Y-Axis of the device in a smooth manner with minimal friction between the components.

Suitable materials for the first linear bearing may be selected from silicone, PEEK, nylon, Delrin, PTFE (Teflon), aluminum, steel, bronze with bonded PTFE liner to reduce friction, metal alloys, UHMWPE (ultra-high molecular weight polyethylene), thermoplastics, composites, and lubricants.

Collectively, the first drive pin 1584, second drive pin 1585, and third drive pin 1586 may be positioned in a manner such that when the strut connector 1540 is displaced along the longitudinal axis Y of the dynamization tab 1500, the displacement is limited to axial displacement along the vertical axis Y of the dynamization tab 1500. While the embodiments of FIGS. 15A-D illustrate a first drive pin 1584, a second drive pin 1585, and a third drive pin 1586, it should be appreciated that the collective functionality of all three drive pins may be accomplished by a single drive pin, e.g. a first drive pin 1584, any two drive pins, e.g. a first drive pin 1584 and a second drive pin 1585, or more than three drive pins, e.g. a fourth drive pin, a fourth drive pin and a fifth drive pin, etc.

The dynamization tab 1500 may further comprise a first set screw 1587 and a second set screw 1591. According to some embodiments, a first set screw 1587 may be positioned such that it is parallel to the vertical axis Y of the dynamization tab 1500 and in contact with the top surface 1543 of the strut connector 1540. The first set screw 1587 may be configured such that it traverses the set screw bore 1513 of the superior member 1504 in a manner such that when the first set screw 1587 is tightened, movement of the strut connector 1540 along the vertical axis Y of the dynamization tab 1500 is limited. The second set screw 1591 may also be positioned parallel to the vertical axis Y of the dynamization tab 1500 and in contact with the bottom surface 1544 of the strut connector 1540. The second set screw 1591 may be configured such that it traverses the set screw bore 1522 of the inferior member 1505 in a manner such that as the second set screw 1591 is tightened, movement of the strut connector 1540 along the vertical axis Y of the dynamization tab 1500 is limited. The first and second set screws (1587, 1591) may include a fitting for receiving a set screw driver, such as a hexagonal receptacle, a Phillips-head receptacle, a flat-head receptacle, a star-wrench receptacle, or any other suitable driver that would be understood in the art. By adjusting the relative positions of the first and second set screws (1587, 1591) within the set screw bores (1513, 1522), the amount of dynamization provided by this device can be controlled.

A first elastic member 1588 and a second elastic member 1589 may each comprise a spring, a resilient device, or an elastomeric material. In some embodiments, the first elastic member 1588 may be positioned parallel to the vertical axis Y of the dynamization tab 1500 in a manner such that it is in contact with the bottom surface 1544 of the strut connector 1540 and the top surface 1517 of the inferior member 1505. Preferably, the outer diameter of the first elastic member 1588 should be similar to or less than the outer diameter of the annular collar of the second linear bearing 1582 to ensure that first elastic member 1588 is biased against the strut connector 1540. Preferably, the outer diameter of the second elastic member 1589 should be similar to or less than the outer diameter of the annular collar of the third linear bearing 1583 to ensure that second elastic member 1589 is biased against the strut connector 1540.

The first elastic member 1588 may be configured such that when the strut connector 1540 is displaced along the longitudinal axis Y of the dynamization tab 1500, the first elastic member 1588 provides a biasing force sufficient to return the strut connector 1540 to its original position. The second elastic member 1589 may also be configured such that when the strut connector 1540 is displaced along the longitudinal axis Y of the dynamization tab 1500, the second elastic member 1589 also provides a biasing force sufficient to return the strut connector 1540 to its original position. One or both of the elastic members may be utilized in the dynamization tab 1500, consistent with the scope of the invention.

Figure 15E:
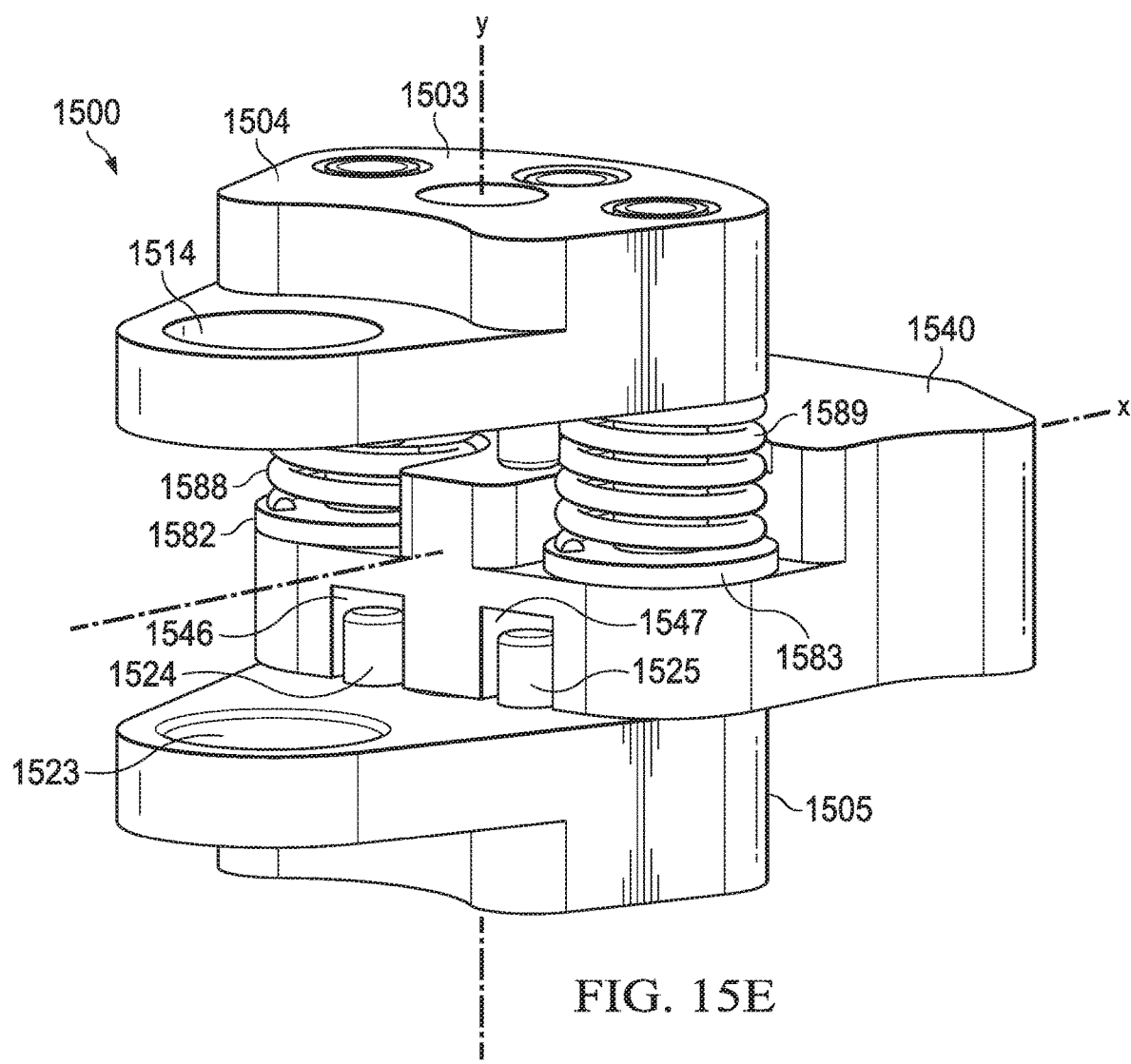
FIG. 15E illustrates a perspective side view of an embodiment of an alternative dynamization device.

A side and perspective view of the complete assembly of the dynamization tab 1500 is found in FIG. 15E. As illustrated, the dynamization tab 1500 comprises a ring connector 1503, including a superior member 1504 and an inferior member 1505. Each of the superior member 1504 and the inferior member 1505 includes a ring connector bore 1514, 1523, which is used to secure the dynamization tab 1500 to an external fixation ring (not shown) using a connecting bolt (not shown). Further, the first and second stabilizing features of the inferior member of the ring connector 1524, 1525 are shown. The dynamization tab 1500 further comprises a strut connector 1540, which is positioned between the superior member of the ring connector 1504 and the inferior member of the ring connector 1505. As shown in FIG. 15E, the first stabilizing feature cavity of the strut connector 1546 and the second stabilizing feature cavity of the strut connector 1547 securely house the first stabilizing feature of the inferior member of the ring connector 1524 and the second stabilizing feature of the inferior member of the ring connector 1525, respectively, in a manner such that rotation of the strut connector 1540 about the vertical axis Y of the dynamization tab 1500 is limited. Also shown, the dynamization tab 1500 comprises a first and a second elastic member 1588, 1589. In the embodiment of FIG. 15E, each comprises a spring which has been traversed by the second linear bearing 1582 and the third linear bearing 1583, respectively. In this configuration, as the strut connector 1540 is displaced from the longitudinal axis X of the dynamization tab 1500, in a linear fashion and along the vertical axis Y, the first and second elastic members 1588, 1589, provide the biasing force sufficient to return the strut connector 1540 to its original position.

Figure 15F:
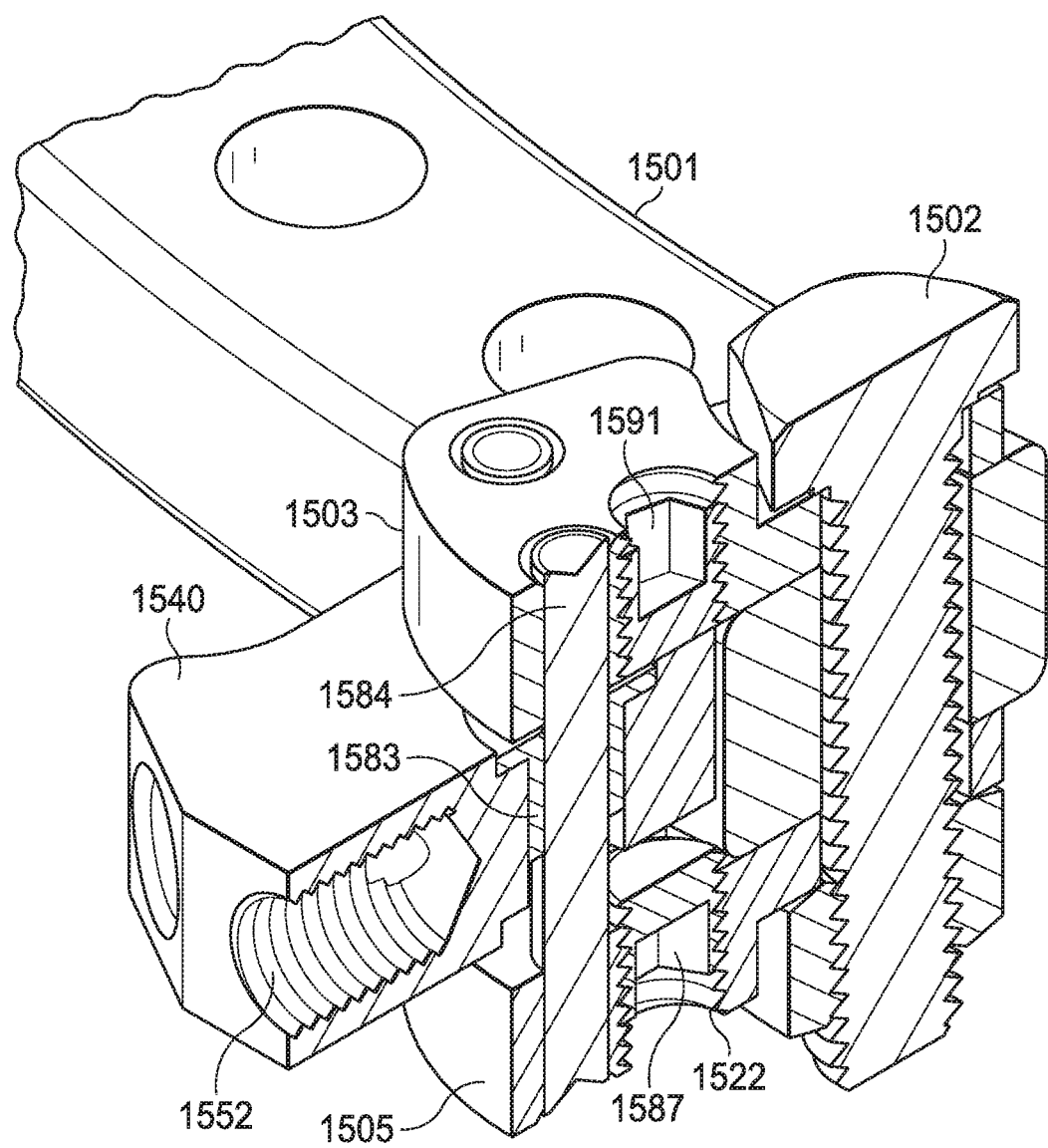
FIG. 15F illustrates a cross-sectional perspective view of an embodiment of an alternative dynamization device mounted to a ring fixator.

A cross-sectional and perspective view of the complete assembly of the dynamization tab 1500 as connected to a external fixation ring 1501 by a connecting bolt 1502 is found in FIG. 15F. As shown in FIG. 15G, when the dynamization tab 1500 is mounted onto an external fixation ring 1501, the superior member 1504 and the inferior member 1505 become rigidly connected to the external fixation ring 1501 by the connecting bolt 1502, thus locking the positions of the superior member 1504 and the inferior member 1505 with respect to each other. In this arrangement, the amount of longitudinal movement of the strut connector 1540 can be controlled by driving or withdrawing the first and second set screws (1587, 1591). As shown in FIG. 15G, the first set screw 1587 has been withdrawn from the set screw bore 1522 of the inferior member 1505, thus providing a limited amount of translational movement (i.e., dynamization) to the strut connector 1540 with respect to the external fixation ring 1501. The degree of translational movement or dynamization of the strut connector 1540 can be controlled with a great deal of accuracy based on the amount of turns that are applied to the first and second set screws (1587, 1591).

An alternate embodiment of a dynamization device is depicted in FIG. 16. In FIG. 16, a dynamization tab 1600 is connected to an external fixation ring 1601 by a connecting bolt 1602. The dynamization tab 1600 includes a ring connector 1603, a strut connector 1640, and a biasing mechanism 1670. Like the previous embodiments, the dynamization tab 1600 may also include one or more strut apertures 1653 to receive a strut fastener of an external fixation strut (not shown). Also shown in FIG. 16 is a locking screw aperture 1659, which can be used to secure the one or more of the external fixation struts to the dynamization tab 1600. The locking screw aperture 1659 may be configured to accept a locking screw, which may be configured to secure the strut fasteners when they are placed inside of the strut apertures 1653. The locking screw aperture 1659 may be threaded to accept a correspondingly threaded locking screw. The locking screw may secure the strut fasteners through contact with the strut fasteners in a manner which prevents the movement of the strut fasteners with respect to the strut apertures 1653 when the locking screw is in place. Several examples of such a locking arrangement are found in U.S. Pat. No. 9,295,493, hereby incorporated by reference into this patent.

An alternate embodiment of a dynamization tab, illustrated in FIGS. 16A-E, may provide dynamization through the use of a hinging mechanism comprising multiple pins. In this embodiment, dynamization may be both axial (along the vertical axis) and rotational (about the transverse axis). Biasing force is provided through the use of an elastomeric material, resilient device, or spring, placed between the strut connector and the ring connector. The arrangement of the hinging mechanism, i.e. a four-bar linkage parallelogram comprising a revolute joint at each junction, allows for the quasi-linear movement and resulting dynamization described above. Further, this arrangement provides for a stable structure that limits the motion to two degrees of movement, i.e. mostly translational and some limited rotational movement, while also providing that the hinges are not subject to stick slip if the external load is not perfectly axial.

Depicted in FIG. 16, this embodiment of a dynamization tab 1600 is connected to an external fixation ring 1601 by a connecting bolt 1602. The dynamization tab includes a ring connector 1603 and a strut connector 1640 and, like the previous embodiments, the dynamization tab 1600 may also include one or more strut apertures 1653 to receive a strut fastener of an external fixation strut (not shown). Also shown in FIG. 16 is a locking screw aperture 1659, which can be used to secure the one or more of the external fixation struts to the dynamization tab 1600. The locking screw aperture 1659 may be configured to accept a locking screw, which may be configured to secure the strut fasteners when they are placed inside of the strut apertures 1653. As shown in FIG. 15, the locking screw aperture 1659 may be threaded to accept a correspondingly threaded locking screw. The locking screw may secure the strut fasteners through contact with the strut fasteners in a manner which prevents the movement of the strut fasteners with respect to the strut apertures 1653 when the locking screw is in place. Several examples of such a locking arrangement are found in U.S. Pat. No. 9,295,493, hereby incorporated by reference into this patent.

Figure 16A:
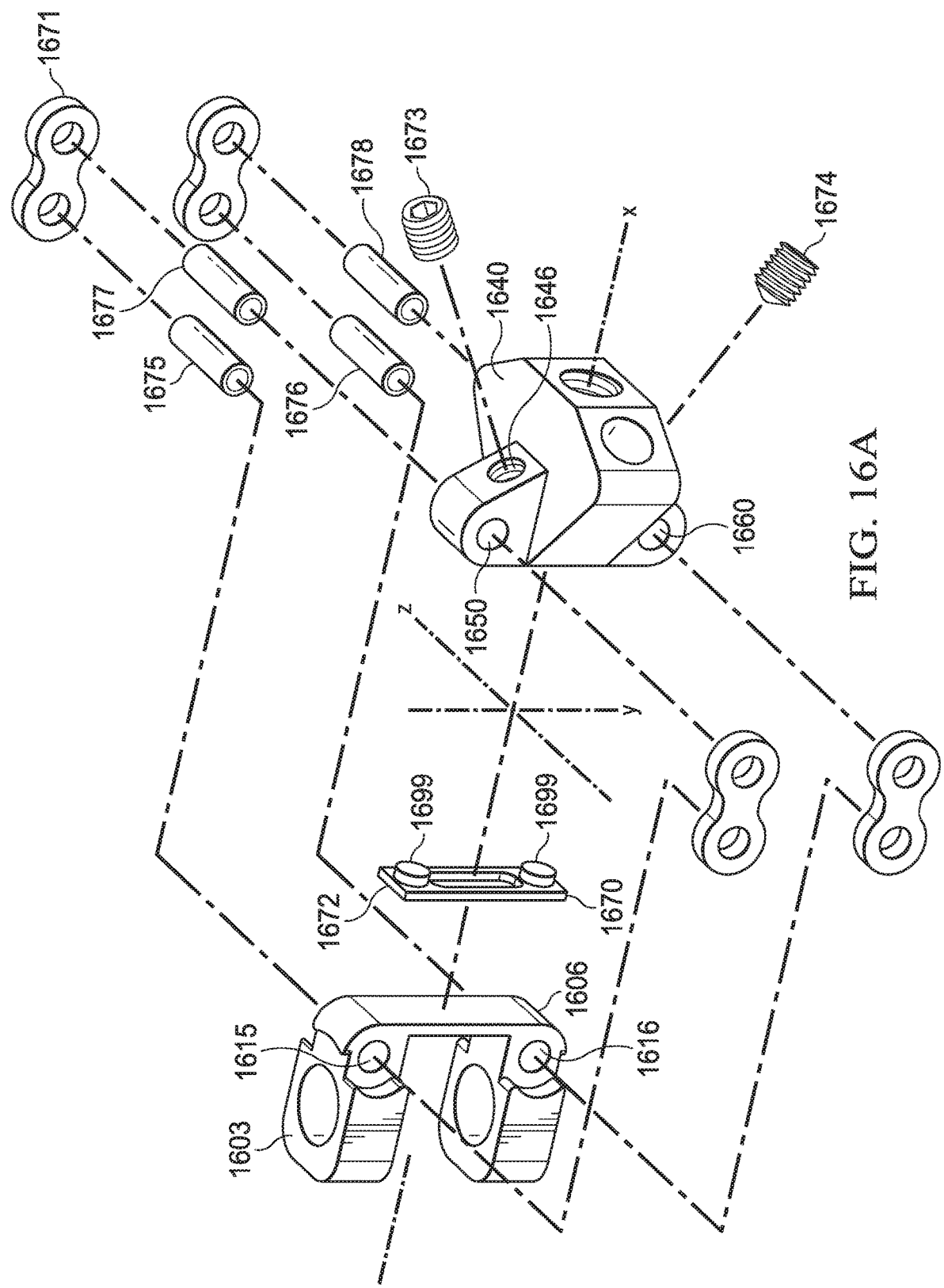
FIG. 16A illustrates an exploded perspective view of an embodiment of an alternative dynamization device.

FIG. 16A is an exploded perspective view of an embodiment of a dynamization tab 1600 with a longitudinal axis X, a vertical axis Y, a transverse axis Z, and may comprise a ring connector 1603, a strut connector 1640, and a biasing mechanism 1670. The biasing mechanism 1670 may comprise a hinging mechanism 1671, an elastic element 1672, a first set screw 1673, and a second set screw 1674. The hinging mechanism 1671 is positioned such that it allows for the strut connector 1640 to be rotationally displaced along the longitudinal axis Y of the dynamization tab 1600.

Figure 16B:
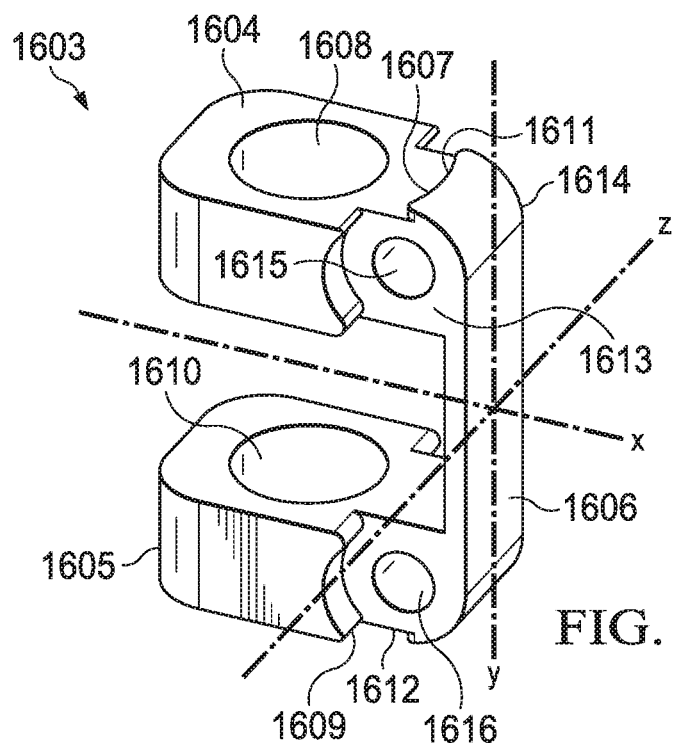
FIG. 16B illustrates a perspective view of a ring connector of an alternative dynamization device.

The ring connector 1603, illustrated in FIG. 16B, may comprise a first stabilizer 1604, a second stabilizer 1605, and a third stabilizer 1606. The first stabilizer 1604 may have a distal end 1609 and be positioned superior and parallel to the longitudinal axis X of the dynamization tab 1600. The first stabilizer 1604 may comprise a ring connector bore 1608, which may be configured to accept a connecting bolt 1602 (not shown). The second stabilizer 1605 may have a distal end 1609 and be positioned inferior and parallel to the longitudinal axis X of the dynamization tab 1600 and may comprise a ring connector bore 1610. The third stabilizer 1606 has a superior end 1611, an inferior end 1612, a first surface 1613, and a second surface 1614, and may be positioned parallel to the vertical axis Y of the dynamization tab 1600 in a manner such that the superior end 1611 is in contact with the distal end of the first stabilizer 1607 and the inferior end 1612 is in contact with the distal end of the second stabilizer 1609. The third stabilizer 1606 may further comprise a first pin bore 1615 and a second pin bore 1616, which may each be positioned parallel to the longitudinal axis X of the dynamization tab 1600 and extend from the first surface of the third stabilizer 1613 to the second surface of the third stabilizer 1614. The first pin bore 1615 and the second pin bore 1616 may be configured to accept the first pin and the second pin (elements 1675 and 1676 of FIG. 16E), respectively.

Figure 16C:
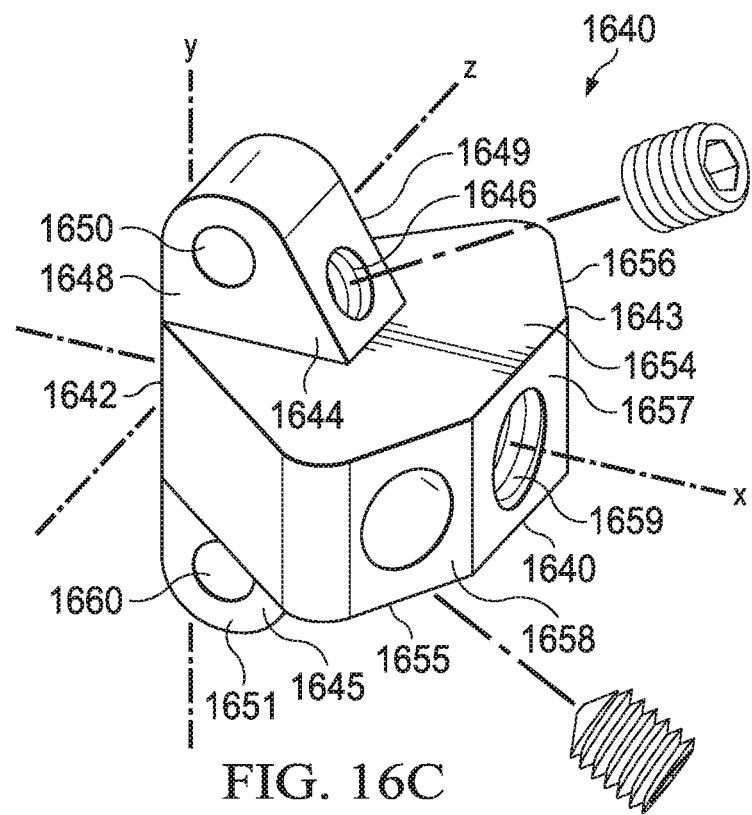
FIG. 16C illustrates a perspective view of a strut connector of an alternative dynamization device.

FIG. 16C illustrates a strut connector 1640, which may have a distal end 1641, a proximal end 1642, and be positioned along the longitudinal axis X of the dynamization tab 1600. The strut connector 1640 may further comprise a head 1643, a first knob 1644, a second knob 1645, a first set screw bore 1646, and a second set screw bore 1647. The head of the strut connector 1643 may have a top surface 1654 and a bottom surface 1655 and may further comprise a first distal-facing surface 1656, a second distal-facing surface 1657, and a third distal-facing surface 1658. The first and third distal facing surfaces (1656, 1658), may additionally comprise a strut aperture 1653. The strut aperture 1653 may be configured to secure the dynamization tab 1600 to an external fixation strut.

The first knob 1644, according to some embodiments, may be positioned parallel to the vertical axis Y of the dynamization tab 1600 in a manner such that it is in contact with top surface 1654 of the head of the strut connector 1643. The first knob 1644 may comprise a first surface 1648, a second surface 1649, and a third pin bore 1650. The third pin bore 1650 may be positioned parallel to the transverse axis Z of the dynamization tab 1600 and may extend from the first surface of the first knob 1648 to the second surface of the first knob 1649 and may be configured to accept a third pin (element 1677 of FIG. 16E). The second knob 1645, according to some embodiments, may be positioned parallel to the vertical axis Y of the dynamization tab 1600 in a manner such that it is in contact with the bottom surface of the head of the strut connector 1655. The second knob 1645 may comprise a first surface 1651, a second surface 1652, and a fourth pin bore 1660. The fourth pin bore 1660 may be positioned parallel to the transverse axis Z of the dynamization tab 1600 and may extend from the first surface of the second knob 1651 to the second surface of the second knob 1652 and may be configured to accept a fourth pin (element 1678 of FIG. 16E).

Figure 16D:
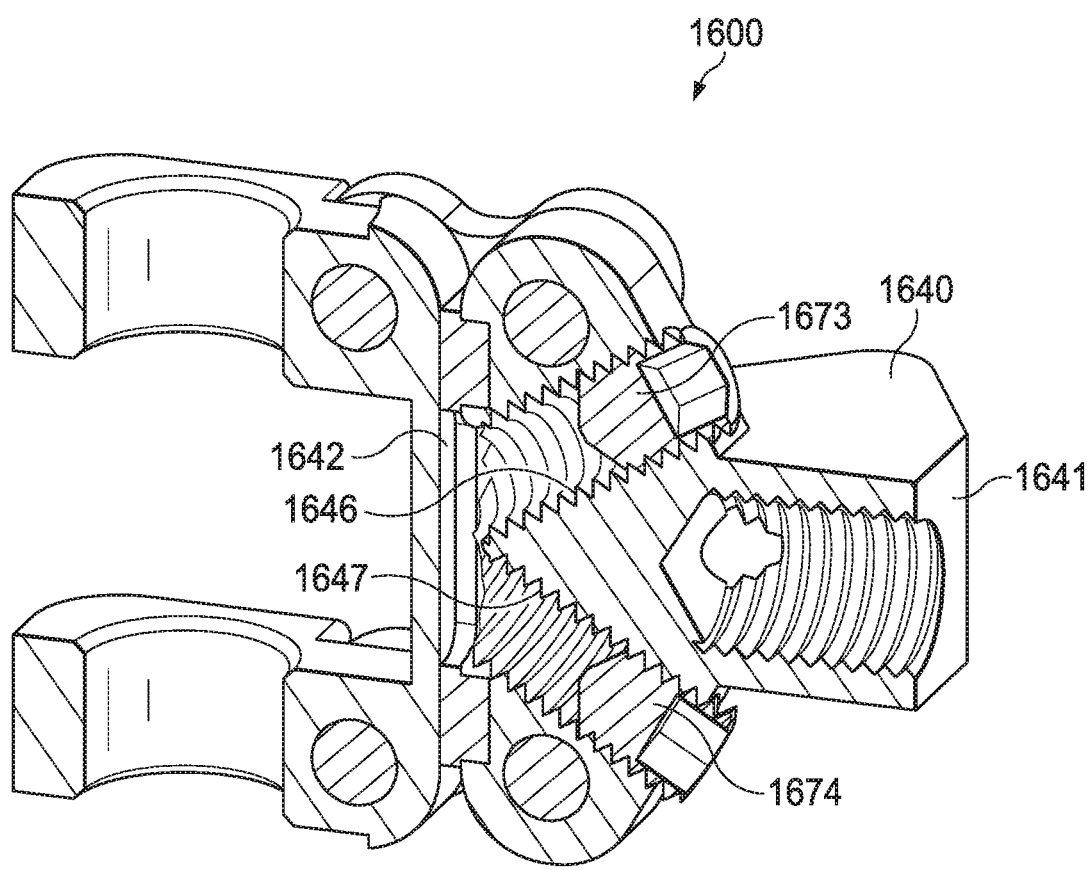
FIG. 16D illustrates a cross-sectional view of an alternative dynamization device.

A perspective and cross-sectional view of the dynamization tab 1600 is illustrated in FIG. 16D. In FIG. 16D, the first set screw bore 1646 of the strut connector 1640 may extend in an angular fashion from the proximal end 1642 of the strut connector 1640 to the distal end 1641 of the strut connector 1640 and be configured to accept a first set screw 1673. The second set screw bore 1647 may extend in an angular fashion from the proximal end 1642 of the strut connector 1640 to the distal end 1641 of the strut connector 1640 and be configured to accept a second set screw 1674.

Figure 16E:
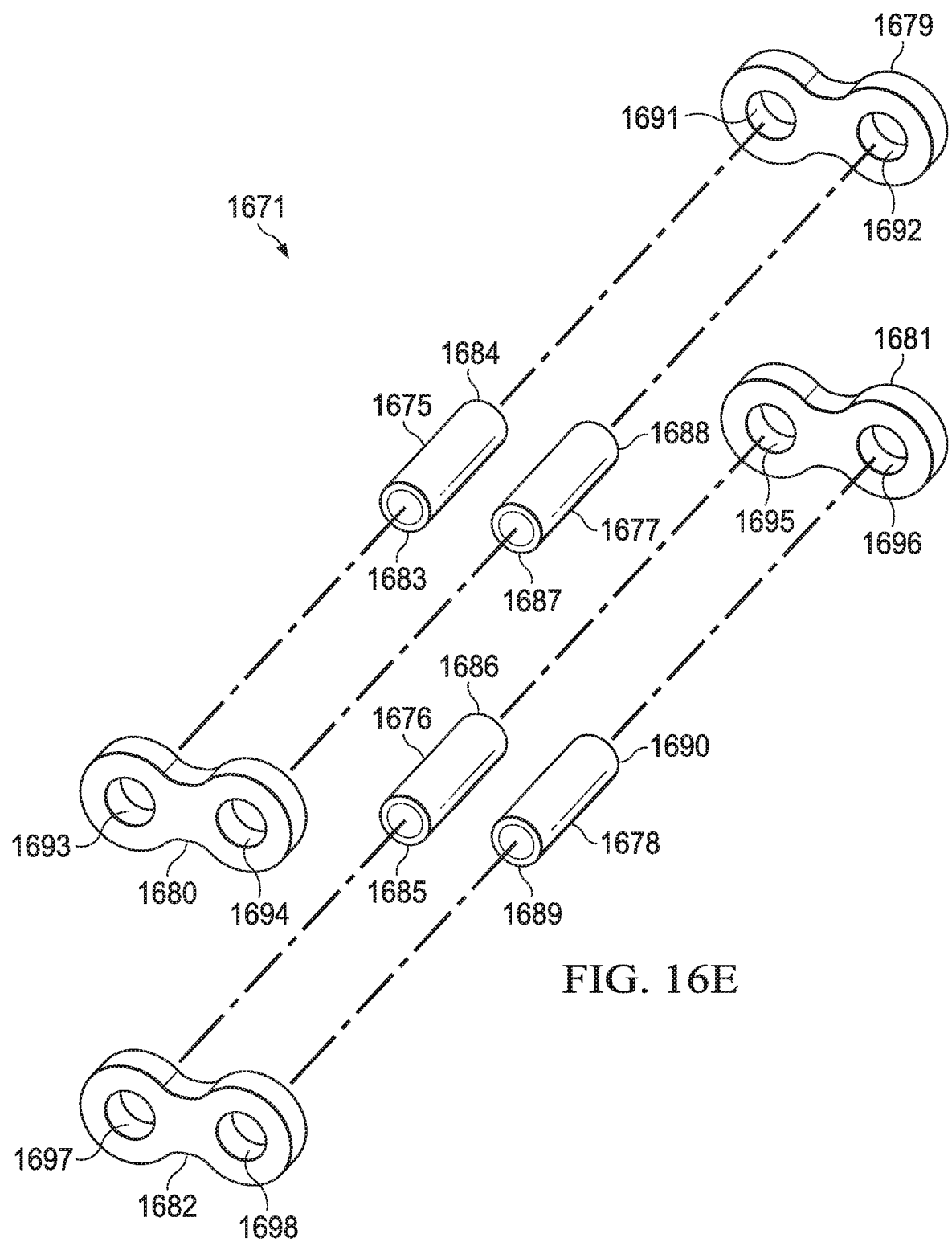
FIG. 16E illustrates an exploded view of a hinging mechanism of an embodiment of an alternative dynamization device.

In the embodiment of FIG. 16E, the hinging mechanism 1671 comprises a first pin 1675, a second pin 1676, a third pin 1677, a fourth pin 1678, a first link 1679, a second link 1680, a third link 1681, and fourth link 1682. The first pin 1675 comprises a first end 1683 and a second end 1684, the second pin 1676 comprises a first end 1685 and a second end 1686, the third pin 1677 comprises a first end 1687 and a second end 1688, and the fourth pin 1678 comprises a first end 1689 and a second end 1690. The first link 1679 comprises a first eye 1691 and a second eye 1692 and is positioned such that the first eye 1691 accepts and secures second end of the first pin 1684 and the second eye 1692 accepts and secures second end of the third pin 1688. The second link 1680 comprises a first eye 1693 and a second eye 1694 and is positioned such that the first eye 1693 accepts and secures the first end of the first pin 1683 and the second eye 1694 accepts and secures the first end of the third pin 1687. The third link 1681 comprises a first eye 1695 and a second eye 1696 and is positioned such that the first eye 1695 accepts and secures the second end of the second pin 1686 and the second eye 1696 accepts and secures the second end of the fourth pin 1690. The fourth link 1682 comprises a first eye 1697 and a second eye 1698 and is positioned such that the first eye 1697 accepts and secures the first end of the second pin 1685 and the second eye 1698 accepts and secures the first end of the fourth pin 1689.

As illustrated in FIG. 16A, the first pin 1675 is positioned such that it traverses the first pin bore of the third stabilizer of the ring connector 1615. The second pin 1676 is positioned such that it traverses the second pin bore of the third stabilizer of the ring connector 1616. The third pin 1677 is positioned such that it traverses the third pin bore of the first knob of the strut connector 1650 and the fourth pin 1678 is positioned such that it traverses the fourth pin bore 1660 of the second knob of the strut connector.

The biasing mechanism 1670 may further comprise an elastic element 1672. The elastic element 1672 may comprise an elastomeric material, resilient device, or a spring and be positioned such that it is in contact with the third stabilizer 1606 of the ring connector and may be configured to provide a biasing force, when the strut connector 1640 is displaced along the longitudinal axis Y of the dynamization tab 1600, sufficient to return the strut connector 1640 to its original position. According to some embodiments, the biasing mechanism 1670 may also comprise a first set screw 1673 and a second set screw 1674, which may be configured to traverse the first set screw bore 1646 and the second set screw bore (element 1647 of FIG. 16D), respectively. Each of the first set screw 1673 and the second set screw 1674 may be configured such that as the screw is tightened, rotational movement of the strut connector 1640 about the transverse axis Z of the dynamization tab 1600 may be limited. According to some embodiments, each of the first set screw 1673 and the second set screw 1674 may be in contact with the elastic element 1672. This contact may be through direct contact between the set screws 1673, 1674 and the elastic element 1672 or, according to some embodiments, through contact between the set screws 1673, 1674 and apertures 1699 located on the elastic element 1672. In these embodiments, as the strut connector 1640 is displaced along the longitudinal axis Y, the contact between the set screws 1673, 1674 and the apertures of the elastic element 1699 will allow for flexibility, i.e. freedom to be displaced, as well as an appropriate biasing force to return the strut connector 1640 to its original position. The first and second set screws (1673, 1674) may include a fitting for receiving a set screw driver, such as a hexagonal receptacle, a Phillips-head receptacle, a flat-head receptacle, a star-wrench receptacle, or any other suitable driver that would be understood in the art. By adjusting the relative positions of the first and second set screws (1673, 1674) within the set screw bores (1646 and 1647 of FIG. 16D), the amount of dynamization provided by this device can be controlled.

Figure 16F:
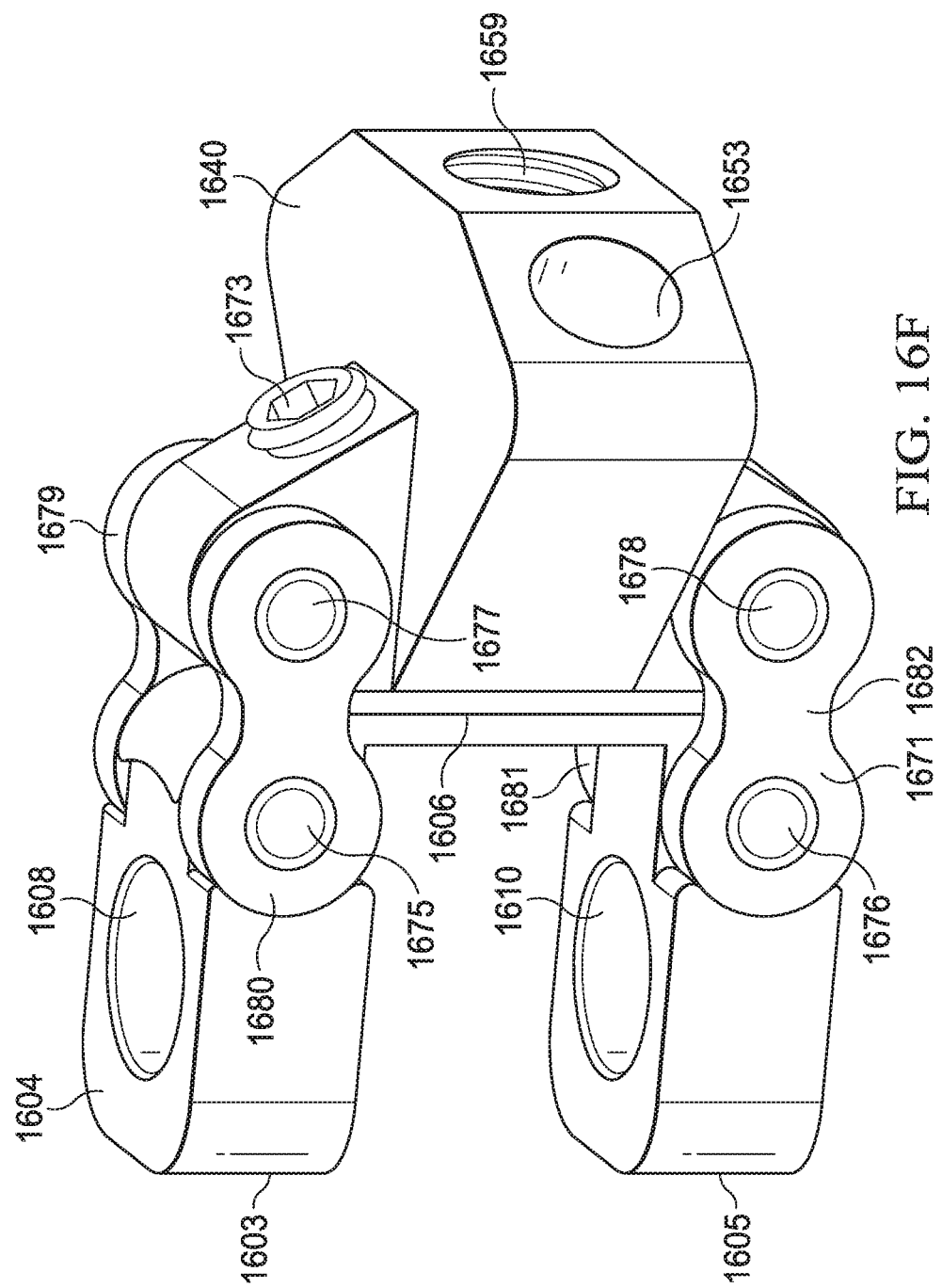
FIG. 16F illustrates a perspective view of an embodiment of an alternative dynamization device mounted to a ring fixator.

A side and perspective view of the complete assembly of the dynamization tab 1600 is found in FIG. 16F. The complete assembly embodied by FIG. 16F comprises a ring connector 1603 including a first stabilizer 1604, a second stabilizer 1506, and a third stabilizer 1606, with each of the first stabilizer 1604 and the second stabilizer 1605 comprising a ring connector bore (1608, 1610, respectively). The ring connector bores 1608, 1610 may be used to secure the dynamization tab 1600 to an external fixation ring (not shown) using a connecting bolt (not shown). The dynamization tab 1600 further comprises a strut connector 1640 including a strut aperture 1653 and a locking-screw aperture 1659, each described in detail above. The ring connector 1603 and strut connector 1640 are adjoined by the hinging mechanism 1671. Shown in FIG. 16F, the complete assembly of the hinging mechanism 1671 comprises the first link 1679, the second link 1680, the third link 1681, the fourth link 1682, the first pin 1675, the second pin 1676, the third pin 1677, and the fourth pin 1678, arranged in a four-barlinkage parallelogram which allows for the quasi-linear movement of the strut connector 1640 under loading.

Figure 16G:
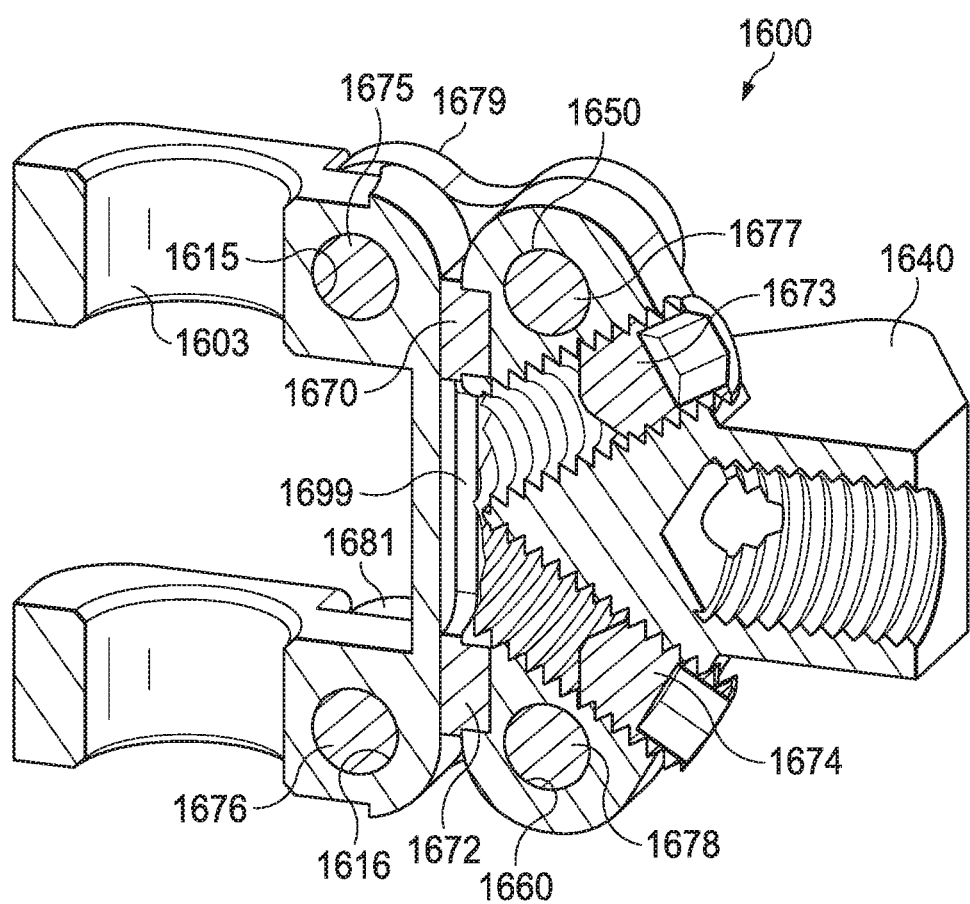
FIG. 16G illustrates another cross-sectional view of an alternative dynamization device.

A cross-sectional and perspective view of the complete assembly of the dynamization tab 1600 is found in FIG. 16G. As illustrated, the dynamization tab comprises a ring connector 1603 and a strut connector 1640, described in detail above. Further, FIG. 16G provides a cross-sectional and perspective view of the biasing mechanism 1670, particularly the parallelogram arrangement of the pins and links, i.e. first pin 1675 as it traverses the first link 1679 and the first pin bore of the ring connector 1615, the second pin 1676 as it traverses the third link 1681 and the second pin bore of the ring connector 1616, the third pin 1677 as it traverses the first link 1679 and the third pin bore of the strut connector 1650, and the fourth pin 1678 as it traverses the third link 1681 and the fourth pin bore of the strut connector 1660. This arrangement works as described above to allow for the quasi-linear movement of the strut connector 1640 under loading. Further, FIG. 16G illustrates the arrangement of the first set screw 1673 and the second set screw 1672 within the strut connector 1640. As shown, each of the set screws 1673, 1672 are withdrawn and are not in contact with the elastic member 1672. As described above, as the set screws 1673, 1672 are driven within the strut connector 1640 and come into contact with an aperture of the elastic member 1699, the degree of dynamization allowed in the dynamization tab 1600 is decreased.

Figure 17:
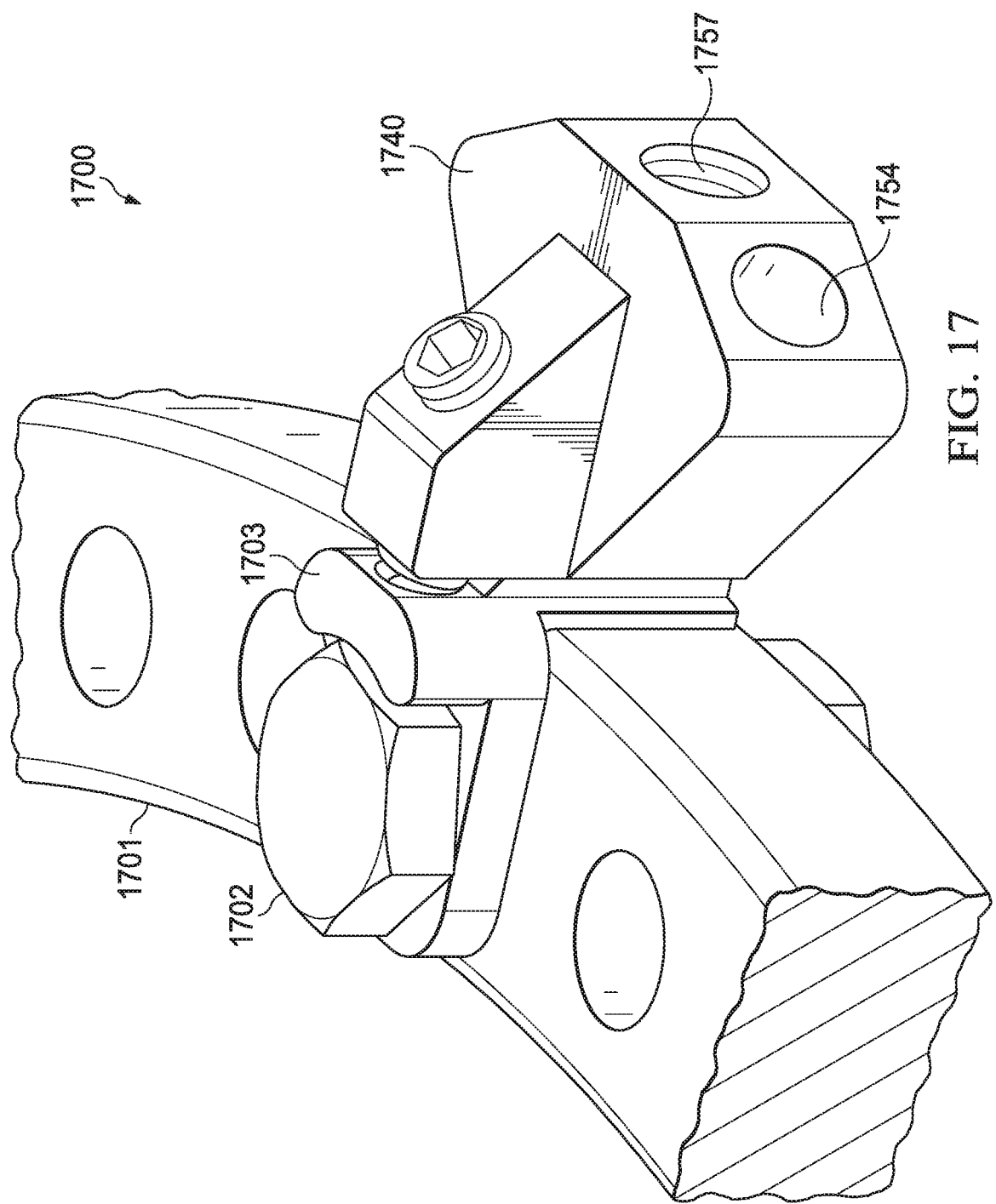
FIG. 17 illustrates a perspective view of an embodiment of an alternative dynamization device mounted to a ring fixator.

An alternate embodiment of a dynamization device is depicted in FIG. 17. In FIG. 17, a dynamization tab 1700 is connected to an external fixation ring 1701 by a connecting bolt 1702. The dynamization tab includes a ring connector 1703 and a strut connector 1740. Like the previous embodiments, the dynamization tab 1700 may also include one or more strut apertures 1754 to receive a strut fastener of an external fixation strut (not shown). Also shown in FIG. 17 is a locking screw aperture 1757, which can be used to secure the one or more of the external fixation struts to the dynamization tab 1700. The locking screw aperture 1757 may be configured to accept a locking screw, which may be configured to secure the strut fasteners when they are placed inside of the strut apertures 1754. The locking screw aperture 1757 may be threaded to accept a correspondingly threaded locking screw. The locking screw may secure the strut fasteners through contact with the strut fasteners in a manner which prevents the movement of the strut fasteners with respect to the strut apertures 1754 when the locking screw is in place. Several examples of such a locking arrangement are found in U.S. Pat. No. 9,295,493, hereby incorporated by reference into this patent.

Figure 17A:
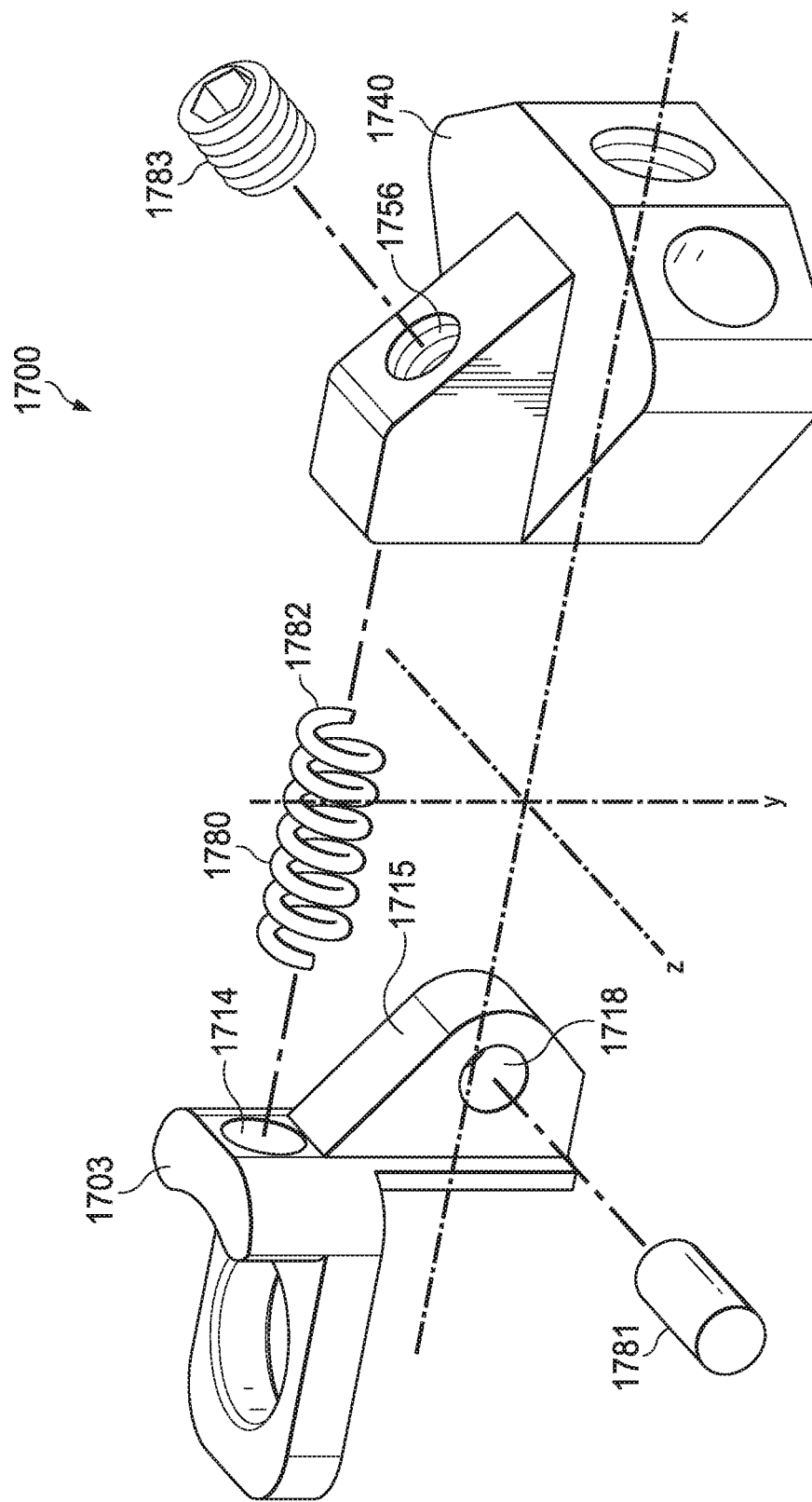
FIG. 17A illustrates an exploded perspective view of an embodiment of an alternative dynamization device.

Detailed illustrations of the dynamization device 1700, providing for rotational displacement of the strut connector to achieve dynamization, are found in FIGS. 17A-E. Illustrated in FIG. 17A is an exploded perspective view of a dynamization tab 1700 with a longitudinal axis X, a vertical axis Y, and a transverse axis Z, and is comprised of a ring connector 1703, a strut connector 1740, and a biasing mechanism 1780. Also shown in FIG. 17A are a hinge pin 1781 and a set screw 1783.

Figure 17B:
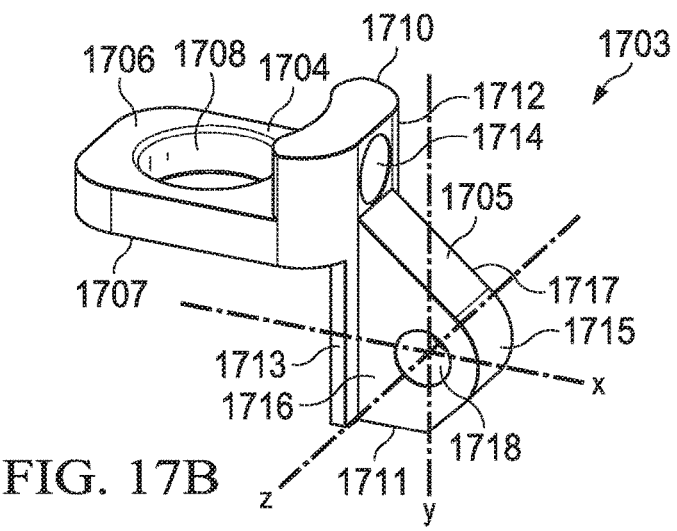
FIG. 17B illustrates a perspective view of a ring connector of an alternative dynamization device.

The ring connector 1703, illustrated in FIG. 17B, comprises a first stabilizer 1704 and a second stabilizer 1705. The first stabilizer 1704, according to some embodiments, is positioned parallel to the longitudinal axis X of the dynamization tab 1700 and comprises a top surface 1706, a bottom surface 1707, and a ring connector bore 1708 extending from the top surface 1706 to the bottom surface 1707. The ring connector bore 1708 may be configured to accept a connecting bolt (not shown) which may secure the dynamization tab 1700 to an external fixation ring. The second stabilizer 1705 may have a superior end 1710 and an inferior end 1711 and may be positioned parallel to the vertical axis Y of the dynamization tab 1700. The second stabilizer 1705 may further comprise a distal-facing surface 1712, a proximal-facing surface 1713, an elastic member recess 1714, and a ring connector knob 1715. The elastic member recess 1714, according to some embodiments, comprises a partial bore extending from the distal-facing surface of the second stabilizer 1712 towards the proximal-facing surface of the second stabilizer 1713 and may be configured to accept an elastic member (for example, element 1782 of FIG. 17A). The ring connector knob 1715 may have a first surface 1716 and a second surface 1717 and may further comprise a hinge pin bore 1718 extending from the first surface 1716 to the second surface 1717.

Figure 17C:
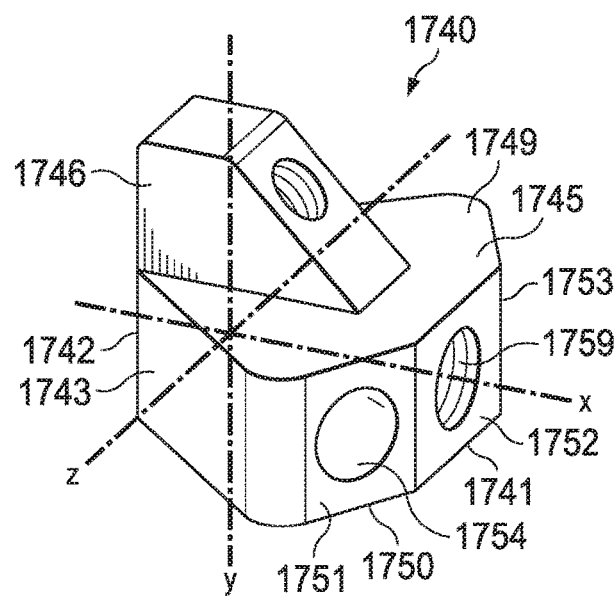
FIG. 17C illustrates a perspective view of a strut connector of an alternative dynamization device.

Illustrated in FIG. 17C, the strut connector 1740 has a distal end 1741 and a proximal end 1742 and be positioned along the longitudinal axis X of the dynamization tab 1700. The strut connector 1740 may further comprise a head 1745 and a strut connector knob 1746. The head of the strut connector 1745 may have a top surface 1749 and a bottom surface 1750 and may further comprise a first distal-facing surface 1751, a second distal-facing surface 1752, and a third distal-facing surface 1753. Each of the first distal-facing surface 1751 and the third distal-facing surface 1753 may comprise a strut aperture 1754, which may be a partial bore extending from the distal end of the strut connector 1741 to the proximal end of the strut connector 1742 and may be configured to secure the dynamization tab 1700 to a strut. Also shown in FIG. 17C is a locking screw aperture 1759, which can be used to secure the one or more of the external fixation struts to the dynamization tab 1700. The locking screw aperture 1759 may be configured to accept a locking screw, which may be configured to secure the strut fasteners when they are placed inside of the strut apertures 1754. The locking screw aperture 1759 may be threaded to accept a correspondingly threaded locking screw. The locking screw may secure the strut fasteners through contact with the strut fasteners in a manner which prevents the movement of the strut fasteners with respect to the strut apertures 1754 when the locking screw is in place. Several examples of such a locking arrangement are found in U.S. Pat. No. 9,295,493, hereby incorporated by reference into this patent.

Figure 17D:
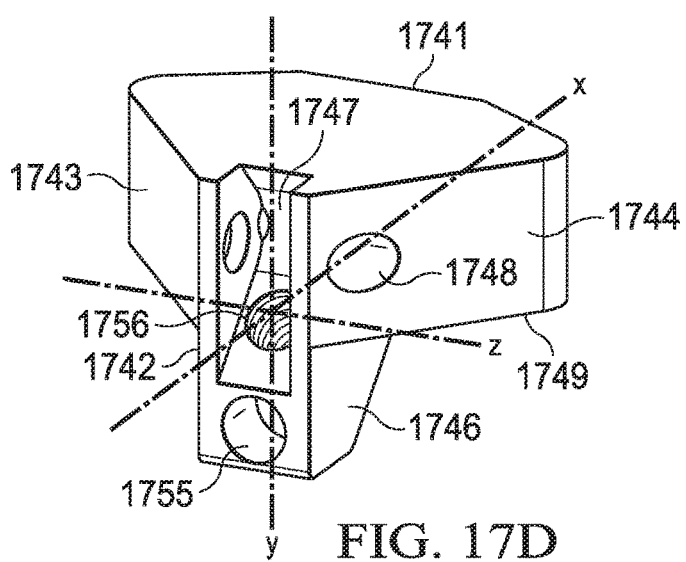
FIG. 17D illustrates another perspective view of a strut connector of an alternative dynamization device.

In the embodiment of FIG. 17D, the strut connector knob 1746 is positioned parallel to the vertical axis Y of the dynamization tab 1700 in a manner such that it is in contact with the top surface of the head 1749. The strut connector knob 1746 may further comprise a strut connector recess 1747, a hinge pin bore 1748, a elastic member recess 1755, and a set screw bore 1756. The elastic member recess 1755 may be a partial bore extending from the proximal end of the strut connector 1742 towards the distal end of the strut connector 1741 and may be configured to accept the elastic member (element 1782 of FIG. 17A). The set screw bore 1756 may extend in an angular fashion from the proximal end of the strut connector 1742 to the distal end of the strut connector 1741 and may be configured to accept a set screw (element 1783 of FIG. 17A). The strut connector recess 1747 is positioned at the proximal end of the strut connector 1742 and is configured to accept at least a portion of the ring connector knob 1715 of FIG. 17B. The hinge pin bore 1748 extends from the first surface of the strut connector 1743 to the second surface of the strut connector 1744.

Referring now back to FIG. 17A, the biasing mechanism 1780 may comprise the hinge pin 1781, the elastic member 1782, and the set screw 1783. The hinge pin 1781 may be positioned along the transverse axis Z of the dynamization tab 1700 in a manner such that it traverses the hinge pin bore of the strut connector (element 1748 of FIG. 17D) and the hinge pin bore of the ring connector 1718 and allows for the rotational displacement of the strut connector 1740 about the transverse axis Z of the dynamization tab 1700. The elastic element 1782 may comprise an elastomeric material, resilient device, or a spring and may be positioned superior and parallel to the longitudinal axis X of the dynamization tab 1700 in a manner such that it is in contact with the elastic element recess of the ring connector 1714 and the elastic element recess of the strut connector (element 1755 of FIG. 17D). The elastic member 1782 may be configured to apply a biasing force, as the strut connector 1740 is pivoted about the transverse axis Z of the dynamization tab 1700, sufficient to return the strut connector 1740 to its original position. The set screw 1783 may be configured to traverse the set screw bore of the strut connector 1756 and be in contact with the ring connector knob 1715 in a manner such that, as the set screw 1783 is tightened, rotational movement of the strut connector 1740 about the transverse axis Z is limited. The set screw 1783 may include a fitting for receiving a set screwdriver, such as a hexagonal receptacle, a Phillips-head receptacle, a flat-head receptacle, a star-wrench receptacle, or any other suitable driver that would be understood in the art. By adjusting the relative position of the set screw 1783 within the set screw bores 1756, the amount of dynamization provided by this device can be controlled. This generally may be done by driving or withdrawing the set screw 1783.

Figure 17E:
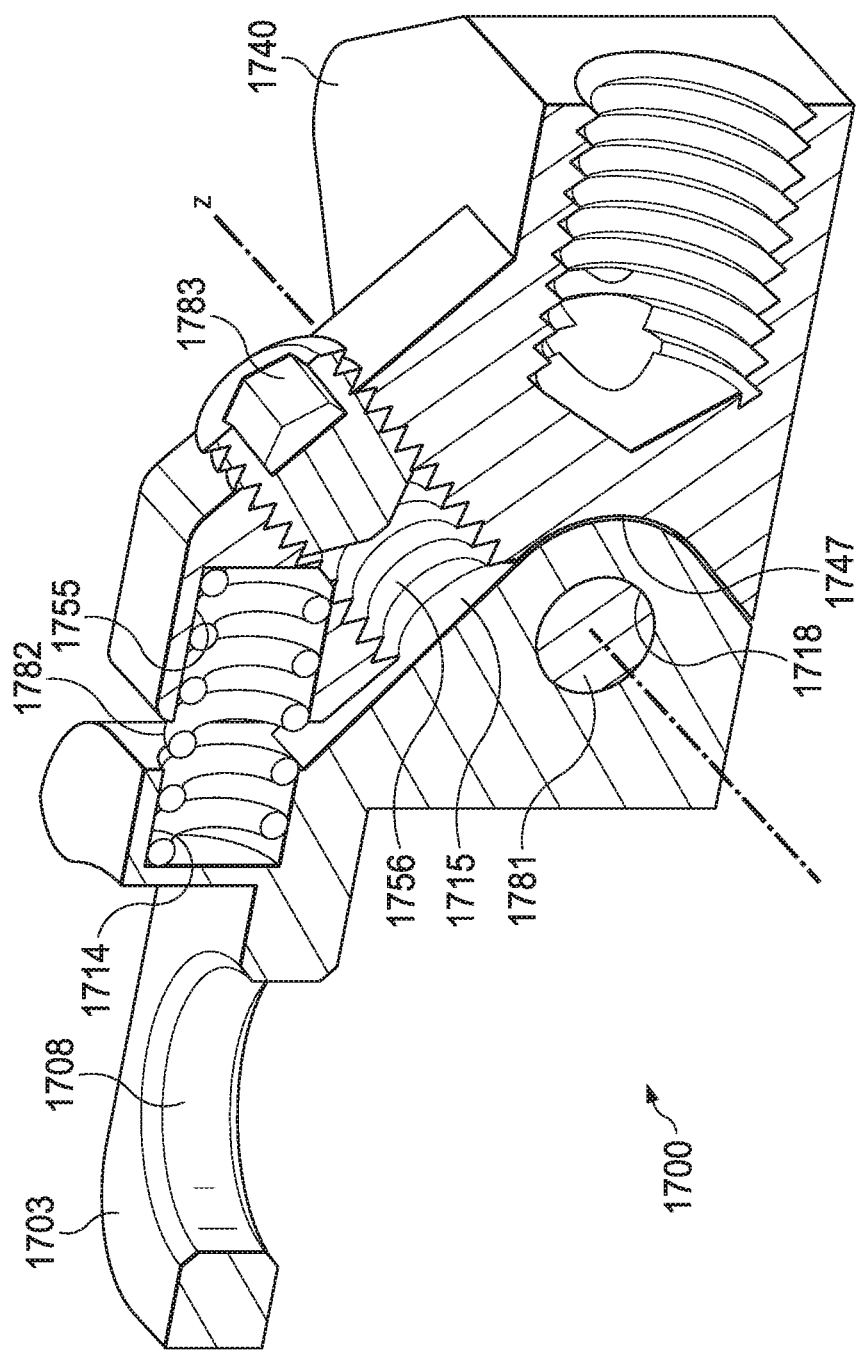
FIG. 17E illustrates a cross-sectional view of an alternative dynamization device.

A cross-sectional and perspective view of the complete assembly of the dynamization tab 1700 is depicted in FIG. 17E. As illustrated, the dynamization tab 1700 comprises a ring connector 1703 and a strut connector 1740. The ring connector 1703 includes a ring connector bore 1708, which is used in conjunction with a connecting bolt (not shown) to secure the dynamization tab 1700 to an external fixation ring (not shown) in the manner described above. Further, the hinge pin 1781 can be seen as it traverses the hinge pin bore of the strut connector (not shown) and the hinge pin bore of the ring connector 1718. This arrangement, combined with the complimentary shape of the ring connector knob 1715 with the strut connector recess 1747, allows for the rotational movement of the strut connector 1740 about the transverse axis Z of the dynamization tab 1700. As shown, the elastic member 1782 is mated within the elastic member recess of the ring connector 1814 and the elastic member recess of the strut connector 1755. Preferably, as shown in FIG. 17G, the ring connector 1703 and the strut connector 1740 will be configured such that, when fully assembled, there is space between the two elements, allowing for the pivotal movement of the strut connector 1740 with respect to the ring connector 1703. As the strut connector is rotationally displaced around the transverse axis Z of the dynamization tab 1700, the elastic member 1782 provides a biasing force sufficient to return the strut connector 1740 to its original position. The set screw 1783 is depicted as partially withdrawn in the set screw bore 1756, thus allowing pivotal movement of the strut connector 1740 with respect to the ring connector 1703. As the set screw 1783 is driven in to the set screw bore 1756, it will become increasingly engaged in the space between the ring connector 1703 and the strut connector 1740 in a manner such that the set screw 1756 comes in contact with the ring connector knob 1715 as the strut connector 1740 is displaced. This arrangement provides control over the amount of dynamization permitted by the device. For example, as the set screw 1783 is increasingly driven, the amount of rotation allowed by the strut connector 1740 before the set screw 1783 contacts the ring connector knob 1715 decreases, thus limiting the amount of dynamization. Similarly, as the set screw 1783 is backed out of the set screw bore 1756, the amount of rotation allowed by the strut connector 1740 before the set screw 1783 contacts the ring connector knob 1715 increases, thus increasing the amount of dynamization.

Figure 18:
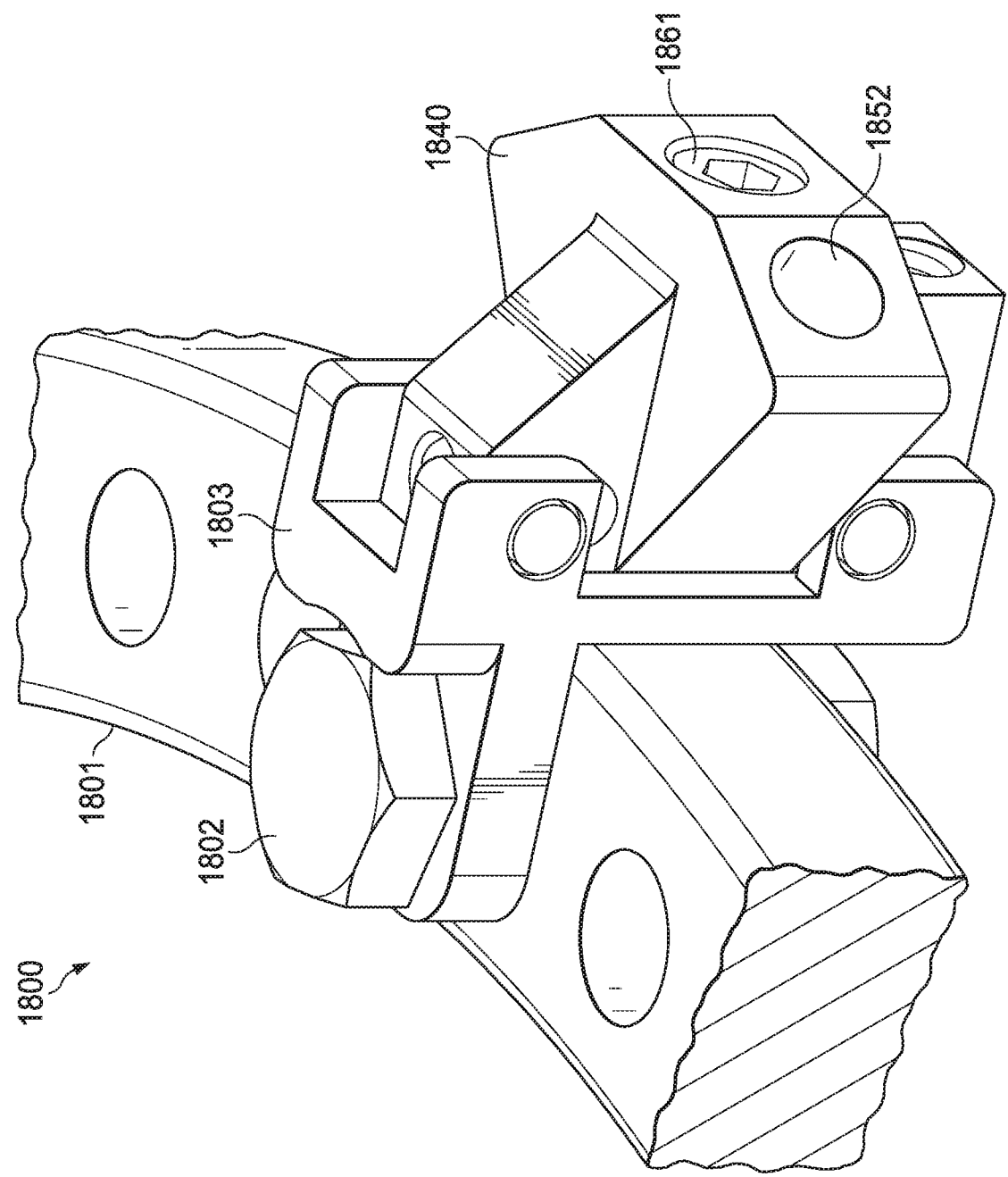
FIG. 18 illustrates a perspective view of an embodiment of an alternative dynamization device mounted to a ring fixator.

An alternate embodiment of a dynamization device is depicted in FIG. 18. In FIG. 18, a dynamization tab 1800 is connected to an external fixation ring 1801 by a connecting bolt 1802. The dynamization tab includes a ring connector 1803 and a strut connector 1840. Like the previous embodiments, the dynamization tab 1800 may also include one or more strut apertures 1852 to receive a strut fastener of an external fixation strut (not shown). Also shown in FIG. 18 is a locking screw aperture 1861, which can be used to secure the one or more of the external fixation struts to the dynamization tab 1800. The locking screw aperture 1861 may be configured to accept a locking screw, which may be configured to secure the strut fasteners when they are placed inside of the strut apertures 1852. As shown in FIG. 18, the locking screw aperture 1861 may be threaded to accept a correspondingly threaded locking screw. The locking screw may secure the strut fasteners through contact with the strut fasteners in a manner which prevents the movement of the strut fasteners with respect to the strut apertures 1852 when the locking screw is in place. Several examples of such a locking arrangement are found in U.S. Pat. No. 9,295,493, hereby incorporated by reference into this patent. Detailed illustrations of the dynamization device 1800, providing for linear displacement of the strut connector to achieve dynamization, are found in FIGS. 18A-D. Specifically, this embodiment provides for dynamization through axial displacement along the vertical axis while additionally protecting the biasing mechanisms by placing them internal to the strut connector.

Figure 18A:
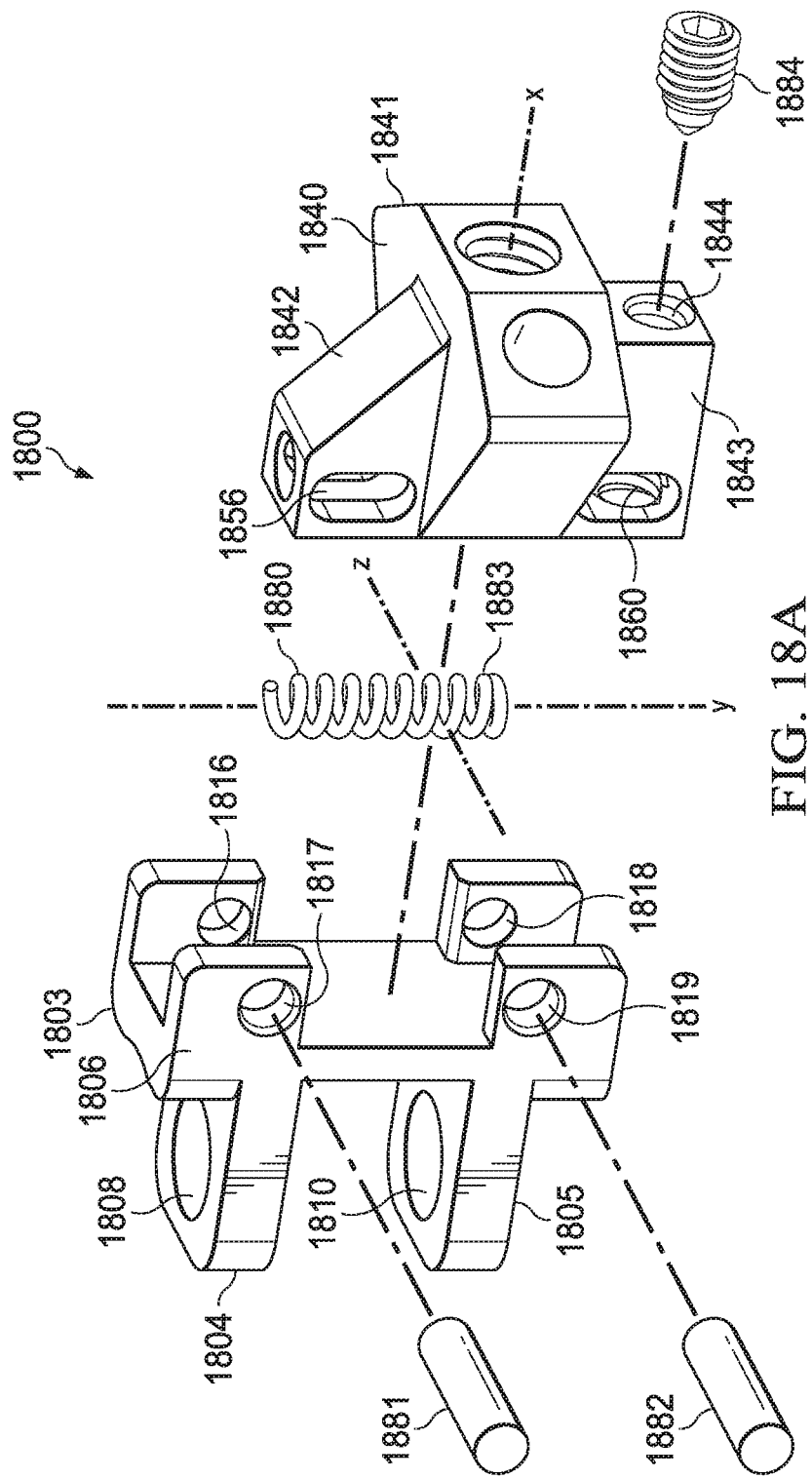
FIG. 18A illustrates an exploded perspective view of an embodiment of an alternative dynamization device.

FIG. 18A is an exploded perspective view of this embodiment of the dynamization tab 1800. The dynamization tab 1800 has a longitudinal axis X, a vertical axis Y, and a transverse axis Z and comprises a ring connector 1803, a strut connector 1840, and a biasing mechanism 1880. The strut connector 1840 may comprise a head 1841, a first knob 1842, a second knob 1843, and a set screw bore 1844. The biasing mechanism 1880 may comprise a first pin 1881, a second pin 1882, an elastic element 1883, and a set screw 1884. Ring connector 1803 may comprise a first stabilizer 1804, a second stabilizer 1805, and a third stabilizer 1806. The first stabilizer 1804 may further comprise a ring connector bore 1808 and the second stabilizer 1805 may also comprise a ring connector bore 1810 that is aligned with ring connector bore 1808. The third stabilizer 1806, according to some embodiments, may comprise a first wall comprising a first pin bore 1816, a second wall comprising a second pin bore 1817, a third wall comprising a third pin bore 1818, and a fourth wall comprising a fourth pin bore 1819. The first pin 1881, according to some embodiments, may be positioned superior and parallel to the transverse axis Z of the dynamization tab 1800 such that it traverses the first pin bore of a first wall of the third stabilizer 1816, the stadium-shaped bore of a first knob of the strut connector 1856, and the second pin bore of the second wall of the third stabilizer 1817. The second pin 1882 may be positioned inferior and parallel to the transverse axis Z of the dynamization tab 1800 such that it traverses the third pin bore of the third wall of the ring connector 1818, the stadium-shaped bore of a second knob of the strut connector 1860, and the fourth pin bore of a fourth wall of the third stabilizer 1819. Preferably, the third stabilizer of the ring connector 1806 will have a complimentary shape to both the first knob of the strut connector 1842 and the second knob of the strut connector 1843, allowing the two to securely mate in a manner which prevents the rotation of the strut connector 1840, when the dynamization tab 1800 is fully assembled, about the vertical axis Y of the dynamization tab 1800. In this way, dynamization may be limited to axial translation under loading.

Figure 18B:
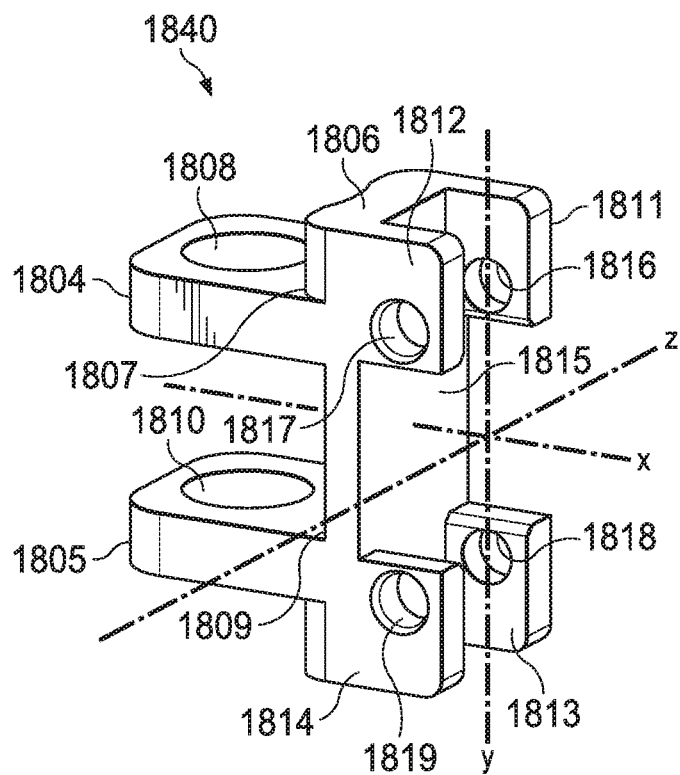
FIG. 18B illustrates a perspective view of a ring connector of an alternative dynamization device.

FIG. 18B illustrates a ring connector 1803 comprising a first stabilizer 1804, a second stabilizer 1805, and a third stabilizer 1806. According to some embodiments, the first stabilizer 1804 has a distal end 1807 and is positioned superior and parallel to the longitudinal axis X of the dynamization tab 1800. The first stabilizer 1804 may further comprise a ring connector bore 1808, which may be configured to accept a connecting bolt (not shown), which may secure the dynamization tab 1800 to an external fixation ring. The second stabilizer 1805 may have a distal end 1809 and be positioned inferior and parallel to the longitudinal axis X of the dynamization tab 1800. The second stabilizer 1805 may also comprise a ring connector bore 1810. The third stabilizer 1806, according to some embodiments, may comprise a first wall 1811 comprising a first pin bore 1816, a second wall 1812 comprising a second pin bore 1817, a third wall 1813 comprising a third pin bore 1818, a fourth wall 1814 comprising a fourth pin bore 1819, and a distal-facing surface 1815. Each of the pin bores of the first wall 1816 and the second wall 1817, and the pin bores of the third wall 1818 and fourth wall 1818, may be positioned such that they are parallel to the transverse axis Z of the dynamization tab 1800. The distal-facing surface of the third stabilizer 1815 may be positioned parallel to the vertical axis Y of the dynamization tab 1800.

Figure 18C:
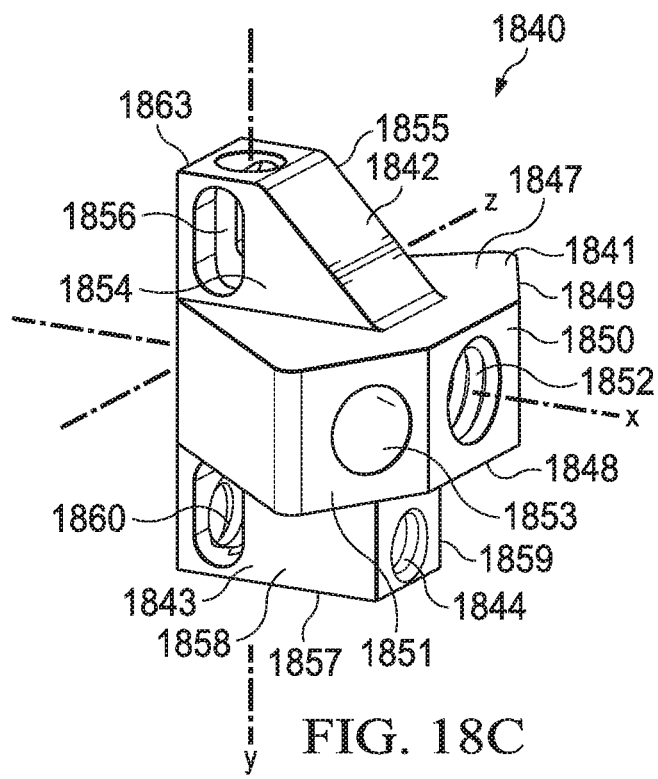
FIG. 18C illustrates a perspective view of a strut connector of an alternative dynamization device.

Referring now to FIG. 18C, the head of the strut connector 1841 has a top surface 1847 and a bottom surface 1848 and further comprises a first distal-facing surface 1849, a second distal-facing surface 1850, and a third distal-facing surface 1851. Each of the first distal-facing surface 1849 and the third distal-facing surface 1851 may comprise a strut aperture 1853, which may be a partial bore extending from the distal end of the strut connector 1841 and may be configured to secure the dynamization tab 1800 to a strut. Also shown in FIG. 18C is a locking screw aperture 1852, which can be used to secure the one or more of the external fixation struts to the dynamization tab 1800. The locking screw aperture 1852 may be configured to accept a locking screw, which may be configured to secure the strut fasteners when they are placed inside of the strut apertures 1853. The locking screw aperture 1852 may be threaded to accept a correspondingly threaded locking screw. The locking screw may secure the strut fasteners through contact with the strut fasteners in a manner which prevents the movement of the strut fasteners with respect to the strut apertures 1853 when the locking screw is in place. Several examples of such a locking arrangement are found in U.S. Pat. No. 9,295,493, hereby incorporated by reference into this patent.

The first knob of the strut connector 1842 may be positioned in a manner such that it is in contact with the top surface of the head of the strut connector 1847. The first knob 1842 may, according to some embodiments, comprise a top surface 1863, a first surface 1854, a second surface 1855, and a stadium-shaped bore 1856. The stadium-shaped bore 1856 may extend from the first surface of the first knob 1854 to the second surface of the first knob 1855. The second knob of the strut connector 1843 may be positioned in a manner such that it is in contact with the bottom surface of the head 1848. According to some embodiments, the second knob 1843 may comprise a bottom surface 1857, a first surface 1858, a second surface 1859, and a stadium-shaped bore 1860. The stadium-shaped bore 1860 may extend from the first surface of the second knob 1858 to the second surface of the second knob 1859. The set screw bore of the strut connector 1844, according to some embodiments, extends inferior and parallel to the longitudinal axis X of the dynamization tab 1800.

Figure 18D:
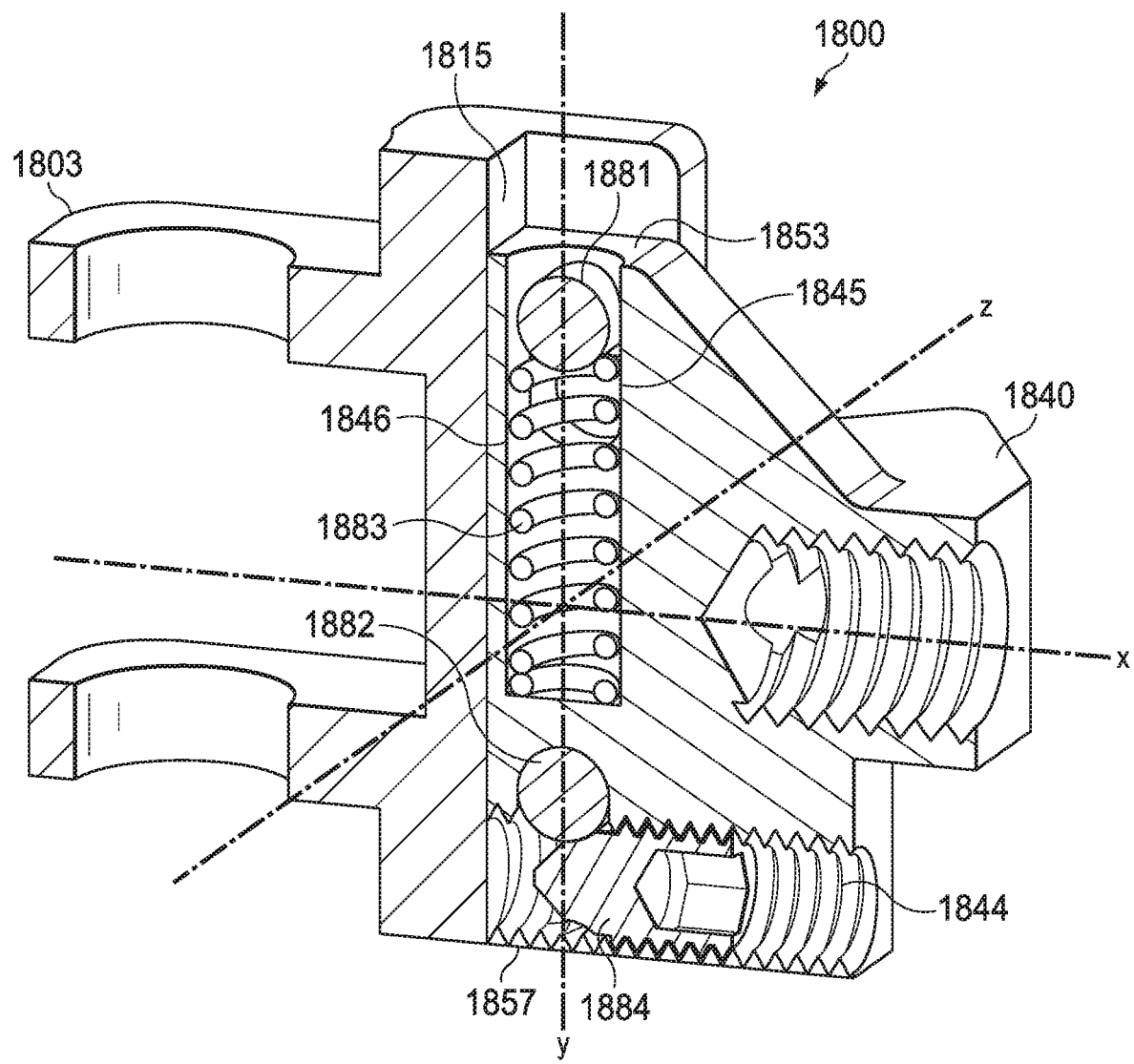
FIG. 18D illustrates a cross-sectional view of an alternative dynamization device.

A cross-sectional and perspective view of the complete assembly of the dynamization tab 1800 is depicted in FIG. 18D. As illustrated, the dynamization tab 1800 comprises a ring connector 1803 and a strut connector 1840. The ring connector 1803 includes ring connector bores 1808 and 1810, which are used in conjunction with a connecting bolt (not shown) to secure the dynamization tab 1800 to an external fixation ring (not shown). An elastic element housing 1845 is depicted as comprising a partial bore, extending from the top surface of the first knob of the strut connector 1853 towards the bottom surface of the second knob of the strut connector 1857 and be positioned along the vertical axis Y of the dynamization tab 1800. The elastic element housing 1845 may be configured to accept the elastic element 1883. The proximal-facing surface of the strut connector 1846 may be positioned proximal and parallel to the vertical axis Y of the dynamization tab 1800. According to some embodiments, the proximal-facing surface of the strut connector 1846 may be in contact with the distal facing surface of the ring connector 1815 in a manner such that rotational displacement of the strut connector 1840 about the transverse axis Z of the dynamization tab 1800 is limited.

With reference to FIGS. 18A and 18D, the first pin 1881, according to some embodiments, may be positioned superior and parallel to the transverse axis Z of the dynamization tab 1800 such that it traverses the first pin bore of the first wall of the third stabilizer 1816, the stadium-shaped bore of the first knob of the strut connector 1856, and the second pin bore of the second wall of the third stabilizer 1817, allowing the strut connector 1840 to be displaced along the vertical axis Y of the dynamization tab 1800 to an extent allowed by the length of the stadium-shaped bore of the first knob of the strut connector 1856. The second pin 1882 may be positioned inferior and parallel to the transverse axis Z of the dynamization tab 1800 such that it traverses the third pin bore of the third wall of the ring connector 1818, the stadium-shaped bore of the second knob of the strut connector 1860, and the fourth pin bore of the fourth wall of the third stabilizer 1819, allowing the strut connector 1840 to be displaced along the vertical axis Y of the dynamization tab 1800 to the extent allowed by the length of the stadium-shaped bore of the second knob of the strut connector 1860. Preferably, the third stabilizer of the ring connector 1806 will have a complimentary shape to both the first knob of the strut connector 1842 and the second knob of the strut connector 1843, allowing the two to securely mate in a manner which prevents the rotation of the strut connector 1840, when the dynamization tab 1800 is fully assembled, about the vertical axis Y of the dynamization tab 1800. Instead, dynamization may be provided by allowing the strut connector 1840 to translate along the vertical axis Y, with limited axial translation under loading.

The elastic element of the biasing mechanism 1883 may comprise an elastomeric material, resilient device, or a spring and may be positioned along the vertical axis Y of the dynamization tab 1800 in a manner such that it traverses the elastic element housing 1845. Preferably, the elastic element 1845 should traverse the space between the first pin 1881 and the second pin 1882 in a manner such that, as the stadium-shaped bores 1856, 1860 are allowed to slide along the pins 1881, 1882, the elastic element 1880 provides a biasing force necessary to return the strut connector 1840 to its original position. The set screw of the biasing mechanism 1884 may be configured to traverse the set screw bore of the strut connector 1844 and may include a fitting for receiving a set screw driver, such as a hexagonal receptacle, a Phillips-head receptacle, a flat-head receptacle, a star-wrench receptacle, or any other suitable driver that would be understood in the art. By adjusting the relative positions of the set screw 1884 within the set screw bore 1844, the amount of dynamization provided by this device can be controlled. Shown in FIG. 18D, as the set screw 1884 is driven into the set screw bore 1844, it becomes increasingly in contact with the second pin 1882, i.e. between the second pin and the bottom surface of the second knob of the strut connector 1857. In this arrangement, as the set screw 1884 is driven, the second pin 1882 is displaced within the stadium-shaped bore of the second knob of the strut connector (not shown) in a manner which restricts the ability of the strut connector 1840 to be displaced along the vertical axis of the dynamization tab 1800. In this manner, dynamization may be controlled by driving or withdrawing the set screw 1884 within the set screw bore 1844.

Figure 19:
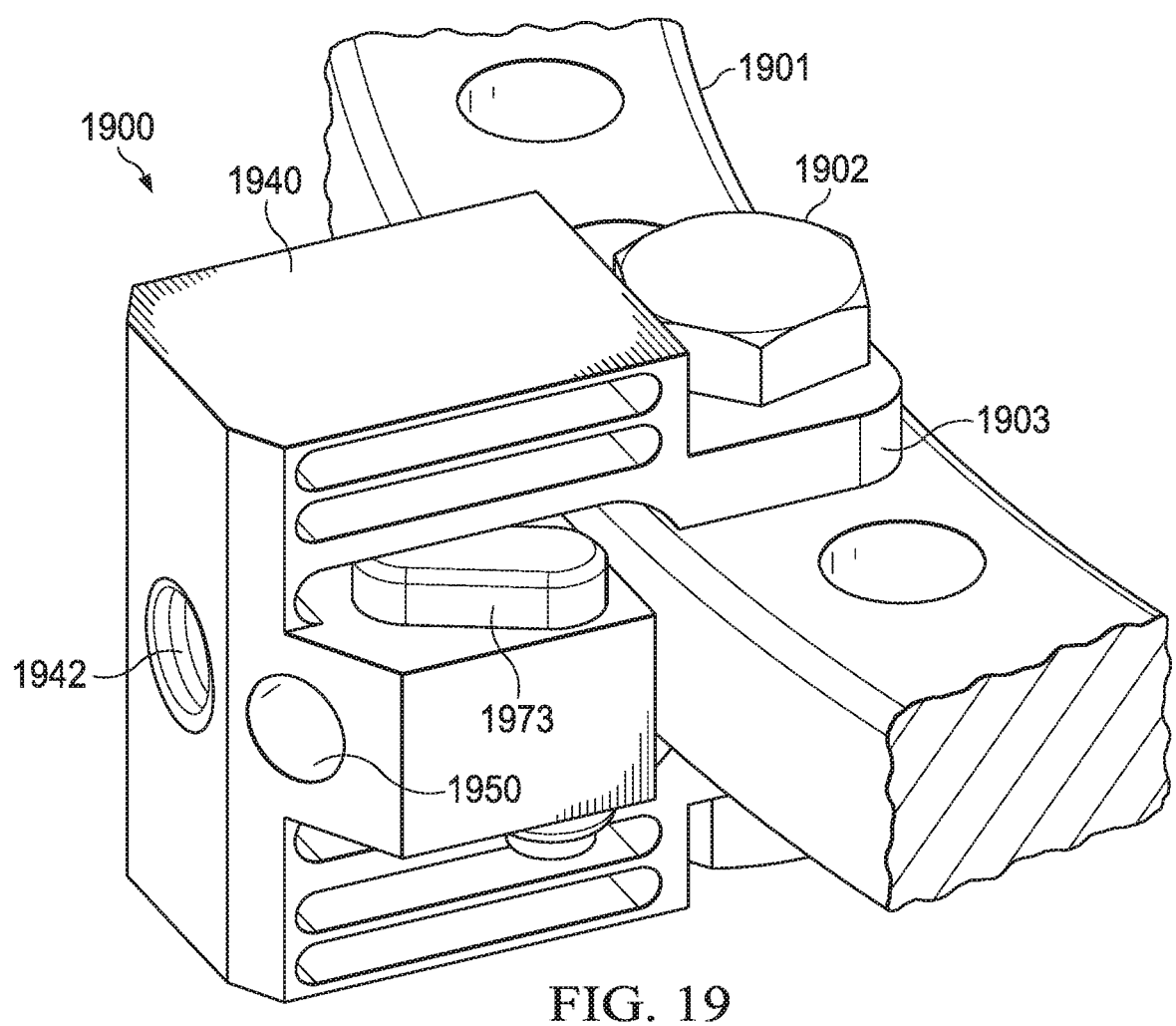
FIG. 19 illustrates a perspective view of an embodiment of a parallel tab dynamization device.
Figure 19A:
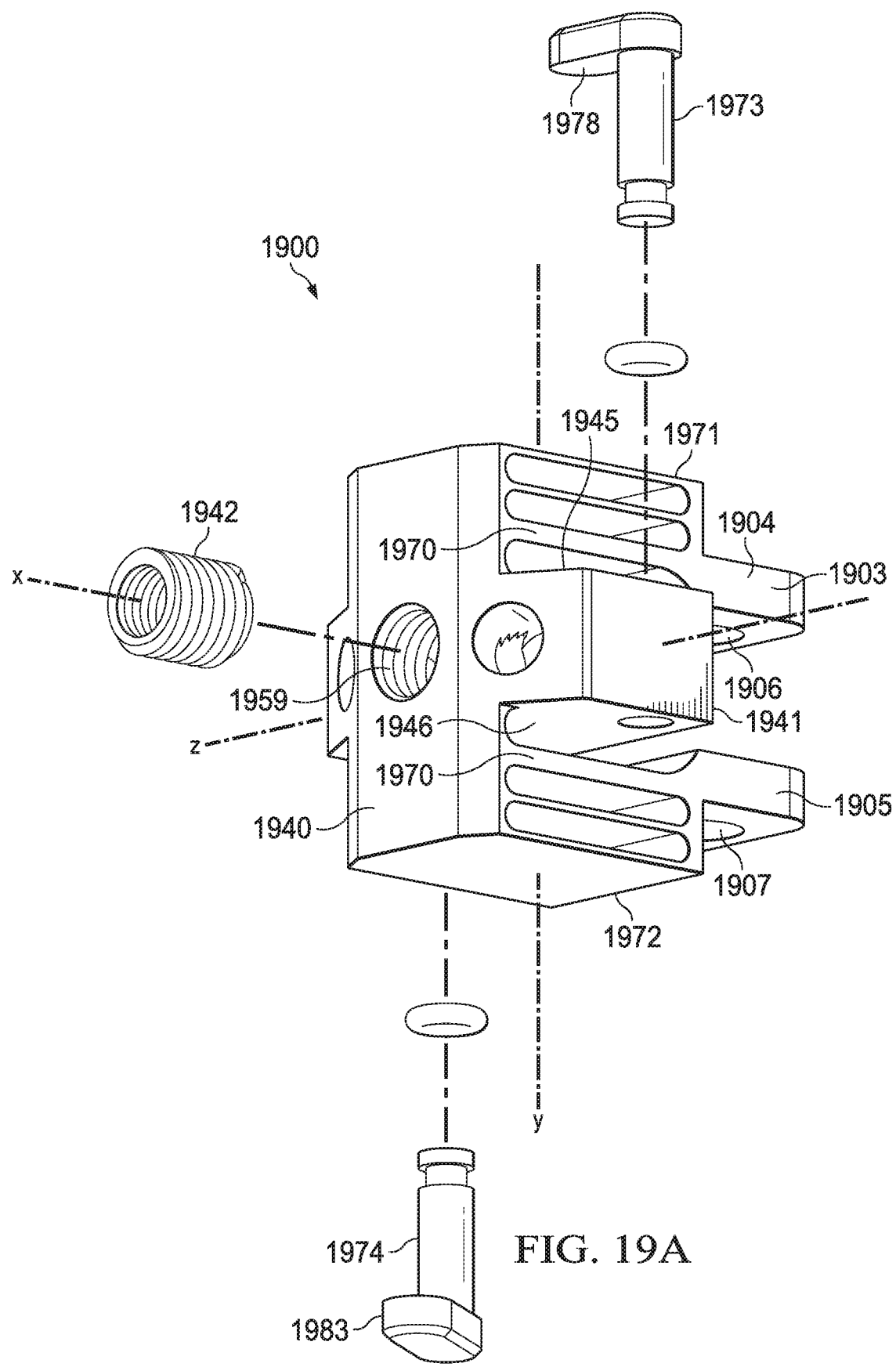
FIG. 19A illustrates an exploded perspective view of an embodiment of a parallel tab dynamization device.

An alternate embodiment of a dynamization device is depicted in FIG. 19. In FIG. 19, a dynamization tab 1900 is connected to an external fixation ring 1901 by a connecting bolt 1902. The dynamization tab includes a ring connector 1903 and a strut connector 1940. Like the previous embodiments, the dynamization tab 1900 may also include one or more strut apertures 1950 to receive a strut fastener of an external fixation strut (not shown). Also shown in FIG. 19 is a locking screw aperture 1942, which can be used to secure the one or more of the external fixation struts to the dynamization tab 1900. The locking screw aperture 1942 may be configured to accept a locking screw, which may be configured to secure the strut fasteners when they are placed inside of the strut apertures 1950. As shown in FIG. 19, the locking screw aperture 1942 may be threaded to accept a correspondingly threaded locking screw. The locking screw may secure the strut fasteners through contact with the strut fasteners in a manner which prevents the movement of the strut fasteners with respect to the strut apertures 1950 when the locking screw is in place. Several examples of such a locking arrangement are found in U.S. Pat. No. 9,295,493, hereby incorporated by reference into this patent.

Detailed illustrations of the dynamization tab 1900, which provides for dynamization through axial translation of the strut connector due to the intrinsic elasticity of the dynamization tab itself, are found in FIGS. 19A-D. In this embodiment, the geometry of the dynamization tab provides that every section of the tab is uniformly loaded. Illustrated in FIG. 19A, the dynamization tab 1900 has a longitudinal axis X, a vertical axis Y, and a transverse axis Z, and comprises a ring connector 1903, a strut connector 1940, and a biasing mechanism 1970. The ring connector 1903, according to some embodiments, may comprise a first stabilizer 1904 and a second stabilizer 1905. The first stabilizer 1904 is positioned superior and parallel to the longitudinal axis X of the dynamization tab 1900 and comprises a ring connector bore 1906. The second stabilizer 1905 is positioned inferior and parallel to the longitudinal axis X and comprises a ring connector bore 1907. Each of the ring connector bores 1905, 1906 may be configured to accept a connecting bolt (not shown) and may be used to secure the dynamization tab 1900 to an external fixation ring. The strut connector 1940 may comprise a head 1941, and a strut set screw 1942. The head of the strut connector 1941, according to some embodiments, has a top surface 1945 and a bottom surface 1946, a locking screw 1942, and locking screw aperture 1959. The locking screw aperture 1959 can be used to secure the one or more of the external fixation struts to the dynamization tab 1900. The locking screw aperture 1959 may be configured to accept locking screw 1942, which may be configured to secure the strut fasteners when they are placed inside of the strut apertures 1950. The locking screw aperture 1959 may be threaded to accept a correspondingly threaded locking screw 1942. The locking screw 1942 may secure the strut fasteners through contact with the strut fasteners in a manner which prevents the movement of the strut fasteners with respect to the strut apertures 1950 when the locking screw is in place. Several examples of such a locking arrangement are found in U.S. Pat. No. 9,295,493, hereby incorporated by reference into this patent. The biasing mechanism 1970 of the dynamization tab 1900 may also comprise a first biasing region 1971, a second biasing region 1972, a first dynamization stop 1973, and a second dynamization stop 1974.

Figure 19C:
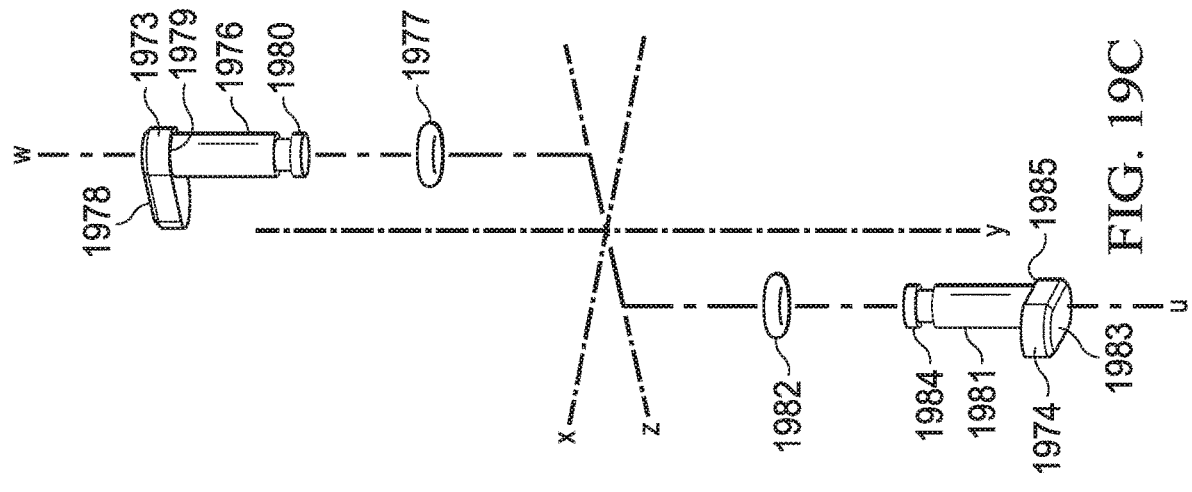
FIG. 19C illustrates a perspective view of a dynamization stop device for use with a parallel tab dynamization device.
Figure 19B:
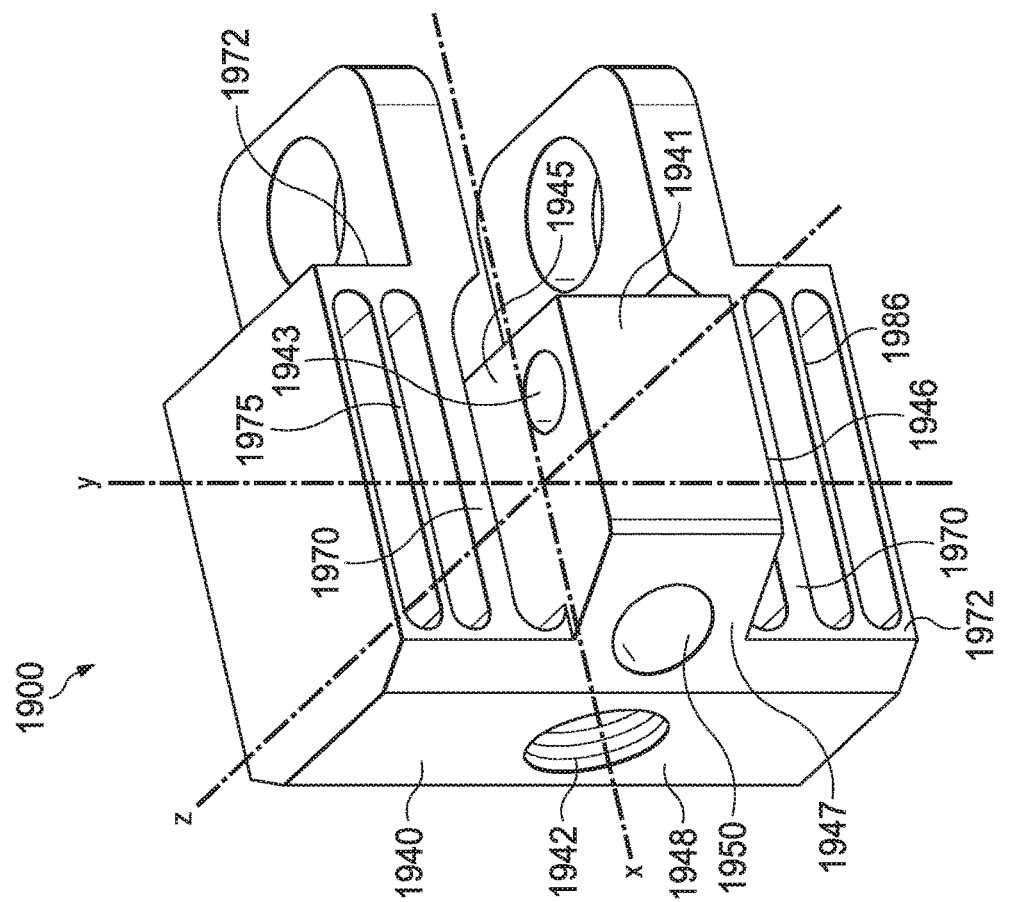
FIG. 19B illustrates a perspective view of an embodiment of a parallel tab dynamization device.

Another view of the dynamization tab 1900 is illustrated in FIG. 19B. In FIG. 19B, the strut connector 1940 may comprise a head 1941, a first dynamization stop bore 1943, and a second dynamization stop bore 1944. The head of the strut connector 1941, according to some embodiments, has a top surface 1945, a bottom surface 1946, and further comprises a first distal-facing surface 1947, a second distal-facing surface 1948, and a third distal-facing surface 1949. Each of the first distal-facing surface 1947 and the third distal-facing surface 1949 may comprise a strut aperture 1950, which may be configured to secure the dynamization tab 1900 to a strut, as described above. The first dynamization stop bore 1943 of the strut connector may extend from the top surface 1945 of the head of the strut connector to the bottom surface 1946 of the head of the strut connector and be positioned parallel to the vertical axis Y of the dynamization tab 1900. The second dynamization stop bore 1944 (not shown) may also extend from the top surface 1945 of the head of the strut connector to the bottom surface 1946 of the head of the strut connector and be positioned parallel to the vertical axis Y of the dynamization tab 1900.

The first biasing region 1971 may be positioned superior and parallel to the longitudinal axis X of the dynamization tab 1900 and comprise one or more biasing plates 1975. The second biasing region 1972 may be positioned inferior and parallel to the longitudinal axis X of the dynamization tab 1900 and comprise one or more biasing plates 1986. The biasing plates 1975, 1986 may be positioned parallel to one another and to the longitudinal axis X of the dynamization tab 1900. Further, the biasing plates 1975, 1986 may comprise a flexible plastic or other elastomeric material and be configured such that, when the strut connector 1940 is displaced along the vertical axis Y of the dynamization tab 1900, the biasing plates 1975, 1986 provide a biasing force sufficient to return the strut connector 1940 to its original position.

Illustrated in FIG. 19C, the first dynamization stop 1973 of the biasing mechanism may comprise a post 1976, an elastic ring 1977, and a first dynamization stop tab 1978. The post of the first dynamization stop 1976 may have a superior end 1979, an inferior end 1980, and a central axis W, and may be configured to be placed within the first dynamization stop bore 1943 of the strut connector (see FIG. 19B) in a manner such that it may rotate about its central axis W. The elastic ring 1977 may be configured to be in contact with the inferior end of the post 1980 in a manner such that it secures the post within the first dynamization stop bore 1943. The first dynamization stop tab 1978 may be positioned parallel to the longitudinal axis X of the dynamization tab 1900 and at the superior end of the post 1979. By rotating the first dynamization stop tab 1978 into the gap found between the top surface 1945 of the head of the strut connector 1941 and the lower surface of the first biasing region 1971, the first biasing region 1971 can be prevented from being deformed along the vertical axis Y.

The second dynamization stop 1974 may comprise a post 1981, an elastic ring 1982, and a second dynamization stop tab 1983. The post of the second dynamization stop 1981 may comprise a superior end 1984, an inferior end 1985, and a central axis U. The post 1981 may be configured to be placed within the second dynamization stop bore of the strut connector (not shown) in a manner such that it may rotate about its central axis U. The elastic ring of the second stop bore 1982 may be configured to be in contact with the superior end of the post 1984 in a manner such that it secures the post 1981 within the second dynamization stop bore (not shown). The second dynamization stop tab 1983 may be positioned parallel to the longitudinal axis X of the dynamization tab 1900 and at the inferior end of the post 1981. By rotating the second dynamization stop tab 1983 into the gap found between the bottom surface 1946 of the head of the strut connector 1941 and the upper surface of the second biasing region 1972, the second biasing region 1972 can be prevented from being deformed along the vertical axis Y.

Figure 19D:
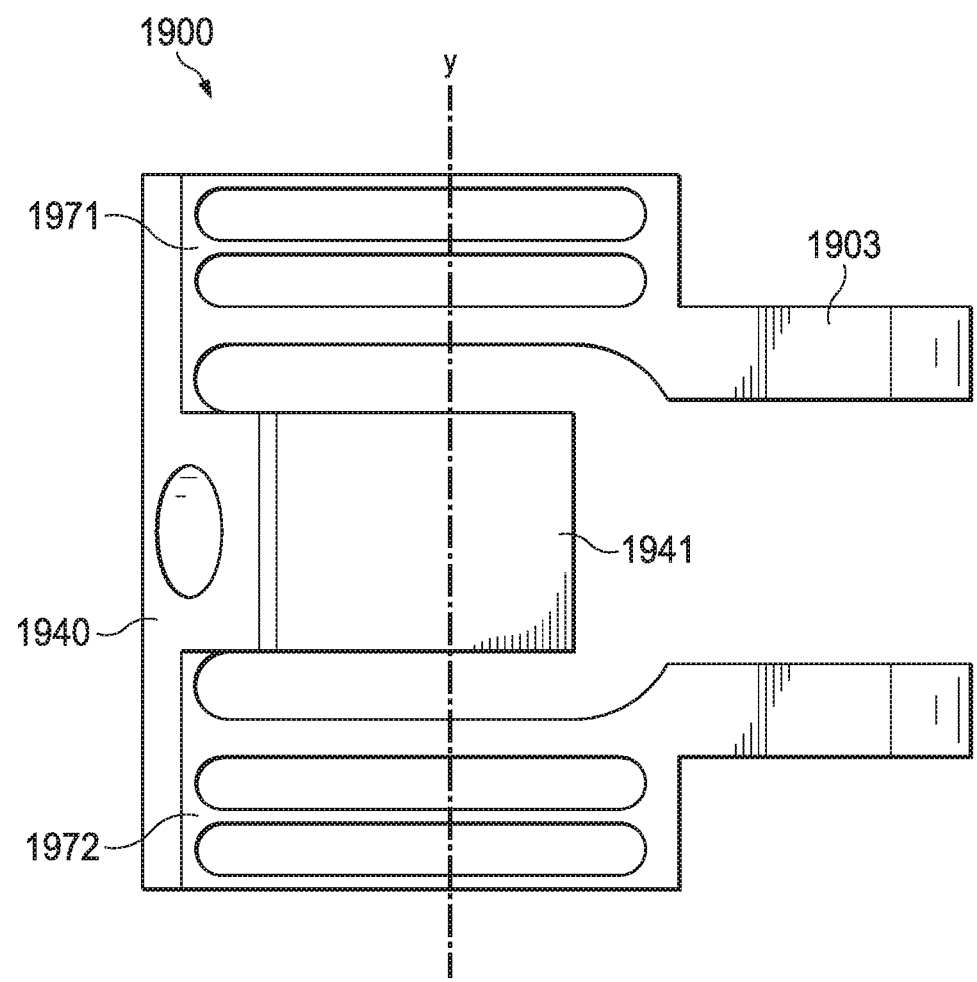
FIG. 19D illustrates a side view of an embodiment of a parallel tab dynamization device.

A side view of the deformed condition of the dynamization tab 1900 is depicted in FIG. 19D. The intrinsic elasticity of the dynamization tab 1900, translated through the first biasing region 1971 and the second biasing region 1972, allows for the movement of the strut connector 1940 along the vertical axis Y of the dynamization tab 1900 under loading. As illustrated, the ring connector 1903 is fixed to an external fixation ring, in a manner described above, and remains stationary with respect to the ring. Under loading, the head of the strut connector 1941 is allowed to move along the vertical axis Y of the dynamization tab 1900 under loading, allowing for dynamization. As shown, the space between the head 1941 and the respective biasing region 1971, 1972, combined with the intrinsic elasticity of the comprising the dynamization tab, determines the degree to which the head is allowed to move under loading. Dynamization may be controlled by limiting the amount of space between the biasing regions 1971, 1972 and the head 1941. This may be achieved by placing a dynamization stop tab (not shown) in the space between the head 1941 and the first biasing region 1971, between the head 1941 and the second biasing region 1972, or both.

The biasing regions, or even the entire tab, may be comprised of a material having appropriate elasticity and shape memory, such material can be selected from plastic, polymer, thermoplastic, metal, metal alloy, composite, resin, ultra-high-molecular-weight polyethylene (UHMW), a polytetrafluroethylene (PTFE), ABS plastic, PLA, polyamide, glass filled polyamide, epoxy, nylon, rayon, polyester, polyacrylate, wood, bamboo, bronze, titanium, steel, stainless steel, a cobalt chromium alloy, ceramic, wax, photopolymer, and polycarbonate. In certain non-limiting examples the polymer can be a thermoplastic polymer, a polyolefin, a polyester, a polysilicone, a polyacrylonitrile resin, a polystyrene, polyvinyl chloride, polyvinylidene chloride, polyvinyl acetate, a fluoroplastic, a phenolic resin, a urea resin, a melamine, an epoxy, a polyurethane, a polyamide, a polyacrylate resin, a polyketone, a polyimide, a polysulfone, a polycarbonate, a polyacetal, poly(hydroxynapthoic acid), a conductive polymer, a poly(3-hexylthiophene), a polyphenylene-vinylene, a poly(phenylene vinylene), a polyaniline, or combinations thereof. Other appropriate and biocompatible materials can be utilized. According to another embodiment, the biasing region or dynamization device can be fabricated by an additive printing process (e.g., a 3D printing process). The biasing region or dynamization device can also be fabricated by machining, forging or casting, based on the specific design and intended use of the device and the material comprising the device. Suitable materials include the medical grade and biocompatible plastics described above, or biocompatible metals, such as titanium, stainless steel, 316L stainless steel, cobalt-chromium, and alloys thereof. According to some embodiments, the devices can be made as a composite or hybrid device with a combination of plastic and metallic components. The selected material must have sufficient plasticity and shape memory to return to its original configuration after having been deformed many times.

Figure 20A:
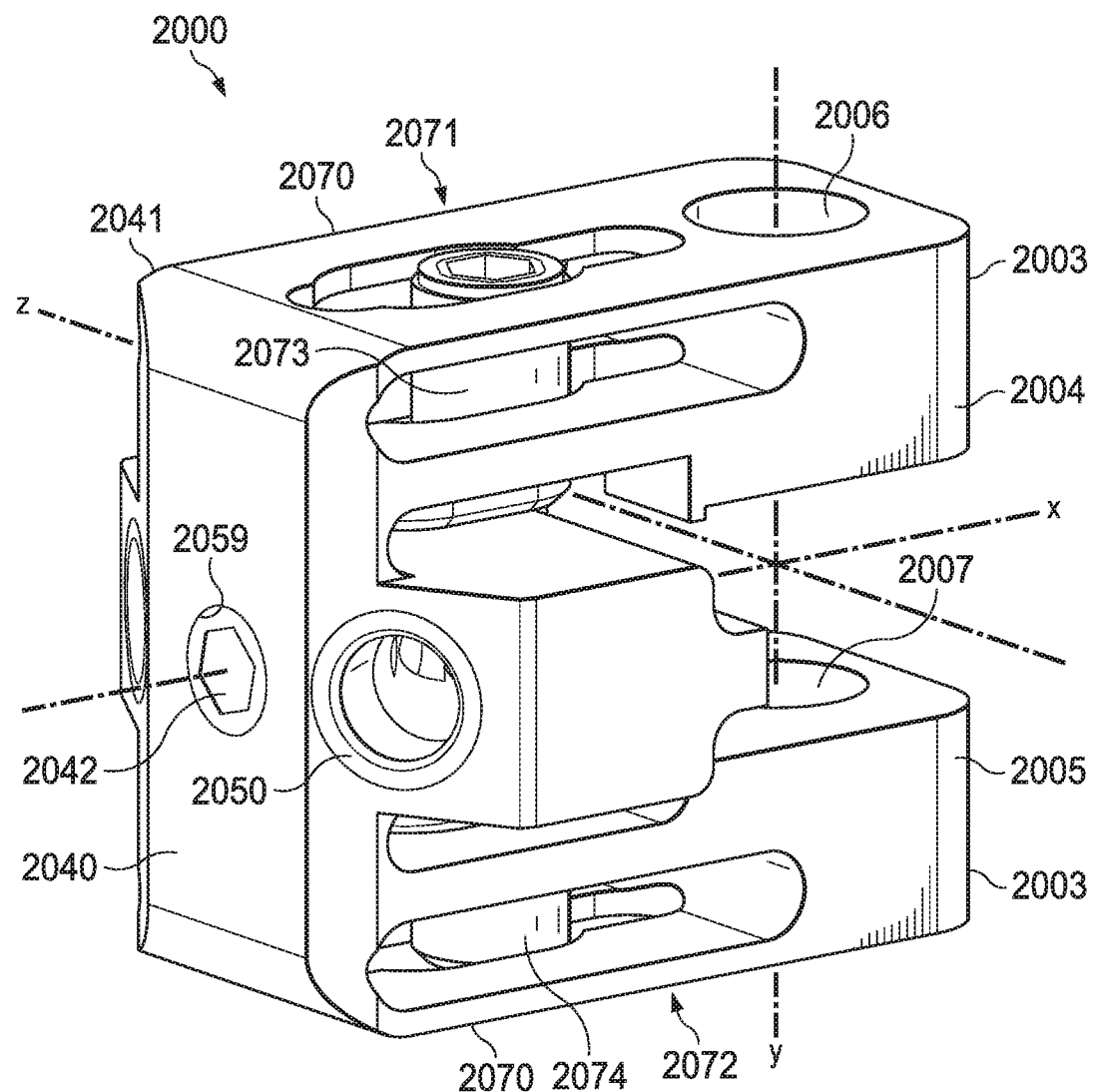
FIG. 20A illustrates a perspective view of another embodiment of a parallel tab dynamization device.

An alternate embodiment of a dynamization device is depicted in FIG. 20A. In FIG. 20A, a dynamization tab 2000 can be connected to an external fixation ring by a connecting bolt. Like the previous embodiments, the dynamization tab 2000 may also include one or more strut apertures 2050 to receive a strut fastener of an external fixation strut (not shown). Also shown in FIG. 20A is a locking screw aperture 2059, which can be used to secure the one or more of the external fixation struts to the dynamization tab 2000. The locking screw aperture 2059 may be configured to accept a locking screw 2042, which may be configured to secure the strut fasteners when they are placed inside of the strut apertures 2050. The locking screw aperture 2059 may be threaded to accept a correspondingly threaded locking screw 2042. The locking screw 2042 may secure the strut fasteners through contact with the strut fasteners in a manner which prevents the movement of the strut fasteners with respect to the strut apertures 2050 when the locking screw is in place. Several examples of such a locking arrangement are found in U.S. Pat. No. 9,295,493, hereby incorporated by reference into this patent.

The dynamization tab 2000 has a longitudinal axis X, a vertical axis Y, and a transverse axis Z, and comprises ring connectors 2003, a strut connector 2040, and biasing mechanisms 2070. The ring connectors 2003, according to some embodiments, may comprise a first stabilizer 2004 and a second stabilizer 2005. The first stabilizer 2004 is positioned superior and parallel to the longitudinal axis X of the dynamization tab 2000 and comprises a ring connector bore 2006. The second stabilizer 2005 is positioned inferior and parallel to the longitudinal axis X and comprises a ring connector bore 2007. Each of the ring connector bores 2006, 2007 may be configured to accept a connecting bolt (not shown) and may be used to secure the dynamization tab 2000 to an external fixation ring. The strut connector 2040 may comprise a locking screw 2042 and locking screw aperture 2059. The locking screw aperture 2059 can be used to secure the one or more of the external fixation struts to the dynamization tab 2000. The locking screw aperture 2059 may be configured to accept locking screw 2042, which may be configured to secure the strut fasteners when they are placed inside of the strut apertures 2050. The locking screw aperture 2059 may be threaded to accept a correspondingly threaded locking screw 2042. The locking screw 2042 may secure the strut fasteners through contact with the strut fasteners in a manner which prevents the movement of the strut fasteners with respect to the strut apertures 2050 when the locking screw is in place. Several examples of such a locking arrangement are found in U.S. Pat. No. 9,295,493, hereby incorporated by reference into this patent. The biasing mechanisms 2070 of the dynamization tab 2000 may also comprise a first biasing region 2071, a second biasing region 2072, a first dynamization stop 2073, and a second dynamization stop 2074.

Figure 20B:
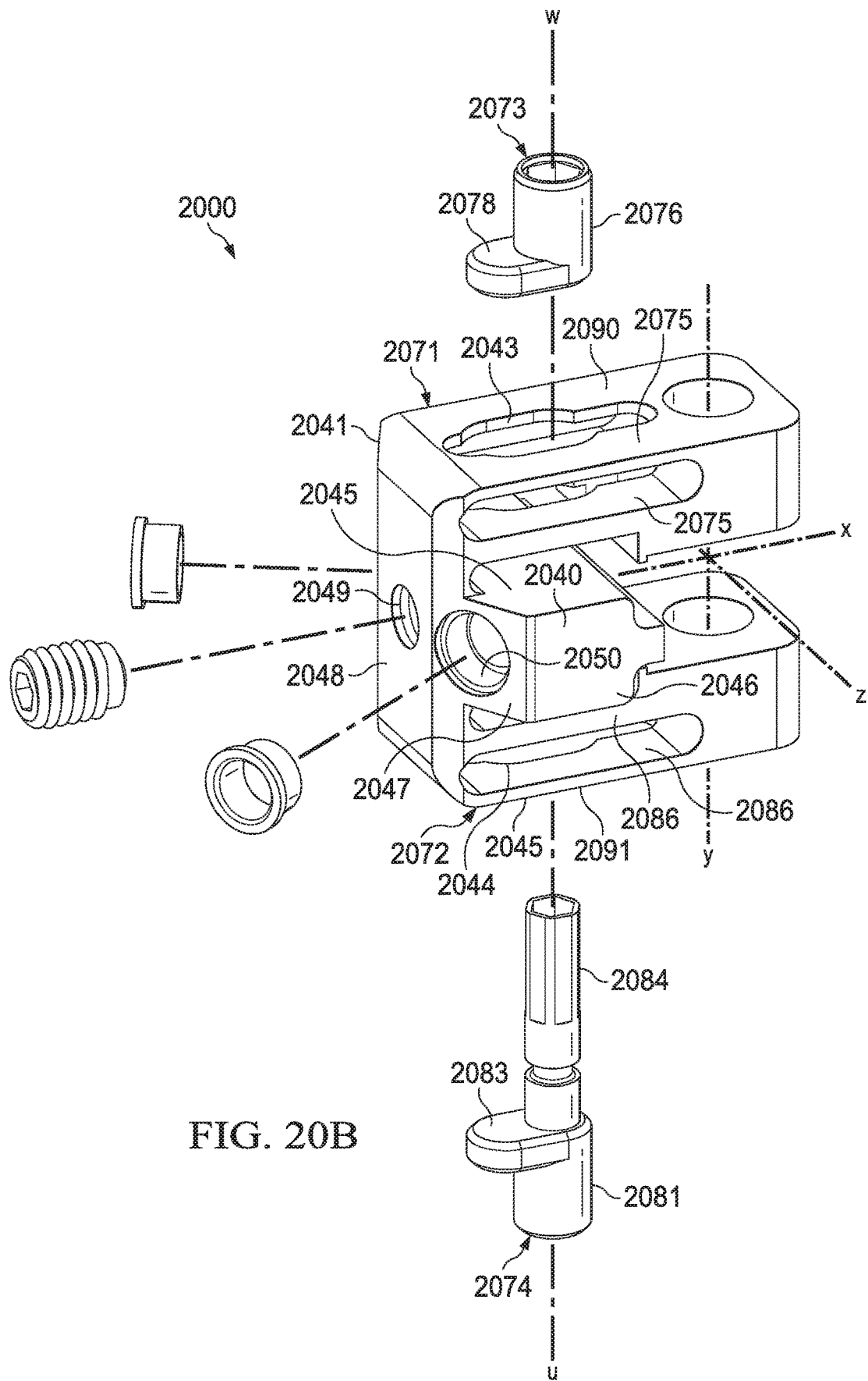
FIG. 20B illustrates an exploded perspective view of an embodiment of a parallel tab dynamization device.

An exploded view of the dynamization tab 2000 is illustrated in FIG. 20B. In FIG. 20B, the strut connector 2040 may comprise a top surface 2045, a bottom surface 2046, a head 2041, a first dynamization stop bore 2043, and a second dynamization stop bore 2044. The head of the strut connector 2041 further comprises a first distal-facing surface 2047, a second distal-facing surface 2048, and a third distal-facing surface 2049. Each of the first distal-facing surface 2047 and the third distal-facing surface 2049 may comprise a strut aperture 2050, which may be configured to secure the dynamization tab 2000 to a strut, as described above. The first dynamization stop bore 2043 of the strut connector may extend from a top surface 2090 of the first biasing region 2071 to the top surface 2045 of the strut connector 2040 and be positioned parallel to the vertical axis Y of the dynamization tab 2000. The second dynamization stop bore 2044 may also extend from the bottom surface 2045 of the second biasing region 2072 to the bottom surface 2046 of the strut connector 2040 and be positioned parallel to the vertical axis Y of the dynamization tab 2000.

The first biasing region 2071 may be positioned superior and parallel to the longitudinal axis X of the dynamization tab 2000 and comprise one or more biasing plates 2075. The second biasing region 2072 may be positioned inferior and parallel to the longitudinal axis X of the dynamization tab 2000 and comprise one or more biasing plates 2086. The biasing plates 2075, 2086 may be positioned parallel to one another and to the longitudinal axis X of the dynamization tab 2000. Further, the biasing plates 2075, 2086 may comprise a flexible plastic or other elastomeric material and be configured such that, when the strut connector 2040 is displaced along the vertical axis Y of the dynamization tab 2000, the biasing plates 2075, 2086 provide a biasing force sufficient to return the strut connector 2040 to its original position.

Further illustrated in FIG. 20B is the first dynamization stop 2073, which may comprise a post 2076, and a first dynamization stop tab 2078. The post of the first dynamization stop 2076 may have a central axis W, and may be configured to be placed within the first dynamization stop bore 2043 of the strut connector in a manner such that it may rotate about its central axis W. The first dynamization stop tab 2078 may be positioned parallel to the longitudinal axis X of the dynamization tab 2000. By rotating the first dynamization stop tab 2078 into the gap found between the top surface 2045 of the head of the strut connector 2040 and the lower surface of the first biasing region 2071, the first biasing region 2071 can be prevented from being deformed along the vertical axis Y.

The second dynamization stop 2074 may comprise a post 2081, a second dynamization stop tab 2083, and a connecting member 2084. The post of the second dynamization stop 1981 may also comprise a central axis U. The post 2081 may be configured to be placed within the second dynamization stop bore 2044 of the strut connector 2040 in a manner such that it may rotate about its central axis U. The second dynamization stop tab 2083 may be positioned parallel to the longitudinal axis X of the dynamization tab 2000 and at the inferior end of the post 2081. By rotating the second dynamization stop tab 2083 into the gap found between the bottom surface 2046 of the strut connector 2040 and the upper surface of the second biasing region 2072, the second biasing region 2072 can be prevented from being deformed along the vertical axis Y.

The connecting member 2084 can be attached to the superior end of the second dynamization stop 2074 and pass through both of the first and second dynamization stop bores (2043, 2044) so as to be attached to the inferior end of the first dynamization stop 2073. The connecting member 2084 may further comprise fluted edges or other similar features that can engage with matching features inside the first dynamization stop 2073. In this manner, the connection of the first dynamization stop 2073 to the second dynamization stop 2074 will cause both stops (2073, 2074) to rotate at the same time, thereby locking or releasing the dynamization feature of the first and second biasing regions (2071, 2072) at the same time. When the dynamization stops (2073, 2074) are disengaged (i.e., the dynamization stop tabs (2078, 2083) are moved parallel to the X axis of the device), thus allowing the stop tabs to pass through the first and second dynamization stop bores (2043, 2044) when the first and second biasing regions (2071, 2072) are deformed. The first and second biasing regions (2071, 2072) of the dynamization tab 2000 can therefore be deformed in a manner similar the deformation of the tab 1900 depicted in FIG. 19D.

The intrinsic elasticity of the dynamization tab 2000, translated through the first biasing region 2071 and the second biasing region 2072, allows for the movement of the strut connector 2040 along the vertical axis Y of the dynamization tab 2000 under loading. The ring connectors 2003 remain fixed to an external fixation ring and remain stationary with respect to the ring. Under loading, the head of the strut connector 2041 is allowed to move along the vertical axis Y of the dynamization tab 2000, allowing for dynamization. As shown in FIG. 19D, the space between the head 1941 and the respective biasing regions 1971, 1972, combined with the intrinsic elasticity of the comprising the dynamization tab, determines the degree to which the head is allowed to move under loading. Dynamization may be controlled by limiting the amount of space between the biasing regions 1971, 1972 and the head 1941.

Figure 20C:
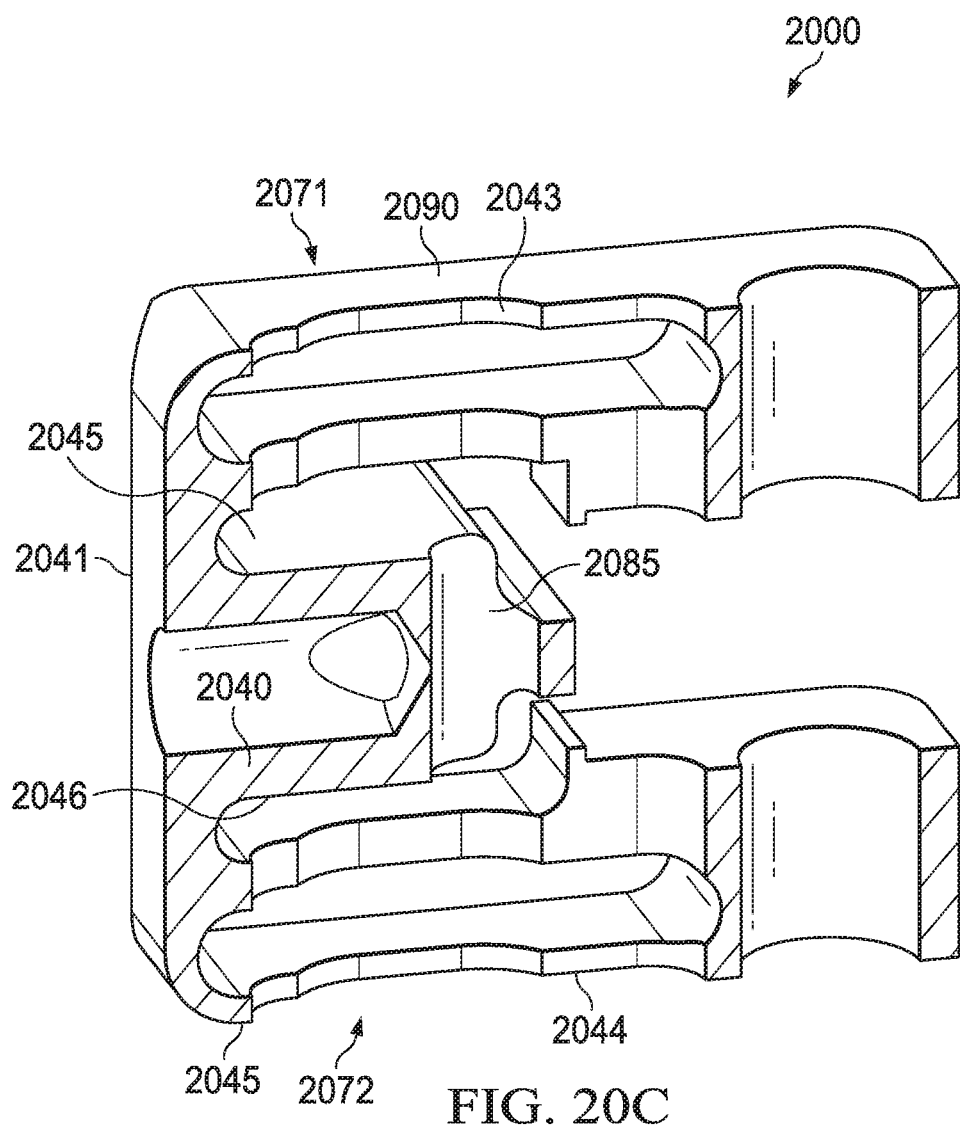
FIG. 20C illustrates a cross sectional view of an embodiment of a parallel tab dynamization device.

A cross-sectional view of an alternative embodiment of the dynamization tab 2000 is depicted in FIG. 20C. In FIG. 20C, the strut connector 2040 may comprise a top surface 2045, a bottom surface 2046, a head 2041, a first dynamization stop bore 2043, and a second dynamization stop bore 2044. The first dynamization stop bore 2043 may extend from a top surface 2090 of the first biasing region 2071 to the top surface 2045 of the strut connector 2040. The second dynamization stop bore 2044 may also extend from the bottom surface 2045 of the second biasing region 2072 to the bottom surface 2046 of the strut connector 2040. Also shown in FIG. 20C is a central recess 2085 in a proximal end of the strut connector 2040. The central recess 2085 is sized to receive the connecting member 2084 between the first and second dynamization stops (2073, 2074). The central recess 2085 is therefore aligned with the first and second dynamization stop bores (2043, 2044), thus allowing the dynamization stops (2073, 2074) to rotate at the same time, thereby locking or releasing the dynamization feature of the first and second biasing regions (2071, 2072) at the same time.

Figure 21A:
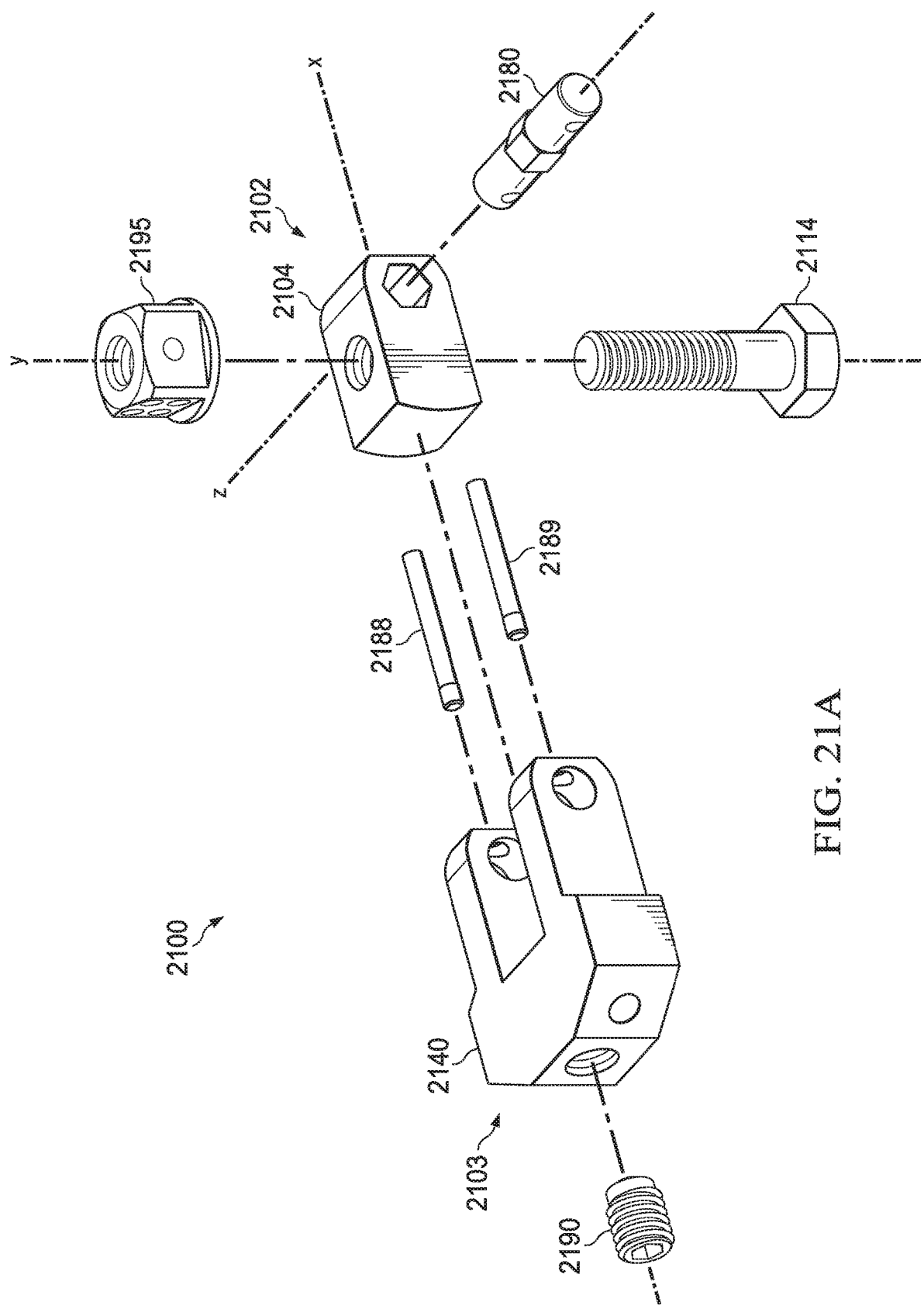
FIG. 21A illustrates an exploded perspective view of an alternative embodiment of a hinged dynamization tab.

FIG. 21A is an exploded perspective view of an embodiment of a cantilevered dynamization tab (cantilevered tab 2100) of the present disclosure. The cantilevered tab 2100 has a longitudinal axis X, a vertical axis Y, and a transverse axis Z defined therein and comprises a proximal end 2102, a distal end 2103, a ring connector body 2104, a strut connector 2140, and a pivot pin 2180 that provides an axis of rotation that is aligned with the transverse axis Z. Further, according to some embodiments, the cantilevered tab 2100 may comprise a connecting bolt 2114, a first connecting nut 2195, a first elastic element 2188, a second elastic element 2189, and a locking screw 2190. The cantilevered tab 2100 may be securely attached to the top surface of a fixator ring by passing the connecting bolt 2114 through an aperture in the ring and threading the ring connector body 2104 onto the connecting bolt 2114.

Figure 21B:
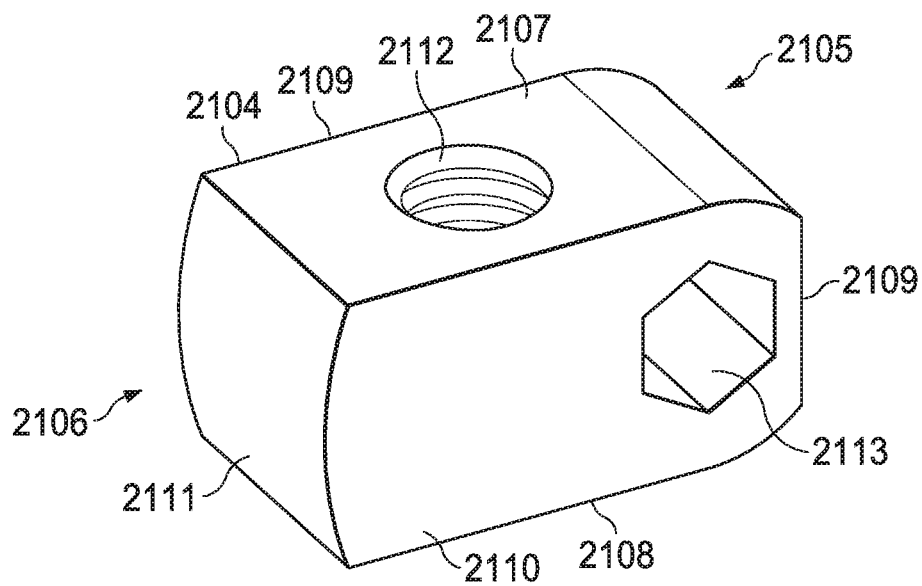
FIG. 21B illustrates a perspective view of a ring connector used with an alternative embodiment of a hinged dynamization tab.

A closer view of the ring connector body (also called a ring connector) 2104 according to this embodiment is depicted in FIG. 21B. In FIG. 21B, the ring connector body 2104 comprises a top surface 2107, a bottom surface 2108, a first lateral surface 2109, a second lateral surface 2110, and a distal surface 2111. According to one embodiment, the distal surface 2111 may comprise a surface with a curved profile with respect to the vertical axis of the cantilevered tab 2100, as shown in FIG. 21B. The ring connector 2104 has a proximal end 2105 and a distal end 2106 and is positioned along the longitudinal axis X of the cantilevered tab 2100. The ring connector 2104 may further comprise a threaded bore 2112, and a second bore 2113. In some embodiments, the threaded bore 2112 extends parallel and distal to the vertical axis Y from the top surface 2105 to the bottom surface 2106. The threaded bore 412 may threadably engage with the connecting bolt 2114, as depicted in FIG. 21A. The second bore 2113 may extend along the transverse axis Z of the cantilevered tab 2100 from the first lateral surface 2109 of the ring connector to the second lateral surface 2110 of the ring connector and may be configured to accept the pivot pin 2180 of FIG. 21A. The second bore 2113 may comprise a plurality of flat surfaces that are parallel to the transverse axis. As shown in FIG. 21B, these flat surfaces may comprise a hexagonal or other symmetrical shape that act as a key to mate with a corresponding portion of the pivot pin 2180.

Figure 21C:
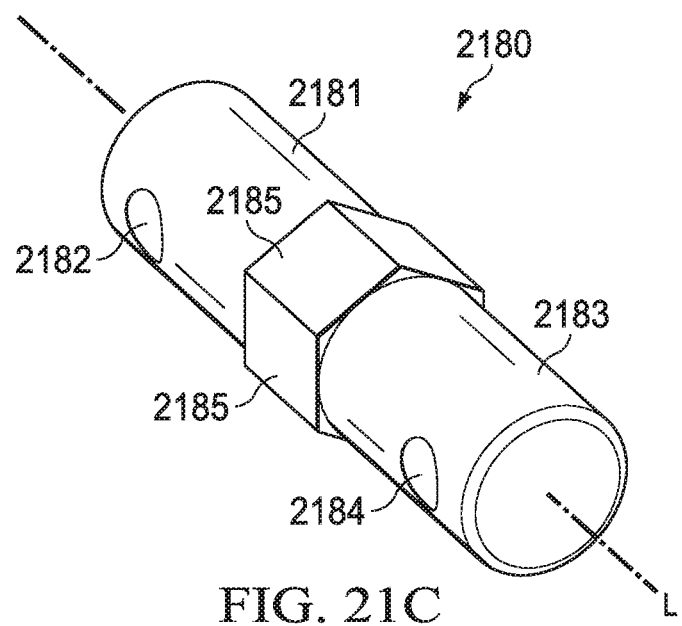
FIG. 21C illustrates a perspective view of a pivot pin used with an alternative embodiment of a hinged dynamization tab.

A closer view of the pivot pin 2180 according to this embodiment is depicted in FIG. 21C. In FIG. 21C, a pivot pin is shown as having a longitudinal axis L that is aligned with the transverse axis of the device X. The pivot pin 2180 is depicted as having a first lateral end 2181 having a substantially cylindrical shape. The first lateral end 2181 may further comprise a cantilever bore 2182 that is substantially orthogonal to the longitudinal axis L of the pivot pin 2180. According one embodiment, the cantilever bore 2182 may pass entirely through the pivot pin. The pivot pin 2180 is also depicted as having a second lateral end 2183 having a substantially cylindrical shape. The second lateral end 2183 may further comprise a cantilever bore 2184 that is substantially orthogonal to the longitudinal axis L of the pivot pin 2180. According one embodiment, the cantilever bore 2184 may pass entirely through the pivot pin. The pivot pin 2180 may further comprise a medial section comprising a plurality of flat surfaces 2185 that are parallel to the longitudinal axis of the pin 2180. Preferably, these plurality of flat surfaces are designed to securely mate with the plurality of flat surfaces found in the of the second bore 2113 of the ring connector body 2104 (see FIG. 21A). The pivot pin 2180 may be suitable for a press fit into the second bore 2113. The pivot pin can pivotally connect the strut connector 2140 with the ring connector body 2104 so that the strut connector 2140 may pivot about the transverse axis Z of the device.

Figure 21D:
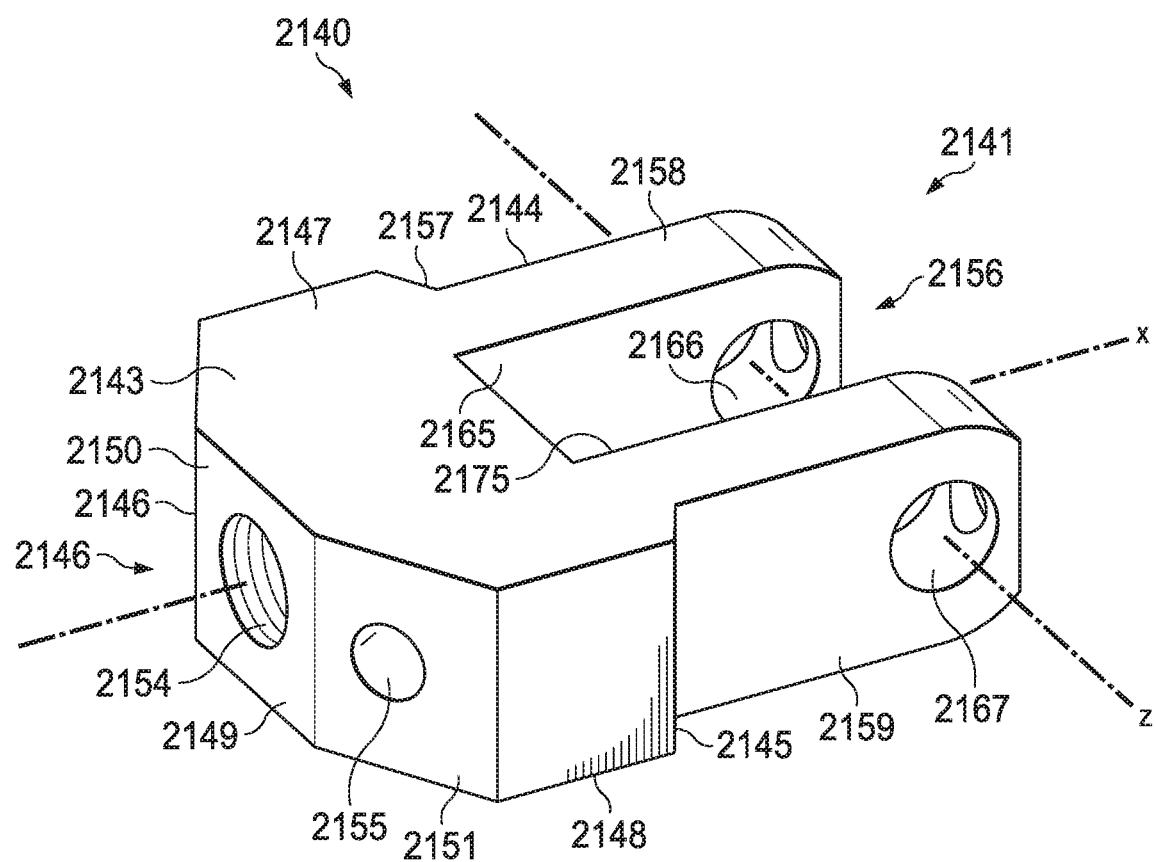
FIG. 21D illustrates a perspective view of a strut connector used with an alternative embodiment of a hinged dynamization tab.

A closer view of the strut connector 2140 according to this embodiment is depicted in FIG. 21D. In some embodiments, the strut connector 2140 may have a proximal end 2141 and a distal end 2146 and may further comprise a head 2143 and strut connector knuckle 2144. The head 2143 may have a proximal end 2145 and a distal end 2146 and be positioned along the longitudinal axis X of the tab 2140. The head 2143 may further comprise a top surface 2147, a bottom surface 2148, a first distal-facing surface 2149, a second distal-facing surface 2150, and a third distal-facing surface 2151. In some embodiments, the strut connector knuckle 2144 may comprise a proximal end 2156 and a distal end 2157 and be positioned along the longitudinal axis X of the tab 2140 so that the distal end 2157 of the strut connector knuckle 2144 is in contact with the proximal end 2145 of the head 2143. The strut connector knuckle 2144 may further comprise a first arm 2158 and a second arm 2159. The first arm 2158 may be positioned parallel to the longitudinal axis X of the tab so that the distal end 2157 is in contact with the proximal end 2145 of the head. The second arm 2159 may also be positioned parallel to the longitudinal axis X of the tab so that the distal end 2157 is in contact with the proximal end 2145 of the head 2143. According to some embodiments, the proximal ends of the first and second arms (2158, 2159) may be connected by a lateral member (not shown in FIG. 21D), which forms a rigid connection between the first and second arms (2158, 2159) and further strengthens the proximal end 2141 of the strut connector 2140.

The first arm 2158 of the strut connector knuckle 2144 may further comprise a first arm bore 2166 that is sized to receive the first lateral end 2181 of the pivot pin 2180. Similarly, the second arm 2159 may further comprise a second arm bore 2167 that extends along the transverse axis Z of the cantilevered tab 2100 and is sized to receive the second lateral end 2183 the pivot pin 2180. The first arm 2158 also comprises a first inner wall 2165 that may be placed in contact with the first lateral surface 2109 of the ring connector 2104 when those components are mated together. The second arm 2159 also comprises a second inner wall 2175 that may be placed in contact with the second lateral surface 2110 of the ring connector 2104 when those components are mated together. The relatively large surface areas of the first and second inner walls (2165, 2175) that are in contact with the first and second lateral surfaces (2109, 2110) allow the strut connector 2140 to pivot about the transverse axis Z with respect to the ring connector 2104 while minimizing any lateral displacement that may occur along the transverse axis Z. According to one embodiment, the first distal-facing surface 2149 may comprise a locking-screw aperture 2154, which may be a partial bore that extends from the distal end of the head 2146 towards the proximal end of the head 2145 and may be threaded to accept a locking screw. The second distal-facing surface 2150 and the third distal-facing surface 2151 may further comprise strut apertures 2155, which may be a partial bore that extends from the distal end of the head 2146 to the proximal end of the head 2145 and may be each be configured to secure a strut to the strut connector 2140.

Figure 21E:
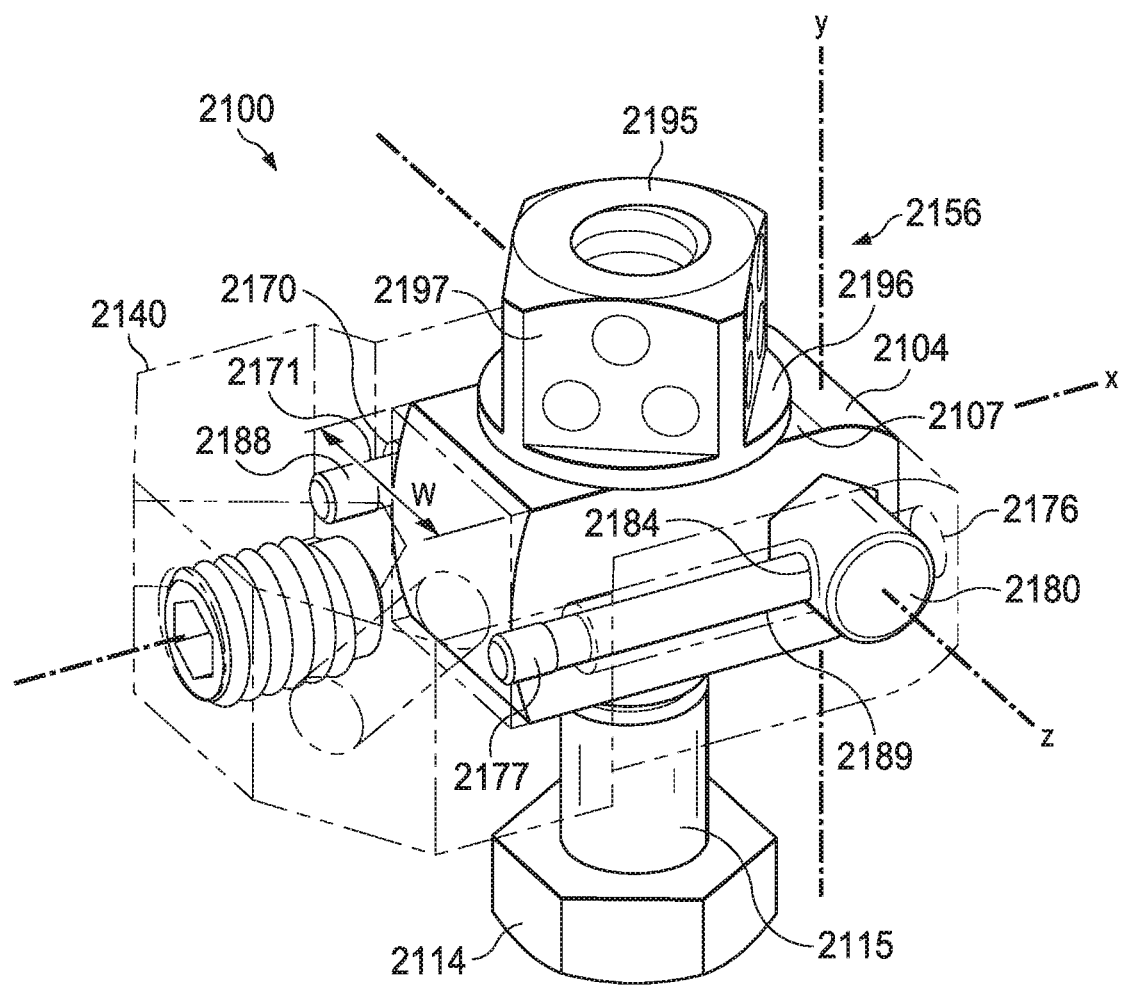
FIG. 21E illustrates a transparent perspective view of an alternative embodiment of a hinged dynamization tab.
Figure 21F:
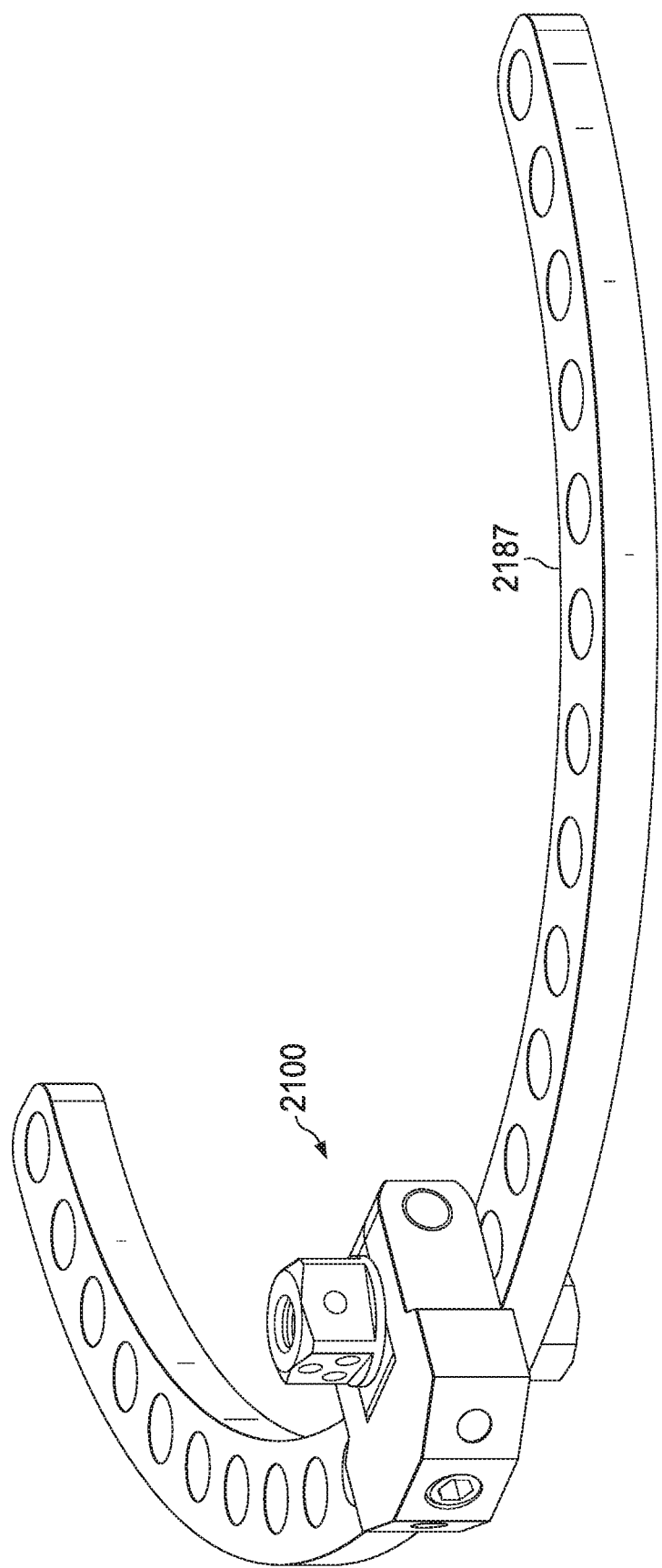
FIG. 21F illustrates a perspective view of an alternative embodiment of a hinged dynamization tab mounted to a fixation ring.

A transparent perspective view of one embodiment of the cantilevered tab 2100 is depicted in FIG. 21E. In FIG. 21E, a fully assembled cantilevered tab 2100 is depicted with a strut connector 2140, a ring connector body 2104, a connecting bolt 2114, a connecting nut 2195, and a pivot pin 2180. Also depicted in FIG. 21F is a first longitudinal cantilever bore 2170 extending from a proximal end 2156 of the first arm 2158 into the first arm and is parallel to the longitudinal axis X. The first longitudinal cantilever bore 2170 further comprises a smaller circumference 2171 at a distal end of the bore 2170, and a larger circumference at a proximal end of the bore 2170. Also shown is a second longitudinal cantilever bore 2176 extending from a proximal end 2156 of the second arm 2159 into the second arm and is parallel to the longitudinal axis X. The second longitudinal cantilever bore 2176 further comprises a smaller circumference 2177 at a distal end of the bore 2176, and a larger circumference at a proximal end of the bore 2176.

Also shown in FIG. 21F is a cantilever bore 2184 that is located in the second lateral end 2183 of the pivot pin 2180, and which is substantially orthogonal to the longitudinal axis of the pivot pin. A similar corresponding cantilever bore is located in the first lateral end 2181 of the pivot pin 2180 but is not visible in FIG. 21E. The cantilever bores (2182, 2184) in the pivot pin 2180 are designed to align with the first and second longitudinal cantilever bores (2170, 2176) when the cantilever tab 2100 is in its resting position. Also shown in FIG. 21E are the first elastic element 2188 and the second elastic element 2189. Each of the these elastic elements (2188, 2189) may be comprised of a flexible or elastic material, such as steel, titanium, bronze, metal alloys, nylon, PEEK, Polyethylene, silicone elastomers, natural and synthetic rubber, polyethylene terephthalate, polymer containing composites, etc. Preferably, each of the elastic elements (2188, 2189) has a cylindrical shape that is uniform along the entire respective lengths. Each of the elastic elements (2188, 2189) has a proximal end (to be disposed near the proximal end of the device 2100) and a distal end (to be disposed near the distal end of the device 2100). The first elastic element 2188 is positioned within the first longitudinal cantilever bore 2170 and within the cantilever bore 2182 at the first lateral end 2181 of the pivot pin (2180). Similarly, the second elastic element 2189 is positioned within the second longitudinal cantilever bore 2176 and within the cantilever bore 2184 at the second lateral end 2183 of the pivot pin (2180). The distal end of the first elastic element 2188 can be mated with the smaller circumference at the distal end 2171 of the first longitudinal cantilever bore, while the proximal end of the first elastic element has an outer circumference that is smaller than the circumference of the proximal end of the first longitudinal cantilever bore 2170. In a similar manner, the distal end of the second elastic element 2189 can be mated with the smaller circumference at the distal end 2177 of the second longitudinal cantilever bore, while the proximal end of the first elastic element has an outer circumference that is smaller than the circumference of the proximal end of the first longitudinal cantilever bore 2170. According to this arrangement, the first and second elastic elements (2188, 2189) can bend and deform within the first and second longitudinal cantilever bores (2170, 2176), respectively. This cantilever movement of the first and second elastic elements (2188, 2189) applies a mechanical bias to the strut connector 2140 as it is pivoted with respect to the ring connector 2104 that encourages the strut connector 2140 to move back to a resting position. The first and second elastic elements (2188, 2189) will deform until the elements impinge upon the surface of the larger diameter first and second longitudinal cantilever bores (2170, 2176), respectively. At this point, no further pivoting movement of the strut connector 2140 is permitted with respect to the ring connector 2104.

Another aspect of this embodiment is the flanged surface 2196 that is found on an end of the connecting nut 2195. As shown in FIG. 21E, the diameter of the flanged surface 2196 of the connecting nut is greater than the lateral width W of the ring connector body. As such, the connecting nut 2195 can be adjustably positioned along the threaded portion of the connecting bolt 2114 so that when the flanged surface 2196 of the connecting nut 2195 impinges upon the top surface 2107 of the ring connector body 2104, the flanged surface 2196 will prevents the pivotal movement of the strut connector 2140 with respect to the ring connector body 2104. On the other hand, when the flanged surface 2196 of the connecting nut 2195 is displaced away from the top surface 2107 of the ring connector body 2104, pivotal movement of the strut connector with respect to the ring connector body can be controllably engaged. According to one embodiment, the connecting nut 2195 may comprise one or more flat surfaces 2197 with markers, such as the three divots seen on the flat surface 2197 of the connecting nut 2195. These markers can be used as an indicator as to how much pivotal movement (and therefore how much dynamization) can be added to or removed from the cantilevered tab 2100. As such, the amount of dynamization to be applied to the device can be controlled.

Figure 21G:
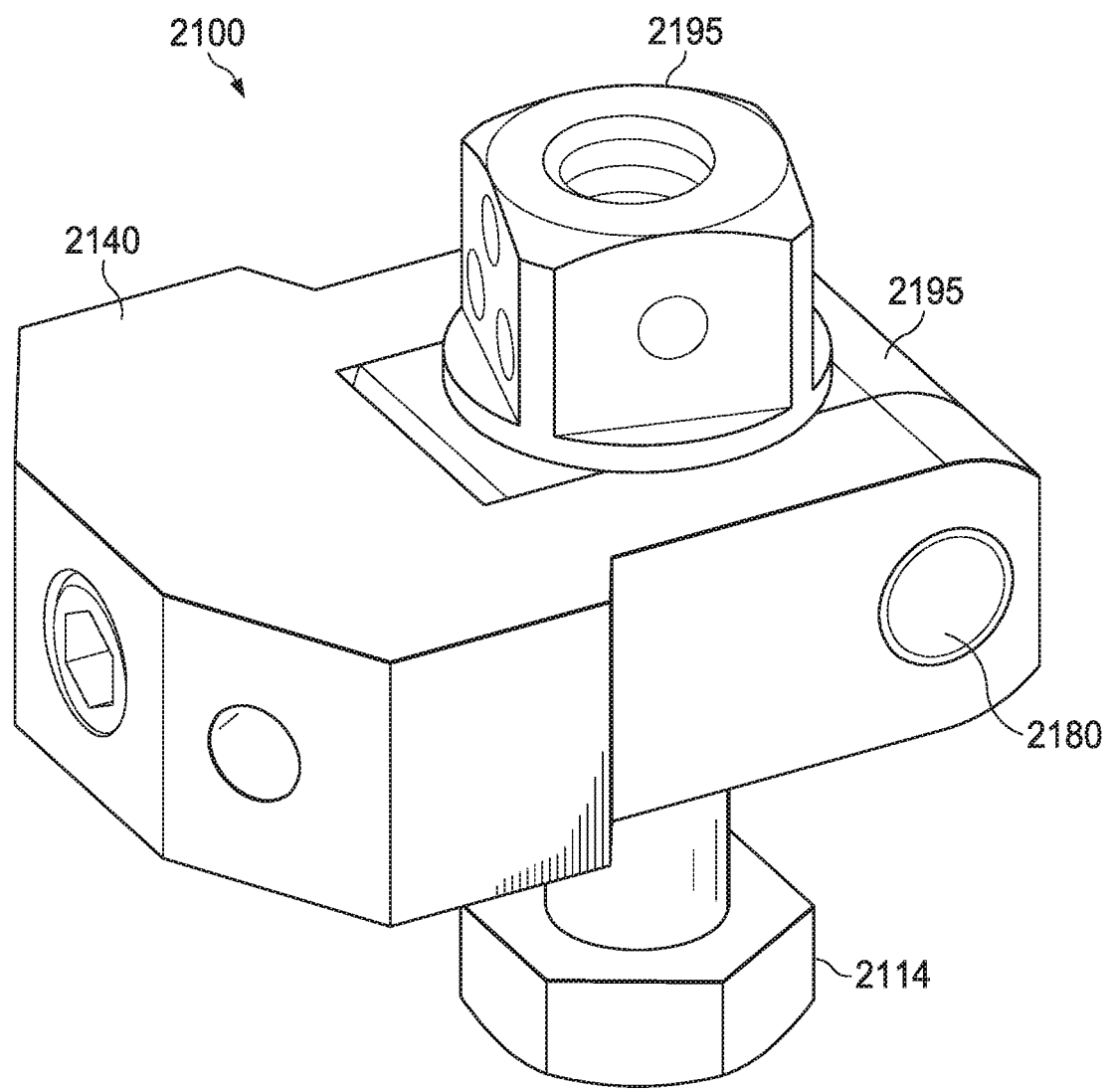
FIG. 21G illustrates another perspective view of a an alternative embodiment of a hinged dynamization tab.

Also shown in FIG. 21E is a smooth portion 2115 of the connecting bolt 2114 that is not threaded. Preferably, the outer diameter of the connecting bolt 2114 is similar to the inner diameter of the apertures found in the fixation ring, so that the connecting bolt 2114 can securely mount the cantilevered tab 2100 to a fixation ring with minimal play between the connecting bolt 2114 and the ring. This is depicted in FIG. 21F, where the cantilevered tab 2100 is securely mounted to a fixation ring 2187. Another perspective view of one embodiment of the cantilevered tab 2100 is depicted in FIG. 21G. In FIG. 21G, a fully-assembled cantilevered tab 2100 is depicted with a strut connector 2140, a ring connector body 2104, a connecting bolt 2114, a connecting nut 2195, and a pivot pin 2180.

With respect to all of the disclosed embodiments, the biasing regions, or even the entire tab, may be comprised of a material having appropriate elasticity and shape memory, such material can be selected from plastic, polymer, thermoplastic, metal, metal alloy, composite, resin, ultra-high-molecular-weight polyethylene (UHMW), a polytetrafluoroethylene (PTFE), ABS plastic, PLA, polyamide, glass filled polyamide, epoxy, nylon, rayon, polyester, polyacrylate, wood, bamboo, bronze, titanium, steel, stainless steel, a cobalt chromium alloy, ceramic, wax, photopolymer, and polycarbonate. In certain non-limiting examples the polymer can be a thermoplastic polymer, a polyolefin, a polyester, a polysilicone, a polyacrylonitrile resin, a polystyrene, polyvinyl chloride, polyvinylidene chloride, polyvinyl acetate, a fluoroplastic, a phenolic resin, a urea resin, a melamine, an epoxy, a polyurethane, a polyamide, a polyacrylate resin, a polyketone, a polyimide, a polysulfone, a polycarbonate, a polyacetal, poly(hydroxynapthoic acid), a conductive polymer, a poly(3-hexylthiophene), a polyphenylene-vinylene, a poly(phenylene vinylene), a polyaniline, or combinations thereof. Other appropriate and biocompatible materials can be utilized. According to another embodiment, the biasing region or dynamization device can be fabricated by an additive printing process (e.g., a 3D printing process). The biasing region or dynamization device can also be fabricated by machining, forging or casting, based on the specific design and intended use of the device and the material comprising the device. Suitable materials include the medical grade and biocompatible plastics described above, or biocompatible metals, such as titanium, stainless steel, 316L stainless steel, cobalt-chromium, and alloys thereof. According to some embodiments, the devices can be made as a composite or hybrid device with a combination of plastic and metallic components. The selected material must have sufficient plasticity and shape memory to return to its original configuration after having been deformed many times.

It will be understood that particular embodiments described herein are shown by way of illustration and do not act as limitations of the disclosure. The principle features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be in the scope of this disclosure and are covered by the claims.

The use of the word "a" or "an" when used in conjunction with the term "comprising" in the claims and/or in the specification may mean "one," but is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise," "comprises," etc.), "having" (and any form of having, such as "have" and "has"), "including" (and any form of including, such as "includes" and "include"), or "containing" (and any form of containing, such as "contains" and "contain"), are inclusive and open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or the sequence of steps of the method described herein without departing from the concept, spirit, and scope of the disclosure. All such familiar substitutes and modification apparent to those skilled in the art are deemed to be within the spirit, scope, and concept of the disclosure as defined by the appended claims.

What is claimed is:

1. A dynamization system comprising:
an external fixation ring; and
a dynamization tab having a longitudinal axis defined therein, the dynamization tab comprising:
a ring connector being configured to releasably couple the dynamization tab to the external fixation ring;
a strut connector being configured to releasably couple the dynamization tab to one or more struts and be positioned along the longitudinal axis of the dynamization tab in a resting position and in a manner such that it that it is capable of being displaced from the longitudinal axis under loading; and
a biasing mechanism, the biasing mechanism being configured to, in response to the strut connector being displaced from the longitudinal axis of the dynamization tab, apply a biasing force sufficient to return the strut connector to the resting position.

2. The dynamization system according to claim 1, wherein the ring connector comprises a ring connector body having a proximal end and a distal end and being positioned along the longitudinal axis of the dynamization tab, the ring connector body further comprising:
a ring connector knob that is positioned at the distal end of the ring connector body and comprises a top surface and a bottom surface;
a first bore that extends from the top surface of the ring connector knob to the bottom surface of the ring connector knob and is parallel to a vertical axis of the dynamization tab, the first bore being configured to accept an adjustment screw;
a second bore that extends from a first upper lateral surface of the ring connector body to a second upper lateral surface of the ring connector body and is positioned parallel to a transverse axis of the dynamization tab at the proximal end of the ring connector body, the second bore being configured to accept a pivot pin; and
a connecting bolt that extends from the bottom surface of the ring connector body and is positioned parallel to the vertical axis of the dynamization tab and is configured to accept a connecting nut;
wherein the strut connector is positioned along the longitudinal axis of the dynamization tab such that the strut connector is in contact with the ring connector, the strut connector further comprising:
a head comprising a proximal end and a distal end, the head further comprising:
a first distal-facing surface positioned parallel to the transverse axis of the dynamization tab;
a locking screw aperture comprising a partial bore extending from a distal end of the head towards a proximal end of the head, the locking screw aperture being configured to accept a locking screw;
second and third distal-facing surfaces, each of the second and third distal-facing surfaces comprising a strut aperture comprising a partial bore extending from the distal end of the head towards the proximal end of the head, each strut aperture being configured to secure the strut connector to a strut; and
a ring connector aperture that is formed in the top surface of the head and extends down into the head and has an inner circumference large enough to allow the strut connector to pivot without outer walls of the ring connector knob impinging upon inner walls of the ring connector aperture.

3. The dynamization system according to claim 2, wherein the strut connector further comprises:
a first arm comprising a proximal end and a distal end, wherein the first arm is positioned along the longitudinal axis of the dynamization tab and further comprises:
a top surface;

a bottom surface, the bottom surface being positioned such that it is parallel to the longitudinal axis of the dynamization tab;
a first inner wall surface;
a first lateral wall surface; and
a first lateral pin bore extending through the first lateral wall surface and the first inner wall surface so that the first lateral pin bore is parallel to the transverse axis of the dynamization tab, the first lateral pin bore being configured to accept the pivot pin;
wherein the strut connector further comprises a second arm comprising a proximal end and a distal end, wherein the second arm is positioned along the longitudinal axis of the dynamization tab and further comprises:
a top surface;
a bottom surface, the bottom surface being positioned such that it is parallel to the longitudinal axis of the dynamization tab;
a second inner wall surface;
a second lateral wall surface; and
a second lateral pin bore extending through the second lateral wall surface and the second inner wall surface so that the second lateral pin bore is parallel to the transverse axis of the dynamization tab, the second lateral pin bore being configured to accept the pivot pin.

4. The dynamization system according to claim 3, wherein the first and second arms are connected by a lateral member at a proximal end of the arms.

5. The dynamization system according to claim 1, wherein the ring connector comprises a ring connector body comprising:
a first roughened surface comprising a plurality of ridges on a bottom surface of the ring connector body, the first roughened surface being positioned at a distal end of the ring connector body in a manner such that it contacts a surface of the external fixation ring and provides a frictional connection that limits rotation of the ring connector with respect to an external fixation ring; and
a second roughened surface comprising a plurality of ridges on the bottom surface of the ring connector body, the second roughened surface being positioned at a proximal end of the ring connector body in a manner such that it contacts a surface of the external fixation ring and provides a frictional connection that limits rotation of the ring connector with respect to an external fixation ring.

6. A dynamization tab according to claim 5, wherein the ring connector body further comprises a first motion limiting face positioned at the distal end of the ring connector body and parallel to a transverse axis of the dynamization tab in a manner such that the first motion limiting face is parallel and superior to the bottom surface of the ring connector body; and
wherein a head of the strut connector comprises a second motion limiting face positioned at a proximal end of the head and in contact with a top surface of the head in a manner such that the degree of rotational displacement of the strut connector about the transverse axis of the dynamization tab is limited by contact between the second motion limiting face of the strut connector and the first motion limiting face of the ring connector body.

7. The dynamization system according to claim 1, wherein the biasing mechanism further comprises a compression spring positioned between a bottom surface of a distal knob of the ring connector and a bottom of a ring connector aperture such that the biasing mechanism provides a mechanical bias that opposes pivotal movement of the strut connector with respect to the ring connector.

8. The dynamization system according to claim 1, further comprising an adjustment screw disposed within a threaded bore of the ring connector that can be driven to traverse the threaded bore; wherein when a distal end of the adjustment screw is driven to impinge upon a bottom of a ring connector aperture, pivotal movement of the strut connector with respect to the ring connector is limited; and wherein when the distal end of the adjustment screw is driven away from the bottom of the ring connector aperture, pivotal movement of the strut connector with respect to the ring connector can be controllably engaged.

9. The dynamization system according to claim 1, wherein a locking-screw aperture is threaded to receive a threaded locking screw and wherein the locking-screw aperture intersects with a proximal end of strut apertures so that a proximal end of the locking screw can impinge upon a proximal end of the strut connector to prevent movement of strut fasteners with respect to the strut apertures when the locking screw is in place.

10. A dynamization tab having a longitudinal axis, a vertical axis, and a transverse axis, the dynamization tab comprising:
a ring connector, the ring connector having a proximal end and a distal end and being positioned along the longitudinal axis of the dynamization tab, the ring connector further comprising:
a ring connector body, the ring connector body having a proximal end and a distal end and being positioned along the longitudinal axis of the dynamization tab, the ring connector body further comprising:
a top surface;
a bottom surface;
a first upper lateral surface;
a second upper lateral surface;
a first bore that extends from the top surface of a ring connector knob to the bottom surface of the ring connector knob and is parallel to the vertical axis of the dynamization tab, the first bore being configured to accept an adjustment screw;
a second bore that extends from the first upper lateral surface of the ring connector body to the second upper lateral surface of the ring connector body and is positioned parallel to the transverse axis of the dynamization tab at the proximal end of the ring connector body, the second bore being configured to accept a pivot pin;
a connecting bolt that extends from the bottom surface of the ring connector body and is positioned parallel to the vertical axis of the dynamization tab and is configured to accept a connecting nut; and
a strut connector, the strut connector having a proximal end and a distal end and being positioned along the longitudinal axis of the dynamization tab such that the strut connector is in contact with the ring connector, the strut connector further comprising:
a head, wherein the head comprises a proximal end and a distal end and is positioned along the longitudinal axis of the dynamization tab, the head further comprising:
a top surface; and a bottom surface;
wherein the ring connector can be mated with the strut connector so that a pivot pin pivotably secures to the ring connector to the strut connector and allows the strut connector to pivot about the transverse axis with respect to the ring connector; and
a biasing element positioned between the ring connector and the strut connector such that the biasing element provides a mechanical bias that opposes pivotal movement of the strut connector with respect to the ring connector.

11. A dynamization tab according to claim 10, wherein the head of the strut connector further comprises:
a first distal-facing surface, the first distal-facing surface comprising:
a top edge and a bottom edge, the first distal-facing surface being positioned parallel to the transverse axis of the dynamization tab and in a manner such that the top edge is in contact with the top surface of the head and the bottom edge is in contact with the bottom surface of the head; and
a locking screw aperture comprising a partial bore extending from the distal end of the head towards the proximal end of the head, the locking screw aperture being configured to accept a locking screw; and
second and third distal-facing surfaces, each of the second and third distal-facing surfaces comprising a strut aperture comprising a partial bore extending from the distal end of the head towards the proximal end of the head, the strut aperture being configured to secure the strut connector to a strut.

12. A dynamization tab according to claim 11, wherein the strut connector further comprises:
a first arm comprising a proximal end and a distal end, wherein the first arm is positioned along the longitudinal axis of the dynamization tab and further comprises:
a top surface;
a bottom surface, the bottom surface being positioned such that it is parallel to the longitudinal axis of the dynamization tab;
a first inner wall surface;
a first lateral wall surface; and
a first lateral pin bore extending through the first lateral wall surface and the first inner wall surface so that the first lateral pin bore is parallel to the transverse axis of the dynamization tab, the first lateral pin bore being configured to accept the pivot pin; and
a second arm comprising a proximal end and a distal end, wherein the second arm is positioned along the longitudinal axis of the dynamization tab and further comprises:
a top surface;
a bottom surface, the bottom surface being positioned such that it is parallel to the longitudinal axis of the dynamization tab;
a second inner wall surface;
a second lateral wall surface; and
a second lateral pin bore extending through the second lateral wall surface and the second inner wall surface so that the second lateral pin bore is parallel to the transverse axis of the dynamization tab, the second lateral pin bore being configured to accept the pivot pin;
wherein the first and second arms are connected by a lateral member at a proximal end of the arms; and
wherein the first and second upper lateral surfaces of the ring connector can slidably engage with the first and second inner wall surfaces of the strut connector when the ring connector is pivotably secured to the strut connector.

13. A dynamization tab according to claim 10, wherein the ring connector body further comprises a first motion limiting face positioned at the distal end of the ring connector body and parallel to the transverse axis of the dynamization tab in a manner such that the first motion limiting face is parallel and superior to the bottom surface of the ring connector body; and
wherein the head of the strut connector further comprises a second motion limiting face positioned at the proximal end of the head and in contact with the top surface of the head in a manner such that a degree of rotational displacement of the strut connector about the transverse axis of the dynamization tab is limited by contact between the second motion limiting face of the strut connector and the first motion limiting face of the ring connector body.

14. A dynamization tab according to claim 10, wherein the ring connector body further comprises:
a first roughened surface comprising a plurality of ridges on the bottom surface of the ring connector body, the first roughened surface being positioned at the distal end of the ring connector body in a manner such that it may contact a surface of an external fixation ring and provide a frictional connection that limits rotation of the ring connector with respect to the external fixation ring; and
a second roughened surface comprising a plurality of ridges on the bottom surface of the ring connector body, the second roughened surface being positioned at the proximal end of the ring connector body in a manner such that it may contact a surface of the external fixation ring and provide a frictional connection that limits rotation of the ring connector with respect to an external fixation ring.

15. A dynamization tab according to claim 10, wherein the biasing element comprises a compression spring.

16. A dynamization tab according to claim 10,
wherein the ring connector knob is positioned at the distal end of the ring connector body;
wherein the head of the strut connector further comprises a ring connector aperture that is formed in the top surface of the head and extends down into the head and has an inner circumference large enough to allow the strut connector to pivot without outer walls of the ring connector knob impinging upon inner walls of the ring connector aperture; and
wherein when a distal end of the adjustment screw is driven to impinge upon the bottom of the ring connector aperture, pivotal movement of the strut connector with respect to the ring connector is limited and, when the distal end of the adjustment screw is driven away from the bottom of the ring connector aperture, pivotal movement of the strut connector with respect to the ring connector can be controllably engaged.

17. A dynamization tab according to claim 10, wherein a locking-screw aperture is threaded to receive a threaded locking screw and wherein the locking-screw aperture intersects with a proximal end of strut apertures so that a proximal end of the locking screw can impinge upon a proximal end of the strut connector to prevent movement of strut fasteners with respect to the strut apertures when the locking screw is in place.

\* \* \* \* \*